(12) United States Patent
Movahedi et al.

(10) Patent No.: US 9,101,674 B2
(45) Date of Patent: Aug. 11, 2015

(54) TARGETING AND IN VIVO IMAGING OF TUMOR-ASSOCIATED MACROPHAGES

(75) Inventors: Kiavash Movahedi, Frankfurt am Main (DE); Damya Laoui, Limal (BE); Steve Schoonooghe, Kessel-Lo (BE); Geert Raes, Sint-Genesius-Rode (BE); Patrick De Baetselier, Berchem (BE); Jo Van Ginderachter, Ninove (BE); Nick Devoogdt, Zemst (BE); Tony Lahoutte, Ganshoren (BE)

(73) Assignees: VIB VZW, Gent (BE); Vrije Universiteit Brussel, Brussel (BE)

( * ) Notice: Subject to any disclaimer, the term of this patent is extended or adjusted under 35 U.S.C. 154(b) by 0 days.

(21) Appl. No.: 13/480,350

(22) Filed: May 24, 2012

(65) Prior Publication Data

US 2012/0301394 A1 Nov. 29, 2012

Related U.S. Application Data

(63) Continuation-in-part of application No. 13/065,794, filed on Mar. 29, 2011, now abandoned.

(60) Provisional application No. 61/341,356, filed on Mar. 29, 2010.

(51) Int. Cl.
| | |
|---|---|
| *A61K 51/10* | (2006.01) |
| *A61K 47/48* | (2006.01) |
| *C07K 16/28* | (2006.01) |
| *B82Y 5/00* | (2011.01) |

(52) U.S. Cl.
CPC ....... *A61K 51/1027* (2013.01); *A61K 47/48484* (2013.01); *A61K 47/48561* (2013.01); *A61K 47/48761* (2013.01); *B82Y 5/00* (2013.01); *C07K 16/2851* (2013.01); *C07K 2317/22* (2013.01); *C07K 2317/35* (2013.01)

(58) Field of Classification Search
CPC ............... A61K 51/1027; A61K 47/48484; A61K 47/48561; A61K 47/48761; C07K 2317/22; C07K 16/2851
See application file for complete search history.

(56) References Cited

U.S. PATENT DOCUMENTS

| 2010/0070191 A1 | 3/2010 | Gold et al. |
| 2011/0262348 A1 | 10/2011 | Movahedi et al. |

FOREIGN PATENT DOCUMENTS

| WO | 9404678 A1 | 3/1994 |
| WO | 9937681 A2 | 7/1999 |
| WO | 9937681 A3 | 10/1999 |
| WO | 0043507 A1 | 7/2000 |
| WO | 0190190 A2 | 11/2001 |
| WO | 0190190 A3 | 8/2002 |
| WO | 02085945 A2 | 10/2002 |
| WO | 02085945 A3 | 3/2003 |
| WO | 03025020 A1 | 3/2003 |
| WO | 03035694 A2 | 5/2003 |
| WO | 03035694 A3 | 10/2003 |

OTHER PUBLICATIONS

Harmsen et al., Properties, production, and applications of camelid single-domain antibody fragments. Appl. Microbiol. Biotechnol. 77:13-22, 2007.*
Gottlin et al., Isolation of Novel EGFR-Specific VHH Domains, J Biomol Screen, 2009, pp. 77-85, vol. 14.
Cortez-Retamozo et al., Efficient Cancer Therapy with a Nanobody-Based Conjugate, Cancer Res., 2004, pp. 2853-2857, vol. 64.
Heusinkveld M, van der Burg SH. Identification and manipulation of tumor associated macrophages in human cancers. Journal of Translational Medicine. 2011; 9:216.
Algars A, Irjala H, Vaittinen S, Huhtinen H, Sundstrom J, Salmi M, et al. Type and location of tumor-infiltrating macrophages and lymphatic vessels predict survival of colorectal cancer •atients. Int J Cancer 2012. 131:864.

* cited by examiner

*Primary Examiner* — Ruixiang Li
(74) *Attorney, Agent, or Firm* — TraskBritt, P.C.

(57) ABSTRACT

The invention relates to activities and characteristics of tumor-associated macrophages (TAMs). In particular, immunoglobulin single variable domains are provided against markers of TAMs, and methods using the same for in vivo imaging of tumor cells, as well as cancer diagnostics and therapeutics.

14 Claims, 36 Drawing Sheets
(25 of 36 Drawing Sheet(s) Filed in Color)

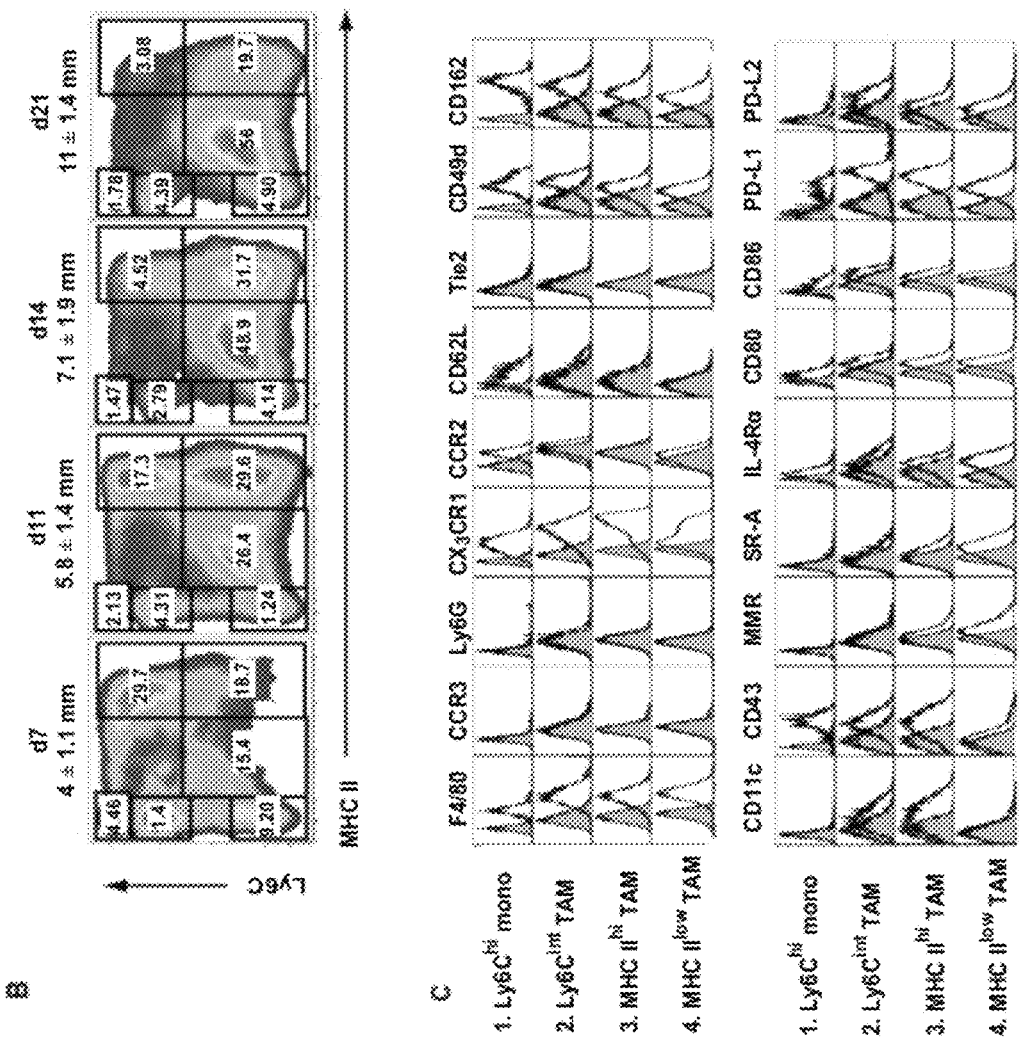

FIG. 2
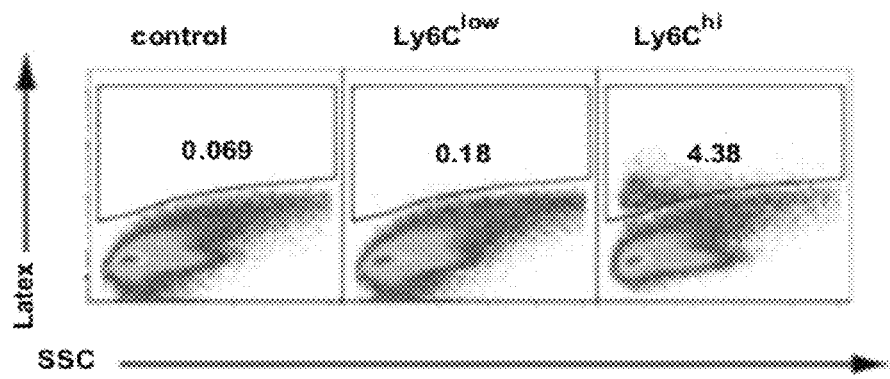
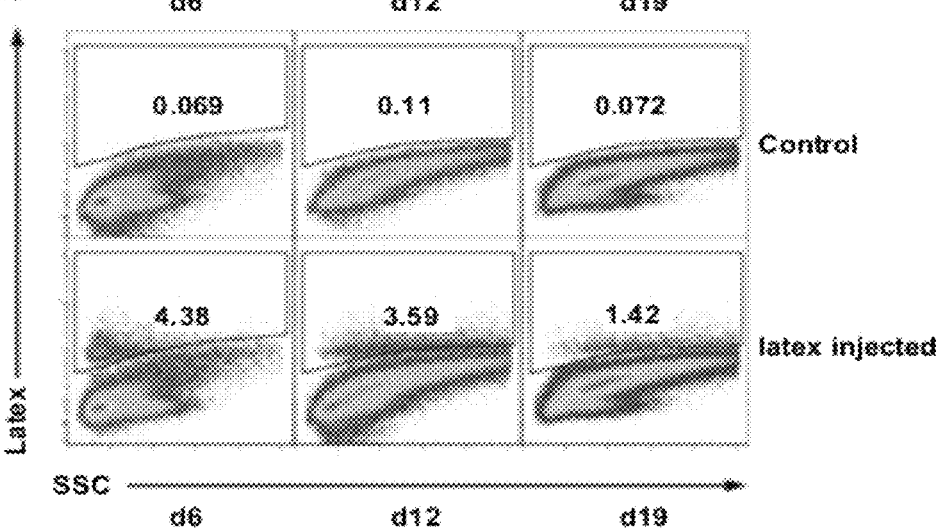
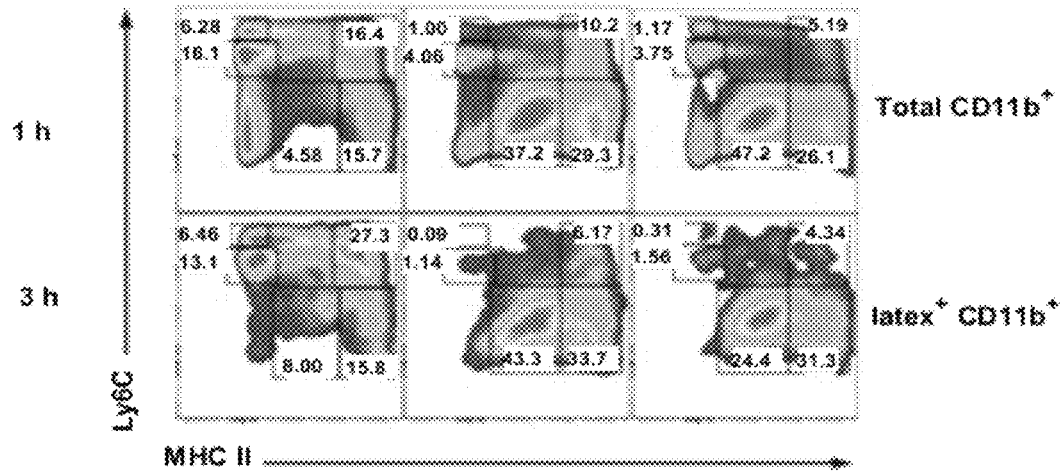

FIG. 2 (continued)
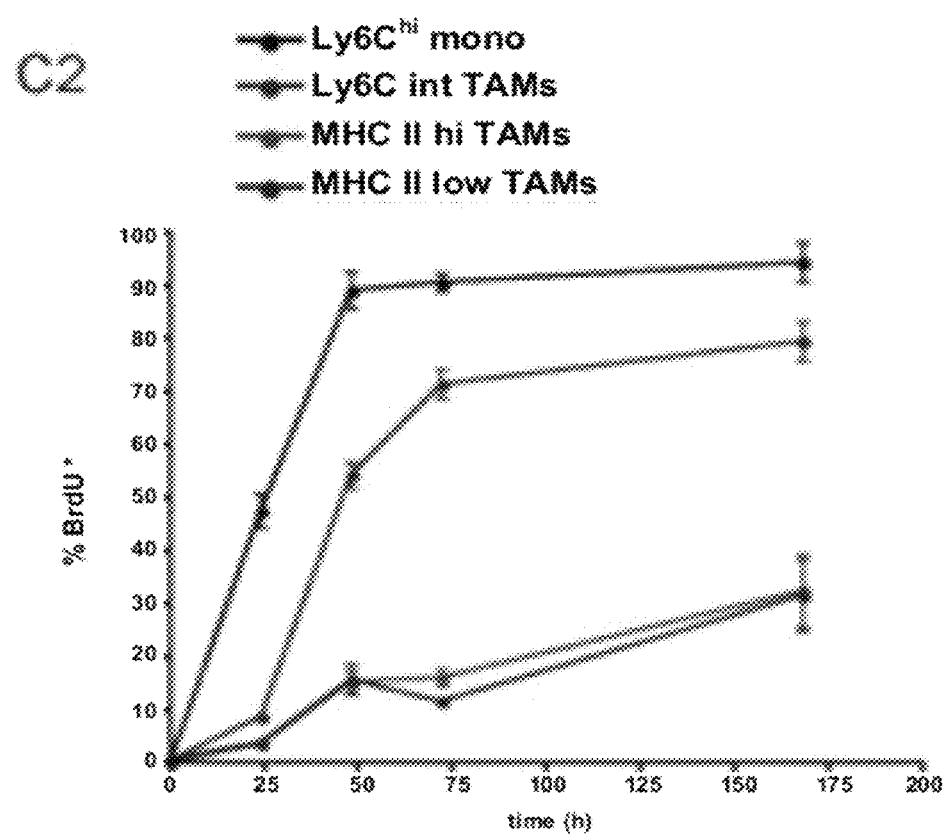
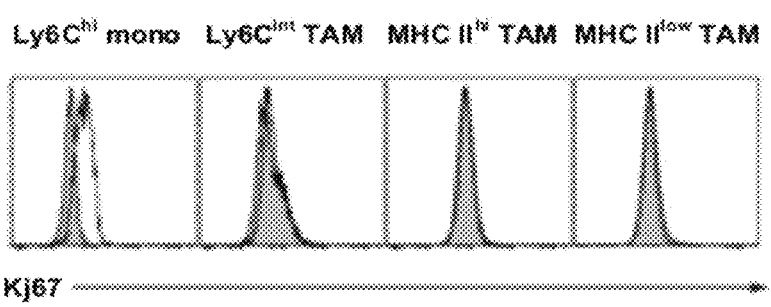

FIG. 4
A
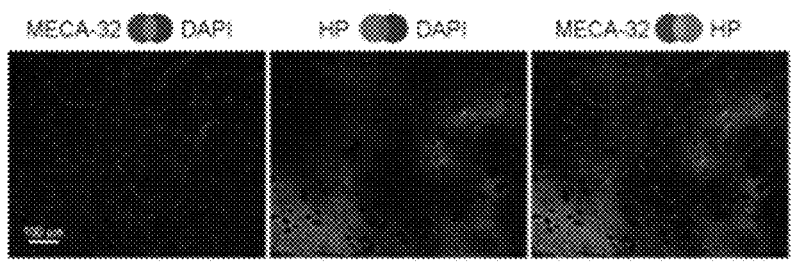
B
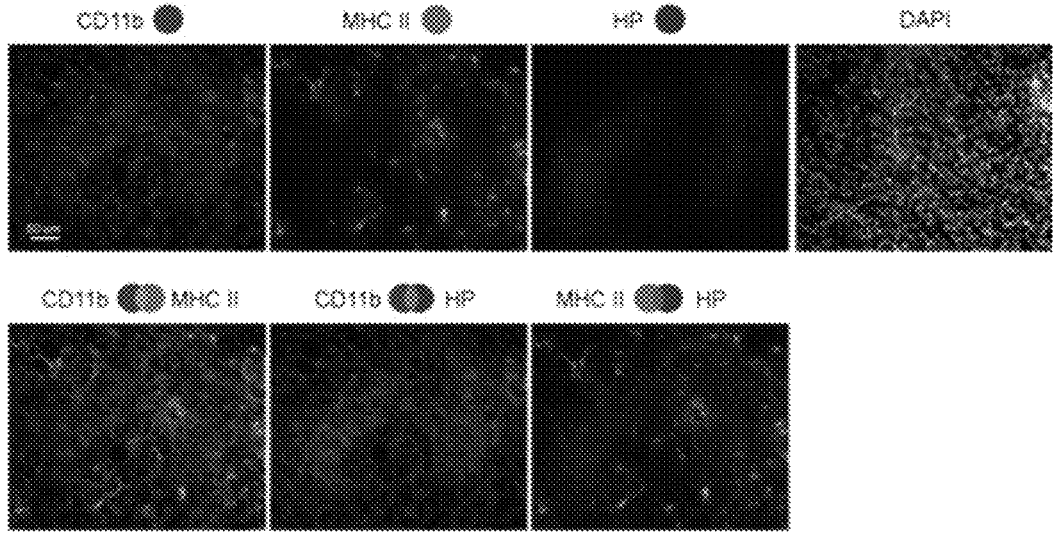
C
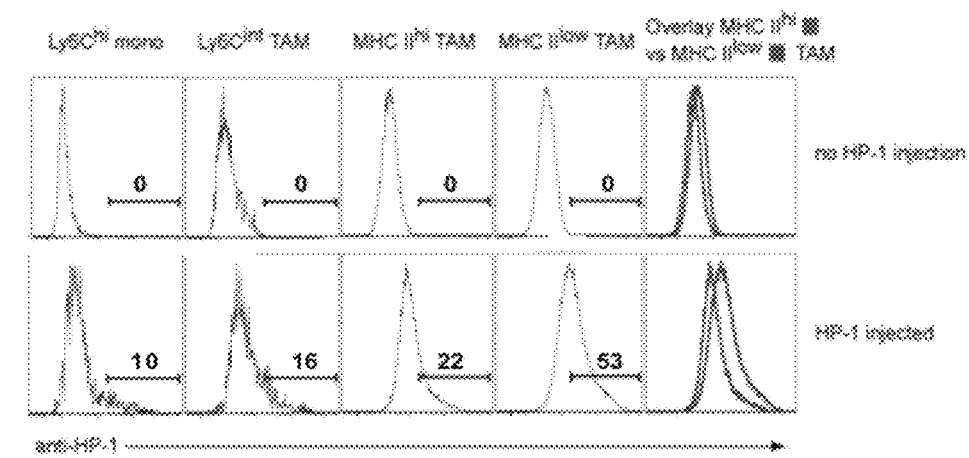

FIG. 7
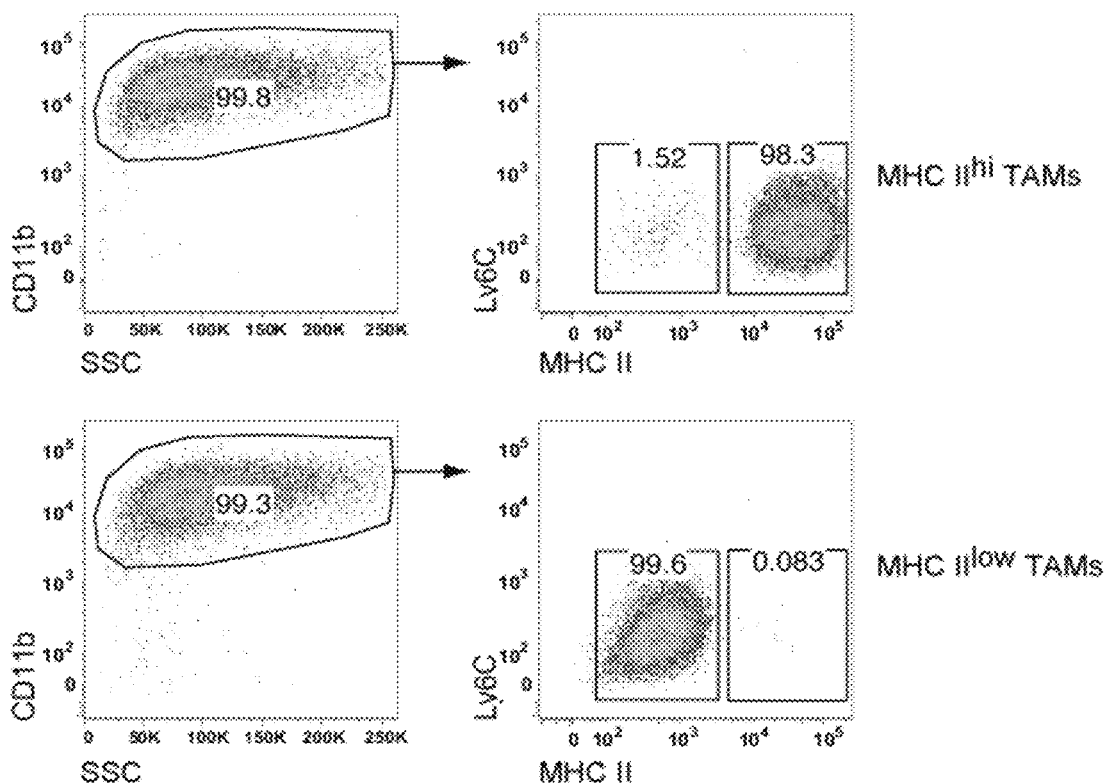
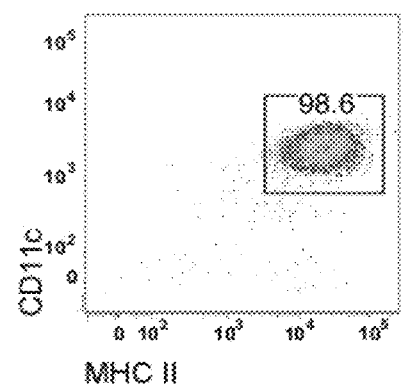

FIG. 8
A
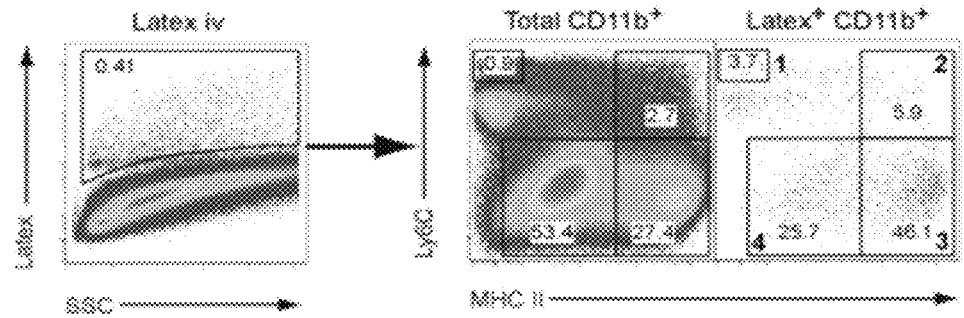
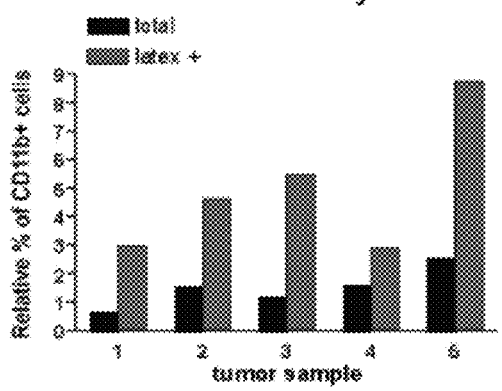
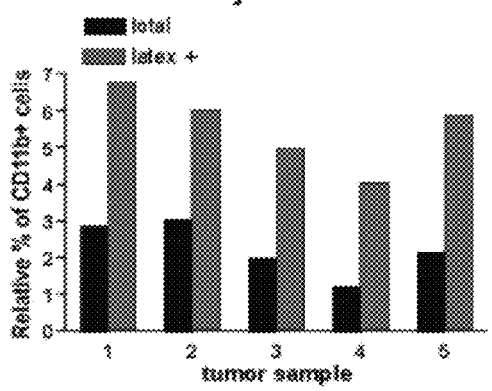
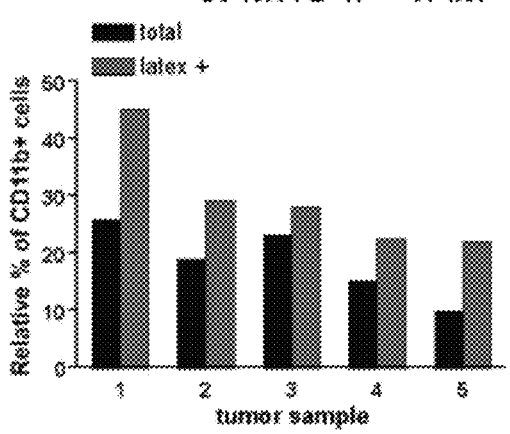
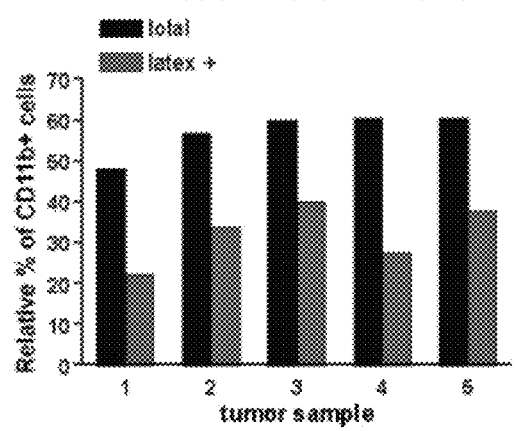

FIG. 13
A
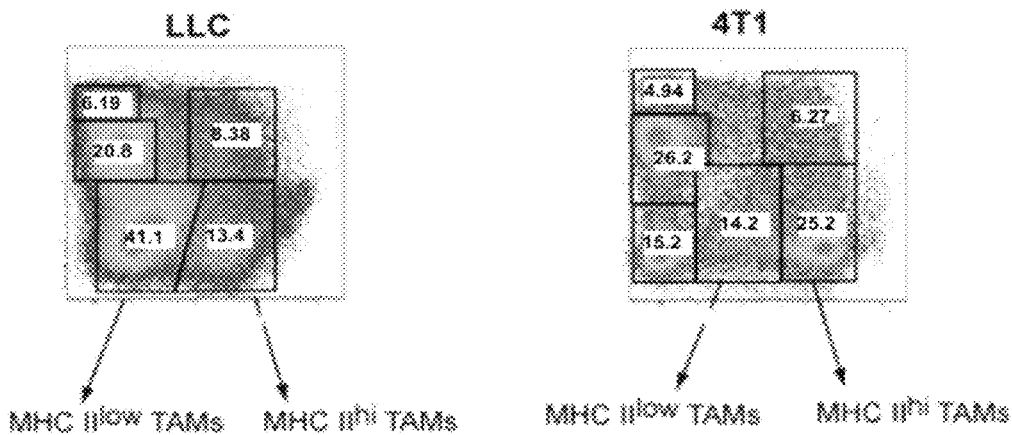
B
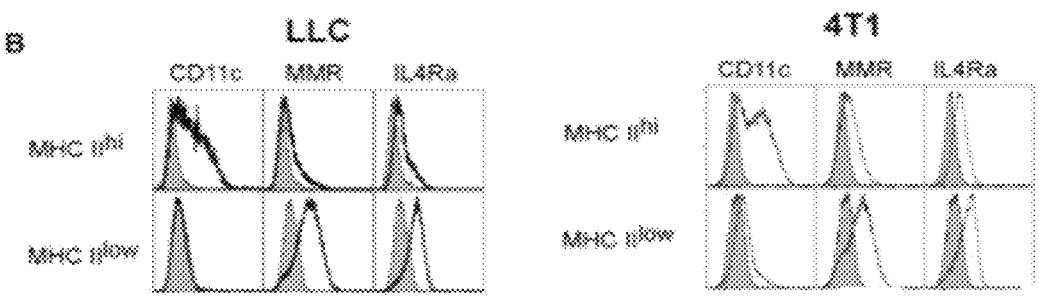
C
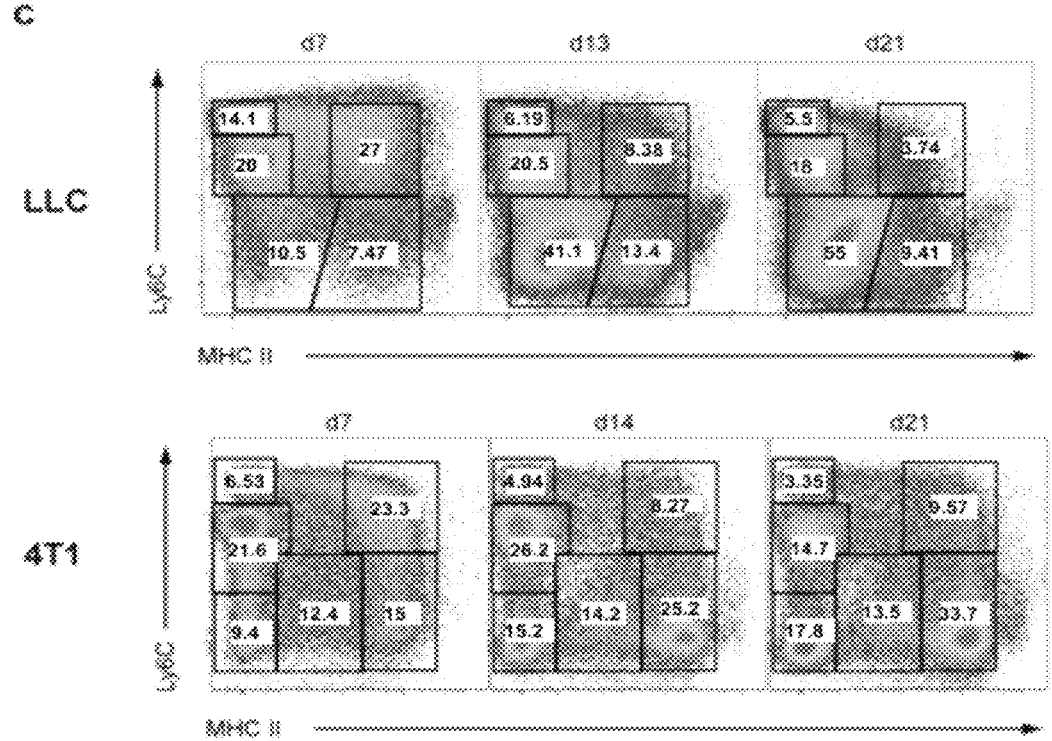

FIG. 21
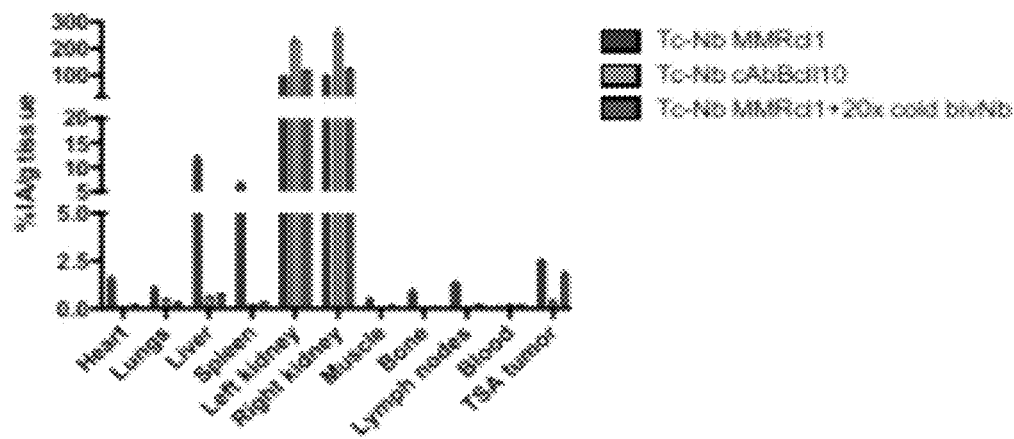
FIG. 22
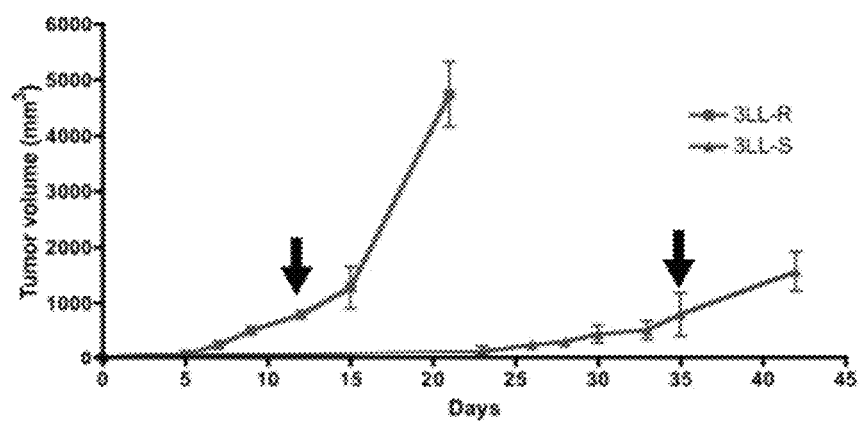
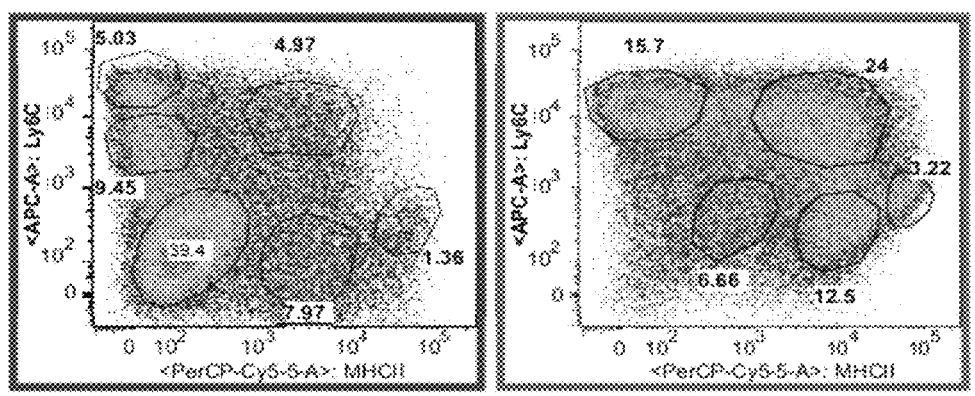

A

FIG. 25 (continued)
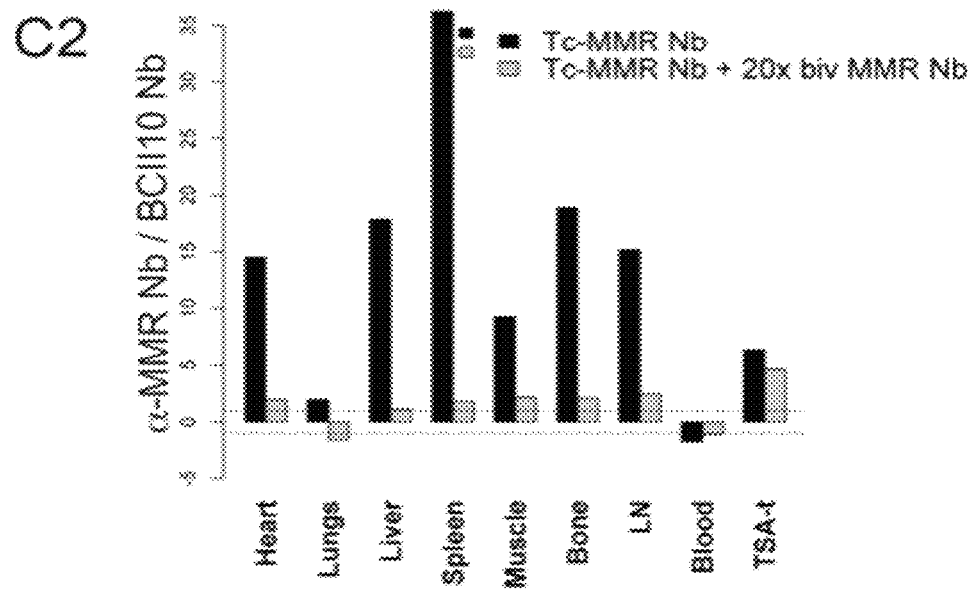
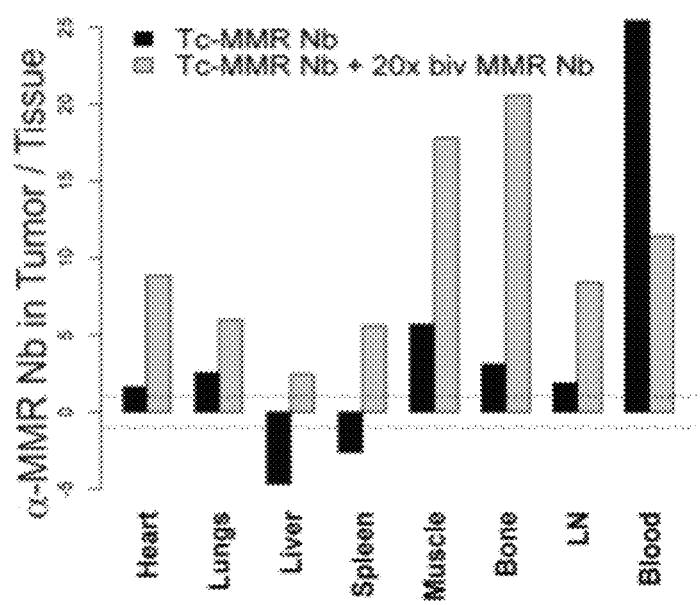

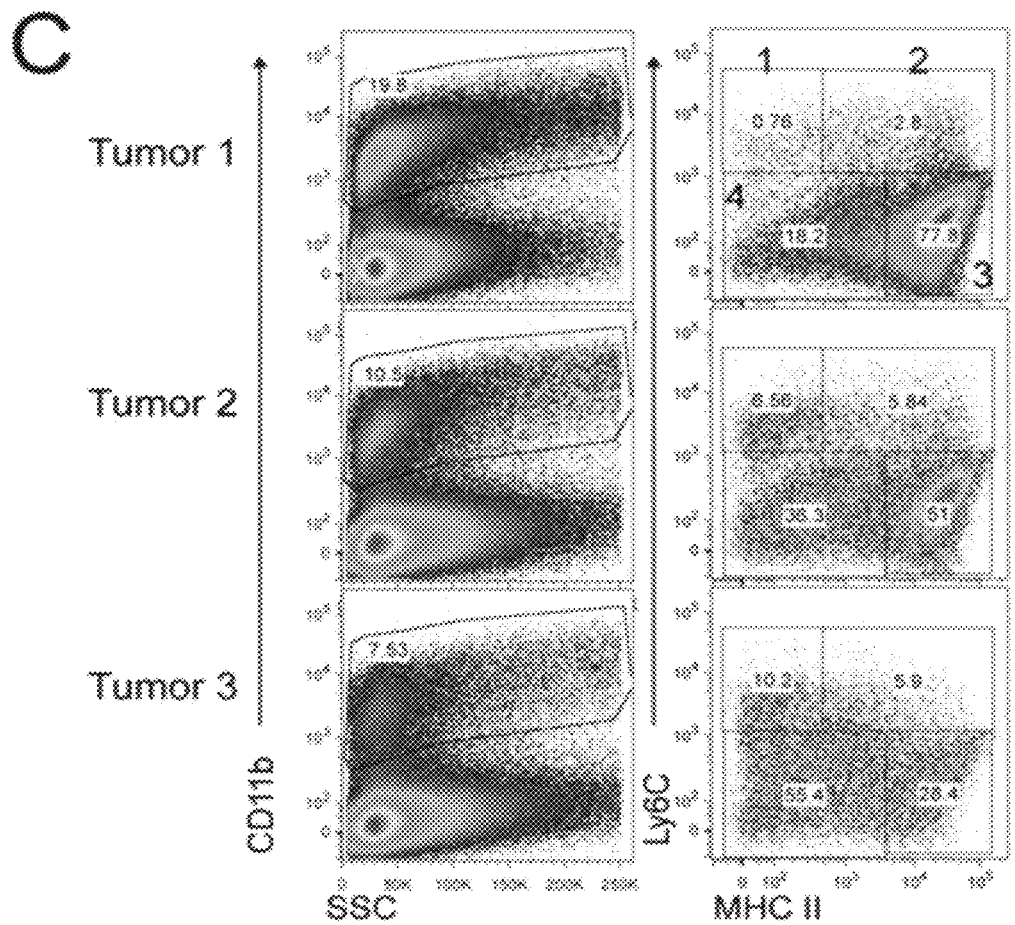

SEQUENCE LISTING

<160> NUMBER OF SEQ ID NOS: 263

<210> SEQ ID NO 1
<211> LENGTH: 375
<212> TYPE: DNA
<213> ORGANISM: Vicugna pacos

<400> SEQUENCE: 1

```
caggtgcagc tgcaggagtc tggaggaggc ttggtgcagc ctgggggtc tctgagactc       60
tcctgtgcag cctctggaaa catcttcagt atcaatgcca tcggctggta ccgccaggct     120
ccagggaagc agcgcgagtt ggtcgcaact attactctta gtggtagcac aaactatgca     180
gactccgtga agggccgatt ctccatctcc agagacaacg ccaagaacac ggtgtatctg     240
caaatgaaca gcctgaaacc tgaggacacg gccgtctatt actgtaatgc taacacctat     300
agcgactctg acgtttatgg ctactggggc caggggaccc aggtcaccgt ctcctcacac     360
caccatcacc atcac                                                     375
```

<210> SEQ ID NO 2
<211> LENGTH: 357
<212> TYPE: DNA
<213> ORGANISM: Vicugna pacos

<400> SEQUENCE: 2

```
caggtgcagc tgcaggagtc tggaggaggc ttggtgcagc ctgggggtc tctgagactc       60
tcctgtgcag cctctggaaa catcttcagt atcaatgcca tcggctggta ccgccaggct     120
ccagggaagc agcgcgagtt ggtcgcaact attactctta gtggtagcac aaactatgca     180
gactccgtga agggccgatt ctccatctcc agagacaacg ccaagaacac ggtgtatctg     240
caaatgaaca gcctgaaacc tgaggacacg gccgtctatt actgtaatgc taacacctat     300
agcgactctg acgtttatgg ctactggggc caggggaccc aggtcaccgt ctcctca        357
```

<210> SEQ ID NO 3
<211> LENGTH: 125
<212> TYPE: PRT
<213> ORGANISM: Vicugna pacos

<400> SEQUENCE: 3

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Ile Gly Trp Tyr Arg Gln Ala Pro Gly Lys Gln Arg Glu Leu Val
        35                  40                  45

Ala Thr Ile Thr Leu Ser Gly Ser Thr Asn Tyr Ala Asp Ser Val Lys
    50                  55                  60

Gly Arg Phe Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Thr Tyr Ser Asp Ser Asp Val Tyr Gly Tyr Trp Gly Gln Gly
            100                 105                 110

Thr Gln Val Thr Val Ser Ser His His His His His
        115                 120                 125

<210> SEQ ID NO 4
<211> LENGTH: 119

<212> TYPE: PRT
<213> ORGANISM: Vicugna pacos

<400> SEQUENCE: 4

```
Gln Val Gln Leu Gln Glu Ser Gly Gly Gly Leu Val Gln Pro Gly Gly
1               5                   10                  15
Ser Leu Arg Leu Ser Cys Ala Ala Ser Gly Asn Ile Phe Ser Ile Asn
            20                  25                  30
Ala Ile Gly Trp Tyr Arg Gln Ala Pro Gly Lys Gln Arg Glu Leu Val
        35                  40                  45
Ala Thr Ile Thr Leu Ser Gly Ser Thr Asn Tyr Ala Asp Ser Val Lys
    50                  55                  60
Gly Arg Phe Ser Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ala Asn Thr Tyr Ser Asp Ser Asp Val Tyr Gly Tyr Trp Gly Gln Gly
            100                 105                 110
Thr Gln Val Thr Val Ser Ser
        115
```

<210> SEQ ID NO 5
<211> LENGTH: 390
<212> TYPE: DNA
<213> ORGANISM: Vicugna pacos

<400> SEQUENCE: 5

```
caggtgcagc tgcaggagtc tggaggagga ttggtgcagg ctggggctc tctgagactc     60
tcctgtgcag cctctggacg caccttcagt agagatgcca tgggctggtt ccgccaggct   120
ccagggaagg agcgtgagtt tgtagcaggt attagctgga gtggtggtag cacatactat   180
gcagactccg tgaagggccg attcaccatc tccaggacg cgccaagaa cacggtaaat    240
ctgcaaatga acagcctgaa acctgaggac acggccgttt attactgtgc agcatcgtcg   300
atttatggga gtgcggtagt agatgggctg tatgactact ggggccaggg gacccaggtc   360
accgtctcct cacaccacca tcaccatcac                                     390
```

<210> SEQ ID NO 6
<211> LENGTH: 372
<212> TYPE: DNA
<213> ORGANISM: Vicugna pacos

<400> SEQUENCE: 6

```
caggtgcagc tgcaggagtc tggaggagga ttggtgcagg ctggggctc tctgagactc     60
tcctgtgcag cctctggacg caccttcagt agagatgcca tgggctggtt ccgccaggct   120
ccagggaagg agcgtgagtt tgtagcaggt attagctgga gtggtggtag cacatactat   180
gcagactccg tgaagggccg attcaccatc tccaggacg cgccaagaa cacggtaaat    240
ctgcaaatga acagcctgaa acctgaggac acggccgttt attactgtgc agcatcgtcg   300
atttatggga gtgcggtagt agatgggctg tatgactact ggggccaggg gacccaggtc   360
accgtctcct ca                                                        372
```

<210> SEQ ID NO 7
<211> LENGTH: 130
<212> TYPE: PRT
<213> ORGANISM: Vicugna pacos -continued

<400> SEQUENCE: 7

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Asp
            20                  25                  30

Ala Met Gly Trp Phe Arg Gln Ala Pro Gly Lys Glu Arg Glu Phe Val
        35                  40                  45

Ala Gly Ile Ser Trp Ser Gly Gly Ser Thr Tyr Tyr Ala Asp Ser Val
    50                  55                  60

Lys Gly Arg Phe Thr Ile Ser Arg Asp Gly Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Ala Ser Ser Ile Tyr Gly Ser Ala Val Val Asp Gly Leu Tyr Asp
            100                 105                 110

Tyr Trp Gly Gln Gly Thr Gln Val Thr Val Ser Ser His His His His
        115                 120                 125

His His
    130

<210> SEQ ID NO 8
<211> LENGTH: 124
<212> TYPE: PRT
<213> ORGANISM: Vicugna pacos

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Asp
            20                  25                  30

Ala Met Gly Trp Phe Arg Gln Ala Pro Gly Lys Glu Arg Glu Phe Val
        35                  40                  45

Ala Gly Ile Ser Trp Ser Gly Gly Ser Thr Tyr Tyr Ala Asp Ser Val
    50                  55                  60

Lys Gly Arg Phe Thr Ile Ser Arg Asp Gly Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Ala Ser Ser Ile Tyr Gly Ser Ala Val Val Asp Gly Leu Tyr Asp
            100                 105                 110

Tyr Trp Gly Gln Gly Thr Gln Val Thr Val Ser Ser
        115                 120

<210> SEQ ID NO 9
<211> LENGTH: 20
<212> TYPE: DNA
<213> ORGANISM: artificial sequence
<220> FEATURE:
<223> OTHER INFORMATION: Primer

<400> SEQUENCE: 9
cccatgaaga ccttcacctc                                           20

<210> SEQ ID NO 10
<211> LENGTH: 20
<212> TYPE: DNA
<213> ORGANISM: artificial sequence
<220> FEATURE:

<223> OTHER INFORMATION: Primer

<400> SEQUENCE: 10
catccctgga acactccact                                                20

<210> SEQ ID NO 11
<211> LENGTH: 20
<212> TYPE: DNA
<213> ORGANISM: artificial sequence
<220> FEATURE:
<223> OTHER INFORMATION: Primer

<400> SEQUENCE: 11
actccttgat tggtggaagc                                                20

<210> SEQ ID NO 12
<211> LENGTH: 20
<212> TYPE: DNA
<213> ORGANISM: artificial sequence
<220> FEATURE:
<223> OTHER INFORMATION: Primer

<400> SEQUENCE: 12
caaaatggca cagacattgg                                                20

<210> SEQ ID NO 13
<211> LENGTH: 20
<212> TYPE: DNA
<213> ORGANISM: artificial sequence
<220> FEATURE:
<223> OTHER INFORMATION: Primer

<400> SEQUENCE: 13
tcctttcccc aaatatcacg                                                20

<210> SEQ ID NO 14
<211> LENGTH: 20
<212> TYPE: DNA
<213> ORGANISM: artificial sequence
<220> FEATURE:
<223> OTHER INFORMATION: Primer

<400> SEQUENCE: 14
cagccatccc taccattcat                                                20

<210> SEQ ID NO 15
<211> LENGTH: 20
<212> TYPE: DNA
<213> ORGANISM: artificial sequence
<220> FEATURE:
<223> OTHER INFORMATION: Primer

<400> SEQUENCE: 15
gtgcccacgt caaggagtat                                                20

<210> SEQ ID NO 16
<211> LENGTH: 20
<212> TYPE: DNA
<213> ORGANISM: artificial sequence
<220> FEATURE:
<223> OTHER INFORMATION: Primer

<400> SEQUENCE: 16
agcaagcaat gacagggaag                                                20

```
<210> SEQ ID NO 17
<211> LENGTH: 20
<212> TYPE: DNA
<213> ORGANISM: artificial sequence
<220> FEATURE:
<223> OTHER INFORMATION: Primer

<400> SEQUENCE: 17
gtcttctgga gtaccatagc                                              20

<210> SEQ ID NO 18
<211> LENGTH: 20
<212> TYPE: DNA
<213> ORGANISM: artificial sequence
<220> FEATURE:
<223> OTHER INFORMATION: Primer

<400> SEQUENCE: 18
gtcagatacc tgacaacagg                                              20

<210> SEQ ID NO 19
<211> LENGTH: 20
<212> TYPE: DNA
<213> ORGANISM: artificial sequence
<220> FEATURE:
<223> OTHER INFORMATION: Primer

<400> SEQUENCE: 19
tctgagtcct cgctcaagtg                                              20

<210> SEQ ID NO 20
<211> LENGTH: 20
<212> TYPE: DNA
<213> ORGANISM: artificial sequence
<220> FEATURE:
<223> OTHER INFORMATION: Primer

<400> SEQUENCE: 20
ccttgggaag atggtggtta                                              20

<210> SEQ ID NO 21
<211> LENGTH: 20
<212> TYPE: DNA
<213> ORGANISM: artificial sequence
<220> FEATURE:
<223> OTHER INFORMATION: Primer

<400> SEQUENCE: 21
tcaacaaaag agctgccaaa                                              20

<210> SEQ ID NO 22
<211> LENGTH: 20
<212> TYPE: DNA
<213> ORGANISM: artificial sequence
<220> FEATURE:
<223> OTHER INFORMATION: Primer

<400> SEQUENCE: 22
gcagaggcca gaagagagaa                                              20

<210> SEQ ID NO 23
<211> LENGTH: 20
<212> TYPE: DNA
<213> ORGANISM: artificial sequence
<220> FEATURE:
<223> OTHER INFORMATION: Primer
```

<400> SEQUENCE: 23
gaaagaccct gaccatcact                                          20

<210> SEQ ID NO 24
<211> LENGTH: 20
<212> TYPE: DNA
<213> ORGANISM: artificial sequence
<220> FEATURE:
<223> OTHER INFORMATION: Primer

<400> SEQUENCE: 24
ccttctctgc agacagagac                                          20

<210> SEQ ID NO 25
<211> LENGTH: 20
<212> TYPE: DNA
<213> ORGANISM: artificial sequence
<220> FEATURE:
<223> OTHER INFORMATION: Primer

<400> SEQUENCE: 25
gtgtggatcc aaagcaatac                                          20

<210> SEQ ID NO 26
<211> LENGTH: 20
<212> TYPE: DNA
<213> ORGANISM: artificial sequence
<220> FEATURE:
<223> OTHER INFORMATION: Primer

<400> SEQUENCE: 26
gtctgctcat tcatgacaag                                          20

<210> SEQ ID NO 27
<211> LENGTH: 20
<212> TYPE: DNA
<213> ORGANISM: artificial sequence
<220> FEATURE:
<223> OTHER INFORMATION: Primer

<400> SEQUENCE: 27
gcactgtgtg ccgataaaga                                          20

<210> SEQ ID NO 28
<211> LENGTH: 20
<212> TYPE: DNA
<213> ORGANISM: artificial sequence
<220> FEATURE:
<223> OTHER INFORMATION: Primer

<400> SEQUENCE: 28
tacctccggg aaatgacatc                                          20

<210> SEQ ID NO 29
<211> LENGTH: 20
<212> TYPE: DNA
<213> ORGANISM: artificial sequence
<220> FEATURE:
<223> OTHER INFORMATION: Primer

<400> SEQUENCE: 29
tgaatcagct ggcttttgtg                                          20

<210> SEQ ID NO 30
<211> LENGTH: 20

```
<212> TYPE: DNA
<213> ORGANISM: artificial sequence
<220> FEATURE:
<223> OTHER INFORMATION: Primer

<400> SEQUENCE: 30
gtggatagct cggtggtgtt                                              20

<210> SEQ ID NO 31
<211> LENGTH: 20
<212> TYPE: DNA
<213> ORGANISM: artificial sequence
<220> FEATURE:
<223> OTHER INFORMATION: Primer

<400> SEQUENCE: 31
caggctgaac ttcgaaacag                                              20

<210> SEQ ID NO 32
<211> LENGTH: 20
<212> TYPE: DNA
<213> ORGANISM: artificial sequence
<220> FEATURE:
<223> OTHER INFORMATION: Primer

<400> SEQUENCE: 32
cagctacgaa aacccaatca                                              20

<210> SEQ ID NO 33
<211> LENGTH: 21
<212> TYPE: DNA
<213> ORGANISM: artificial sequence
<220> FEATURE:
<223> OTHER INFORMATION: Primer

<400> SEQUENCE: 33
gcttctggtc gatgtcatga g                                            21

<210> SEQ ID NO 34
<211> LENGTH: 20
<212> TYPE: DNA
<213> ORGANISM: artificial sequence
<220> FEATURE:
<223> OTHER INFORMATION: Primer

<400> SEQUENCE: 34
tccaccagga gatgttgaac                                              20

<210> SEQ ID NO 35
<211> LENGTH: 20
<212> TYPE: DNA
<213> ORGANISM: artificial sequence
<220> FEATURE:
<223> OTHER INFORMATION: Primer

<400> SEQUENCE: 35
gcatgtggtc cttccaactt                                              20

<210> SEQ ID NO 36
<211> LENGTH: 20
<212> TYPE: DNA
<213> ORGANISM: artificial sequence
<220> FEATURE:
<223> OTHER INFORMATION: Primer

<400> SEQUENCE: 36
```

-continued gatcctcagc cacaaccttc                                                20

<210> SEQ ID NO 37
<211> LENGTH: 20
<212> TYPE: DNA
<213> ORGANISM: artificial sequence
<220> FEATURE:
<223> OTHER INFORMATION: Primer

<400> SEQUENCE: 37
tgacttgggt ccttgtcctc                                                20

<210> SEQ ID NO 38
<211> LENGTH: 20
<212> TYPE: DNA
<213> ORGANISM: artificial sequence
<220> FEATURE:
<223> OTHER INFORMATION: Primer

<400> SEQUENCE: 38
aaggaagcca ccaatgacac                                                20

<210> SEQ ID NO 39
<211> LENGTH: 20
<212> TYPE: DNA
<213> ORGANISM: artificial sequence
<220> FEATURE:
<223> OTHER INFORMATION: Primer

<400> SEQUENCE: 39
acttcgcagg agaactggag                                                20

<210> SEQ ID NO 40
<211> LENGTH: 20
<212> TYPE: DNA
<213> ORGANISM: artificial sequence
<220> FEATURE:
<223> OTHER INFORMATION: Primer

<400> SEQUENCE: 40
aagaagctgt tgggaggaca                                                20

<210> SEQ ID NO 41
<211> LENGTH: 20
<212> TYPE: DNA
<213> ORGANISM: artificial sequence
<220> FEATURE:
<223> OTHER INFORMATION: Primer

<400> SEQUENCE: 41
caggctgctg taacgatgaa                                                20

<210> SEQ ID NO 42
<211> LENGTH: 20
<212> TYPE: DNA
<213> ORGANISM: artificial sequence
<220> FEATURE:
<223> OTHER INFORMATION: Primer

<400> SEQUENCE: 42
aatgctttct ccgctctgaa                                                20

<210> SEQ ID NO 43
<211> LENGTH: 20
<212> TYPE: DNA
<213> ORGANISM: artificial sequence

```
<220> FEATURE:
<223> OTHER INFORMATION: Primer

<400> SEQUENCE: 43
gaaagcatac ctggctggac                                          20

<210> SEQ ID NO 44
<211> LENGTH: 20
<212> TYPE: DNA
<213> ORGANISM: artificial sequence
<220> FEATURE:
<223> OTHER INFORMATION: Primer

<400> SEQUENCE: 44
acaaaagagc cgtacctgga                                          20

<210> SEQ ID NO 45
<211> LENGTH: 20
<212> TYPE: DNA
<213> ORGANISM: artificial sequence
<220> FEATURE:
<223> OTHER INFORMATION: Primer

<400> SEQUENCE: 45
tttcaaaagg aagggggacaa                                         20

<210> SEQ ID NO 46
<211> LENGTH: 20
<212> TYPE: DNA
<213> ORGANISM: artificial sequence
<220> FEATURE:
<223> OTHER INFORMATION: Primer

<400> SEQUENCE: 46
ccacctagaa aaccctgctg                                          20

<210> SEQ ID NO 47
<211> LENGTH: 21
<212> TYPE: DNA
<213> ORGANISM: artificial sequence
<220> FEATURE:
<223> OTHER INFORMATION: Primer

<400> SEQUENCE: 47
actcaataca cactgcaggt g                                        21

<210> SEQ ID NO 48
<211> LENGTH: 20
<212> TYPE: DNA
<213> ORGANISM: artificial sequence
<220> FEATURE:
<223> OTHER INFORMATION: Primer

<400> SEQUENCE: 48
ggactttaag ggttacttgg                                          20

<210> SEQ ID NO 49
<211> LENGTH: 20
<212> TYPE: DNA
<213> ORGANISM: artificial sequence
<220> FEATURE:
<223> OTHER INFORMATION: Primer

<400> SEQUENCE: 49
gtctcctgcc tccactttct                                          20
```

<210> SEQ ID NO 50
<211> LENGTH: 20
<212> TYPE: DNA
<213> ORGANISM: artificial sequence
<220> FEATURE:
<223> OTHER INFORMATION: Primer

<400> SEQUENCE: 50
ctaagggcag aggggctatt                                                    20

<210> SEQ ID NO 51
<211> LENGTH: 20
<212> TYPE: DNA
<213> ORGANISM: artificial sequence
<220> FEATURE:
<223> OTHER INFORMATION: Primer

<400> SEQUENCE: 51
ccttcacaga gcaatgactc                                                    20

<210> SEQ ID NO 52
<211> LENGTH: 21
<212> TYPE: DNA
<213> ORGANISM: artificial sequence
<220> FEATURE:
<223> OTHER INFORMATION: Primer

<400> SEQUENCE: 52
gtctactccc aggttctctt c                                                  21

<210> SEQ ID NO 53
<211> LENGTH: 20
<212> TYPE: DNA
<213> ORGANISM: artificial sequence
<220> FEATURE:
<223> OTHER INFORMATION: Primer

<400> SEQUENCE: 53
cgttgccatt ggaatagaga                                                    20

<210> SEQ ID NO 54
<211> LENGTH: 20
<212> TYPE: DNA
<213> ORGANISM: artificial sequence
<220> FEATURE:
<223> OTHER INFORMATION: Primer

<400> SEQUENCE: 54
tggcaaagag tcaaaactgg                                                    20

<210> SEQ ID NO 55
<211> LENGTH: 20
<212> TYPE: DNA
<213> ORGANISM: artificial sequence
<220> FEATURE:
<223> OTHER INFORMATION: Primer

<400> SEQUENCE: 55
caccattagt ctgggcgtct                                                    20

<210> SEQ ID NO 56
<211> LENGTH: 20
<212> TYPE: DNA
<213> ORGANISM: artificial sequence
<220> FEATURE:
<223> OTHER INFORMATION: Primer

```
<400> SEQUENCE: 56
gatgcggaag tagcaaaagc                                           20

<210> SEQ ID NO 57
<211> LENGTH: 20
<212> TYPE: DNA
<213> ORGANISM: artificial sequence
<220> FEATURE:
<223> OTHER INFORMATION: Primer

<400> SEQUENCE: 57
cttttagcgg cacgaacgat                                           20

<210> SEQ ID NO 58
<211> LENGTH: 20
<212> TYPE: DNA
<213> ORGANISM: artificial sequence
<220> FEATURE:
<223> OTHER INFORMATION: Primer

<400> SEQUENCE: 58
aagaacagcg gtgcaggtaa                                           20

<210> SEQ ID NO 59
<211> LENGTH: 20
<212> TYPE: DNA
<213> ORGANISM: artificial sequence
<220> FEATURE:
<223> OTHER INFORMATION: Primer

<400> SEQUENCE: 59
tgacatgccc aagactcaga                                           20

<210> SEQ ID NO 60
<211> LENGTH: 20
<212> TYPE: DNA
<213> ORGANISM: artificial sequence
<220> FEATURE:
<223> OTHER INFORMATION: Primer

<400> SEQUENCE: 60
aggttgctca agcagcaaag                                           20

<210> SEQ ID NO 61
<211> LENGTH: 20
<212> TYPE: DNA
<213> ORGANISM: artificial sequence
<220> FEATURE:
<223> OTHER INFORMATION: Primer

<400> SEQUENCE: 61
ccggtactac tgctgctcct                                           20

<210> SEQ ID NO 62
<211> LENGTH: 20
<212> TYPE: DNA
<213> ORGANISM: artificial sequence
<220> FEATURE:
<223> OTHER INFORMATION: Primer

<400> SEQUENCE: 62
cacacaccga gctgtgagat                                           20

<210> SEQ ID NO 63
```

```
<211> LENGTH: 20
<212> TYPE: DNA
<213> ORGANISM: artificial sequence
<220> FEATURE:
<223> OTHER INFORMATION: Primer

<400> SEQUENCE: 63
ctcagttcat ccacggcata                                              20

<210> SEQ ID NO 64
<211> LENGTH: 20
<212> TYPE: DNA
<213> ORGANISM: artificial sequence
<220> FEATURE:
<223> OTHER INFORMATION: Primer

<400> SEQUENCE: 64
caaggctcac catcatcgta                                              20

<210> SEQ ID NO 65
<211> LENGTH: 20
<212> TYPE: DNA
<213> ORGANISM: artificial sequence
<220> FEATURE:
<223> OTHER INFORMATION: Primer

<400> SEQUENCE: 65
tctcctgggc aagtgtagga                                              20

<210> SEQ ID NO 66
<211> LENGTH: 20
<212> TYPE: DNA
<213> ORGANISM: artificial sequence
<220> FEATURE:
<223> OTHER INFORMATION: Primer

<400> SEQUENCE: 66
gcctgtgcag agtgaacaaa                                              20

<210> SEQ ID NO 67
<211> LENGTH: 20
<212> TYPE: DNA
<213> ORGANISM: artificial sequence
<220> FEATURE:
<223> OTHER INFORMATION: Primer

<400> SEQUENCE: 67
ctccacagcg cttctattcc                                              20

<210> SEQ ID NO 68
<211> LENGTH: 20
<212> TYPE: DNA
<213> ORGANISM: artificial sequence
<220> FEATURE:
<223> OTHER INFORMATION: Primer

<400> SEQUENCE: 68
cttcttcttg gggtcagcac                                              20

<210> SEQ ID NO 69
<211> LENGTH: 20
<212> TYPE: DNA
<213> ORGANISM: artificial sequence
<220> FEATURE:
<223> OTHER INFORMATION: Primer

<400> SEQUENCE: 69
```
ctgggcaaga aatctgatga                                           20

<210> SEQ ID NO 70
<211> LENGTH: 20
<212> TYPE: DNA
<213> ORGANISM: artificial sequence
<220> FEATURE:
<223> OTHER INFORMATION: Primer

<400> SEQUENCE: 70
tggttgtggc aggaaagata                                           20

<210> SEQ ID NO 71
<211> LENGTH: 20
<212> TYPE: DNA
<213> ORGANISM: artificial sequence
<220> FEATURE:
<223> OTHER INFORMATION: Primer

<400> SEQUENCE: 71
ggatgttgac agcaagagca                                           20

<210> SEQ ID NO 72
<211> LENGTH: 20
<212> TYPE: DNA
<213> ORGANISM: artificial sequence
<220> FEATURE:
<223> OTHER INFORMATION: Primer

<400> SEQUENCE: 72
ctcatcttca ccccggttag                                           20

<210> SEQ ID NO 73
<211> LENGTH: 20
<212> TYPE: DNA
<213> ORGANISM: artificial sequence
<220> FEATURE:
<223> OTHER INFORMATION: Primer

<400> SEQUENCE: 73
ccaaggagac ggaatacagg                                           20

<210> SEQ ID NO 74
<211> LENGTH: 20
<212> TYPE: DNA
<213> ORGANISM: artificial sequence
<220> FEATURE:
<223> OTHER INFORMATION: Primer

<400> SEQUENCE: 74
tctctgtgga gctgaagcaa                                           20

<210> SEQ ID NO 75
<211> LENGTH: 21
<212> TYPE: DNA
<213> ORGANISM: artificial sequence
<220> FEATURE:
<223> OTHER INFORMATION: Primer

<400> SEQUENCE: 75
tcatagccac actcaagaat g                                         21

<210> SEQ ID NO 76
<211> LENGTH: 21
<212> TYPE: DNA

```
<213> ORGANISM: artificial sequence
<220> FEATURE:
<223> OTHER INFORMATION: Primer

<400> SEQUENCE: 76
aagcagaact gaactaccat c                                              21

<210> SEQ ID NO 77
<211> LENGTH: 20
<212> TYPE: DNA
<213> ORGANISM: artificial sequence
<220> FEATURE:
<223> OTHER INFORMATION: Primer

<400> SEQUENCE: 77
tctacgcagt gcttctttgc                                                20

<210> SEQ ID NO 78
<211> LENGTH: 20
<212> TYPE: DNA
<213> ORGANISM: artificial sequence
<220> FEATURE:
<223> OTHER INFORMATION: Primer

<400> SEQUENCE: 78
ccacttctgt gtgggtcta                                                 20

<210> SEQ ID NO 79
<211> LENGTH: 20
<212> TYPE: DNA
<213> ORGANISM: artificial sequence
<220> FEATURE:
<223> OTHER INFORMATION: Primer

<400> SEQUENCE: 79
gcagatggct catgtctgaa                                                20

<210> SEQ ID NO 80
<211> LENGTH: 20
<212> TYPE: DNA
<213> ORGANISM: artificial sequence
<220> FEATURE:
<223> OTHER INFORMATION: Primer

<400> SEQUENCE: 80
ctctgggaag ctgggtgtag                                                20

<210> SEQ ID NO 81
<211> LENGTH: 20
<212> TYPE: DNA
<213> ORGANISM: artificial sequence
<220> FEATURE:
<223> OTHER INFORMATION: Primer

<400> SEQUENCE: 81
tcacctgagc tttgatgtcg                                                20

<210> SEQ ID NO 82
<211> LENGTH: 20
<212> TYPE: DNA
<213> ORGANISM: artificial sequence
<220> FEATURE:
<223> OTHER INFORMATION: Primer

<400> SEQUENCE: 82
ttatggttac cctcccgttg                                                20
```

```
<210> SEQ ID NO 83
<211> LENGTH: 20
<212> TYPE: DNA
<213> ORGANISM: artificial sequence
<220> FEATURE:
<223> OTHER INFORMATION: Primer

<400> SEQUENCE: 83
gcttggctta tggactgagg                                              20

<210> SEQ ID NO 84
<211> LENGTH: 20
<212> TYPE: DNA
<213> ORGANISM: artificial sequence
<220> FEATURE:
<223> OTHER INFORMATION: Primer

<400> SEQUENCE: 84
cttgtccttg tggctgtgaa                                              20

<210> SEQ ID NO 85
<211> LENGTH: 20
<212> TYPE: DNA
<213> ORGANISM: artificial sequence
<220> FEATURE:
<223> OTHER INFORMATION: Primer

<400> SEQUENCE: 85
gcctcctgct catagctacc                                              20

<210> SEQ ID NO 86
<211> LENGTH: 20
<212> TYPE: DNA
<213> ORGANISM: artificial sequence
<220> FEATURE:
<223> OTHER INFORMATION: Primer

<400> SEQUENCE: 86
gggtcagcac agatctcctt                                              20

<210> SEQ ID NO 87
<211> LENGTH: 20
<212> TYPE: DNA
<213> ORGANISM: artificial sequence
<220> FEATURE:
<223> OTHER INFORMATION: Primer

<400> SEQUENCE: 87
atgtccagct ttgtgggttc                                              20

<210> SEQ ID NO 88
<211> LENGTH: 20
<212> TYPE: DNA
<213> ORGANISM: artificial sequence
<220> FEATURE:
<223> OTHER INFORMATION: Primer

<400> SEQUENCE: 88
aggtcaggtt ccgcagataa                                              20

<210> SEQ ID NO 89
<211> LENGTH: 20
<212> TYPE: DNA
<213> ORGANISM: artificial sequence
<220> FEATURE:
```

<223> OTHER INFORMATION: Primer

<400> SEQUENCE: 89
cccacttcct gctgtttctc                                              20

<210> SEQ ID NO 90
<211> LENGTH: 20
<212> TYPE: DNA
<213> ORGANISM: artificial sequence
<220> FEATURE:
<223> OTHER INFORMATION: Primer

<400> SEQUENCE: 90
gagcaaggac gcttctcagt                                              20

<210> SEQ ID NO 91
<211> LENGTH: 21
<212> TYPE: DNA
<213> ORGANISM: artificial sequence
<220> FEATURE:
<223> OTHER INFORMATION: Primer

<400> SEQUENCE: 91
ccttcgcgat tatcagaatc c                                            21

<210> SEQ ID NO 92
<211> LENGTH: 20
<212> TYPE: DNA
<213> ORGANISM: artificial sequence
<220> FEATURE:
<223> OTHER INFORMATION: Primer

<400> SEQUENCE: 92
tacttatggt ggacccagca                                              20

<210> SEQ ID NO 93
<211> LENGTH: 20
<212> TYPE: DNA
<213> ORGANISM: artificial sequence
<220> FEATURE:
<223> OTHER INFORMATION: Primer

<400> SEQUENCE: 93
ccagatcaca catgcaacag                                              20

<210> SEQ ID NO 94
<211> LENGTH: 25
<212> TYPE: DNA
<213> ORGANISM: artificial sequence
<220> FEATURE:
<223> OTHER INFORMATION: Primer

<400> SEQUENCE: 94
ctataaaaat aaacacttag agcca                                        25

<210> SEQ ID NO 95
<211> LENGTH: 21
<212> TYPE: DNA
<213> ORGANISM: artificial sequence
<220> FEATURE:
<223> OTHER INFORMATION: Primer

<400> SEQUENCE: 95
cggaagattc cacgccaatt c                                            21

```
<210> SEQ ID NO 96
<211> LENGTH: 21
<212> TYPE: DNA
<213> ORGANISM: artificial sequence
<220> FEATURE:
<223> OTHER INFORMATION: Primer

<400> SEQUENCE: 96
ggtgaggaac gtgtcctgaa g                                            21

<210> SEQ ID NO 97
<211> LENGTH: 20
<212> TYPE: DNA
<213> ORGANISM: artificial sequence
<220> FEATURE:
<223> OTHER INFORMATION: Primer

<400> SEQUENCE: 97
atcgaaccca gagtggaatg                                              20

<210> SEQ ID NO 98
<211> LENGTH: 20
<212> TYPE: DNA
<213> ORGANISM: artificial sequence
<220> FEATURE:
<223> OTHER INFORMATION: Primer

<400> SEQUENCE: 98
gctagaaacc ccagcatgag                                              20

<210> SEQ ID NO 99
<211> LENGTH: 25
<212> TYPE: DNA
<213> ORGANISM: artificial sequence
<220> FEATURE:
<223> OTHER INFORMATION: Primer

<400> SEQUENCE: 99
cactcacctg ctgctactca ttcac                                        25

<210> SEQ ID NO 100
<211> LENGTH: 24
<212> TYPE: DNA
<213> ORGANISM: artificial sequence
<220> FEATURE:
<223> OTHER INFORMATION: Primer

<400> SEQUENCE: 100
ggattcacag agagggaaaa atgg                                         24

<210> SEQ ID NO 101
<211> LENGTH: 20
<212> TYPE: DNA
<213> ORGANISM: artificial sequence
<220> FEATURE:
<223> OTHER INFORMATION: Primer

<400> SEQUENCE: 101
gacaaagaag ggcatggaag                                              20

<210> SEQ ID NO 102
<211> LENGTH: 20
<212> TYPE: DNA
<213> ORGANISM: artificial sequence
<220> FEATURE:
<223> OTHER INFORMATION: Primer
```

<400> SEQUENCE: 102
cattccttag gcgtgaccat    20

<210> SEQ ID NO 103
<211> LENGTH: 20
<212> TYPE: DNA
<213> ORGANISM: artificial sequence
<220> FEATURE:
<223> OTHER INFORMATION: Primer

<400> SEQUENCE: 103
gcaaatggag ccgtctgtgc    20

<210> SEQ ID NO 104
<211> LENGTH: 20
<212> TYPE: DNA
<213> ORGANISM: artificial sequence
<220> FEATURE:
<223> OTHER INFORMATION: Primer

<400> SEQUENCE: 104
ctcgtggatc tccgtgacac    20

<210> SEQ ID NO 105
<211> LENGTH: 20
<212> TYPE: DNA
<213> ORGANISM: artificial sequence
<220> FEATURE:
<223> OTHER INFORMATION: Primer

<400> SEQUENCE: 105
acgggaaact gcttgatgtc    20

<210> SEQ ID NO 106
<211> LENGTH: 20
<212> TYPE: DNA
<213> ORGANISM: artificial sequence
<220> FEATURE:
<223> OTHER INFORMATION: Primer

<400> SEQUENCE: 106
actcagcgtc atgttgtcca    20

<210> SEQ ID NO 107
<211> LENGTH: 20
<212> TYPE: DNA
<213> ORGANISM: artificial sequence
<220> FEATURE:
<223> OTHER INFORMATION: Primer

<400> SEQUENCE: 107
gagcatgaat gaagtgtccg    20

<210> SEQ ID NO 108
<211> LENGTH: 20
<212> TYPE: DNA
<213> ORGANISM: artificial sequence
<220> FEATURE:
<223> OTHER INFORMATION: Primer

<400> SEQUENCE: 108
tgctgaagtt gtcgtcacac    20

<210> SEQ ID NO 109
<211> LENGTH: 20

```
<212> TYPE: DNA
<213> ORGANISM: artificial sequence
<220> FEATURE:
<223> OTHER INFORMATION: Primer

<400> SEQUENCE: 109
ctggctgttt gctacgtgaa                                                      20

<210> SEQ ID NO 110
<211> LENGTH: 20
<212> TYPE: DNA
<213> ORGANISM: artificial sequence
<220> FEATURE:
<223> OTHER INFORMATION: Primer

<400> SEQUENCE: 110
catgaaactt gcctcgtgtg                                                      20

<210> SEQ ID NO 111
<211> LENGTH: 780
<212> TYPE: DNA
<213> ORGANISM: Vicugna pacos

<400> SEQUENCE: 111
caggtgcagc ttcaggagtc tggaggaggc ttggtgcagc tggggggtc tctgagactc            60 tcctgtgcag cctctggaaa catcttcagt atcaatgcca tcggctggta ccgccaggct          120
ccagggaagc agcgcgagtt ggtcgcaact attactctta gtggtagcac aaactatgca          180
gactccgtga agggccgatt ctccatctcc agagacaacg ccaagaacac ggtgtatctg          240
caaatgaaca gcctgaaacc tgaggacacg gccgtctatt actgtaatgc taacacctat          300
agcgactctg acgtttatgg ctactggggc caggggaccc aggtcaccgt ctcctcaagc          360
ccatctacac ctcccacacc atcaccatcc acaccaccgg caagtcaggt gcagctgcag          420
gagtctggag gaggcttggt gcagcctggg gggtctctga actctcctg tgcagcctct           480 ggaaacatct tcagtatcaa tgccatcggc tggtaccgcc aggctccagg gaagcagcgc          540
gagttggtcg caactattac tcttagtggt agcacaaact atgcagactc cgtgaagggc          600
cgattctcca tctccagaga caacgccaag aacacggtgt atctgcaaat gaacagcctg          660
aaacctgagg acacggccgt ctattactgt aatgctaaca cctatagcga ctctgacgtt          720
tatggctact ggggccaggg gacccaggtc accgtctcct cacaccacca tcaccatcac          780

<210> SEQ ID NO 112
<211> LENGTH: 260
<212> TYPE: PRT
<213> ORGANISM: Vicugna pacos

<400> SEQUENCE: 112

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Ile Gly Trp Tyr Arg Gln Ala Pro Gly Lys Gln Arg Glu Leu Val
        35                  40                  45

Ala Thr Ile Thr Leu Ser Gly Ser Thr Asn Tyr Ala Asp Ser Val Lys
    50                  55                  60

Gly Arg Phe Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
```

```
            85                  90                  95
Ala Asn Thr Tyr Ser Asp Ser Asp Val Tyr Gly Tyr Trp Gly Gln Gly
            100                 105                 110

Thr Gln Val Thr Val Ser Ser Pro Ser Thr Pro Pro Thr Pro Ser
            115                 120                 125

Pro Ser Thr Pro Pro Ala Ser Gln Val Gln Leu Gln Glu Ser Gly Gly
    130                 135                 140

Gly Leu Val Gln Pro Gly Gly Ser Leu Arg Leu Ser Cys Ala Ala Ser
145                 150                 155                 160

Gly Asn Ile Phe Ser Ile Asn Ala Ile Gly Trp Tyr Arg Gln Ala Pro
                165                 170                 175

Gly Lys Gln Arg Glu Leu Val Ala Thr Ile Thr Leu Ser Gly Ser Thr
            180                 185                 190

Asn Tyr Ala Asp Ser Val Lys Gly Arg Phe Ser Ile Ser Arg Asp Asn
        195                 200                 205

Ala Lys Asn Thr Val Tyr Leu Gln Met Asn Ser Leu Lys Pro Glu Asp
    210                 215                 220

Thr Ala Val Tyr Tyr Cys Asn Ala Asn Thr Tyr Ser Asp Ser Asp Val
225                 230                 235                 240

Tyr Gly Tyr Trp Gly Gln Gly Thr Gln Val Thr Val Ser Ser His His
                245                 250                 255

His His His His
        260

<210> SEQ ID NO 113
<211> LENGTH: 777
<212> TYPE: DNA
<213> ORGANISM: Vicugna pacos

<400> SEQUENCE: 113
caggtgcagc ttcaggagtc tggaggaggc ttggtgcagc ctggggggtc tctgagactc     60
tcctgtgcag cctctggaaa catcttcagt atcaatgcca tcggctggta ccgccaggct    120
ccagggaagc agcgcgagtt ggtcgcaact attactctta gtggtagcac aaactatgca    180
gactccgtga agggccgatt ctccatctcc agagacaacg ccaagaacac ggtgtatctg    240
caaatgaaca gcctgaaacc tgaggacacg gccgtctatt actgtaatgc taacacctat    300
agcgactctg acgtttatgg ctactgggcc aggggacccc aggtcaccgt ctcctcaggc    360
ggaggcggta gtggcggagg tggatctgga ggcggcggta gtcaggtgca gctgcaggag    420
tctggaggag gcttggtgca gcctgggggg tctctgagac tctcctgtgc agcctctgga    480
aacatcttca gtatcaatgc catcggctgg taccgccagg ctccagggaa gcagcgcgag    540
ttggtcgcaa ctattactct tagtggtagc acaaactatg cagactccgt gaagggccga    600
ttctccatct ccagagacaa cgccaagaac acggtgtatc tgcaaatgaa cagcctgaaa    660
cctgaggaca cggccgtcta ttactgtaat gctaacacct atagcgactc tgacgtttat    720
ggctactggg gccaggggac ccaggtcacc gtctcctcac accaccatca ccatcac     777

<210> SEQ ID NO 114
<211> LENGTH: 259
<212> TYPE: PRT
<213> ORGANISM: Vicugna pacos

<400> SEQUENCE: 114

Gln Val Gln Leu Gln Glu Ser Gly Gly Gly Leu Val Gln Pro Gly Gly
1               5                   10                  15
```

Ser Leu Arg Leu Ser Cys Ala Ala Ser Gly Asn Ile Phe Ser Ile Asn
            20                  25                  30

Ala Ile Gly Trp Tyr Arg Gln Ala Pro Gly Lys Gln Arg Glu Leu Val
        35                  40                  45

Ala Thr Ile Thr Leu Ser Gly Ser Thr Asn Tyr Ala Asp Ser Val Lys
 50                  55                  60

Gly Arg Phe Ser Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                85                  90                  95

Ala Asn Thr Tyr Ser Asp Ser Asp Val Tyr Gly Tyr Trp Gly Gln Gly
            100                 105                 110

Thr Gln Val Thr Val Ser Ser Gly Gly Gly Gly Ser Gly Gly Gly Gly
        115                 120                 125

Ser Gly Gly Gly Gly Ser Gln Val Gln Leu Gln Glu Ser Gly Gly Gly
130                 135                 140

Leu Val Gln Pro Gly Gly Ser Leu Arg Leu Ser Cys Ala Ala Ser Gly
145                 150                 155                 160

Asn Ile Phe Ser Ile Asn Ala Ile Gly Trp Tyr Arg Gln Ala Pro Gly
                165                 170                 175

Lys Gln Arg Glu Leu Val Ala Thr Ile Thr Leu Ser Gly Ser Thr Asn
            180                 185                 190

Tyr Ala Asp Ser Val Lys Gly Arg Phe Ser Ile Ser Arg Asp Asn Ala
        195                 200                 205

Lys Asn Thr Val Tyr Leu Gln Met Asn Ser Leu Lys Pro Glu Asp Thr
210                 215                 220

Ala Val Tyr Tyr Cys Asn Ala Asn Thr Tyr Ser Asp Ser Asp Val Tyr
225                 230                 235                 240

Gly Tyr Trp Gly Gln Gly Thr Gln Val Thr Val Ser Ser His His His
                245                 250                 255

His His His

<210> SEQ ID NO 115
<211> LENGTH: 783
<212> TYPE: DNA
<213> ORGANISM: Vicugna pacos

<400> SEQUENCE: 115

```
caggtgcagc ttcaggagtc tggaggaggc ttggtgcagc ctgggggtc tctgagactc      60
tcctgtgcag cctctggaaa catcttcagt atcaatgcca tcggctggta ccgccaggct    120
ccagggaagc agcgcgagtt ggtcgcaact attactctta gtggtagcac aaactatgca    180
gactccgtga agggccgatt ctccatctcc agagacaacg ccaagaacac ggtgtatctg    240
caaatgaaca gcctgaaacc tgaggacacg gccgtctatt actgtaatgc taacacctat    300
agcgactctg acgtttatgg ctactgggc aggggaccc aggtcaccgt ctcctcagcg      360
caccacagcg aagaccccag ctccaaagct cccaaagctc aatggcaca ggtgcagctg     420
caggagtctg gaggaggctt ggtgcagcct gggggtctc tgagactctc ctgtgcagcc    480
tctggaaaca tcttcagtat caatgccatc ggctggtacc gccaggctcc agggaagcag   540
cgcgagttgg tcgcaactat tactcttagt ggtagcacaa actatgcaga ctccgtgaag   600
ggccgattct ccatctccag agacaacgcc aagaacacgg tgtatctgca aatgaacagc   660
ctgaaacctg aggacacggc cgtctattac tgtaatgcta acacctatag cgactctgac   720
```

```
gtttatggct actggggcca ggggacccag gtcaccgtct cctcacacca ccatcaccat    780
cac                                                                  783
```

```
<210> SEQ ID NO 116
<211> LENGTH: 261
<212> TYPE: PRT
<213> ORGANISM: Vicugna pacos

<400> SEQUENCE: 116
```

| | | | | | | | | | | | | | | |
|---|---|---|---|---|---|---|---|---|---|---|---|---|---|---|
| Gln | Val | Gln | Leu | Gln | Glu | Ser | Gly | Gly | Gly | Leu | Val | Gln | Pro | Gly |
| 1 | | | | 5 | | | | | 10 | | | | | 15 |
| Gly | | | | | | | | | | | | | | |

Ser Leu Arg Leu Ser Cys Ala Ala Ser Gly Asn Ile Phe Ser Ile Asn
                20                  25                  30

Ala Ile Gly Trp Tyr Arg Gln Ala Pro Gly Lys Gln Arg Glu Leu Val
            35                  40                  45

Ala Thr Ile Thr Leu Ser Gly Ser Thr Asn Tyr Ala Asp Ser Val Lys
        50                  55                  60

Gly Arg Phe Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Thr Tyr Ser Asp Ser Asp Val Tyr Gly Tyr Trp Gly Gln Gly
            100                 105                 110

Thr Gln Val Thr Val Ser Ser Ala His His Ser Glu Asp Pro Ser Ser
        115                 120                 125

Lys Ala Pro Lys Ala Pro Met Ala Gln Val Gln Leu Gln Glu Ser Gly
    130                 135                 140

Gly Gly Leu Val Gln Pro Gly Gly Ser Leu Arg Leu Ser Cys Ala Ala
145                 150                 155                 160

Ser Gly Asn Ile Phe Ser Ile Asn Ala Ile Gly Trp Tyr Arg Gln Ala
                165                 170                 175

Pro Gly Lys Gln Arg Glu Leu Val Ala Thr Ile Thr Leu Ser Gly Ser
            180                 185                 190

Thr Asn Tyr Ala Asp Ser Val Lys Gly Arg Phe Ser Ile Ser Arg Asp
        195                 200                 205

Asn Ala Lys Asn Thr Val Tyr Leu Gln Met Asn Ser Leu Lys Pro Glu
    210                 215                 220

Asp Thr Ala Val Tyr Tyr Cys Asn Ala Asn Thr Tyr Ser Asp Ser Asp
225                 230                 235                 240

Val Tyr Gly Tyr Trp Gly Gln Gly Thr Gln Val Thr Val Ser Ser His
                245                 250                 255

His His His His His
            260

```
<210> SEQ ID NO 117
<211> LENGTH: 41
<212> TYPE: DNA
<213> ORGANISM: Artificial Sequence
<220> FEATURE:
<223> OTHER INFORMATION: Primer

<400> SEQUENCE: 117
ccggccatgg cccaggtgca gcttcaggag tctggaggag g                        41

<210> SEQ ID NO 118
<211> LENGTH: 88
```

<210> SEQ ID NO 118
<211> LENGTH: 88 (implied)
<212> TYPE: DNA
<213> ORGANISM: Artificial Sequence
<220> FEATURE:
<223> OTHER INFORMATION: Primer

<400> SEQUENCE: 118
tgattcctgc agctgcacct gactaccgcc gcctccagat ccacctccgc cactaccgcc    60
tccgcctgag gagacggtga cctgggtc                                       88

<210> SEQ ID NO 119
<211> LENGTH: 94
<212> TYPE: DNA
<213> ORGANISM: Artificial Sequence
<220> FEATURE:
<223> OTHER INFORMATION: Primer

<400> SEQUENCE: 119
tgattcctgc agctgcacct gtgccattgg agctttggga gctttggagc tggggtcttc    60
gctgtggtgc gctgaggaga cggtgacctg ggtc                                94

<210> SEQ ID NO 120
<211> LENGTH: 91
<212> TYPE: DNA
<213> ORGANISM: Artificial Sequence
<220> FEATURE:
<223> OTHER INFORMATION: Primer

<400> SEQUENCE: 120
tgattcctgc agctgcacct gacttgccgg tggtgtggat ggtgatggtg tgggaggtgt    60
agatgggctt gaggagacgg tgacctgggt c                                   91

<210> SEQ ID NO 121
<211> LENGTH: 15
<212> TYPE: PRT
<213> ORGANISM: Artificial Sequence
<220> FEATURE:
<223> OTHER INFORMATION: Linker

<400> SEQUENCE: 121

Gly Gly Gly Gly Ser Gly Gly Gly Gly Ser Gly Gly Gly Gly Ser
 1               5                  10                  15

<210> SEQ ID NO 122
<211> LENGTH: 17
<212> TYPE: PRT
<213> ORGANISM: Artificial Sequence
<220> FEATURE:
<223> OTHER INFORMATION: Linker

<400> SEQUENCE: 122

Ala His His Ser Glu Asp Pro Ser Ser Lys Ala Pro Lys Ala Pro Met
 1               5                  10                  15

Ala

<210> SEQ ID NO 123
<211> LENGTH: 16
<212> TYPE: PRT
<213> ORGANISM: Artificial Sequence
<220> FEATURE:
<223> OTHER INFORMATION: Linker

<400> SEQUENCE: 123

Ser Pro Ser Thr Pro Pro Thr Pro Ser Pro Ser Thr Pro Pro Ala Ser
 1               5                  10                  15

<210> SEQ ID NO 124
<211> LENGTH: 40
<212> TYPE: DNA
<213> ORGANISM: Artificial Sequence
<220> FEATURE:
<223> OTHER INFORMATION: Primer

<400> SEQUENCE: 124
attgaattct attagtggtg gtggtggtgg tgctcgagtg            40

<210> SEQ ID NO 125
<211> LENGTH: 33
<212> TYPE: DNA
<213> ORGANISM: Artificial Sequence
<220> FEATURE:
<223> OTHER INFORMATION: Primer

<400> SEQUENCE: 125
ttaactgcag atggccgaag agggcggcag cct            33

<210> SEQ ID NO 126
<211> LENGTH: 133
<212> TYPE: PRT
<213> ORGANISM: Vicugna pacos

<400> SEQUENCE: 126

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asn Tyr
            20                  25                  30

Thr Val Ala Trp Phe Arg Gln Ala Pro Gly Lys Glu Arg Glu Gly Val
        35                  40                  45

Ser Cys Ile Ser Ser Ser Gly Gly Ser Thr Asn Tyr Ala Asp Ser Val
    50                  55                  60

Lys Gly Arg Phe Thr Ile Ser Arg Asp Asn Ser Lys Lys Ser Val Tyr
65                  70                  75                  80

Leu Gln Met Asn Ser Leu Lys Pro Glu Asp Thr Ala Ile Tyr Thr Cys
                85                  90                  95

Ala Ala Glu Arg Ala Pro Pro Tyr Tyr Ser Gly Tyr Tyr Phe Phe Asp
            100                 105                 110

Ser Thr Cys Val Ala Ala Ser Tyr Asp Tyr Trp Gly Gln Gly Thr Gln
        115                 120                 125

Val Thr Val Ser Ser
    130

<210> SEQ ID NO 127
<211> LENGTH: 121
<212> TYPE: PRT
<213> ORGANISM: Vicugna pacos

<400> SEQUENCE: 127

Gln Val Gln Leu Gln Glu Ser Gly Gly Gly Leu Val Gln Pro Gly Gly
1               5                   10                  15

Ser Leu Lys Leu Ser Cys Ala Ala Ser Gly Ser Ile Phe Ser Ile Lys
            20                  25                  30

Thr Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

-continued

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Asp Gly Val Val Ala Trp Asp Gln Pro Tyr Asp Asn Tyr Trp Gly
            100                 105                 110

Gln Gly Thr Gln Val Thr Val Ser Ser
        115                 120

<210> SEQ ID NO 128
<211> LENGTH: 125
<212> TYPE: PRT
<213> ORGANISM: Vicugna pacos

<400> SEQUENCE: 128

Gln Val Gln Leu Gln Glu Ser Gly Gly Gly Leu Val Gln Ala Gly Asp
  1               5                  10                  15

Ser Leu Ser Ile Ser Cys Ala Ala Ser Gly Asp Thr Phe Asn His Tyr
                 20                  25                  30

Ser Trp Gly Trp Phe Arg Gln Ala Pro Gly Lys Ala Arg Glu Phe Val
             35                  40                  45

Ala Ala Ile Ser Trp Asn Gly Gly Ser Lys Tyr Ala Asp Ser Val Lys
         50                  55                  60

Gly Arg Phe Ala Ile Ser Arg Asp Ile Ala Lys Asn Thr Val Ser Leu
 65                  70                  75                  80

Gln Met Asn Ser Leu Glu Pro Glu Asp Thr Ala Val Tyr Tyr Cys Ala
                 85                  90                  95

Ala Asp Arg Arg Pro Tyr Asn Asp Trp Trp Asp Trp Ser Trp Trp
            100                 105                 110

Val Tyr Trp Gly Gln Gly Thr Gln Val Thr Val Ser Ser
        115                 120                 125

<210> SEQ ID NO 129
<211> LENGTH: 127
<212> TYPE: PRT
<213> ORGANISM: Vicugna pacos

<400> SEQUENCE: 129

Gln Val Gln Leu Gln Glu Ser Gly Gly Gly Leu Val Gln Pro Gly Glu
  1               5                  10                  15

Ser Leu Arg Leu Ser Cys Lys Leu Ser Gly Phe Thr Leu Asp Tyr Tyr
                 20                  25                  30

Asp Ile Gly Trp Phe Arg Gln Ala Pro Gly Lys Glu Arg Glu Gly Val
             35                  40                  45

Ser Cys Ile Ser Ser Ile Gly Gly Ser Ala Asn Tyr Ala Asp Ser Val
         50                  55                  60

Lys Gly Arg Phe Thr Ile Ser Arg Asp Asn Val Lys Asn Thr Val Tyr
 65                  70                  75                  80

Leu Gln Met Asn Ser Leu Lys Pro Glu Asp Thr Ala Ile Tyr Tyr Cys
                 85                  90                  95

Ala Ala Glu Ala Gln Thr Pro Tyr Asn Asp Gly Asp Cys Thr Arg Ala
            100                 105                 110

Ser Tyr Asp Tyr Trp Gly Gln Gly Ile Gln Val Thr Val Ser Ser
        115                 120                 125

<210> SEQ ID NO 130
```

<211> LENGTH: 118
<212> TYPE: PRT
<213> ORGANISM: Vicugna pacos

<400> SEQUENCE: 130

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Ile
        35                  40                  45

Ser Cys Ile Ser Tyr Lys Gly Gly Ser Thr Thr Tyr Ala Asp Ser Val
50                  55                  60

Lys Gly Arg Phe Thr Ile Ser Lys Asp Asn Ala Lys Asn Thr Ala Tyr
65                  70                  75                  80

Leu Gln Met Asn Asn Leu Lys Pro Glu Asp Thr Gly Ile Tyr Tyr Cys
            85                  90                  95

Ala Ala Gly Phe Val Cys Tyr Asn Tyr Asp Tyr Trp Gly Pro Gly Thr
        100                 105                 110

Gln Val Thr Val Ser Ser
        115

<210> SEQ ID NO 131
<211> LENGTH: 131
<212> TYPE: PRT
<213> ORGANISM: Vicugna pacos

<400> SEQUENCE: 131

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Asp Asp Asp Tyr
            20                  25                  30

Asp Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Asp Phe Phe Arg Trp Asp Ser Gly Ser Tyr Tyr Val Arg Gly
        100                 105                 110

Cys Arg His Ala Thr Tyr Asp Tyr Trp Gly Gln Gly Thr Gln Val Thr
        115                 120                 125

Val Ser Ser
    130

<210> SEQ ID NO 132
<211> LENGTH: 119
<212> TYPE: PRT
<213> ORGANISM: Vicugna pacos

<400> SEQUENCE: 132

Gln Val Gln Leu Gln Glu Ser Gly Gly Gly Leu Val Gln Pro Gly Gly
1               5                   10                  15

Ser Leu Arg Leu Ser Cys Val Val Ser Gly Ser Phe Leu Ser Ile Asn
            20                  25                  30

His Met Gly Trp Tyr Arg Gln Val Ser Gly Glu Gln Arg Glu Leu Val
            35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Ser Ala Lys Asn Thr Val Tyr Leu
 65                  70                  75                  80

Gln Met Asn Ser Leu Lys Pro Glu Asp Thr Ala Val Tyr Tyr Cys Asn
                85                  90                  95

Ala Asp Ala Leu Thr Met Leu Pro Pro Phe Asp Phe Trp Gly Gln Gly
            100                 105                 110

Thr Gln Val Thr Val Ser Ser
        115

<210> SEQ ID NO 133
<211> LENGTH: 120
<212> TYPE: PRT
<213> ORGANISM: Vicugna pacos

<400> SEQUENCE: 133

Gln Val Gln Leu Gln Glu Ser Gly Gly Gly Leu Val Gln Pro Gly Gly
 1               5                  10                  15

Ser Leu Met Leu Ser Cys Ala Ala Ser Gly Asn Ile Phe Thr Ile Asn
            20                  25                  30

Arg Met Gly Trp Tyr Arg Gln Ala Pro Gly Lys Gln Arg Glu Leu Val
            35                  40                  45

Ala Ala Ile Thr Ser Gly Gly Asn Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                85                  90                  95

Ala Ala Ile Val Thr Met Thr Ser Pro Tyr Ser Asp Tyr Trp Gly Gln
            100                 105                 110

Gly Thr Gln Val Thr Val Ser Ser
        115                 120

<210> SEQ ID NO 134
<211> LENGTH: 112
<212> TYPE: PRT
<213> ORGANISM: Vicugna pacos

<400> SEQUENCE: 134

Gln Val Gln Leu Gln Glu Ser Gly Gly Thr Leu Val Gln Pro Gly Gly
 1               5                  10                  15

Ser Leu Arg Leu Ser Cys Ala Ser Gly Ser Thr Phe Ser Ile Asn
            20                  25                  30

Asn Met Gly Trp Tyr Arg Gln Ala Pro Gly Lys Gln Arg Glu Leu Val
            35                  40                  45

Ala Gly Ile Thr Gly Gly Asn Thr His Tyr Ala Asp Ser Val Lys Gly
        50                  55                  60

Arg Phe Thr Ile Ser Arg Asp Asn Ala Lys Asn Thr Met Tyr Leu Gln
 65                  70                  75                  80

Met Asn Gly Leu Lys Pro Glu Asp Thr Ala Val Tyr Tyr Cys Asn Ala
                85                  90                  95

Asn Trp Gly Ala Tyr Trp Gly Gln Gly Thr Gln Val Thr Val Ser Ser
            100                 105                 110

```
<210> SEQ ID NO 135
<211> LENGTH: 121
<212> TYPE: PRT
<213> ORGANISM: Vicugna pacos

<400> SEQUENCE: 135

Gln Val Gln Leu Gln Glu Ser Gly Gly Gly Leu Val Gln Pro Gly Gly
1               5                   10                  15

Ser Leu Gly Leu Ser Cys Ala Ala Ser Gly Arg Ile Ala Ser Ile Ser
            20                  25                  30

Ala Met Gly Trp Tyr Arg Gln Ala Pro Gly Lys Gln Arg Glu Leu Val
        35                  40                  45

Ala Ala Ile Thr Gly Ser Gly Arg Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Leu Met Val Asp Tyr Gly Leu Gly Leu Gly Thr Asp Tyr Trp Gly
            100                 105                 110

Gln Gly Thr Gln Val Thr Val Ser Ser
        115                 120

<210> SEQ ID NO 136
<211> LENGTH: 130
<212> TYPE: PRT
<213> ORGANISM: Vicugna pacos

<400> SEQUENCE: 136

Gln Val Gln Leu Gln Glu Ser Gly Gly Gly Leu Val Gln Pro Gly Gly
1               5                   10                  15

Ser Leu Arg Leu Ser Cys Ala Ala Ser Gly Pro Gly Phe Lys Leu Asp
            20                  25                  30

Tyr Tyr Ala Ile Ala Trp Phe Arg Gln Ala Pro Gly Lys Glu Arg Glu
        35                  40                  45

Gly Val Ser Cys Ile Gly Gly Ser Gly Ser Gly Leu Thr Thr Tyr Val
    50                  55                  60

Glu Asn Ser Val Lys Asp Arg Phe Thr Ile Ser Arg Asp Asn Ala Gln
65                  70                  75                  80

Asn Thr Val Tyr Leu His Met Asn Ser Leu Lys Pro Glu Asp Thr Gly
                85                  90                  95

Ile Tyr Tyr Cys Ala Ala Asp Thr Tyr Tyr Cys Ser Lys Arg Val
            100                 105                 110

Trp Arg Asn Asp Tyr Gly Ser Trp Gly Gln Gly Thr Gln Val Thr Val
        115                 120                 125

Ser Ser
    130

<210> SEQ ID NO 137
<211> LENGTH: 122
<212> TYPE: PRT
<213> ORGANISM: Vicugna pacos

<400> SEQUENCE: 137

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ile Asn
```

```
                    20                  25                  30
Tyr Met Gly Trp Tyr Arg Gln Ala Pro Gly Lys Gln Arg Glu Leu Val
                35                  40                  45

Ala Ala Ile Thr Ser Gly Ser Gly Ser Thr Asn Tyr Ala Asp Ser Val
         50                  55                  60

Lys Gly Arg Phe Thr Ile Ser Arg Asp Asn Ala Lys Asn Thr Met Tyr
 65                  70                  75                  80

Leu Gln Met Asn Ser Leu Lys Pro Glu Asp Thr Ala Val Tyr Tyr Cys
                 85                  90                  95

Asn Ala Asp Met Asp Ser Ser Leu Ser Gly Gly Tyr Val Asp Val Trp
                100                 105                 110

Gly Gln Gly Thr Gln Val Thr Val Ser Ser
                115                 120

<210> SEQ ID NO 138
<211> LENGTH: 125
<212> TYPE: PRT
<213> ORGANISM: Vicugna pacos

<400> SEQUENCE: 138

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Gly Thr Phe Asp Asp Ser
                 20                  25                  30

Val Ile Gly Trp Phe Arg Gln Ala Pro Gly Lys Glu Arg Glu Gly Val
                 35                  40                  45

Ser Cys Ile Ser Ser Asn Asp Gly Thr Thr His Tyr Ala Ser Pro Val
             50                  55                  60

Lys Gly Arg Phe Thr Ile Ser Ser Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Glu Thr Pro Ser Ile Gly Ser Pro Cys Thr Ser Ala Ser Tyr
                100                 105                 110

Asp Tyr Trp Gly Gln Gly Thr Gln Val Thr Val Ser Ser
            115                 120                 125

<210> SEQ ID NO 139
<211> LENGTH: 125
<212> TYPE: PRT
<213> ORGANISM: Vicugna pacos

<400> SEQUENCE: 139

Gln Val Gln Leu Gln Glu Ser Gly Gly Gly Leu Val Gln Pro Gly Gly
 1               5                  10                  15

Ser Leu Arg Leu Ser Cys Thr Ala Thr Gly Phe Thr Leu Lys Asn His
                 20                  25                  30

His Ile Gly Trp Leu Arg Gln Ala Pro Gly Lys Glu Arg Glu Gly Val
                 35                  40                  45

Ala Ser Ile Asn Ser Ser Gly Gly Ser Thr Asn Tyr Ala Asp Ser Val
             50                  55                  60

Gln Gly Arg Phe Thr Ile Ser Arg Asp Asn Ala Lys Asn Thr Val Phe
 65                  70                  75                  80

Leu Gln Met Asn Ser Leu Lys Ser Glu Asp Thr Ala Val Tyr Tyr Cys
                 85                  90                  95

Ala Arg Leu Arg Arg Tyr Tyr Gly Leu Asn Leu Asp Pro Gly Ser Tyr
```

```
              100                 105                 110

Asp Tyr Trp Gly Gln Gly Thr Gln Val Thr Val Ser Ser
        115                 120                 125

<210> SEQ ID NO 140
<211> LENGTH: 124
<212> TYPE: PRT
<213> ORGANISM: Vicugna pacos

<400> SEQUENCE: 140

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ala Tyr
            20                  25                  30

Ala Met Gly Trp Phe Arg Gln Ala Pro Gly Lys Glu Arg Glu Phe Val
        35                  40                  45

Ala Ala Ile Ser Arg Ser Gly Asp Ser Thr Asp Tyr Ala Asp Ser Val
    50                  55                  60

Lys Gly Arg Phe Thr Ile Ser Arg Asp Ser Ala Lys Asn Met Val Tyr
65                  70                  75                  80

Leu Gln Met Asn Ser Leu Lys Pro Glu Asp Thr Ala Leu Tyr His Cys
                85                  90                  95

Ala Ala Arg Thr Val Ser Ala Pro Pro Ser Ala Trp Gly Tyr Gly
            100                 105                 110

Tyr Trp Gly Gln Gly Thr Gln Val Thr Val Ser Ser
        115                 120

<210> SEQ ID NO 141
<211> LENGTH: 118
<212> TYPE: PRT
<213> ORGANISM: Vicugna pacos

<400> SEQUENCE: 141

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Asp Tyr Tyr
            20                  25                  30

Ala Ile Gly Trp Phe Arg Gln Ala Pro Gly Lys Glu Arg Glu Gly Ile
        35                  40                  45

Ser Cys Ile Ser Tyr Lys Gly Gly Ser Thr Thr Tyr Ala Asp Ser Val
    50                  55                  60

Lys Gly Arg Phe Thr Ile Ser Lys Asp Asn Ala Lys Asn Thr Ala Tyr
65                  70                  75                  80

Leu Gln Met Asn Ser Leu Lys Pro Glu Asp Thr Gly Ile Tyr Ser Cys
                85                  90                  95

Ala Ala Gly Phe Val Cys Tyr Asn Tyr Asp Tyr Trp Gly Gln Gly Thr
            100                 105                 110

Gln Val Thr Val Ser Ser
        115

<210> SEQ ID NO 142
<211> LENGTH: 130
<212> TYPE: PRT
<213> ORGANISM: Vicugna pacos

<400> SEQUENCE: 142

Gln Val Gln Leu Gln Glu Ser Gly Gly Gly Leu Val Gln Pro Gly Gly
1               5                   10                  15
```

Ser Leu Arg Leu Ser Cys Ala Ala Ser Gly Arg Thr Phe Ser Asn Tyr
            20                  25                  30

Val Asn Tyr Ala Met Gly Trp Phe Arg Gln Phe Pro Gly Lys Glu Arg
            35                  40                  45

Glu Phe Val Ala Ser Ile Ser Trp Ser Val Thr Thr Tyr Tyr Ala
 50                  55                  60

Asp Ser Val Lys Gly Arg Phe Thr Ile Ser Arg Asp Asn Ala Lys Asn
 65                  70                  75                  80

Thr Val Tyr Leu Gln Met Asn Ser Leu Lys Pro Glu Asp Thr Ala Val
                 85                  90                  95

Tyr Tyr Cys Ala Ala His Leu Ala Gln Tyr Ser Asp Tyr Ala Tyr Arg
            100                 105                 110

Asp Pro His Gln Phe Gly Ala Trp Gly Gln Gly Thr Gln Val Thr Val
            115                 120                 125

Ser Ser
    130

<210> SEQ ID NO 143
<211> LENGTH: 117
<212> TYPE: PRT
<213> ORGANISM: Vicugna pacos

<400> SEQUENCE: 143

Gln Val Gln Leu Gln Glu Ser Gly Gly Gly Leu Val Gln Ala Gly Gly
 1               5                  10                  15

Ser Leu Arg Leu Ser Cys Leu Ala Ser Gly Asp Thr Phe Ser Asn Tyr
            20                  25                  30

Val Met Ala Trp Phe Arg Gln Ala Pro Gly Lys Glu Arg Glu Ile Val
            35                  40                  45

Ala Ala Ile Arg Leu Ser Gly Ala Arg Tyr Val Pro Asp Ser Val Lys
 50                  55                  60

Gly Arg Phe Thr Ile Ser Arg Asp Asn Ala Lys Asn Ala Met Tyr Leu
 65                  70                  75                  80

Gln Met Thr Ser Leu Lys Pro Glu Asp Thr Ala Arg Tyr Tyr Cys Ala
                 85                  90                  95

Ala Gly His Thr Trp Gly Gln Tyr Ala Tyr Trp Gly Gln Gly Thr Gln
            100                 105                 110

Val Thr Val Ser Ser
            115

<210> SEQ ID NO 144
<211> LENGTH: 119
<212> TYPE: PRT
<213> ORGANISM: Vicugna pacos

<400> SEQUENCE: 144

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Ala
            20                  25                  30

Ala Met Gly Trp Phe Arg Gln Ala Pro Gly Lys Glu Arg Glu Pro Val
            35                  40                  45

Ala Leu Ile Asn Leu Asp Asp Gly Glu Thr Tyr Tyr Ala Asp Ile Ala
 50                  55                  60

Lys Gly Arg Phe Thr Leu Ser Lys Asp Asn Ala Lys Asn Ser Val Tyr
 65                  70                  75                  80

```
Leu Gln Met Asn Ser Leu Lys Pro Glu Asp Thr Ala Val Tyr Tyr Cys
                 85                  90                  95

Ala Val Arg Gly Arg Phe Asp Asp Asn Tyr Glu Tyr Trp Gly Gln Gly
            100                 105                 110

Thr Gln Val Thr Val Ser Ser
        115

<210> SEQ ID NO 145
<211> LENGTH: 122
<212> TYPE: PRT
<213> ORGANISM: Vicugna pacos

<400> SEQUENCE: 145

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ile Asn
            20                  25                  30

Tyr Met Gly Trp Tyr Arg Gln Ala Pro Gly Lys Gln Arg Glu Leu Val
        35                  40                  45

Ala Ala Ile Thr Ser Gly Ser Gly Ser Thr Asn Tyr Ala Asp Ser Val
    50                  55                  60

Lys Gly Arg Phe Thr Ile Ser Arg Asp Asn Ala Lys Lys Thr Met Tyr
65                  70                  75                  80

Leu Gln Met Asn Ser Leu Lys Pro Glu Asp Thr Ala Val Tyr Tyr Cys
                85                  90                  95

Asn Ala Asp Met Asp Ser Ser Leu Ser Gly Tyr Val Asp Val Trp
            100                 105                 110

Gly Gln Gly Thr Gln Val Thr Val Ser Ser
        115                 120

<210> SEQ ID NO 146
<211> LENGTH: 112
<212> TYPE: PRT
<213> ORGANISM: Vicugna pacos

<400> SEQUENCE: 146

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Asn
            20                  25                  30

Asn Met Gly Trp Tyr Arg Gln Ala Pro Gly Lys Gln Arg Glu Leu Val
        35                  40                  45

Ala Gly Ile Thr Gly Gly Asn Thr His Tyr Ala Asp Ser Val Lys Gly
    50                  55                  60

Arg Phe Thr Ile Ser Arg Asp Asn Ala Lys Asn Thr Met Tyr Leu Gln
65                  70                  75                  80

Met Asn Ser Leu Lys Pro Glu Asp Thr Ala Val Tyr Tyr Cys Asn Ala
                85                  90                  95

Asn Trp Gly Ala Tyr Trp Gly Gln Gly Thr Gln Val Thr Val Ser Ser
            100                 105                 110

<210> SEQ ID NO 147
<211> LENGTH: 119
<212> TYPE: PRT
<213> ORGANISM: Vicugna pacos

<400> SEQUENCE: 147
```

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Val Ser Ile Asn
            20                  25                  30

Ala Met Gly Trp Tyr Arg Gln Ala Pro Gly Lys Gln Arg Glu Leu Val
        35                  40                  45

Ala Leu Val Thr Gly Ser Gly Arg Thr Asn Leu Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Val Leu Val Ile Gly Pro Leu Glu Gly Tyr Asp Tyr Trp Gly Gln Gly
        100                 105                 110

Thr Gln Val Thr Val Ser Ser
    115

<210> SEQ ID NO 148
<211> LENGTH: 121
<212> TYPE: PRT
<213> ORGANISM: Vicugna pacos

<400> SEQUENCE: 148

Gln Val Gln Leu Gln Glu Ser Gly Gly Gly Leu Val Gln Pro Gly Gly
1               5                   10                  15

Ser Leu Lys Leu Ser Cys Ala Ala Ser Gly Ser Ile Phe Ser Ile Lys
            20                  25                  30

Thr Met Gly Trp Tyr Arg Gln Ala Pro Gly Lys Gln Arg Glu Leu Val
        35                  40                  45

Ala Ala Val Ser Ser Gly Gly Ser Thr Asn Tyr Ala Asp Ser Val Lys
    50                  55                  60

Gly Arg Phe Thr Ile Ser Arg Asp Asn Ala Lys Asn Ala Val Tyr Leu
65                  70                  75                  80

Gln Met Asn Ser Leu Lys Pro Glu Asp Thr Ala Val Tyr Tyr Cys Asn
            85                  90                  95

Ala Asp Gly Val Val Ala Trp Asp Gln Pro Tyr Asp Asn Tyr Trp Gly
        100                 105                 110

Gln Gly Thr Gln Val Thr Val Ser Ser
    115                 120

<210> SEQ ID NO 149
<211> LENGTH: 118
<212> TYPE: PRT
<213> ORGANISM: Vicugna pacos

<400> SEQUENCE: 149

Gln Val Gln Leu Gln Glu Ser Gly Gly Gly Leu Val Gln Ala Gly Gly
1               5                   10                  15

Ser Leu Arg Leu Ser Cys Val Asp Gln Gly Arg Thr Phe Ser Val Asn
            20                  25                  30

Ala Met Ala Trp Tyr Arg Gln Ala Pro Gly Lys Gln Arg Glu Leu Val
        35                  40                  45

Ala Ser Ile Thr Ser Ser Gly Leu Asp Thr Gln Tyr Ala Glu Gly Met
    50                  55                  60

Lys Gly Arg Phe Thr Ile Ser Lys Gly Asn Asp Lys Phe Ser Thr Tyr
65                  70                  75                  80

```
Leu Gln Met Asn Asn Leu Lys Pro Asp Asp Thr Ala Val Tyr Tyr Cys
                85                  90                  95

Asn Ala Glu Arg Trp Asp Asn Gly Met Val Tyr Trp Gly Lys Gly Thr
            100                 105                 110

Gln Val Thr Val Ser Ser
        115

<210> SEQ ID NO 150
<211> LENGTH: 132
<212> TYPE: PRT
<213> ORGANISM: Vicugna pacos

<400> SEQUENCE: 150

Gln Val Gln Leu Gln Glu Ser Gly Gly Gly Leu Val Gln Ala Gly Asp
1               5                   10                  15

Ser Leu Arg Leu Ser Cys Leu Ala Thr Gly Ser Met Phe Ser Ile Asn
            20                  25                  30

Ala Trp Gly Trp Tyr Arg Gln Ala Pro Gly Lys Gln Arg Glu Leu Val
        35                  40                  45

Ala Ser Ile Thr Ser Gly Gly Ser Thr Glu Tyr Ala Glu Ser Val
    50                  55                  60

Lys Gly Arg Phe Thr Ile Ser Arg Asp Ser Ala Lys Asn Met Leu Tyr
65                  70                  75                  80

Leu Gln Met Asn Ser Leu Arg Pro Glu Asp Thr Ala Val Tyr Tyr Cys
                85                  90                  95

Asn Ala Glu Arg Trp Asp Gly Tyr Ala Leu Gly Tyr Ser Pro Asn His
            100                 105                 110

Gly Ser Gly His Arg Pro Tyr Asn Tyr Trp Gly Gln Gly Thr Gln Val
        115                 120                 125

Thr Val Ser Ser
    130

<210> SEQ ID NO 151
<211> LENGTH: 120
<212> TYPE: PRT
<213> ORGANISM: Vicugna pacos

<400> SEQUENCE: 151

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Trp Gly Trp Tyr Arg Gln Ala Pro Gly Lys Gln Arg Glu Leu Val
        35                  40                  45

Ala Glu Ile Thr Ser Ser Gly Ser Thr Asn Tyr Ala Asp Ser Val Lys
    50                  55                  60

Gly Arg Phe Thr Ile Ser Gly Asp Asn Ala Lys Asn Ser Val Tyr Leu
65                  70                  75                  80

His Met Asn Asn Leu Glu Pro Glu Asp Thr Ala Val Tyr Tyr Cys Lys
                85                  90                  95

Ala Val Ala Val Thr Phe Thr Thr Pro Arg Ser Asp Tyr Trp Gly Arg
            100                 105                 110

Gly Thr Gln Val Thr Val Ser Ser
        115                 120

<210> SEQ ID NO 152
<211> LENGTH: 116
```

<212> TYPE: PRT
<213> ORGANISM: Vicugna pacos

<400> SEQUENCE: 152

Gln Val Gln Leu Gln Glu Ser Gly Gly Gly Leu Val Gln Pro Gly Gly
1               5                   10                  15

Ser Leu Arg Leu Ser Cys Ala Pro Ser Gly Ser Ile Ile Ser Ile Asn
            20                  25                  30

Ala Met Ala Trp Tyr Arg Gln Ala Pro Gly Lys Glu Arg Glu Leu Val
        35                  40                  45

Ala Ala Ile Ser Ser Gly Gly Ser Thr Tyr Tyr Ala Asp Ser Val Lys
    50                  55                  60

Gly Arg Phe Thr Ile Ser Gly Asp Ile Ala Lys Asn Leu Leu Trp Leu
65                  70                  75                  80

Gln Met Asn Ser Leu Lys Pro Glu Asp Thr Ala Met Tyr Tyr Cys Ala
                85                  90                  95

Pro Gly Gly Gly Trp Arg Pro Gly Ala Trp Gly Gln Gly Thr Gln Val
            100                 105                 110

Thr Val Ser Ser
        115

<210> SEQ ID NO 153
<211> LENGTH: 116
<212> TYPE: PRT
<213> ORGANISM: Vicugna pacos

<400> SEQUENCE: 153

Gln Val Gln Leu Gln Glu Ser Gly Gly Gly Leu Val Gln Pro Gly Gly
1               5                   10                  15

Ser Leu Arg Leu Ser Cys Ala Gly Ser Gly Phe Thr Val Ser Thr Ser
            20                  25                  30

Met Ile Asn Trp Ala Arg Gln Val Pro Gly Lys Glu Leu Glu Trp Leu
        35                  40                  45

Val Asp Val Leu Pro Ser Gly Ser Thr Tyr Tyr Ala Asp Pro Val Lys
    50                  55                  60

Gly Arg Phe Thr Ile Ser Arg Asp Asn Ala Gln Asn Thr Ile Tyr Leu
65                  70                  75                  80

Gln Met Asn Tyr Leu Lys Pro Glu Asp Thr Ala Ile Tyr Tyr Cys Ala
                85                  90                  95

Ile Asn Arg Glu Thr Met Pro Pro Phe Arg Gly Gln Gly Thr Gln Val
            100                 105                 110

Thr Val Ser Ser
        115

<210> SEQ ID NO 154
<211> LENGTH: 121
<212> TYPE: PRT
<213> ORGANISM: Vicugna pacos

<400> SEQUENCE: 154

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Pro Phe Ser Ser Ala
            20                  25                  30

Pro Met Ser Trp Val Arg Gln Ala Pro Gly Lys Glu Leu Glu Trp Val
        35                  40                  45

Ser Tyr Ile Gly Tyr Thr Gly Thr Ile Thr Asp Tyr Ala Asn Ser Val

```
                    50                  55                  60
Lys Gly Arg Phe Thr Ile Ser Arg Asp Asn Ala Lys Asn Arg Leu Tyr
 65                  70                  75                  80

Leu Gln Met Asn Ser Leu Lys Pro Glu Asp Thr Ala Val Tyr Phe Cys
                 85                  90                  95

Ala Gln Gly Tyr Ala Arg Leu Ile Ala Asp Ser Asp Leu Val Arg Gly
                100                 105                 110

Gln Gly Thr Gln Val Thr Val Ser Ser
        115                 120

<210> SEQ ID NO 155
<211> LENGTH: 121
<212> TYPE: PRT
<213> ORGANISM: Vicugna pacos

<400> SEQUENCE: 155

Gln Val Gln Leu Gln Glu Ser Gly Gly Arg Leu Gly Ala Ala Gly Gly
 1               5                  10                  15

Ser Leu Arg Leu Ser Cys Thr Ala Ser Gly Phe Pro Phe Asn Ile Tyr
                20                  25                  30

Pro Met Ser Trp Val Arg Gln Ala Pro Gly Lys Gly Phe Glu Trp Val
            35                  40                  45

Ser Tyr Ile Ser His Gly Gly Thr Thr Thr Asp Tyr Ser Asp Ala Val
         50                  55                  60

Lys Gly Arg Phe Thr Ile Ser Arg Asp Asn Ala Lys Asn Arg Leu Tyr
 65                  70                  75                  80

Leu Gln Met Asp Ser Leu Lys Pro Glu Asp Thr Ala Val Tyr Phe Cys
                 85                  90                  95

Ala Gln Gly Tyr Ala Arg Leu Met Thr Asp Ser Glu Leu Val Arg Gly
                100                 105                 110

Gln Gly Thr Gln Val Thr Val Ser Ser
        115                 120

<210> SEQ ID NO 156
<211> LENGTH: 11
<212> TYPE: PRT
<213> ORGANISM: Vicugna pacos

<400> SEQUENCE: 156

Ser Gly Asn Ile Phe Ser Ile Asn Ala Ile Gly
 1               5                  10

<210> SEQ ID NO 157
<211> LENGTH: 11
<212> TYPE: PRT
<213> ORGANISM: Vicugna pacos

<400> SEQUENCE: 157

Ser Gly Arg Thr Phe Ser Arg Asp Ala Met Gly
 1               5                  10

<210> SEQ ID NO 158
<211> LENGTH: 10
<212> TYPE: PRT
<213> ORGANISM: Vicugna pacos

<400> SEQUENCE: 158

Gly Phe Thr Leu Asp Asn Tyr Thr Val Ala
 1               5                  10
```

<210> SEQ ID NO 159
<211> LENGTH: 10
<212> TYPE: PRT
<213> ORGANISM: Vicugna pacos

<400> SEQUENCE: 159

Gly Ser Ile Phe Ser Ile Lys Thr Met Gly
1               5                   10

<210> SEQ ID NO 160
<211> LENGTH: 10
<212> TYPE: PRT
<213> ORGANISM: Vicugna pacos

<400> SEQUENCE: 160

Gly Asp Thr Phe Asn His Tyr Ser Trp Gly
1               5                   10

<210> SEQ ID NO 161
<211> LENGTH: 10
<212> TYPE: PRT
<213> ORGANISM: Vicugna pacos

<400> SEQUENCE: 161

Gly Phe Thr Leu Asp Tyr Tyr Asp Ile Gly
1               5                   10

<210> SEQ ID NO 162
<211> LENGTH: 10
<212> TYPE: PRT
<213> ORGANISM: Vicugna pacos

<400> SEQUENCE: 162

Gly Phe Thr Leu Asp Tyr Tyr Ala Ile Gly
1               5                   10

<210> SEQ ID NO 163
<211> LENGTH: 10
<212> TYPE: PRT
<213> ORGANISM: Vicugna pacos

<400> SEQUENCE: 163

Gly Phe Thr Asp Asp Asp Tyr Asp Ile Gly
1               5                   10

<210> SEQ ID NO 164
<211> LENGTH: 10
<212> TYPE: PRT
<213> ORGANISM: Vicugna pacos

<400> SEQUENCE: 164

Gly Ser Phe Leu Ser Ile Asn His Met Gly
1               5                   10

<210> SEQ ID NO 165
<211> LENGTH: 10
<212> TYPE: PRT
<213> ORGANISM: Vicugna pacos

<400> SEQUENCE: 165

Gly Asn Ile Phe Thr Ile Asn Arg Met Gly
1               5                   10

<210> SEQ ID NO 166

```
<211> LENGTH: 10
<212> TYPE: PRT
<213> ORGANISM: Vicugna pacos

<400> SEQUENCE: 166

Gly Ser Thr Phe Ser Ile Asn Asn Met Gly
1               5                   10

<210> SEQ ID NO 167
<211> LENGTH: 10
<212> TYPE: PRT
<213> ORGANISM: Vicugna pacos

<400> SEQUENCE: 167

Gly Arg Ile Ala Ser Ile Ser Ala Met Gly
1               5                   10

<210> SEQ ID NO 168
<211> LENGTH: 11
<212> TYPE: PRT
<213> ORGANISM: Vicugna pacos

<400> SEQUENCE: 168

Pro Gly Phe Lys Leu Asp Tyr Tyr Ala Ile Ala
1               5                   10

<210> SEQ ID NO 169
<211> LENGTH: 10
<212> TYPE: PRT
<213> ORGANISM: Vicugna pacos

<400> SEQUENCE: 169

Gly Arg Thr Phe Ser Ile Asn Tyr Met Gly
1               5                   10

<210> SEQ ID NO 170
<211> LENGTH: 10
<212> TYPE: PRT
<213> ORGANISM: Vicugna pacos

<400> SEQUENCE: 170

Gly Gly Thr Phe Asp Asp Ser Val Ile Gly
1               5                   10

<210> SEQ ID NO 171
<211> LENGTH: 10
<212> TYPE: PRT
<213> ORGANISM: Vicugna pacos

<400> SEQUENCE: 171

Gly Phe Thr Leu Lys Asn His His Ile Gly
1               5                   10

<210> SEQ ID NO 172
<211> LENGTH: 10
<212> TYPE: PRT
<213> ORGANISM: Vicugna pacos

<400> SEQUENCE: 172

Gly Arg Ile Phe Ser Ala Tyr Ala Met Gly
1               5                   10

<210> SEQ ID NO 173
<211> LENGTH: 10
<212> TYPE: PRT
```

-continued

<213> ORGANISM: Vicugna pacos

<400> SEQUENCE: 173

Gly Phe Ser Leu Asp Tyr Tyr Ala Ile Gly
1               5                   10

<210> SEQ ID NO 174
<211> LENGTH: 13
<212> TYPE: PRT
<213> ORGANISM: Vicugna pacos

<400> SEQUENCE: 174

Gly Arg Thr Phe Ser Asn Tyr Val Asn Tyr Ala Met Gly
1               5                   10

<210> SEQ ID NO 175
<211> LENGTH: 10
<212> TYPE: PRT
<213> ORGANISM: Vicugna pacos

<400> SEQUENCE: 175

Gly Asp Thr Phe Ser Asn Tyr Val Met Ala
1               5                   10

<210> SEQ ID NO 176
<211> LENGTH: 10
<212> TYPE: PRT
<213> ORGANISM: Vicugna pacos

<400> SEQUENCE: 176

Gly Arg Thr Phe Ser Ser Ala Ala Met Gly
1               5                   10

<210> SEQ ID NO 177
<211> LENGTH: 10
<212> TYPE: PRT
<213> ORGANISM: Vicugna pacos

<400> SEQUENCE: 177

Gly Arg Thr Phe Ser Ile Asn Tyr Met Gly
1               5                   10

<210> SEQ ID NO 178
<211> LENGTH: 10
<212> TYPE: PRT
<213> ORGANISM: Vicugna pacos

<400> SEQUENCE: 178

Gly Ser Thr Phe Ser Ile Asn Asn Met Gly
1               5                   10

<210> SEQ ID NO 179
<211> LENGTH: 10
<212> TYPE: PRT
<213> ORGANISM: Vicugna pacos

<400> SEQUENCE: 179

Gly Ser Ile Val Ser Ile Asn Ala Met Gly
1               5                   10

<210> SEQ ID NO 180
<211> LENGTH: 10
<212> TYPE: PRT
<213> ORGANISM: Vicugna pacos

```
<400> SEQUENCE: 180

Gly Ser Ile Phe Ser Ile Lys Thr Met Gly
1               5                   10

<210> SEQ ID NO 181
<211> LENGTH: 10
<212> TYPE: PRT
<213> ORGANISM: Vicugna pacos

<400> SEQUENCE: 181

Gly Arg Thr Phe Ser Val Asn Ala Met Ala
1               5                   10

<210> SEQ ID NO 182
<211> LENGTH: 10
<212> TYPE: PRT
<213> ORGANISM: Vicugna pacos

<400> SEQUENCE: 182

Gly Ser Met Phe Ser Ile Asn Ala Trp Gly
1               5                   10

<210> SEQ ID NO 183
<211> LENGTH: 10
<212> TYPE: PRT
<213> ORGANISM: Vicugna pacos

<400> SEQUENCE: 183

Gly Ser Ile Phe Ser Ile Asn Ala Trp Gly
1               5                   10

<210> SEQ ID NO 184
<211> LENGTH: 10
<212> TYPE: PRT
<213> ORGANISM: Vicugna pacos

<400> SEQUENCE: 184

Gly Ser Ile Ile Ser Ile Asn Ala Met Ala
1               5                   10

<210> SEQ ID NO 185
<211> LENGTH: 10
<212> TYPE: PRT
<213> ORGANISM: Vicugna pacos

<400> SEQUENCE: 185

Gly Phe Thr Val Ser Thr Ser Met Ile Asn
1               5                   10

<210> SEQ ID NO 186
<211> LENGTH: 10
<212> TYPE: PRT
<213> ORGANISM: Vicugna pacos

<400> SEQUENCE: 186

Gly Phe Pro Phe Ser Ser Ala Pro Met Ser
1               5                   10

<210> SEQ ID NO 187
<211> LENGTH: 10
<212> TYPE: PRT
<213> ORGANISM: Vicugna pacos

<400> SEQUENCE: 187
```

```
Gly Phe Pro Phe Asn Ile Tyr Pro Met Ser
1               5                   10
```

<210> SEQ ID NO 188
<211> LENGTH: 9
<212> TYPE: PRT
<213> ORGANISM: Vicugna pacos

<400> SEQUENCE: 188

```
Thr Ile Thr Leu Ser Gly Ser Thr Asn
1               5
```

<210> SEQ ID NO 189
<211> LENGTH: 9
<212> TYPE: PRT
<213> ORGANISM: Vicugna pacos

<400> SEQUENCE: 189

```
Gly Ile Ser Trp Ser Gly Gly Ser Thr
1               5
```

<210> SEQ ID NO 190
<211> LENGTH: 9
<212> TYPE: PRT
<213> ORGANISM: Vicugna pacos

<400> SEQUENCE: 190

```
Cys Ile Ser Ser Ser Gly Gly Ser Thr
1               5
```

<210> SEQ ID NO 191
<211> LENGTH: 8
<212> TYPE: PRT
<213> ORGANISM: Vicugna pacos

<400> SEQUENCE: 191

```
Ala Ile Thr Ser Gly Gly Ser Thr
1               5
```

<210> SEQ ID NO 192
<211> LENGTH: 8
<212> TYPE: PRT
<213> ORGANISM: Vicugna pacos

<400> SEQUENCE: 192

```
Ala Ile Ser Trp Asn Gly Gly Ser
1               5
```

<210> SEQ ID NO 193
<211> LENGTH: 9
<212> TYPE: PRT
<213> ORGANISM: Vicugna pacos

<400> SEQUENCE: 193

```
Cys Ile Ser Ser Ile Gly Gly Ser Ala
1               5
```

<210> SEQ ID NO 194
<211> LENGTH: 9
<212> TYPE: PRT
<213> ORGANISM: Vicugna pacos

<400> SEQUENCE: 194

```
Cys Ile Ser Tyr Lys Gly Gly Ser Thr
1               5
```

```
<210> SEQ ID NO 195
<211> LENGTH: 9
<212> TYPE: PRT
<213> ORGANISM: Vicugna pacos

<400> SEQUENCE: 195

Cys Ile Ser Ser Ser Asp Gly Ser Thr
1               5

<210> SEQ ID NO 196
<211> LENGTH: 8
<212> TYPE: PRT
<213> ORGANISM: Vicugna pacos

<400> SEQUENCE: 196

Ala Ile Thr Ser Gly Gly Ser Thr
1               5

<210> SEQ ID NO 197
<211> LENGTH: 8
<212> TYPE: PRT
<213> ORGANISM: Vicugna pacos

<400> SEQUENCE: 197

Ala Ile Thr Ser Gly Gly Asn Thr
1               5

<210> SEQ ID NO 198
<211> LENGTH: 7
<212> TYPE: PRT
<213> ORGANISM: Vicugna pacos

<400> SEQUENCE: 198

Gly Ile Thr Gly Gly Asn Thr
1               5

<210> SEQ ID NO 199
<211> LENGTH: 8
<212> TYPE: PRT
<213> ORGANISM: Vicugna pacos

<400> SEQUENCE: 199

Ala Ile Thr Gly Ser Gly Arg Thr
1               5

<210> SEQ ID NO 200
<211> LENGTH: 10
<212> TYPE: PRT
<213> ORGANISM: Vicugna pacos

<400> SEQUENCE: 200

Cys Ile Gly Gly Ser Gly Ser Gly Leu Thr
1               5                   10

<210> SEQ ID NO 201
<211> LENGTH: 9
<212> TYPE: PRT
<213> ORGANISM: Vicugna pacos

<400> SEQUENCE: 201

Ala Ile Thr Ser Gly Ser Gly Ser Thr
1               5
```

-continued

```
<210> SEQ ID NO 202
<211> LENGTH: 9
<212> TYPE: PRT
<213> ORGANISM: Vicugna pacos

<400> SEQUENCE: 202

Cys Ile Ser Ser Asn Asp Gly Thr Thr
1               5

<210> SEQ ID NO 203
<211> LENGTH: 9
<212> TYPE: PRT
<213> ORGANISM: Vicugna pacos

<400> SEQUENCE: 203

Ser Ile Asn Ser Ser Gly Gly Ser Thr
1               5

<210> SEQ ID NO 204
<211> LENGTH: 9
<212> TYPE: PRT
<213> ORGANISM: Vicugna pacos

<400> SEQUENCE: 204

Ala Ile Ser Arg Ser Gly Asp Ser Thr
1               5

<210> SEQ ID NO 205
<211> LENGTH: 9
<212> TYPE: PRT
<213> ORGANISM: Vicugna pacos

<400> SEQUENCE: 205

Cys Ile Ser Tyr Lys Gly Gly Ser Thr
1               5

<210> SEQ ID NO 206
<211> LENGTH: 9
<212> TYPE: PRT
<213> ORGANISM: Vicugna pacos

<400> SEQUENCE: 206

Ser Ile Ser Trp Ser Ser Val Thr Thr
1               5

<210> SEQ ID NO 207
<211> LENGTH: 8
<212> TYPE: PRT
<213> ORGANISM: Vicugna pacos

<400> SEQUENCE: 207

Ala Ile Arg Leu Ser Gly Ala Arg
1               5

<210> SEQ ID NO 208
<211> LENGTH: 9
<212> TYPE: PRT
<213> ORGANISM: Vicugna pacos

<400> SEQUENCE: 208

Leu Ile Asn Leu Asp Asp Gly Glu Thr
1               5

<210> SEQ ID NO 209
<211> LENGTH: 9
```

-continued

```
<212> TYPE: PRT
<213> ORGANISM: Vicugna pacos

<400> SEQUENCE: 209

Ala Ile Thr Ser Gly Ser Gly Ser Thr
1               5

<210> SEQ ID NO 210
<211> LENGTH: 7
<212> TYPE: PRT
<213> ORGANISM: Vicugna pacos

<400> SEQUENCE: 210

Gly Ile Thr Gly Gly Asn Thr
1               5

<210> SEQ ID NO 211
<211> LENGTH: 8
<212> TYPE: PRT
<213> ORGANISM: Vicugna pacos

<400> SEQUENCE: 211

Leu Val Thr Gly Ser Gly Arg Thr
1               5

<210> SEQ ID NO 212
<211> LENGTH: 8
<212> TYPE: PRT
<213> ORGANISM: Vicugna pacos

<400> SEQUENCE: 212

Ala Val Ser Ser Gly Gly Ser Thr
1               5

<210> SEQ ID NO 213
<211> LENGTH: 9
<212> TYPE: PRT
<213> ORGANISM: Vicugna pacos

<400> SEQUENCE: 213

Ser Ile Thr Ser Ser Gly Leu Asp Thr
1               5

<210> SEQ ID NO 214
<211> LENGTH: 9
<212> TYPE: PRT
<213> ORGANISM: Vicugna pacos

<400> SEQUENCE: 214

Ser Ile Thr Ser Gly Gly Gly Ser Thr
1               5

<210> SEQ ID NO 215
<211> LENGTH: 8
<212> TYPE: PRT
<213> ORGANISM: Vicugna pacos

<400> SEQUENCE: 215

Glu Ile Thr Ser Ser Gly Ser Thr
1               5

<210> SEQ ID NO 216
<211> LENGTH: 8
<212> TYPE: PRT
<213> ORGANISM: Vicugna pacos
```

<400> SEQUENCE: 216

Ala Ile Ser Ser Gly Gly Ser Thr
1               5

<210> SEQ ID NO 217
<211> LENGTH: 8
<212> TYPE: PRT
<213> ORGANISM: Vicugna pacos

<400> SEQUENCE: 217

Asp Val Leu Pro Ser Gly Ser Thr
1               5

<210> SEQ ID NO 218
<211> LENGTH: 9
<212> TYPE: PRT
<213> ORGANISM: Vicugna pacos

<400> SEQUENCE: 218

Tyr Ile Gly Tyr Thr Gly Thr Ile Thr
1               5

<210> SEQ ID NO 219
<211> LENGTH: 9
<212> TYPE: PRT
<213> ORGANISM: Vicugna pacos

<400> SEQUENCE: 219

Tyr Ile Ser His Gly Gly Thr Thr Thr
1               5

<210> SEQ ID NO 220
<211> LENGTH: 11
<212> TYPE: PRT
<213> ORGANISM: Vicugna pacos

<400> SEQUENCE: 220

Asn Thr Tyr Ser Asp Ser Asp Val Tyr Gly Tyr
1               5                   10

<210> SEQ ID NO 221
<211> LENGTH: 15
<212> TYPE: PRT
<213> ORGANISM: Vicugna pacos

<400> SEQUENCE: 221

Ser Ser Ile Tyr Gly Ser Ala Val Val Asp Gly Leu Tyr Asp Tyr
1               5                   10                  15

<210> SEQ ID NO 222
<211> LENGTH: 24
<212> TYPE: PRT
<213> ORGANISM: Vicugna pacos

<400> SEQUENCE: 222

Glu Arg Ala Pro Pro Tyr Tyr Ser Gly Tyr Tyr Phe Phe Asp Ser Thr
1               5                   10                  15

Cys Val Ala Ala Ser Tyr Asp Tyr
            20

<210> SEQ ID NO 223
<211> LENGTH: 13
<212> TYPE: PRT

```
<213> ORGANISM: Vicugna pacos

<400> SEQUENCE: 223

Asp Gly Val Val Ala Trp Asp Gln Pro Tyr Asp Asn Tyr
1               5                   10

<210> SEQ ID NO 224
<211> LENGTH: 17
<212> TYPE: PRT
<213> ORGANISM: Vicugna pacos

<400> SEQUENCE: 224

Asp Arg Arg Pro Tyr Asn Asp Trp Trp Asp Trp Ser Trp Trp Val
1               5                   10                  15

Tyr

<210> SEQ ID NO 225
<211> LENGTH: 18
<212> TYPE: PRT
<213> ORGANISM: Vicugna pacos

<400> SEQUENCE: 225

Glu Ala Gln Thr Pro Tyr Asn Asp Gly Asp Cys Thr Arg Ala Ser Tyr
1               5                   10                  15

Asp Tyr

<210> SEQ ID NO 226
<211> LENGTH: 9
<212> TYPE: PRT
<213> ORGANISM: Vicugna pacos

<400> SEQUENCE: 226

Gly Phe Val Cys Tyr Asn Tyr Asp Tyr
1               5

<210> SEQ ID NO 227
<211> LENGTH: 22
<212> TYPE: PRT
<213> ORGANISM: Vicugna pacos

<400> SEQUENCE: 227

Asp Phe Phe Arg Trp Asp Ser Gly Ser Tyr Tyr Val Arg Gly Cys Arg
1               5                   10                  15

His Ala Thr Tyr Asp Tyr
            20

<210> SEQ ID NO 228
<211> LENGTH: 11
<212> TYPE: PRT
<213> ORGANISM: Vicugna pacos

<400> SEQUENCE: 228

Asp Ala Leu Thr Met Leu Pro Pro Phe Asp Phe
1               5                   10

<210> SEQ ID NO 229
<211> LENGTH: 12
<212> TYPE: PRT
<213> ORGANISM: Vicugna pacos

<400> SEQUENCE: 229

Ala Ile Val Thr Met Thr Ser Pro Tyr Ser Asp Tyr
1               5                   10
```

<210> SEQ ID NO 230
<211> LENGTH: 5
<212> TYPE: PRT
<213> ORGANISM: Vicugna pacos

<400> SEQUENCE: 230

Asn Trp Gly Ala Tyr
1               5

<210> SEQ ID NO 231
<211> LENGTH: 13
<212> TYPE: PRT
<213> ORGANISM: Vicugna pacos

<400> SEQUENCE: 231

Leu Met Val Asp Tyr Gly Leu Gly Leu Gly Thr Asp Tyr
1               5                   10

<210> SEQ ID NO 232
<211> LENGTH: 17
<212> TYPE: PRT
<213> ORGANISM: Vicugna pacos

<400> SEQUENCE: 232

Asp Thr Tyr Tyr Tyr Cys Ser Lys Arg Val Trp Arg Asn Asp Tyr Gly
1               5                   10                  15

Ser

<210> SEQ ID NO 233
<211> LENGTH: 13
<212> TYPE: PRT
<213> ORGANISM: Vicugna pacos

<400> SEQUENCE: 233

Asp Met Asp Ser Ser Leu Ser Gly Gly Tyr Val Asp Val
1               5                   10

<210> SEQ ID NO 234
<211> LENGTH: 16
<212> TYPE: PRT
<213> ORGANISM: Vicugna pacos

<400> SEQUENCE: 234

Glu Thr Pro Ser Ile Gly Ser Pro Cys Thr Ser Ala Ser Tyr Asp Tyr
1               5                   10                  15

<210> SEQ ID NO 235
<211> LENGTH: 16
<212> TYPE: PRT
<213> ORGANISM: Vicugna pacos

<400> SEQUENCE: 235

Leu Arg Arg Tyr Tyr Gly Leu Asn Leu Asp Pro Gly Ser Tyr Asp Tyr
1               5                   10                  15

<210> SEQ ID NO 236
<211> LENGTH: 15
<212> TYPE: PRT
<213> ORGANISM: Vicugna pacos

<400> SEQUENCE: 236

Arg Thr Val Ser Ala Pro Pro Ser Ala Ala Trp Gly Tyr Gly Tyr
1               5                   10                  15

```
<210> SEQ ID NO 237
<211> LENGTH: 9
<212> TYPE: PRT
<213> ORGANISM: Vicugna pacos

<400> SEQUENCE: 237

Gly Phe Val Cys Tyr Asn Tyr Asp Tyr
1               5

<210> SEQ ID NO 238
<211> LENGTH: 18
<212> TYPE: PRT
<213> ORGANISM: Vicugna pacos

<400> SEQUENCE: 238

His Leu Ala Gln Tyr Ser Asp Tyr Ala Tyr Arg Asp Pro His Gln Phe
1               5                   10                  15

Gly Ala

<210> SEQ ID NO 239
<211> LENGTH: 9
<212> TYPE: PRT
<213> ORGANISM: Vicugna pacos

<400> SEQUENCE: 239

Gly His Thr Trp Gly Gln Tyr Ala Tyr
1               5

<210> SEQ ID NO 240
<211> LENGTH: 10
<212> TYPE: PRT
<213> ORGANISM: Vicugna pacos

<400> SEQUENCE: 240

Arg Gly Arg Phe Asp Asp Asn Tyr Glu Tyr
1               5                   10

<210> SEQ ID NO 241
<211> LENGTH: 13
<212> TYPE: PRT
<213> ORGANISM: Vicugna pacos

<400> SEQUENCE: 241

Asp Met Asp Ser Ser Leu Ser Gly Gly Tyr Val Asp Val
1               5                   10

<210> SEQ ID NO 242
<211> LENGTH: 5
<212> TYPE: PRT
<213> ORGANISM: Vicugna pacos

<400> SEQUENCE: 242

Asn Trp Gly Ala Tyr
1               5

<210> SEQ ID NO 243
<211> LENGTH: 11
<212> TYPE: PRT
<213> ORGANISM: Vicugna pacos

<400> SEQUENCE: 243

Leu Val Ile Gly Pro Leu Glu Gly Tyr Asp Tyr
1               5                   10
```

<210> SEQ ID NO 244
<211> LENGTH: 13
<212> TYPE: PRT
<213> ORGANISM: Vicugna pacos

<400> SEQUENCE: 244

Asp Gly Val Val Ala Trp Asp Gln Pro Tyr Asp Asn Tyr
1               5                   10

<210> SEQ ID NO 245
<211> LENGTH: 9
<212> TYPE: PRT
<213> ORGANISM: Vicugna pacos

<400> SEQUENCE: 245

Glu Arg Trp Asp Asn Gly Met Val Tyr
1               5

<210> SEQ ID NO 246
<211> LENGTH: 23
<212> TYPE: PRT
<213> ORGANISM: Vicugna pacos

<400> SEQUENCE: 246

Glu Arg Trp Asp Gly Tyr Ala Leu Gly Tyr Ser Pro Asn His Gly Ser
1               5                   10                  15

Gly His Arg Pro Tyr Asn Tyr
            20

<210> SEQ ID NO 247
<211> LENGTH: 12
<212> TYPE: PRT
<213> ORGANISM: Vicugna pacos

<400> SEQUENCE: 247

Val Ala Val Thr Phe Thr Thr Pro Arg Ser Asp Tyr
1               5                   10

<210> SEQ ID NO 248
<211> LENGTH: 8
<212> TYPE: PRT
<213> ORGANISM: Vicugna pacos

<400> SEQUENCE: 248

Gly Gly Gly Trp Arg Pro Gly Ala
1               5

<210> SEQ ID NO 249
<211> LENGTH: 8
<212> TYPE: PRT
<213> ORGANISM: Vicugna pacos

<400> SEQUENCE: 249

Asn Arg Glu Thr Met Pro Pro Phe
1               5

<210> SEQ ID NO 250
<211> LENGTH: 12
<212> TYPE: PRT
<213> ORGANISM: Vicugna pacos

<400> SEQUENCE: 250

Gly Tyr Ala Arg Leu Ile Ala Asp Ser Asp Leu Val

```
1               5                    10
```

<210> SEQ ID NO 251
<211> LENGTH: 12
<212> TYPE: PRT
<213> ORGANISM: Vicugna pacos

<400> SEQUENCE: 251

```
Gly Tyr Ala Arg Leu Met Thr Asp Ser Glu Leu Val
1               5                   10
```

<210> SEQ ID NO 252
<211> LENGTH: 22
<212> TYPE: DNA
<213> ORGANISM: Artificial Sequence
<220> FEATURE:
<223> OTHER INFORMATION: Primer

<400> SEQUENCE: 252
gtcctggctc tcttctacaa gg                                                22

<210> SEQ ID NO 253
<211> LENGTH: 23
<212> TYPE: DNA
<213> ORGANISM: Artificial Sequence
<220> FEATURE:
<223> OTHER INFORMATION: Primer

<400> SEQUENCE: 253
ggtacgtgct gttgaactgt tcc                                               23

<210> SEQ ID NO 254
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (24)..(24)
<223> OTHER INFORMATION: n can be a or g

<400> SEQUENCE: 254
gatgtgcagc tgcaggagtc tggn                                              24

<210> SEQ ID NO 255
<211> LENGTH: 30
<212> TYPE: DNA
<213> ORGANISM: Artificial Sequence
<220> FEATURE:
<223> OTHER INFORMATION: Primer

<400> SEQUENCE: 255
ctagtgcggc cgctgaggag acggtgacct                                        30

<210> SEQ ID NO 256
<211> LENGTH: 10
<212> TYPE: PRT
<213> ORGANISM: Artificial Sequence
<220> FEATURE:
<223> OTHER INFORMATION: HA tag

<400> SEQUENCE: 256

```
Tyr Pro Tyr Asp Val Pro Asp Tyr Gly Ser
1               5                   10
```

```
<210> SEQ ID NO 257
<211> LENGTH: 19
<212> TYPE: PRT
<213> ORGANISM: Artificial Sequence
<220> FEATURE:
<223> OTHER INFORMATION: C-terminal extension

<400> SEQUENCE: 257

Ala Ala Ala Tyr Pro Tyr Asp Val Pro Asp Tyr Gly Ser His His His
1               5                  10                  15

His His His

<210> SEQ ID NO 258
<211> LENGTH: 1456
<212> TYPE: PRT
<213> ORGANISM: Homo sapiens

<400> SEQUENCE: 258

Met Arg Leu Pro Leu Leu Leu Val Phe Ala Ser Val Ile Pro Gly Ala
1               5                   10                  15

Val Leu Leu Leu Asp Thr Arg Gln Phe Leu Ile Tyr Asn Glu Asp His
                20                  25                  30

Lys Arg Cys Val Asp Ala Val Ser Pro Ser Ala Val Gln Thr Ala Ala
        35                  40                  45

Cys Asn Gln Asp Ala Glu Ser Gln Lys Phe Arg Trp Val Ser Glu Ser
    50                  55                  60

Gln Ile Met Ser Val Ala Phe Lys Leu Cys Leu Gly Val Pro Ser Lys
65                  70                  75                  80

Thr Asp Trp Val Ala Ile Thr Leu Tyr Ala Cys Asp Ser Lys Ser Glu
                85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
    130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
    210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
    290                 295                 300
```

-continued

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
            325                 330                 335

Gly Tyr Ile Cys Lys Lys Gly Asn Thr Thr Leu Asn Ser Phe Val Ile
            340                 345                 350

Pro Ser Glu Ser Asp Val Pro Thr His Cys Pro Ser Gln Trp Trp Pro
            355                 360                 365

Tyr Ala Gly His Cys Tyr Lys Ile His Arg Asp Glu Lys Lys Ile Gln
370                 375                 380

Arg Asp Ala Leu Thr Thr Cys Arg Lys Glu Gly Asp Leu Thr Ser
385                 390                 395                 400

Ile His Thr Ile Glu Glu Leu Asp Phe Ile Ile Ser Gln Leu Gly Tyr
                    405                 410                 415

Glu Pro Asn Asp Glu Leu Trp Ile Gly Leu Asn Asp Ile Lys Ile Gln
                    420                 425                 430

Met Tyr Phe Glu Trp Ser Asp Gly Thr Pro Val Thr Phe Thr Lys Trp
            435                 440                 445

Leu Arg Gly Glu Pro Ser His Glu Asn Asn Arg Gln Glu Asp Cys Val
450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                485                 490                 495

Ile Val Glu Val Glu Lys Gly Cys Arg Lys Gly Trp Lys Lys His His
                500                 505                 510

Phe Tyr Cys Tyr Met Ile Gly His Thr Leu Ser Thr Phe Ala Glu Ala
            515                 520                 525

Asn Gln Thr Cys Asn Asn Glu Asn Ala Tyr Leu Thr Thr Ile Glu Asp
530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                565                 570                 575

Gln Trp Thr Ile Glu Glu Val Arg Phe Thr His Trp Asn Ser Asp
            580                 585                 590

Met Pro Gly Arg Lys Pro Gly Cys Val Ala Met Arg Thr Gly Ile Ala
            595                 600                 605

Gly Gly Leu Trp Asp Val Leu Lys Cys Asp Glu Lys Ala Lys Phe Val
            610                 615                 620

Cys Lys His Trp Ala Glu Gly Val Thr His Pro Pro Lys Pro Thr Thr
625                 630                 635                 640

Thr Pro Glu Pro Lys Cys Pro Glu Asp Trp Gly Ala Ser Ser Arg Thr
                645                 650                 655

Ser Leu Cys Phe Lys Leu Tyr Ala Lys Gly Lys His Glu Lys Lys Thr
            660                 665                 670

Trp Phe Glu Ser Arg Asp Phe Cys Arg Ala Leu Gly Gly Asp Leu Ala
            675                 680                 685

Ser Ile Asn Asn Lys Glu Glu Gln Gln Thr Ile Trp Arg Leu Ile Thr
            690                 695                 700

Ala Ser Gly Ser Tyr His Lys Leu Phe Trp Leu Gly Leu Thr Tyr Gly
705                 710                 715                 720

Ser Pro Ser Glu Gly Phe Thr Trp Ser Asp Gly Ser Pro Val Ser Tyr

-continued

```
                725                 730                 735
Glu Asn Trp Ala Tyr Gly Glu Pro Asn Asn Tyr Gln Asn Val Glu Tyr
            740                 745                 750
Cys Gly Glu Leu Lys Gly Asp Pro Thr Met Ser Trp Asn Asp Ile Asn
        755                 760                 765
Cys Glu His Leu Asn Asn Trp Ile Cys Gln Ile Gln Lys Gly Gln Thr
    770                 775                 780
Pro Lys Pro Glu Pro Thr Pro Ala Pro Gln Asp Asn Pro Pro Val Thr
785                 790                 795                 800
Glu Asp Gly Trp Val Ile Tyr Lys Asp Tyr Gln Tyr Tyr Phe Ser Lys
                805                 810                 815
Glu Lys Glu Thr Met Asp Asn Ala Arg Ala Phe Cys Lys Arg Asn Phe
            820                 825                 830
Gly Asp Leu Val Ser Ile Gln Ser Glu Ser Lys Lys Phe Leu Trp
        835                 840                 845
Lys Tyr Val Asn Arg Asn Asp Ala Gln Ser Ala Tyr Phe Ile Gly Leu
    850                 855                 860
Leu Ile Ser Leu Asp Lys Lys Phe Ala Trp Met Asp Gly Ser Lys Val
865                 870                 875                 880
Asp Tyr Val Ser Trp Ala Thr Gly Glu Pro Asn Phe Ala Asn Glu Asp
                885                 890                 895
Glu Asn Cys Val Thr Met Tyr Ser Asn Ser Gly Phe Trp Asn Asp Ile
            900                 905                 910
Asn Cys Gly Tyr Pro Asn Ala Phe Ile Cys Gln Arg His Asn Ser Ser
        915                 920                 925
Ile Asn Ala Thr Thr Val Met Pro Thr Met Pro Ser Val Pro Ser Gly
    930                 935                 940
Cys Lys Glu Gly Trp Asn Phe Tyr Ser Asn Lys Cys Phe Lys Ile Phe
945                 950                 955                 960
Gly Phe Met Glu Glu Arg Lys Asn Trp Gln Glu Ala Arg Lys Ala
                965                 970                 975
Cys Ile Gly Phe Gly Gly Asn Leu Val Ser Ile Gln Asn Glu Lys Glu
            980                 985                 990
Gln Ala Phe Leu Thr Tyr His Met Lys Asp Ser Thr Phe Ser Ala Trp
        995                 1000                1005
Thr Gly Leu Asn Asp Val Asn Ser Glu His Thr Phe Leu Trp Thr
    1010                1015                1020
Asp Gly Arg Gly Val His Tyr Thr Asn Trp Gly Lys Gly Tyr Pro
    1025                1030                1035
Gly Gly Arg Arg Ser Ser Leu Ser Tyr Glu Asp Ala Asp Cys Val
    1040                1045                1050
Val Ile Ile Gly Gly Ala Ser Asn Glu Ala Gly Lys Trp Met Asp
    1055                1060                1065
Asp Thr Cys Asp Ser Lys Arg Gly Tyr Ile Cys Gln Thr Arg Ser
    1070                1075                1080
Asp Pro Ser Leu Thr Asn Pro Pro Ala Thr Ile Gln Thr Asp Gly
    1085                1090                1095
Phe Val Lys Tyr Gly Lys Ser Ser Tyr Ser Leu Met Arg Gln Lys
    1100                1105                1110
Phe Gln Trp His Glu Ala Glu Thr Tyr Cys Lys Leu His Asn Ser
    1115                1120                1125
Leu Ile Ala Ser Ile Leu Asp Pro Tyr Ser Asn Ala Phe Ala Trp
    1130                1135                1140
```

```
Leu Gln Met Glu Thr Ser Asn Glu Arg Val Trp Ile Ala Leu Asn
    1145                1150                1155

Ser Asn Leu Thr Asp Asn Gln Tyr Thr Trp Thr Asp Lys Trp Arg
    1160                1165                1170

Val Arg Tyr Thr Asn Trp Ala Ala Asp Glu Pro Lys Leu Lys Ser
    1175                1180                1185

Ala Cys Val Tyr Leu Asp Leu Asp Gly Tyr Trp Lys Thr Ala His
    1190                1195                1200

Cys Asn Glu Ser Phe Tyr Phe Leu Cys Lys Arg Ser Asp Glu Ile
    1205                1210                1215

Pro Ala Thr Glu Pro Pro Gln Leu Pro Gly Arg Cys Pro Glu Ser
    1220                1225                1230

Asp His Thr Ala Trp Ile Pro Phe His Gly His Cys Tyr Tyr Ile
    1235                1240                1245

Glu Ser Ser Tyr Thr Arg Asn Trp Gly Gln Ala Ser Leu Glu Cys
    1250                1255                1260

Leu Arg Met Gly Ser Ser Leu Val Ser Ile Glu Ser Ala Ala Glu
    1265                1270                1275

Ser Ser Phe Leu Ser Tyr Arg Val Glu Pro Leu Lys Ser Lys Thr
    1280                1285                1290

Asn Phe Trp Ile Gly Leu Phe Arg Asn Val Glu Gly Thr Trp Leu
    1295                1300                1305

Trp Ile Asn Asn Ser Pro Val Ser Phe Val Asn Trp Asn Thr Gly
    1310                1315                1320

Asp Pro Ser Gly Glu Arg Asn Asp Cys Val Ala Leu His Ala Ser
    1325                1330                1335

Ser Gly Phe Trp Ser Asn Ile His Cys Ser Ser Tyr Lys Gly Tyr
    1340                1345                1350

Ile Cys Lys Arg Pro Lys Ile Ile Asp Ala Lys Pro Thr His Glu
    1355                1360                1365

Leu Leu Thr Thr Lys Ala Asp Thr Arg Lys Met Asp Pro Ser Lys
    1370                1375                1380

Pro Ser Ser Asn Val Ala Gly Val Val Ile Ile Val Ile Leu Leu
    1385                1390                1395

Ile Leu Thr Gly Ala Gly Leu Ala Ala Tyr Phe Phe Tyr Lys Lys
    1400                1405                1410

Arg Arg Val His Leu Pro Gln Glu Gly Ala Phe Glu Asn Thr Leu
    1415                1420                1425

Tyr Phe Asn Ser Gln Ser Ser Pro Gly Thr Ser Asp Met Lys Asp
    1430                1435                1440

Leu Val Gly Asn Ile Glu Gln Asn Glu His Ser Val Ile
    1445                1450                1455

<210> SEQ ID NO 259
<211> LENGTH: 1371
<212> TYPE: PRT
<213> ORGANISM: Homo sapiens

<400> SEQUENCE: 259

Leu Leu Asp Thr Arg Gln Phe Leu Ile Tyr Asn Glu Asp His Lys Arg
1               5                   10                  15

Cys Val Asp Ala Val Ser Pro Ser Ala Val Gln Thr Ala Ala Cys Asn
            20                  25                  30

Gln Asp Ala Glu Ser Gln Lys Phe Arg Trp Val Ser Glu Ser Gln Ile
```

-continued

```
                35                  40                  45
Met Ser Val Ala Phe Lys Leu Cys Leu Gly Val Pro Ser Lys Thr Asp
        50                  55                  60
Trp Val Ala Ile Thr Leu Tyr Ala Cys Asp Ser Lys Ser Glu Phe Gln
65                  70                  75                  80
Lys Trp Glu Cys Lys Asn Asp Thr Leu Leu Gly Ile Lys Gly Glu Asp
                85                  90                  95
Leu Phe Phe Asn Tyr Gly Asn Arg Gln Glu Lys Asn Ile Met Leu Tyr
            100                 105                 110
Lys Gly Ser Gly Leu Trp Ser Arg Trp Lys Ile Tyr Gly Thr Thr Asp
            115                 120                 125
Asn Leu Cys Ser Arg Gly Tyr Glu Ala Met Tyr Thr Leu Leu Gly Asn
        130                 135                 140
Ala Asn Gly Ala Thr Cys Ala Phe Pro Phe Lys Phe Glu Asn Lys Trp
145                 150                 155                 160
Tyr Ala Asp Cys Thr Ser Ala Gly Arg Ser Asp Gly Trp Leu Trp Cys
                165                 170                 175
Gly Thr Thr Thr Asp Tyr Asp Thr Asp Lys Leu Phe Gly Tyr Cys Pro
            180                 185                 190
Leu Lys Phe Glu Gly Ser Glu Ser Leu Trp Asn Lys Asp Pro Leu Thr
        195                 200                 205
Ser Val Ser Tyr Gln Ile Asn Ser Lys Ser Ala Leu Thr Trp His Gln
        210                 215                 220
Ala Arg Lys Ser Cys Gln Gln Asn Ala Glu Leu Leu Ser Ile Thr
225                 230                 235                 240
Glu Ile His Glu Gln Thr Tyr Leu Thr Gly Leu Thr Ser Ser Leu Thr
                245                 250                 255
Ser Gly Leu Trp Ile Gly Leu Asn Ser Leu Ser Phe Asn Ser Gly Trp
            260                 265                 270
Gln Trp Ser Asp Arg Ser Pro Phe Arg Tyr Leu Asn Trp Leu Pro Gly
        275                 280                 285
Ser Pro Ser Ala Glu Pro Gly Lys Ser Cys Val Ser Leu Asn Pro Gly
        290                 295                 300
Lys Asn Ala Lys Trp Glu Asn Leu Glu Cys Val Gln Lys Leu Gly Tyr
305                 310                 315                 320
Ile Cys Lys Lys Gly Asn Thr Thr Leu Asn Ser Phe Val Ile Pro Ser
                325                 330                 335
Glu Ser Asp Val Pro Thr His Cys Pro Ser Gln Trp Trp Pro Tyr Ala
            340                 345                 350
Gly His Cys Tyr Lys Ile His Arg Asp Glu Lys Lys Ile Gln Arg Asp
            355                 360                 365
Ala Leu Thr Thr Cys Arg Lys Glu Gly Gly Asp Leu Ala Ser Ile His
        370                 375                 380
Thr Ile Glu Glu Phe Asp Phe Ile Ile Ser Gln Leu Gly Tyr Glu Pro
385                 390                 395                 400
Asn Asp Glu Leu Trp Ile Gly Leu Asn Asp Ile Lys Ile Gln Met Tyr
                405                 410                 415
Phe Glu Trp Ser Asp Gly Thr Pro Val Thr Phe Thr Lys Trp Leu Arg
            420                 425                 430
Gly Glu Pro Ser His Glu Asn Asn Arg Gln Glu Asp Cys Val Val Met
        435                 440                 445
Lys Gly Lys Asp Gly Tyr Trp Ala Asp Arg Gly Cys Glu Trp Pro Leu
        450                 455                 460
```

```
Gly Tyr Ile Cys Lys Met Lys Ser Arg Ser Gln Gly Pro Glu Ile Val
465                 470                 475                 480

Glu Val Glu Lys Gly Cys Arg Lys Gly Trp Lys His His Phe Tyr
            485                 490                 495

Cys Tyr Met Ile Gly His Thr Leu Ser Thr Phe Ala Glu Ala Asn Gln
                500                 505                 510

Thr Cys Asn Asn Glu Asn Ala Tyr Leu Thr Thr Ile Glu Asp Arg Tyr
                515                 520                 525

Glu Gln Ala Phe Leu Thr Ser Phe Val Gly Leu Arg Pro Glu Lys Tyr
                530                 535                 540

Phe Trp Thr Gly Leu Ser Asp Ile Gln Thr Lys Gly Thr Phe Gln Trp
545                 550                 555                 560

Thr Ile Glu Glu Glu Val Arg Phe Thr His Trp Asn Ser Asp Met Pro
                565                 570                 575

Gly Arg Lys Pro Gly Cys Val Ala Met Arg Thr Gly Ile Ala Gly Gly
                580                 585                 590

Leu Trp Asp Val Leu Lys Cys Asp Glu Lys Ala Lys Phe Val Cys Lys
                595                 600                 605

His Trp Ala Glu Gly Val Thr His Pro Pro Lys Pro Thr Thr Thr Pro
                610                 615                 620

Glu Pro Lys Cys Pro Glu Asp Trp Gly Ala Ser Ser Arg Thr Ser Leu
625                 630                 635                 640

Cys Phe Lys Leu Tyr Ala Lys Gly Lys His Glu Lys Lys Thr Trp Phe
                645                 650                 655

Glu Ser Arg Asp Phe Cys Arg Ala Leu Gly Gly Asp Leu Ala Ser Ile
                660                 665                 670

Asn Asn Lys Glu Glu Gln Gln Thr Ile Trp Arg Leu Ile Thr Ala Ser
                675                 680                 685

Gly Ser Tyr His Lys Leu Phe Trp Leu Gly Leu Thr Tyr Gly Ser Pro
                690                 695                 700

Ser Glu Gly Phe Thr Trp Ser Asp Gly Ser Pro Val Ser Tyr Glu Asn
705                 710                 715                 720

Trp Ala Tyr Gly Glu Pro Asn Asn Tyr Gln Asn Val Glu Tyr Cys Gly
                725                 730                 735

Glu Leu Lys Gly Asp Pro Thr Met Ser Trp Asn Asp Ile Asn Cys Glu
                740                 745                 750

His Leu Asn Asn Trp Ile Cys Gln Ile Gln Lys Gly Gln Thr Pro Lys
                755                 760                 765

Pro Glu Pro Thr Pro Ala Pro Gln Asp Asn Pro Pro Val Thr Glu Asp
                770                 775                 780

Gly Trp Val Ile Tyr Lys Asp Tyr Gln Tyr Tyr Phe Ser Lys Glu Lys
785                 790                 795                 800

Glu Thr Met Asp Asn Ala Arg Ala Phe Cys Lys Arg Asn Phe Gly Asp
                805                 810                 815

Leu Val Ser Ile Gln Ser Glu Ser Glu Lys Lys Phe Leu Trp Lys Tyr
                820                 825                 830

Val Asn Arg Asn Asp Ala Gln Ser Ala Tyr Phe Ile Gly Leu Leu Ile
                835                 840                 845

Ser Leu Asp Lys Lys Phe Ala Trp Met Asp Gly Ser Lys Val Asp Tyr
                850                 855                 860

Val Ser Trp Ala Thr Gly Glu Pro Asn Phe Ala Asn Glu Asp Glu Asn
865                 870                 875                 880
```

```
Cys Val Thr Met Tyr Ser Asn Ser Gly Phe Trp Asn Asp Ile Asn Cys
                885                 890                 895

Gly Tyr Pro Asn Ala Phe Ile Cys Gln Arg His Asn Ser Ser Ile Asn
        900                 905                 910

Ala Thr Thr Val Met Pro Thr Met Pro Ser Val Pro Ser Gly Cys Lys
        915                 920                 925

Glu Gly Trp Asn Phe Tyr Ser Asn Lys Cys Phe Lys Ile Phe Gly Phe
        930                 935                 940

Met Glu Glu Arg Lys Asn Trp Gln Glu Ala Arg Lys Ala Cys Ile
945                 950                 955                 960

Gly Phe Gly Gly Asn Leu Val Ser Ile Gln Asn Glu Lys Glu Gln Ala
        965                 970                 975

Phe Leu Thr Tyr His Met Lys Asp Ser Thr Phe Ser Ala Trp Thr Gly
        980                 985                 990

Leu Asn Asp Val Asn Ser Glu His Thr Phe Leu Trp Thr Asp Gly Arg
        995                 1000                1005

Gly Val His Tyr Thr Asn Trp Gly Lys Gly Tyr Pro Gly Gly Arg
        1010                1015                1020

Arg Ser Ser Leu Ser Tyr Glu Asp Ala Asp Cys Val Val Ile Ile
        1025                1030                1035

Gly Gly Ala Ser Asn Glu Ala Gly Lys Trp Met Asp Asp Thr Cys
        1040                1045                1050

Asp Ser Lys Arg Gly Tyr Ile Cys Gln Thr Arg Ser Asp Pro Ser
        1055                1060                1065

Leu Thr Asn Pro Pro Ala Thr Ile Gln Thr Asp Gly Phe Val Lys
        1070                1075                1080

Tyr Gly Lys Ser Ser Tyr Ser Leu Met Arg Gln Lys Phe Gln Trp
        1085                1090                1095

His Glu Ala Glu Thr Tyr Cys Lys Leu His Asn Ser Leu Ile Ala
        1100                1105                1110

Ser Ile Leu Asp Pro Tyr Ser Asn Ala Phe Ala Trp Leu Gln Met
        1115                1120                1125

Glu Thr Ser Asn Glu Arg Val Trp Ile Ala Leu Asn Ser Asn Leu
        1130                1135                1140

Thr Asp Asn Gln Tyr Thr Trp Thr Asp Lys Trp Arg Val Arg Tyr
        1145                1150                1155

Thr Asn Trp Ala Ala Asp Glu Pro Lys Leu Lys Ser Ala Cys Val
        1160                1165                1170

Tyr Leu Asp Leu Asp Gly Tyr Trp Lys Thr Ala His Cys Asn Glu
        1175                1180                1185

Ser Phe Tyr Phe Leu Cys Lys Arg Ser Asp Glu Ile Pro Ala Thr
        1190                1195                1200

Glu Pro Pro Gln Leu Pro Gly Arg Cys Pro Glu Ser Asp His Thr
        1205                1210                1215

Ala Trp Ile Pro Phe His Gly His Cys Tyr Tyr Ile Glu Ser Ser
        1220                1225                1230

Tyr Thr Arg Asn Trp Gly Gln Ala Ser Leu Glu Cys Leu Arg Met
        1235                1240                1245

Gly Ser Ser Leu Val Ser Ile Glu Ser Ala Ala Glu Ser Ser Phe
        1250                1255                1260

Leu Ser Tyr Arg Val Glu Pro Leu Lys Ser Lys Thr Asn Phe Trp
        1265                1270                1275

Ile Gly Leu Phe Arg Asn Val Glu Gly Thr Trp Leu Trp Ile Asn
```

```
                    1280               1285                  1290
Asn Ser Pro Val Ser Phe Val Asn Trp Asn Thr Gly Asp Pro Ser
        1295                1300                1305
Gly Glu Arg Asn Asp Cys Val Ala Leu His Ala Ser Ser Gly Phe
1310                1315                1320
Trp Ser Asn Ile His Cys Ser Ser Tyr Lys Gly Tyr Ile Cys Lys
        1325                1330                1335
Arg Pro Lys Ile Ile Asp Ala Lys Pro Thr His Glu Leu Leu Thr
        1340                1345                1350
Thr Lys Ala Asp Thr Arg Lys Met Asp Pro Ser Lys His His His
        1355                1360                1365
His His His
        1370

<210> SEQ ID NO 260
<211> LENGTH: 1456
<212> TYPE: PRT
<213> ORGANISM: Mus musculus

<400> SEQUENCE: 260

Met Arg Leu Leu Leu Leu Ala Phe Ile Ser Val Ile Pro Val Ser
1               5                   10                  15
Val Gln Leu Leu Asp Ala Arg Gln Phe Leu Ile Tyr Asn Glu Asp His
        20                  25                  30
Lys Arg Cys Val Asp Ala Leu Ser Ala Ile Ser Val Gln Thr Ala Thr
            35                  40                  45
Cys Asn Pro Glu Ala Glu Ser Gln Lys Phe Arg Trp Val Ser Asp Ser
50                  55                  60
Gln Ile Met Ser Val Ala Phe Lys Leu Cys Leu Gly Val Pro Ser Lys
65                  70                  75                  80
Thr Asp Trp Ala Ser Val Thr Leu Tyr Ala Cys Asp Ser Lys Ser Glu
                85                  90                  95
Tyr Gln Lys Trp Glu Cys Lys Asn Asp Thr Leu Phe Gly Ile Lys Gly
                100                 105                 110
Thr Glu Leu Tyr Phe Asn Tyr Gly Asn Arg Gln Glu Lys Asn Ile Lys
            115                 120                 125
Leu Tyr Lys Gly Ser Gly Leu Trp Ser Arg Trp Lys Val Tyr Gly Thr
130                 135                 140
Thr Asp Asp Leu Cys Ser Arg Gly Tyr Glu Ala Met Tyr Ser Leu Leu
145                 150                 155                 160
Gly Asn Ala Asn Gly Ala Val Cys Ala Phe Pro Phe Lys Phe Glu Asn
                165                 170                 175
Lys Trp Tyr Ala Asp Cys Thr Ser Ala Gly Arg Ser Asp Gly Trp Leu
            180                 185                 190
Trp Cys Gly Thr Thr Thr Asp Tyr Asp Lys Asp Lys Leu Phe Gly Phe
            195                 200                 205
Cys Pro Leu His Phe Glu Gly Ser Glu Arg Leu Trp Asn Lys Asp Pro
        210                 215                 220
Leu Thr Gly Ile Leu Tyr Gln Ile Asn Ser Lys Ser Ala Leu Thr Trp
225                 230                 235                 240
His Gln Ala Arg Ala Ser Cys Lys Gln Gln Asn Ala Asp Leu Leu Ser
                245                 250                 255
Val Thr Glu Ile His Glu Gln Met Tyr Leu Thr Gly Leu Thr Ser Ser
                260                 265                 270
```

```
Leu Ser Ser Gly Leu Trp Ile Gly Leu Asn Ser Leu Ser Val Arg Ser
        275                 280                 285

Gly Trp Gln Trp Ala Gly Gly Ser Pro Phe Arg Tyr Leu Asn Trp Leu
        290                 295                 300

Pro Gly Ser Pro Ser Ser Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Asn Thr Leu Asn Pro Phe Ile Ile
                340                 345                 350

Pro Ser Ala Ser Asp Val Pro Thr Gly Cys Pro Asn Gln Trp Trp Pro
            355                 360                 365

Tyr Ala Gly His Cys Tyr Arg Ile His Arg Glu Glu Lys Lys Ile Gln
        370                 375                 380

Lys Tyr Ala Leu Gln Ala Cys Arg Lys Glu Gly Gly Asp Leu Ala Ser
385                 390                 395                 400

Ile His Ser Ile Glu Glu Phe Asp Phe Ile Phe Ser Gln Leu Gly Tyr
                405                 410                 415

Glu Pro Asn Asp Glu Leu Trp Ile Gly Leu Asn Asp Ile Lys Ile Gln
                420                 425                 430

Met Tyr Phe Glu Trp Ser Asp Gly Thr Pro Val Thr Phe Thr Lys Trp
            435                 440                 445

Leu Pro Gly Glu Pro Ser His Glu Asn Asn Arg Gln Glu Asp Cys Val
        450                 455                 460

Val Met Lys Gly Lys Asp Gly Tyr Trp Ala Asp Arg Ala Cys Glu Gln
465                 470                 475                 480

Pro Leu Gly Tyr Ile Cys Lys Met Val Ser Gln Ser His Ala Val Val
                485                 490                 495

Pro Glu Gly Ala Asp Lys Gly Cys Arg Lys Gly Trp Lys Arg His Gly
            500                 505                 510

Phe Tyr Cys Tyr Leu Ile Gly Ser Thr Leu Ser Thr Phe Thr Asp Ala
        515                 520                 525

Asn His Thr Cys Thr Asn Glu Lys Ala Tyr Leu Thr Thr Val Glu Asp
        530                 535                 540

Arg Tyr Glu Gln Ala Phe Leu Thr Ser Leu Val Gly Leu Arg Pro Glu
545                 550                 555                 560

Lys Tyr Phe Trp Thr Gly Leu Ser Asp Val Gln Asn Lys Gly Thr Phe
                565                 570                 575

Arg Trp Thr Val Asp Glu Gln Val Gln Phe Thr His Trp Asn Ala Asp
            580                 585                 590

Met Pro Gly Arg Lys Ala Gly Cys Val Ala Met Lys Thr Gly Val Ala
        595                 600                 605

Gly Gly Leu Trp Asp Val Leu Ser Cys Glu Glu Lys Ala Lys Phe Val
        610                 615                 620

Cys Lys His Trp Ala Glu Gly Val Thr Arg Pro Pro Glu Pro Thr Thr
625                 630                 635                 640

Thr Pro Glu Pro Lys Cys Pro Glu Asn Trp Gly Thr Thr Ser Lys Thr
                645                 650                 655

Ser Met Cys Phe Lys Leu Tyr Ala Lys Gly Lys His Glu Lys Lys Thr
            660                 665                 670

Trp Phe Glu Ser Arg Asp Phe Cys Lys Ala Ile Gly Gly Glu Leu Ala
        675                 680                 685

Ser Ile Lys Ser Lys Asp Glu Gln Gln Val Ile Trp Arg Leu Ile Thr
```

```
                690                 695                 700
Ser Ser Gly Ser Tyr His Glu Leu Phe Trp Leu Gly Leu Thr Tyr Gly
705                 710                 715                 720

Ser Pro Ser Glu Gly Phe Thr Trp Ser Asp Gly Ser Pro Val Ser Tyr
                725                 730                 735

Glu Asn Trp Ala Tyr Gly Glu Pro Asn Asn Tyr Gln Asn Val Glu Tyr
                740                 745                 750

Cys Gly Glu Leu Lys Gly Asp Pro Gly Met Ser Trp Asn Asp Ile Asn
                755                 760                 765

Cys Glu His Leu Asn Asn Trp Ile Cys Gln Ile Gln Lys Gly Lys Thr
                770                 775                 780

Leu Leu Pro Glu Pro Thr Pro Ala Pro Gln Asp Asn Pro Pro Val Thr
785                 790                 795                 800

Ala Asp Gly Trp Val Ile Tyr Lys Asp Tyr Gln Tyr Tyr Phe Ser Lys
                805                 810                 815

Glu Lys Glu Thr Met Asp Asn Ala Arg Ala Phe Cys Lys Lys Asn Phe
                820                 825                 830

Gly Asp Leu Ala Thr Ile Lys Ser Glu Ser Glu Lys Lys Phe Leu Trp
                835                 840                 845

Lys Tyr Ile Asn Lys Asn Gly Gly Gln Ser Pro Tyr Phe Ile Gly Met
850                 855                 860

Leu Ile Ser Met Asp Lys Lys Phe Ile Trp Met Asp Gly Ser Lys Val
865                 870                 875                 880

Asp Phe Val Ala Trp Ala Thr Gly Glu Pro Asn Phe Ala Asn Asp Asp
                885                 890                 895

Glu Asn Cys Val Thr Met Tyr Thr Asn Ser Gly Phe Trp Asn Asp Ile
                900                 905                 910

Asn Cys Gly Tyr Pro Asn Asn Phe Ile Cys Gln Arg His Asn Ser Ser
                915                 920                 925

Ile Asn Ala Thr Ala Met Pro Thr Thr Pro Thr Thr Pro Gly Gly Cys
930                 935                 940

Lys Glu Gly Trp His Leu Tyr Lys Asn Lys Cys Phe Lys Ile Phe Gly
945                 950                 955                 960

Phe Ala Asn Glu Glu Lys Lys Ser Trp Gln Asp Ala Arg Gln Ala Cys
                965                 970                 975

Lys Gly Leu Lys Gly Asn Leu Val Ser Ile Glu Asn Ala Gln Glu Gln
                980                 985                 990

Ala Phe Val Thr Tyr His Met Arg Asp Ser Thr Phe Asn Ala Trp Thr
                995                 1000                1005

Gly Leu Asn Asp Ile Asn Ala Glu His Met Phe Leu Trp Thr Ala
                1010                1015                1020

Gly Gln Gly Val His Tyr Thr Asn Trp Gly Lys Gly Tyr Pro Gly
                1025                1030                1035

Gly Arg Arg Ser Ser Leu Ser Tyr Glu Asp Ala Asp Cys Val Val
                1040                1045                1050

Val Ile Gly Gly Asn Ser Arg Glu Ala Gly Thr Trp Met Asp Asp
                1055                1060                1065

Thr Cys Asp Ser Lys Gln Gly Tyr Ile Cys Gln Thr Gln Thr Asp
                1070                1075                1080

Pro Ser Leu Pro Val Ser Thr Thr Thr Pro Lys Asp Gly Phe
                1085                1090                1095

Val Thr Tyr Gly Lys Ser Ser Tyr Ser Leu Met Lys Leu Lys Leu
                1100                1105                1110
```

```
Pro Trp His Glu Ala Glu Thr Tyr Cys Lys Asp His Thr Ser Leu
1115                1120                1125

Leu Ala Ser Ile Leu Asp Pro Tyr Ser Asn Ala Phe Ala Trp Met
1130                1135                1140

Lys Met His Pro Phe Asn Val Pro Ile Trp Ile Ala Leu Asn Ser
1145                1150                1155

Asn Leu Thr Asn Asn Glu Tyr Thr Trp Thr Asp Arg Trp Arg Val
1160                1165                1170

Arg Tyr Thr Asn Trp Gly Ala Asp Glu Pro Lys Leu Lys Ser Ala
1175                1180                1185

Cys Val Tyr Met Asp Val Asp Gly Tyr Trp Arg Thr Ser Tyr Cys
1190                1195                1200

Asn Glu Ser Phe Tyr Phe Leu Cys Lys Lys Ser Asp Glu Ile Pro
1205                1210                1215

Ala Thr Glu Pro Pro Gln Leu Pro Gly Lys Cys Pro Glu Ser Glu
1220                1225                1230

Gln Thr Ala Trp Ile Pro Phe Tyr Gly His Cys Tyr Tyr Phe Glu
1235                1240                1245

Ser Ser Phe Thr Arg Ser Trp Gly Gln Ala Ser Leu Glu Cys Leu
1250                1255                1260

Arg Met Gly Ala Ser Leu Val Ser Ile Glu Thr Ala Ala Glu Ser
1265                1270                1275

Ser Phe Leu Ser Tyr Arg Val Glu Pro Leu Lys Ser Lys Thr Asn
1280                1285                1290

Phe Trp Ile Gly Met Phe Arg Asn Val Glu Gly Lys Trp Leu Trp
1295                1300                1305

Leu Asn Asp Asn Pro Val Ser Phe Val Asn Trp Lys Thr Gly Asp
1310                1315                1320

Pro Ser Gly Glu Arg Asn Asp Cys Val Val Leu Ala Ser Ser Ser
1325                1330                1335

Gly Leu Trp Asn Asn Ile His Cys Ser Ser Tyr Lys Gly Phe Ile
1340                1345                1350

Cys Lys Met Pro Lys Ile Ile Asp Pro Val Thr Thr His Ser Ser
1355                1360                1365

Ile Thr Thr Lys Ala Asp Gln Arg Lys Met Asp Pro Gln Pro Lys
1370                1375                1380

Gly Ser Ser Lys Ala Ala Gly Val Val Thr Val Leu Leu Ile
1385                1390                1395

Val Ile Gly Ala Gly Val Ala Ala Tyr Phe Phe Tyr Lys Lys Arg
1400                1405                1410

His Ala Leu His Ile Pro Gln Glu Ala Thr Phe Glu Asn Thr Leu
1415                1420                1425

Tyr Phe Asn Ser Asn Leu Ser Pro Gly Thr Ser Asp Thr Lys Asp
1430                1435                1440

Leu Met Gly Asn Ile Glu Gln Asn Glu His Ala Ile Ile
1445                1450                1455

<210> SEQ ID NO 261
<211> LENGTH: 1376
<212> TYPE: PRT
<213> ORGANISM: Mus musculus

<400> SEQUENCE: 261

Leu Leu Asp Ala Arg Gln Phe Leu Ile Tyr Asn Glu Asp His Lys Arg
```

-continued

```
1               5                   10                  15
Cys Val Asp Ala Leu Ser Ala Ile Ser Val Gln Thr Ala Thr Cys Asn
             20                  25                  30

Pro Glu Ala Glu Ser Gln Lys Phe Arg Trp Val Ser Asp Ser Gln Ile
             35                  40                  45

Met Ser Val Ala Phe Lys Leu Cys Leu Gly Val Pro Ser Lys Thr Asp
 50                  55                  60

Trp Ala Ser Val Thr Leu Tyr Ala Cys Asp Ser Lys Ser Glu Tyr Gln
 65                  70                  75                  80

Lys Trp Glu Cys Lys Asn Asp Thr Leu Phe Gly Ile Lys Gly Thr Glu
             85                  90                  95

Leu Tyr Phe Asn Tyr Gly Asn Arg Gln Glu Lys Asn Ile Lys Leu Tyr
             100                 105                 110

Lys Gly Ser Gly Leu Trp Ser Arg Trp Lys Val Tyr Gly Thr Thr Asp
             115                 120                 125

Asp Leu Cys Ser Arg Gly Tyr Glu Ala Met Tyr Ser Leu Leu Gly Asn
             130                 135                 140

Ala Asn Gly Ala Val Cys Ala Phe Pro Phe Lys Phe Glu Asn Lys Trp
145                 150                 155                 160

Tyr Ala Asp Cys Thr Ser Ala Gly Arg Ser Asp Gly Trp Leu Trp Cys
                 165                 170                 175

Gly Thr Thr Thr Asp Tyr Asp Lys Asp Lys Leu Phe Gly Phe Cys Pro
                 180                 185                 190

Leu His Phe Glu Gly Ser Glu Arg Leu Trp Asn Lys Asp Pro Leu Thr
                 195                 200                 205

Gly Ile Leu Tyr Gln Ile Asn Ser Lys Ser Ala Leu Thr Trp His Gln
210                 215                 220

Ala Arg Ala Ser Cys Lys Gln Gln Asn Ala Asp Leu Leu Ser Val Thr
225                 230                 235                 240

Glu Ile His Glu Gln Met Tyr Leu Thr Gly Leu Thr Ser Ser Leu Ser
                 245                 250                 255

Ser Gly Leu Trp Ile Gly Leu Asn Ser Leu Ser Val Arg Ser Gly Trp
                 260                 265                 270

Gln Trp Ala Gly Gly Ser Pro Phe Arg Tyr Leu Asn Trp Leu Pro Gly
                 275                 280                 285

Ser Pro Ser Ser Glu Pro Gly Lys Ser Cys Val Ser Leu Asn Pro Gly
                 290                 295                 300

Lys Asn Ala Lys Trp Glu Asn Leu Glu Cys Val Gln Lys Leu Gly Tyr
305                 310                 315                 320

Ile Cys Lys Lys Gly Asn Asn Thr Leu Asn Pro Phe Ile Ile Pro Ser
                 325                 330                 335

Ala Ser Asp Val Pro Thr Gly Cys Pro Asn Gln Trp Trp Pro Tyr Ala
                 340                 345                 350

Gly His Cys Tyr Arg Ile His Arg Glu Glu Lys Lys Ile Gln Lys Tyr
                 355                 360                 365

Ala Leu Gln Ala Cys Arg Lys Glu Gly Gly Asp Leu Ala Ser Ile His
                 370                 375                 380

Ser Ile Glu Glu Phe Asp Phe Ile Phe Ser Gln Leu Gly Tyr Glu Pro
385                 390                 395                 400

Asn Asp Glu Leu Trp Ile Gly Leu Asn Asp Ile Lys Ile Gln Met Tyr
                 405                 410                 415

Phe Glu Trp Ser Asp Gly Thr Pro Val Thr Phe Thr Lys Trp Leu Pro
                 420                 425                 430
```

-continued

```
Gly Glu Pro Ser His Glu Asn Asn Arg Gln Glu Asp Cys Val Val Met
            435                 440                 445

Lys Gly Lys Asp Gly Tyr Trp Ala Asp Arg Ala Cys Glu Gln Pro Leu
450                 455                 460

Gly Tyr Ile Cys Lys Met Val Ser Gln Ser His Ala Val Val Pro Glu
465                 470                 475                 480

Gly Ala Asp Lys Gly Cys Arg Lys Gly Trp Lys Arg His Gly Phe Tyr
                485                 490                 495

Cys Tyr Leu Ile Gly Ser Thr Leu Ser Thr Phe Thr Asp Ala Asn His
            500                 505                 510

Thr Cys Thr Asn Glu Lys Ala Tyr Leu Thr Thr Val Glu Asp Arg Tyr
            515                 520                 525

Glu Gln Ala Phe Leu Thr Ser Leu Val Gly Leu Arg Pro Glu Lys Tyr
            530                 535                 540

Phe Trp Thr Gly Leu Ser Asp Val Gln Asn Lys Gly Thr Phe Arg Trp
545                 550                 555                 560

Thr Val Asp Glu Gln Val Gln Phe Thr His Trp Asn Ala Asp Met Pro
                565                 570                 575

Gly Arg Lys Ala Gly Cys Val Ala Met Lys Thr Gly Val Ala Gly Gly
            580                 585                 590

Leu Trp Asp Val Leu Ser Cys Glu Glu Lys Ala Lys Phe Val Cys Lys
            595                 600                 605

His Trp Ala Glu Gly Val Thr Arg Pro Pro Glu Pro Thr Thr Thr Pro
            610                 615                 620

Glu Pro Lys Cys Pro Glu Asn Trp Gly Thr Thr Ser Lys Thr Ser Met
625                 630                 635                 640

Cys Phe Lys Leu Tyr Ala Lys Gly Lys His Glu Lys Lys Thr Trp Phe
                645                 650                 655

Glu Ser Arg Asp Phe Cys Lys Ala Ile Gly Gly Glu Leu Ala Ser Ile
            660                 665                 670

Lys Ser Lys Asp Glu Gln Gln Val Ile Trp Arg Leu Ile Thr Ser Ser
            675                 680                 685

Gly Ser Tyr His Glu Leu Phe Trp Leu Gly Leu Thr Tyr Gly Ser Pro
            690                 695                 700

Ser Glu Gly Phe Thr Trp Ser Asp Gly Ser Pro Val Ser Tyr Glu Asn
705                 710                 715                 720

Trp Ala Tyr Gly Glu Pro Asn Asn Tyr Gln Asn Val Glu Tyr Cys Gly
                725                 730                 735

Glu Leu Lys Gly Asp Pro Gly Met Ser Trp Asn Asp Ile Asn Cys Glu
            740                 745                 750

His Leu Asn Asn Trp Ile Cys Gln Ile Gln Lys Gly Lys Thr Leu Leu
            755                 760                 765

Pro Glu Pro Thr Pro Ala Pro Gln Asp Asn Pro Pro Val Thr Ala Asp
770                 775                 780

Gly Trp Val Ile Tyr Lys Asp Tyr Gln Tyr Tyr Phe Ser Lys Glu Lys
785                 790                 795                 800

Glu Thr Met Asp Asn Ala Arg Ala Phe Cys Lys Lys Asn Phe Gly Asp
                805                 810                 815

Leu Ala Thr Ile Lys Ser Glu Ser Glu Lys Lys Phe Leu Trp Lys Tyr
            820                 825                 830

Ile Asn Lys Asn Gly Gly Gln Ser Pro Tyr Phe Ile Gly Met Leu Ile
            835                 840                 845
```

```
Ser Met Asp Lys Lys Phe Ile Trp Met Asp Gly Ser Lys Val Asp Phe
850                 855                 860
Val Ala Trp Ala Thr Gly Glu Pro Asn Phe Ala Asn Asp Asp Glu Asn
865                 870                 875                 880
Cys Val Thr Met Tyr Thr Asn Ser Gly Phe Trp Asn Asp Ile Asn Cys
            885                 890                 895
Gly Tyr Pro Asn Asn Phe Ile Cys Gln Arg His Asn Ser Ser Ile Asn
                900                 905                 910
Ala Thr Ala Met Pro Thr Thr Pro Thr Thr Pro Gly Gly Cys Lys Glu
                915                 920                 925
Gly Trp His Leu Tyr Lys Asn Lys Cys Phe Lys Ile Phe Gly Phe Ala
930                 935                 940
Asn Glu Glu Lys Lys Ser Trp Gln Asp Ala Arg Gln Ala Cys Lys Gly
945                 950                 955                 960
Leu Lys Gly Asn Leu Val Ser Ile Glu Asn Ala Gln Glu Gln Ala Phe
                965                 970                 975
Val Thr Tyr His Met Arg Asp Ser Thr Phe Asn Ala Trp Thr Gly Leu
                980                 985                 990
Asn Asp Ile Asn Ala Glu His Met Phe Leu Trp Thr Ala Gly Gln Gly
                995                 1000                1005
Val His Tyr Thr Asn Trp Gly Lys Gly Tyr Pro Gly Gly Arg Arg
    1010            1015            1020
Ser Ser Leu Ser Tyr Glu Asp Ala Asp Cys Val Val Val Ile Gly
    1025            1030            1035
Gly Asn Ser Arg Glu Ala Gly Thr Trp Met Asp Asp Thr Cys Asp
    1040            1045            1050
Ser Lys Gln Gly Tyr Ile Cys Gln Thr Gln Thr Asp Pro Ser Leu
    1055            1060            1065
Pro Val Ser Pro Thr Thr Thr Pro Lys Asp Gly Phe Val Thr Tyr
    1070            1075            1080
Gly Lys Ser Ser Tyr Ser Leu Met Lys Leu Lys Leu Pro Trp His
    1085            1090            1095
Glu Ala Glu Thr Tyr Cys Lys Asp His Thr Ser Leu Leu Ala Ser
    1100            1105            1110
Ile Leu Asp Pro Tyr Ser Asn Ala Phe Ala Trp Met Lys Met His
    1115            1120            1125
Pro Phe Asn Val Pro Ile Trp Ile Ala Leu Asn Ser Asn Leu Thr
    1130            1135            1140
Asn Asn Glu Tyr Thr Trp Thr Asp Arg Trp Arg Val Arg Tyr Thr
    1145            1150            1155
Asn Trp Gly Ala Asp Glu Pro Lys Leu Lys Ser Ala Cys Val Tyr
    1160            1165            1170
Met Asp Val Asp Gly Tyr Trp Arg Thr Ser Tyr Cys Asn Glu Ser
    1175            1180            1185
Phe Tyr Phe Leu Cys Lys Lys Ser Asp Glu Ile Pro Ala Thr Glu
    1190            1195            1200
Pro Pro Gln Leu Pro Gly Lys Cys Pro Glu Ser Glu Gln Thr Ala
    1205            1210            1215
Trp Ile Pro Phe Tyr Gly His Cys Tyr Tyr Phe Glu Ser Ser Phe
    1220            1225            1230
Thr Arg Ser Trp Gly Gln Ala Ser Leu Glu Cys Leu Arg Met Gly
    1235            1240            1245
Ala Ser Leu Val Ser Ile Glu Thr Ala Ala Glu Ser Ser Phe Leu
```

```
                1250                1255                1260
Ser Tyr Arg Val Glu Pro Leu Lys Ser Lys Thr Asn Phe Trp Ile
    1265                1270                1275

Gly Met Phe Arg Asn Val Glu Gly Lys Trp Leu Trp Leu Asn Asp
    1280                1285                1290

Asn Pro Val Ser Phe Val Asn Trp Lys Thr Gly Asp Pro Ser Gly
    1295                1300                1305

Glu Arg Asn Asp Cys Val Val Leu Ala Ser Ser Gly Leu Trp
    1310                1315                1320

Asn Asn Ile His Cys Ser Ser Tyr Lys Gly Phe Ile Cys Lys Met
    1325                1330                1335

Pro Lys Ile Ile Asp Pro Val Thr Thr His Ser Ser Ile Thr Thr
    1340                1345                1350

Lys Ala Asp Gln Arg Lys Met Asp Pro Gln Pro Lys Gly Ser Ser
    1355                1360                1365

Lys Ala His His His His His His
    1370                1375

<210> SEQ ID NO 262
<211> LENGTH: 1365
<212> TYPE: PRT
<213> ORGANISM: Homo sapiens

<400> SEQUENCE: 262

Leu Leu Asp Thr Arg Gln Phe Leu Ile Tyr Asn Glu Asp His Lys Arg
1               5                   10                  15

Cys Val Asp Ala Val Ser Pro Ser Ala Val Gln Thr Ala Ala Cys Asn
            20                  25                  30

Gln Asp Ala Glu Ser Gln Lys Phe Arg Trp Val Ser Glu Ser Gln Ile
        35                  40                  45

Met Ser Val Ala Phe Lys Leu Cys Leu Gly Val Pro Ser Lys Thr Asp
    50                  55                  60

Trp Val Ala Ile Thr Leu Tyr Ala Cys Asp Ser Lys Ser Glu Phe Gln
65                  70                  75                  80

Lys Trp Glu Cys Lys Asn Asp Thr Leu Leu Gly Ile Lys Gly Glu Asp
                85                  90                  95

Leu Phe Phe Asn Tyr Gly Asn Arg Gln Glu Lys Asn Ile Met Leu Tyr
            100                 105                 110

Lys Gly Ser Gly Leu Trp Ser Arg Trp Lys Ile Tyr Gly Thr Thr Asp
        115                 120                 125

Asn Leu Cys Ser Arg Gly Tyr Glu Ala Met Tyr Thr Leu Leu Gly Asn
    130                 135                 140

Ala Asn Gly Ala Thr Cys Ala Phe Pro Phe Lys Phe Glu Asn Lys Trp
145                 150                 155                 160

Tyr Ala Asp Cys Thr Ser Ala Gly Arg Ser Asp Gly Trp Leu Trp Cys
                165                 170                 175

Gly Thr Thr Thr Asp Tyr Asp Thr Asp Lys Leu Phe Gly Tyr Cys Pro
            180                 185                 190

Leu Lys Phe Glu Gly Ser Glu Ser Leu Trp Asn Lys Asp Pro Leu Thr
        195                 200                 205

Ser Val Ser Tyr Gln Ile Asn Ser Lys Ser Ala Leu Thr Trp His Gln
    210                 215                 220

Ala Arg Lys Ser Cys Gln Gln Gln Asn Ala Glu Leu Leu Ser Ile Thr
225                 230                 235                 240
```

```
Glu Ile His Glu Gln Thr Tyr Leu Thr Gly Leu Thr Ser Ser Leu Thr
            245                 250                 255

Ser Gly Leu Trp Ile Gly Leu Asn Ser Leu Ser Phe Asn Ser Gly Trp
        260                 265                 270

Gln Trp Ser Asp Arg Ser Pro Phe Arg Tyr Leu Asn Trp Leu Pro Gly
    275                 280                 285

Ser Pro Ser Ala Glu Pro Gly Lys Ser Cys Val Ser Leu Asn Pro Gly
290                 295                 300

Lys Asn Ala Lys Trp Glu Asn Leu Glu Cys Val Gln Lys Leu Gly Tyr
305                 310                 315                 320

Ile Cys Lys Lys Gly Asn Thr Thr Leu Asn Ser Phe Val Ile Pro Ser
                325                 330                 335

Glu Ser Asp Val Pro Thr His Cys Pro Ser Gln Trp Trp Pro Tyr Ala
            340                 345                 350

Gly His Cys Tyr Lys Ile His Arg Asp Glu Lys Lys Ile Gln Arg Asp
        355                 360                 365

Ala Leu Thr Thr Cys Arg Lys Glu Gly Gly Asp Leu Thr Ser Ile His
    370                 375                 380

Thr Ile Glu Glu Leu Asp Phe Ile Ile Ser Gln Leu Gly Tyr Glu Pro
385                 390                 395                 400

Asn Asp Glu Leu Trp Ile Gly Leu Asn Asp Ile Lys Ile Gln Met Tyr
                405                 410                 415

Phe Glu Trp Ser Asp Gly Thr Pro Val Thr Phe Thr Lys Trp Leu Arg
            420                 425                 430

Gly Glu Pro Ser His Glu Asn Asn Arg Gln Glu Asp Cys Val Val Met
        435                 440                 445

Lys Gly Lys Asp Gly Tyr Trp Ala Asp Arg Gly Cys Glu Trp Pro Leu
    450                 455                 460

Gly Tyr Ile Cys Lys Met Lys Ser Arg Ser Gln Gly Pro Glu Ile Val
465                 470                 475                 480

Glu Val Glu Lys Gly Cys Arg Lys Gly Trp Lys Lys His His Phe Tyr
                485                 490                 495

Cys Tyr Met Ile Gly His Thr Leu Ser Thr Phe Ala Glu Ala Asn Gln
            500                 505                 510

Thr Cys Asn Asn Glu Asn Ala Tyr Leu Thr Thr Ile Glu Asp Arg Tyr
        515                 520                 525

Glu Gln Ala Phe Leu Thr Ser Phe Val Gly Leu Arg Pro Glu Lys Tyr
    530                 535                 540

Phe Trp Thr Gly Leu Ser Asp Ile Gln Thr Lys Gly Thr Phe Gln Trp
545                 550                 555                 560

Thr Ile Glu Glu Val Arg Phe Thr His Trp Asn Ser Asp Met Pro
                565                 570                 575

Gly Arg Lys Pro Gly Cys Val Ala Met Arg Thr Gly Ile Ala Gly Gly
            580                 585                 590

Leu Trp Asp Val Leu Lys Cys Asp Glu Lys Ala Lys Phe Val Cys Lys
        595                 600                 605

His Trp Ala Glu Gly Val Thr His Pro Pro Lys Pro Thr Thr Thr Pro
    610                 615                 620

Glu Pro Lys Cys Pro Glu Asp Trp Gly Ala Ser Ser Arg Thr Ser Leu
625                 630                 635                 640

Cys Phe Lys Leu Tyr Ala Lys Gly Lys His Glu Lys Lys Thr Trp Phe
                645                 650                 655

Glu Ser Arg Asp Phe Cys Arg Ala Leu Gly Gly Asp Leu Ala Ser Ile
```

-continued

```
                660              665              670
Asn Asn Lys Glu Glu Gln Gln Thr Ile Trp Arg Leu Ile Thr Ala Ser
            675              680              685

Gly Ser Tyr His Lys Leu Phe Trp Leu Gly Leu Thr Tyr Gly Ser Pro
            690              695              700

Ser Glu Gly Phe Thr Trp Ser Asp Gly Ser Pro Val Ser Tyr Glu Asn
705              710              715              720

Trp Ala Tyr Gly Glu Pro Asn Asn Tyr Gln Asn Val Glu Tyr Cys Gly
                725              730              735

Glu Leu Lys Gly Asp Pro Thr Met Ser Trp Asn Asp Ile Asn Cys Glu
            740              745              750

His Leu Asn Asn Trp Ile Cys Gln Ile Gln Lys Gly Gln Thr Pro Lys
            755              760              765

Pro Glu Pro Thr Pro Ala Pro Gln Asp Asn Pro Pro Val Thr Glu Asp
            770              775              780

Gly Trp Val Ile Tyr Lys Asp Tyr Gln Tyr Tyr Phe Ser Lys Glu Lys
785              790              795              800

Glu Thr Met Asp Asn Ala Arg Ala Phe Cys Lys Arg Asn Phe Gly Asp
                805              810              815

Leu Val Ser Ile Gln Ser Glu Ser Glu Lys Lys Phe Leu Trp Lys Tyr
            820              825              830

Val Asn Arg Asn Asp Ala Gln Ser Ala Tyr Phe Ile Gly Leu Leu Ile
            835              840              845

Ser Leu Asp Lys Lys Phe Ala Trp Met Asp Gly Ser Lys Val Asp Tyr
            850              855              860

Val Ser Trp Ala Thr Gly Glu Pro Asn Phe Ala Asn Glu Asp Glu Asn
865              870              875              880

Cys Val Thr Met Tyr Ser Asn Ser Gly Phe Trp Asn Asp Ile Asn Cys
                885              890              895

Gly Tyr Pro Asn Ala Phe Ile Cys Gln Arg His Asn Ser Ser Ile Asn
            900              905              910

Ala Thr Thr Val Met Pro Thr Met Pro Ser Val Pro Ser Gly Cys Lys
            915              920              925

Glu Gly Trp Asn Phe Tyr Ser Asn Lys Cys Phe Lys Ile Phe Gly Phe
            930              935              940

Met Glu Glu Glu Arg Lys Asn Trp Gln Glu Ala Arg Lys Ala Cys Ile
945              950              955              960

Gly Phe Gly Gly Asn Leu Val Ser Ile Gln Asn Glu Lys Glu Gln Ala
                965              970              975

Phe Leu Thr Tyr His Met Lys Asp Ser Thr Phe Ser Ala Trp Thr Gly
            980              985              990

Leu Asn Asp Val Asn Ser Glu His Thr Phe Leu Trp Thr Asp Gly Arg
            995              1000             1005

Gly Val His Tyr Thr Asn Trp Gly Lys Gly Tyr Pro Gly Gly Arg
            1010             1015             1020

Arg Ser Ser Leu Ser Tyr Glu Asp Ala Asp Cys Val Val Ile Ile
            1025             1030             1035

Gly Gly Ala Ser Asn Glu Ala Gly Lys Trp Met Asp Asp Thr Cys
            1040             1045             1050

Asp Ser Lys Arg Gly Tyr Ile Cys Gln Thr Arg Ser Asp Pro Ser
            1055             1060             1065

Leu Thr Asn Pro Pro Ala Thr Ile Gln Thr Asp Gly Phe Val Lys
            1070             1075             1080
```

Tyr Gly Lys Ser Ser Tyr Ser Leu Met Arg Gln Lys Phe Gln Trp
　　　1085　　　　　　1090　　　　　　　　1095

His Glu Ala Glu Thr Tyr Cys Lys Leu His Asn Ser Leu Ile Ala
1100　　　　　　　　1105　　　　　　1110

Ser Ile Leu Asp Pro Tyr Ser Asn Ala Phe Ala Trp Leu Gln Met
1115　　　　　　　　1120　　　　　　1125

Glu Thr Ser Asn Glu Arg Val Trp Ile Ala Leu Asn Ser Asn Leu
1130　　　　　　　　1135　　　　　　1140

Thr Asp Asn Gln Tyr Thr Trp Thr Asp Lys Trp Arg Val Arg Tyr
1145　　　　　　　　1150　　　　　　1155

Thr Asn Trp Ala Ala Asp Glu Pro Lys Leu Lys Ser Ala Cys Val
1160　　　　　　　　1165　　　　　　1170

Tyr Leu Asp Leu Asp Gly Tyr Trp Lys Thr Ala His Cys Asn Glu
1175　　　　　　　　1180　　　　　　1185

Ser Phe Tyr Phe Leu Cys Lys Arg Ser Asp Glu Ile Pro Ala Thr
1190　　　　　　　　1195　　　　　　1200

Glu Pro Pro Gln Leu Pro Gly Arg Cys Pro Glu Ser Asp His Thr
1205　　　　　　　　1210　　　　　　1215

Ala Trp Ile Pro Phe His Gly His Cys Tyr Tyr Ile Glu Ser Ser
1220　　　　　　　　1225　　　　　　1230

Tyr Thr Arg Asn Trp Gly Gln Ala Ser Leu Glu Cys Leu Arg Met
1235　　　　　　　　1240　　　　　　1245

Gly Ser Ser Leu Val Ser Ile Glu Ser Ala Ala Glu Ser Ser Phe
1250　　　　　　　　1255　　　　　　1260

Leu Ser Tyr Arg Val Glu Pro Leu Lys Ser Lys Thr Asn Phe Trp
1265　　　　　　　　1270　　　　　　1275

Ile Gly Leu Phe Arg Asn Val Glu Gly Thr Trp Leu Trp Ile Asn
1280　　　　　　　　1285　　　　　　1290

Asn Ser Pro Val Ser Phe Val Asn Trp Asn Thr Gly Asp Pro Ser
1295　　　　　　　　1300　　　　　　1305

Gly Glu Arg Asn Asp Cys Val Ala Leu His Ala Ser Ser Gly Phe
1310　　　　　　　　1315　　　　　　1320

Trp Ser Asn Ile His Cys Ser Ser Tyr Lys Gly Tyr Ile Cys Lys
1325　　　　　　　　1330　　　　　　1335

Arg Pro Lys Ile Ile Asp Ala Lys Pro Thr His Glu Leu Leu Thr
1340　　　　　　　　1345　　　　　　1350

Thr Lys Ala Asp Thr Arg Lys Met Asp Pro Ser Lys
1355　　　　　　　　1360　　　　　　1365

<210> SEQ ID NO 263
<211> LENGTH: 1370
<212> TYPE: PRT
<213> ORGANISM: Mus musculus

<400> SEQUENCE: 263

Leu Leu Asp Ala Arg Gln Phe Leu Ile Tyr Asn Glu Asp His Lys Arg
1　　　　　　5　　　　　　　　10　　　　　　　　　15

Cys Val Asp Ala Leu Ser Ala Ile Ser Val Gln Thr Ala Thr Cys Asn
　　　　　　20　　　　　　　　25　　　　　　　　　30

Pro Glu Ala Glu Ser Gln Lys Phe Arg Trp Val Ser Ser Gln Ile
　　　　35　　　　　　　　40　　　　　　　　　45

Met Ser Val Ala Phe Lys Leu Cys Leu Gly Val Pro Ser Lys Thr Asp
50　　　　　　　　55　　　　　　　　　60

Trp Ala Ser Val Thr Leu Tyr Ala Cys Asp Ser Lys Ser Glu Tyr Gln

```
                65                  70                  75                  80
Lys Trp Glu Cys Lys Asn Asp Thr Leu Phe Gly Ile Lys Gly Thr Glu
                    85                  90                  95
Leu Tyr Phe Asn Tyr Gly Asn Arg Gln Glu Lys Asn Ile Lys Leu Tyr
                    100                 105                 110
Lys Gly Ser Gly Leu Trp Ser Arg Trp Lys Val Tyr Gly Thr Thr Asp
                    115                 120                 125
Asp Leu Cys Ser Arg Gly Tyr Glu Ala Met Tyr Ser Leu Leu Gly Asn
                    130                 135                 140
Ala Asn Gly Ala Val Cys Ala Phe Pro Phe Lys Phe Glu Asn Lys Trp
145                 150                 155                 160
Tyr Ala Asp Cys Thr Ser Ala Gly Arg Ser Asp Gly Trp Leu Trp Cys
                    165                 170                 175
Gly Thr Thr Thr Asp Tyr Asp Lys Asp Lys Leu Phe Gly Phe Cys Pro
                    180                 185                 190
Leu His Phe Glu Gly Ser Glu Arg Leu Trp Asn Lys Asp Pro Leu Thr
                    195                 200                 205
Gly Ile Leu Tyr Gln Ile Asn Ser Lys Ser Ala Leu Thr Trp His Gln
                    210                 215                 220
Ala Arg Ala Ser Cys Lys Gln Gln Asn Ala Asp Leu Leu Ser Val Thr
225                 230                 235                 240
Glu Ile His Glu Gln Met Tyr Leu Thr Gly Leu Thr Ser Ser Leu Ser
                    245                 250                 255
Ser Gly Leu Trp Ile Gly Leu Asn Ser Leu Ser Val Arg Ser Gly Trp
                    260                 265                 270
Gln Trp Ala Gly Gly Ser Pro Phe Arg Tyr Leu Asn Trp Leu Pro Gly
                    275                 280                 285
Ser Pro Ser Ser Glu Pro Gly Lys Ser Cys Val Ser Leu Asn Pro Gly
                    290                 295                 300
Lys Asn Ala Lys Trp Glu Asn Leu Glu Cys Val Gln Lys Leu Gly Tyr
305                 310                 315                 320
Ile Cys Lys Lys Gly Asn Asn Thr Leu Asn Pro Phe Ile Ile Pro Ser
                    325                 330                 335
Ala Ser Asp Val Pro Thr Gly Cys Pro Asn Gln Trp Trp Pro Tyr Ala
                    340                 345                 350
Gly His Cys Tyr Arg Ile His Arg Glu Glu Lys Lys Ile Gln Lys Tyr
                    355                 360                 365
Ala Leu Gln Ala Cys Arg Lys Glu Gly Gly Asp Leu Ala Ser Ile His
                    370                 375                 380
Ser Ile Glu Glu Phe Asp Phe Ile Phe Ser Gln Leu Gly Tyr Glu Pro
385                 390                 395                 400
Asn Asp Glu Leu Trp Ile Gly Leu Asn Asp Ile Lys Ile Gln Met Tyr
                    405                 410                 415
Phe Glu Trp Ser Asp Gly Thr Pro Val Thr Phe Thr Lys Trp Leu Pro
                    420                 425                 430
Gly Glu Pro Ser His Glu Asn Asn Arg Gln Glu Asp Cys Val Val Met
                    435                 440                 445
Lys Gly Lys Asp Gly Tyr Trp Ala Asp Arg Ala Cys Glu Gln Pro Leu
                    450                 455                 460
Gly Tyr Ile Cys Lys Met Val Ser Gln Ser His Ala Val Val Pro Glu
465                 470                 475                 480
Gly Ala Asp Lys Gly Cys Arg Lys Gly Trp Lys Arg His Gly Phe Tyr
                    485                 490                 495
```

-continued

```
Cys Tyr Leu Ile Gly Ser Thr Leu Ser Thr Phe Thr Asp Ala Asn His
            500                 505                 510

Thr Cys Thr Asn Glu Lys Ala Tyr Leu Thr Thr Val Glu Asp Arg Tyr
            515                 520                 525

Glu Gln Ala Phe Leu Thr Ser Leu Val Gly Leu Arg Pro Glu Lys Tyr
        530                 535                 540

Phe Trp Thr Gly Leu Ser Asp Val Gln Asn Lys Gly Thr Phe Arg Trp
545                 550                 555                 560

Thr Val Asp Glu Gln Val Gln Phe Thr His Trp Asn Ala Asp Met Pro
                565                 570                 575

Gly Arg Lys Ala Gly Cys Val Ala Met Lys Thr Gly Val Ala Gly Gly
            580                 585                 590

Leu Trp Asp Val Leu Ser Cys Glu Glu Lys Ala Lys Phe Val Cys Lys
        595                 600                 605

His Trp Ala Glu Gly Val Thr Arg Pro Pro Glu Pro Thr Thr Thr Pro
    610                 615                 620

Glu Pro Lys Cys Pro Glu Asn Trp Gly Thr Thr Ser Lys Thr Ser Met
625                 630                 635                 640

Cys Phe Lys Leu Tyr Ala Lys Gly Lys His Glu Lys Lys Thr Trp Phe
                645                 650                 655

Glu Ser Arg Asp Phe Cys Lys Ala Ile Gly Gly Glu Leu Ala Ser Ile
            660                 665                 670

Lys Ser Lys Asp Glu Gln Gln Val Ile Trp Arg Leu Ile Thr Ser Ser
        675                 680                 685

Gly Ser Tyr His Glu Leu Phe Trp Leu Gly Leu Thr Tyr Gly Ser Pro
    690                 695                 700

Ser Glu Gly Phe Thr Trp Ser Asp Gly Ser Pro Val Ser Tyr Glu Asn
705                 710                 715                 720

Trp Ala Tyr Gly Glu Pro Asn Asn Tyr Gln Asn Val Glu Tyr Cys Gly
                725                 730                 735

Glu Leu Lys Gly Asp Pro Gly Met Ser Trp Asn Asp Ile Asn Cys Glu
            740                 745                 750

His Leu Asn Asn Trp Ile Cys Gln Ile Gln Lys Gly Lys Thr Leu Leu
        755                 760                 765

Pro Glu Pro Thr Pro Ala Pro Gln Asp Asn Pro Pro Val Thr Ala Asp
    770                 775                 780

Gly Trp Val Ile Tyr Lys Asp Tyr Gln Tyr Tyr Phe Ser Lys Glu Lys
785                 790                 795                 800

Glu Thr Met Asp Asn Ala Arg Ala Phe Cys Lys Lys Asn Phe Gly Asp
                805                 810                 815

Leu Ala Thr Ile Lys Ser Glu Ser Glu Lys Lys Phe Leu Trp Lys Tyr
            820                 825                 830

Ile Asn Lys Asn Gly Gly Gln Ser Pro Tyr Phe Ile Gly Met Leu Ile
        835                 840                 845

Ser Met Asp Lys Lys Phe Ile Trp Met Asp Gly Ser Lys Val Asp Phe
    850                 855                 860

Val Ala Trp Ala Thr Gly Glu Pro Asn Phe Ala Asn Asp Asp Glu Asn
865                 870                 875                 880

Cys Val Thr Met Tyr Thr Asn Ser Gly Phe Trp Asn Asp Ile Asn Cys
                885                 890                 895

Gly Tyr Pro Asn Asn Phe Ile Cys Gln Arg His Asn Ser Ser Ile Asn
        900                 905                 910
```

-continued

```
Ala Thr Ala Met Pro Thr Thr Pro Thr Thr Pro Gly Gly Cys Lys Glu
            915                 920                 925

Gly Trp His Leu Tyr Lys Asn Lys Cys Phe Lys Ile Phe Gly Phe Ala
930                 935                 940

Asn Glu Glu Lys Lys Ser Trp Gln Asp Ala Arg Gln Ala Cys Lys Gly
945                 950                 955                 960

Leu Lys Gly Asn Leu Val Ser Ile Glu Asn Ala Gln Glu Gln Ala Phe
            965                 970                 975

Val Thr Tyr His Met Arg Asp Ser Thr Phe Asn Ala Trp Thr Gly Leu
            980                 985                 990

Asn Asp Ile Asn Ala Glu His Met Phe Leu Trp Thr Ala Gly Gln Gly
            995                 1000                1005

Val His Tyr Thr Asn Trp Gly Lys Gly Tyr Pro Gly Gly Arg Arg
        1010                1015                1020

Ser Ser Leu Ser Tyr Glu Asp Ala Asp Cys Val Val Val Ile Gly
        1025                1030                1035

Gly Asn Ser Arg Glu Ala Gly Thr Trp Met Asp Asp Thr Cys Asp
        1040                1045                1050

Ser Lys Gln Gly Tyr Ile Cys Gln Thr Gln Thr Asp Pro Ser Leu
        1055                1060                1065

Pro Val Ser Pro Thr Thr Thr Pro Lys Asp Gly Phe Val Thr Tyr
        1070                1075                1080

Gly Lys Ser Ser Tyr Ser Leu Met Lys Leu Lys Leu Pro Trp His
        1085                1090                1095

Glu Ala Glu Thr Tyr Cys Lys Asp His Thr Ser Leu Leu Ala Ser
        1100                1105                1110

Ile Leu Asp Pro Tyr Ser Asn Ala Phe Ala Trp Met Lys Met His
        1115                1120                1125

Pro Phe Asn Val Pro Ile Trp Ile Ala Leu Asn Ser Asn Leu Thr
        1130                1135                1140

Asn Asn Glu Tyr Thr Trp Thr Asp Arg Trp Arg Val Arg Tyr Thr
        1145                1150                1155

Asn Trp Gly Ala Asp Glu Pro Lys Leu Lys Ser Ala Cys Val Tyr
        1160                1165                1170

Met Asp Val Asp Gly Tyr Trp Arg Thr Ser Tyr Cys Asn Glu Ser
        1175                1180                1185

Phe Tyr Phe Leu Cys Lys Lys Ser Asp Glu Ile Pro Ala Thr Glu
        1190                1195                1200

Pro Pro Gln Leu Pro Gly Lys Cys Pro Glu Ser Glu Gln Thr Ala
        1205                1210                1215

Trp Ile Pro Phe Tyr Gly His Cys Tyr Tyr Phe Glu Ser Ser Phe
        1220                1225                1230

Thr Arg Ser Trp Gly Gln Ala Ser Leu Glu Cys Leu Arg Met Gly
        1235                1240                1245

Ala Ser Leu Val Ser Ile Glu Thr Ala Ala Glu Ser Ser Phe Leu
        1250                1255                1260

Ser Tyr Arg Val Glu Pro Leu Lys Ser Lys Thr Asn Phe Trp Ile
        1265                1270                1275

Gly Met Phe Arg Asn Val Glu Gly Lys Trp Leu Trp Leu Asn Asp
        1280                1285                1290

Asn Pro Val Ser Phe Val Asn Trp Lys Thr Gly Asp Pro Ser Gly
        1295                1300                1305

Glu Arg Asn Asp Cys Val Val Leu Ala Ser Ser Ser Gly Leu Trp
```

-continued

```
              1310                1315                1320
Asn Asn Ile His Cys Ser Ser Tyr Lys Gly Phe Ile Cys Lys Met
        1325                1330                1335

Pro Lys Ile Ile Asp Pro Val Thr Thr His Ser Ser Ile Thr Thr
        1340                1345                1350

Lys Ala Asp Gln Arg Lys Met Asp Pro Gln Pro Lys Gly Ser Ser
        1355                1360                1365

Lys Ala
    1370
```

TARGETING AND IN VIVO IMAGING OF TUMOR-ASSOCIATED MACROPHAGES

CROSS-REFERENCE TO RELATED APPLICATION

This application is a continuation-in-part of U.S. patent application Ser. No. 13/065,794 filed Mar. 29, 2011, which claims the benefit of U.S. Provisional Patent Application Ser. No. 61/341,356, filed Mar. 29, 2010, the disclosure of each of which is hereby incorporated herein in its entirety by this reference.

STATEMENT ACCORDING TO 37 C.F.R. §1.821(c) OR (e)—SEQUENCE LISTING SUBMITTED AS ASCII TEXT FILE

Pursuant to 37 C.F.R. §1.821(c) or (e), a file containing an ASCII text version of the Sequence Listing has been submitted concomitant with this application, the contents of which are hereby incorporated by reference.

FIELD OF THE INVENTION

The present invention relates to the field of tumor growth and biology. The invention relates to activities and characteristics of tumor-associated macrophages (TAMs). In particular, immunoglobulin single variable domains are provided against markers of TAMs, and methods using the same for in vivo imaging of tumor cells, as well as cancer diagnostics and therapeutics.

BACKGROUND

Tumors harbor dynamic microenvironments in which cancer cells are intimately associated with non-transformed host cells. The tumor-associated stroma is considered to play an important role during tumor growth, influencing phenomena such as angiogenesis, metastasis and immune suppression.[36] As such, the stroma forms an attractive target for diagnostic and therapeutic applications.[37]

Different myeloid cells are important components of the tumor stroma. Myeloid cells are frequently found to infiltrate tumors and have been linked to diverse tumor-promoting activities.[1] In particular, tumor-associated macrophages (TAMs) are an important component of the tumor stroma, both in murine models and human patients.[2] TAMs can promote tumor-growth by affecting angiogenesis, immune suppression and invasion and metastasis.[2,3]

Tissue-resident macrophages can be maintained through local proliferation or differentiation in situ from circulating monocytic precursors.[5] Importantly, discrete subsets of blood monocytes have been described. Mouse monocytes can be classified as $Ly6C^{low}CX_3CR1^{hi}$ ($CCR2^-CD62L^-$) or $Ly6C^{hi}CX_3CR1^{low}$ ($CCR2^+CD62L^+$) and are shown to have distinct functions and migration patterns.[6]

Macrophages are plastic cells that can adopt different phenotypes depending on the immune context. Microenvironmental stimuli can drive a macrophage either towards a "classical" (M1) or an "alternative" (M2) activation state, two extremes in a spectrum.[7] M1 macrophages are typically characterized by the expression of pro-inflammatory cytokines, inducible nitric oxide synthase 2 (Nos2) and MHC Class II molecules. M2 macrophages, have a decreased level of the aforementioned molecules and are identified by their signature-expression of a variety of markers, including arginase-1 and mannose and scavenger receptors. It has been suggested that TAMs display a M2-like phenotype.[8]

Despite the presence of TAM in tumor infiltrate and their potential to produce angiogenic factors, their role in tumor growth and development remains unclear. There remains a need to discover and understand the complexities of the tumor-infiltrating myeloid cell compartment in view of the selective treatment of tumor growth.

SUMMARY OF THE INVENTION

Antibody-based tumor targeting strategies are widely explored.[38] Antibodies can be used for tumor imaging or delivering therapeuticals to tumor cells. However, limitations of conventional antibodies include a poor penetration of solid tumors and high Fc-mediated aspecific binding, highlighting the need for smaller and more specific binding units. Further to that, antibody-based tumor-targeting approaches have mostly been directed against antigens expressed on cancer cells.[38] However, the antigenic profile of cancer cells can be unstable and depends on the cancer type. Tumors also contain a large stromal compartment, which includes myeloid cells such as macrophages.[39] Stromal cells might provide a good alternative for tumor-targeting, since their antigenic profile is more stable and might be similar across different cancer types.

The present invention is based on the inventor's surprising finding of the existence of molecularly and functionally distinct TAM subsets, located in different intratumoral regions and the unraveling of $Ly6C^{hi}$ monocytes as their precursors. In particular, molecular markers for discriminating between these different TAM subsets, and accordingly, between these different intratumoral microenvironments (hypoxic versus normoxic zones), form the basis of the present invention. The present invention relates to the use of these molecular markers for specifically targeting the M1/M2-like or hypoxic/perivascular TAM subsets or their precursors, or, in a preferred embodiment, for selectively targeting the hypoxic/perivascular cells inside a tumor. The invention further relates to combinatorial strategies for optimally "re-educating" the TAM compartment and reverting its tumor-promoting activities.

In particular, selective in vivo targeting and imaging of distinct TAM subpopulations in the tumor stroma is envisaged by making use of specific immunoglobulin single variable domains, including nanobodies, against the corresponding molecular markers. Furthermore, a strategy was developed to reduce extra-tumoral signals to background levels, while persevering an efficient targeting of the tumor. Evidence is provided that TAM subsets can be efficiently targeted in vivo using nanobodies against the macrophage mannose receptor (MMR) in preclinical models, as illustrated in murine models. Moreover, evidence is provided that MMR$^+$ TAMs can be detected in intratumoral hypoxic zones of human samples, as illustrated in human breast cancer samples.

Thus, the invention encompasses novel diagnostic, prognostic and therapeutic applications for the diagnosis and treatment of cancer based on the existence of distinct TAM subsets, corresponding molecular markers and targeting tools, and a selective tumor targeting methodology.

Objects of the present invention will be clear from the description that follows.

BRIEF DESCRIPTION OF THE DRAWINGS

The patent or application file contains at least one drawing executed in color. Copies of this patent or patent application

FIG. 4: MHC II$^{low}$ TAMs are enriched in hypoxic regions, while MHC II$^{hi}$ TAMs are mainly normoxic. (A) Three weeks tumor-bearing mice were injected with pimonidazole (HP-1). Frozen tumor sections were stained with MECA32 and anti-HP-1 antibodies and DAPI. (B) Frozen tumor sections from HP-1 injected mice were stained for CD11b, MHC II, HP-1 adducts and DAPI. (C) Assessment of HP-1 adducts in the distinct tumor myeloid subsets using FACS. n=4 experiments.

FIG. 7: Purities of sorted cell populations. Representative plots are shown of the FACS sorted cell populations that were used throughout the study. (A) MHC II$^{hi}$ TAMs and MHC II$^{low}$ TAMs (B) CD11c+MHC II$^{hi}$B220-Ly6C-splenic cDCs.

FIG. 13: TAM subsets in the Lewis Lung Carcinoma (LLC) model and in the mammary carcinoma model 4T1.

FIG. 21. Uptake values of $^{99m}$Tc-labeled monovalent anti-MMR Nb clone 1 in TS/A tumor-bearing mice upon co-injection with a twenty-fold excess of cold bivalent anti-MMR Nb, based on dissection at 3 hours post injection. Tracer uptake is expressed as injected activity per gram (% IA/g).

FIG. 22. The relative abundance of TAM subsets is different in fast growing 3LL-R versus slow growing 3LL-S tumors. $3 \times 10^6$ cancer cells were injected in the flank and tumor volumes were measured at different time intervals. When tumors reached a volume of about 1000 mm$^3$, tumor single cell suspensions were made and the presence of TAM subsets were assessed via FACS.

Figure 1:
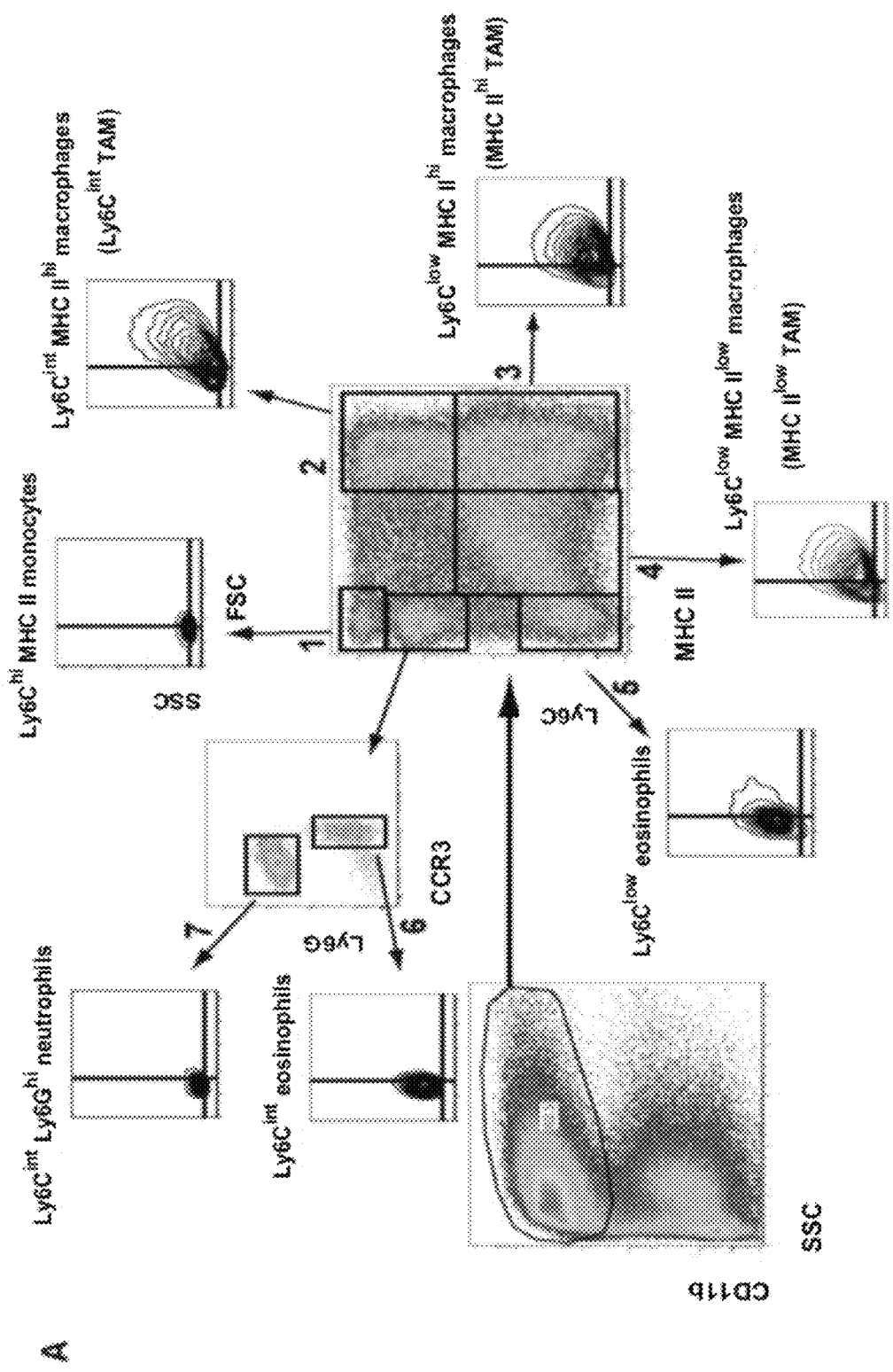
FIG. 1: TS/A tumors are infiltrated by distinct granulocyte and monocyte/macrophage subsets. (A) Single-cell suspensions of 11-day-old tumors were stained for the indicated markers. On gated CD11b+ cells, Ly6C was plotted vs. MHC II, demonstrating at least seven distinct subsets. For each subset, forward scatter (FSC) vs. side scatter (SSC) plots are shown. (B) Staining single-cell suspensions from 7-, 11-, 14- and 21-day-old tumors. Plots are gated on CD11b+ cells. Accompanying mean tumor diameters±SEM are indicated. n=3 experiments. (C) The expression of the indicated markers was assessed on cells present in gates 1-4, as shown in panel A. All markers were analyzed using antibody staining, except for CX3CR1, for which tumors were grown in CX3CR1GFP/+ mice. Shaded histograms are isotype controls or, for CX3CR1, autofluorescence in WT mice.

A clone was selected when the OD405 nm was at least two times higher on specific antigen as compared to irrelevant milk-blocking proteins.

DETAILED DESCRIPTION OF THE INVENTION

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g., "a" or "an," "the," this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Unless otherwise defined herein, scientific and technical terms and phrases used in connection with the present invention shall have the meanings that are commonly understood by those of ordinary skill in the art. Generally, nomenclatures used in connection with, and techniques of molecular and cellular biology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, for example, Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002).

As used herein, the terms "polypeptide," "protein," "peptide" are used interchangeably herein, and refer to a polymeric form of amino acids of any length, which can include coded and non-coded amino acids, chemically or biochemically modified or derivatized amino acids, and polypeptides having modified peptide backbones.

As used herein, the terms "nucleic acid molecule," "polynucleotide," "polynucleic acid," "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A first aspect of the invention relates to an immunoglobulin single variable domain directed against and/or specifically binding to a molecular marker of Table 1.

According to a particular embodiment, the invention relates to an immunoglobulin single variable domain that is directed against and/or specifically binds to the macrophage mannose receptor. The immunoglobulin single variable domains of the present invention may generally be directed against any MMR, in particular a mammalian macrophage mannose receptor, and in particular mouse macrophage mannose receptor (SEQ ID NO:260) and/or human macrophage mannose receptor (SEQ ID NO:258). The present invention is in its broadest sense not particularly limited to or defined by a specific antigenic determinant, epitope, part, domain, subunit or conformation of MMR, and in particular mouse MMR (SEQ ID NO:260) and/or human macrophage mannose receptor (SEQ ID NO:258) against which the immunoglobulin single variable domains are directed. According to a specific preferred embodiment, the immunoglobulin single variable domain specifically binds to the ectodomain of the macrophage mannose receptor, and in particular the ectodomain of the mouse macrophage mannose receptor (SEQ ID NO:263) and/or the ectodomain of the human macrophage mannose receptor (SEQ ID NO:262).

The "macrophage mannose receptor" (MMR), as used herein, refers to a type I transmembrane protein, first identified in mammalian tissue macrophages and later in dendritic cells and a variety of endothelial and epithelial cells. Macrophages are central actors of the innate and adaptive immune responses. They are disseminated throughout most organs to protect against entry of infectious agents by internalizing and most of the time, killing them. Among the surface receptors present on macrophages, the mannose receptor recognizes a variety of molecular patterns generic to microorganisms. The MMR is composed of a single subunit with N- and O-linked glycosylations and consists of five domains: an N-terminal cysteine-rich region, which recognizes terminal sulfated sugar residues; a fibronectin type II domain with unclear function; a series of eight C-type, lectin-like carbohydrate recognition domains (CRDs) involved in $Ca^{2+}$-dependent recognition of mannose, fucose, or N-acetylglucosamine residues on the envelop of pathogens or on endogenous glycoproteins with CRDs 4-8 showing affinity for ligands comparable with that of intact MR; a single transmembrane domain; and a 45 residue-long cytoplasmic tail that contains motifs critical for MR-mediated endocytosis and sorting in endosomes.[47]

Preferably, the macrophage mannose receptor is of mammalian origin, particularly from mouse, rat, human, and the like, and these cross-species variants of the MMR protein are referred to herein as "homologues" of the macrophage mannose receptor. Thus, the macrophage mannose receptor as referred to in the present invention includes homologues as wells as fragments of the full-length MMR protein. Non-limiting examples of homologues of the MMR include the mouse MMR (synonyms: MRC1 or CD206; accession number nucleotide sequence: NM_008625.2; accession number protein sequence: NP_032651.2 and as in SEQ ID NO:260) or the human MMR (synonyms: MRC1 or CD206; accession number nucleotide sequence: NM_002438.2; accession number protein sequence: NP_002429.1 and as in SEQ ID NO:258). The deduced amino acid sequence of mouse mannose receptor has an overall 82% homology with the human mannose receptor, as can be easily measured in a BLASTp alignment.[51] A non-limiting example of a fragment of the full-length MMR protein includes the ectodomain of a particular MMR. The "ectodomain" as used herein, refers to a fragment of the MMR containing an N-terminus that is cysteine-rich, followed by a fibronectin type II domain and eight carbohydrate recognition domains (CRDs). All of the eight CRDs are particularly well conserved, especially CRD4. For example, mouse CRD4 shows 92% homology with the equivalent region of the human protein. The ectodomain of the mouse macrophage mannose receptor is defined as the AA 19-AA 1388 fragment (SEQ ID NO:263) of the corresponding full-length mouse MMR amino acid sequence as defined in NP_032651.2 (SEQ ID NO:260). Or, the ectodomain of the human macrophage mannose receptor is be defined as the AA 19-AA 1383 fragment (SEQ ID NO:262) of the corresponding full-length mouse MMR amino acid sequence as defined in NP_002429.1 (SEQ ID NO:258), see also Table 15.

The present invention thus provides for an immunoglobulin single variable domain specifically recognizing a marker of Table 1, preferably the macrophage mannose receptor (as defined above). As used herein, the term "specifically recognizing" or "specifically binding to" or simply "specific for" refers to the ability of an immunoglobulin or an immunoglobulin fragment, such as an immunoglobulin single variable domain, to preferentially bind to a particular antigen that is present in a homogeneous mixture of different antigens and does not necessarily imply high affinity (as defined further herein). In certain embodiments, a specific binding interaction will discriminate between desirable and undesirable antigens in a sample, in some embodiments more than about 10- to 100-fold or more (e.g., more than about 1000- or 10,000-fold). The terms "specifically bind," "selectively bind," "preferentially bind," and grammatical equivalents thereof, are used interchangeably herein.

The term "affinity," as used herein, refers to the degree to which an immunoglobulin single variable domain, binds to an antigen so as to shift the equilibrium of antigen and immunoglobulin single variable domain toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the antibody (fragment) and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M.

An immunoglobulin single variable domain that can specifically bind to and/or that has affinity for a specific antigen or antigenic determinant (e.g., epitope) is said to be "against" or "directed against" the antigen or antigenic determinant. An immunoglobulin single variable domain according to the invention is said to be "cross-reactive" for two different antigens or antigenic determinants (such as macrophage mannose receptor from two different species of mammal, such as human MMR and mouse MMR) if it is specific for both these different antigens or antigenic determinants.

It will be appreciated that, according to the invention, immunoglobulin single variable domains that are directed against the macrophage mannose receptor from one species may or may not show cross-reactivity with the macrophage mannose receptor from another species. For example, immunoglobulin single variable domains directed against human MMR, in particular human MMR (SEQ ID NO:258) may or may not show cross-reactivity with MMR from one or more other species of animals that are often used in animal models for diseases (for example, mouse, rat, rabbit, pig or dog). It will be clear to the skilled person that such cross-reactivity, when present, may have advantages for diagnostic and/or therapeutic development, since it allows the immunoglobulin single variable domains to be tested in such disease models. It is expected that the immunoglobulin single variable domains according to the invention will generally bind to all naturally occurring or synthetic analogs, variants, mutants, alleles of the MMRs mentioned herein.

As used herein, an "immunoglobulin single variable domain" is an antigen-binding domain or fragment that comprises an amino acid sequence that comprises four framework regions (FR) and three complementarity determining regions (CDR) according to the following formula (1):

FR1-CDR1-FR2-CDR2-FR3-CDR3-FR4 (1);

or any suitable fragment thereof (which will then usually contain at least some of the amino acid residues that form at least one of the complementarity determining regions), and in which FR1 to FR4 refer to framework regions 1 to 4, respectively, and in which CDR1 to CDR3 refer to the complementarity determining regions 1 to 3, respectively.

Immunoglobulin single variable domains comprising 4 FRs and 3 CDRs are known to the person skilled in the art and have been described, as a non-limiting example, in reference (40). Typical, but non-limiting, examples of immunoglobulin single variable domains include light chain variable domain sequences (e.g., a $V_L$ domain sequence), or heavy chain variable domain sequences (e.g., a $V_H$ domain sequence), which are usually derived from conventional four-chain antibodies. Preferably, the immunoglobulin single variable domains are derived from camelid antibodies, preferably from heavy chain camelid antibodies, devoid of light chains, and are known as $V_HH$ domain sequences or nanobodies (as described further herein).

A nanobody (Nb) is the smallest functional fragment or single variable domain ($V_HH$) of a naturally occurring single-chain antibody and is known to the person skilled in the art. They are derived from heavy chain only antibodies, seen in camelids.[26,27] In the family of "camelids" immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody or a $V_HH$ antibody. Nanobody™, Nanobodies™ and Nanoclone™ are trademarks of Ablynx NV (Belgium). The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies (as defined further herein) or attached to reporter molecules.[28] Nbs are stable, survive the gastro-intestinal system and can easily be manufactured. Therefore, Nbs can be used in many applications including drug discovery and therapy, but also as a versatile and valuable tool for purification, functional study and crystallization of proteins.[29]

The nanobodies of the invention generally comprise a single amino acid chain that can be considered to comprise four "framework regions" or FRs and three "complementarity determining regions" or CDRs, according to formula (1) (as define above). The term "complementarity determining region" or "CDR" refers to variable regions in nanobodies and contains the amino acid sequences capable of specifically binding to antigenic targets. These CDR regions account for the basic specificity of the nanobody for a particular antigenic determinant structure. Such regions are also referred to as "hypervariable regions." The nanobodies have three CDR regions, each non-contiguous with the others (termed CDR1, CDR2, CDR3). The delineation of the FR and CDR sequences is often based on the IMGT unique numbering system for V-domains and V-like domains.[35] Alternatively, the delineation of the FR and CDR sequences can be done by using the Kabat numbering system as applied to $V_HH$ domains from Camelids in the article of Riechmann and Muyldermans.[41] As will be known by the person skilled in the art, the nanobodies can in particular be characterized by the presence of one or more Camelidae hallmark residues in one or more of the framework sequences (according to Kabat numbering), as described, for example, in WO 08/020,079, on page 75, Table A-3, incorporated herein by reference).

Non-limiting examples of nanobodies according to the present invention are as described herein and include anti-human, anti-mouse and cross-reactive anti-human/anti-mouse MMR nanobodies. For example, in Table 4, in particular SEQ ID NO:3, SEQ ID NO:4, SEQ ID NO:7, SEQ ID NO:8, SEQ ID NO:112, SEQ ID NO:114, SEQ ID NO:116; in Table 14, in particular SEQ ID NOS:126-155). In a specific embodiment, the nanobodies of the present invention may comprise at least one of the complementarity determining regions (CDRs) as described herein, for example, CDRs with an amino acid sequence selected from SEQ ID NOs:156-251 (see Table 14). Preferably, the nanobodies of the present invention comprise a CDR1, a CDR2 and a CDR3 selected from the group consisting of SEQ ID NOS:156-251 according to the above described formula (1). More specifically, the nanobodies can be selected from the group comprising SEQ ID NO:3, SEQ ID NO:4, SEQ ID NO:7, SEQ ID NO:8, SEQ ID NO:112, SEQ ID NO:114, SEQ ID NO:116, SEQ ID NOS:126-155, or a functional fragment thereof. A "functional fragment" or a "suitable fragment," as used herein, may, for example, comprise one of the CDR loops. Preferably, the functional fragment comprises CDR3. More specifically, the nanobodies consist of any of SEQ ID NO:3, SEQ ID NO:4, SEQ ID NO:7, SEQ ID NO:8, SEQ ID NO:112, SEQ ID NO:114, SEQ ID NO:116, or SEQ ID NOS:126-155. In still another embodiment, a nucleic acid sequence encoding any of the above nanobodies or functional fragments is also part of the present invention (for example, see Table 4; SEQ ID NO:1, SEQ ID NO:2, SEQ ID NO:5, SEQ ID NO:6, SEQ ID NO:111, SEQ ID NO:113, SEQ ID NO:115). Further, the present invention also envisages expression vectors comprising nucleic acid sequences encoding any of the above nanobodies or functional fragments thereof, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the nanobodies can be done according to techniques known by the skilled person in the art. For the sake of clarity, it is expected that at least some of the nanobodies identified herein may also be cross-reactive with macrophage mannose receptors of other mammalian species.

It should be noted that the term nanobody as used herein in its broadest sense is not limited to a specific biological source or to a specific method of preparation. For example, the nanobodies of the invention can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a nanobody using techniques for nucleic acid synthesis known per se, followed by expression of the nucleic acid thus obtained; and/or (8) by any combination of one or more of the foregoing.

One preferred class of nanobodies corresponds to the $V_HH$ domains of naturally occurring heavy chain antibodies directed against a macrophage mannose receptor. As further described herein, such $V_HH$ sequences can generally be generated or obtained by suitably immunizing a species of Camelid with a MMR (i.e., so as to raise an immune response and/or heavy chain antibodies directed against a MMR), by obtaining a suitable biological sample from the Camelid (such as a blood sample, or any sample of B-cells), and by generating $V_HH$ sequences directed against a MMR, starting from the sample, using any suitable technique known per se. Such techniques will be clear to the skilled person. Alternatively, such naturally occurring $V_HH$ domains against MMR can be obtained from naive libraries of Camelid $V_HH$ sequences, for example, by screening such a library using MMR or at least one part, fragment, antigenic determinant or epitope thereof using one or more screening techniques known per se. Such libraries and techniques are, for example, described in WO9937681, WO0190190, WO03025020 and WO03035694. Alternatively, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as, for example, described in WO0043507. Yet another technique for obtaining $V_HH$ sequences directed against a MMR involves suitably immunizing a transgenic mammal that is capable of expressing heavy chain antibodies (i.e., so as to raise an immune response and/or heavy chain antibodies directed against a MMR), obtaining a suitable biological sample from the transgenic mammal (such as a blood sample, or any sample of B-cells), and then generating $V_HH$ sequences directed against a MMR starting from the sample, using any suitable technique known per se. For example, for this purpose, the heavy chain antibody-expressing mice and the further methods and techniques described in WO02085945 and in WO04049794 can be used.

Accordingly, the invention encompasses methods of generating immunoglobulin single variable domains according to the invention. As a non-limiting example, a method is provided of generating nanobodies directed against or specifically binding to the macrophage mannose receptor (as described herein), comprising:
  (i) immunizing an animal with a MMR, in particular a mouse (SEQ ID NOS:260, 261, 263) or human MMR (SEQ ID NOS:258, 259, 262), or a fragment thereof; and
  (ii) screening for nanobodies specifically binding to the MMR.

For the immunization of an animal with a MMR, the MMR may be produced and purified using conventional methods that may employ expressing a recombinant form of the MMR in a host cell, and purifying the MMR using affinity chromatography and/or antibody-based methods. Any suitable animal, e.g., a warm-blooded animal, in particular a mammal such as a rabbit, mouse, rat, camel, sheep, cow, shark, or pig or a bird such as a chicken or turkey, may be immunized using any of the techniques well known in the art suitable for generating an immune response. The screening for nanobodies, as a non-limiting example, specifically binding to a MMR may, for example, be performed by screening a set, collection or library of cells that express heavy chain antibodies on their surface (e.g., B-cells obtained from a suitably immunized Camelid), or bacteriophages that display a fusion of genIII and nanobody at their surface, by screening of a (naïve or immune) library of $V_HH$ sequences or nanobody sequences, or by screening of a (naïve or immune) library of nucleic acid sequences that encode VHH sequences or nanobody sequences, which may all be performed in a manner known per se, and which method may optionally further comprise one or more other suitable steps, such as, for example, and without limitation, a step of affinity maturation, a step of expressing the desired amino acid sequence, a step of screening for binding and/or for activity against the desired antigen (in this case, the MMR), a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

A particularly preferred class of immunoglobulin single variable domains of the invention comprises nanobodies with an amino acid sequence that corresponds to the amino acid sequence of a naturally occurring $V_HH$ domain, but that has been "humanized," i.e., by replacing one or more amino acid residues in the amino acid sequence of the naturally occurring $V_HH$ sequence (and in particular in the framework sequences) by one or more of the amino acid residues that occur at the corresponding position(s) in a VH domain from a conventional four-chain antibody from a human being. This can be performed in a manner known per se, which will be clear to the skilled person, on the basis of the further description herein and the prior art on humanization. Again, it should be noted that such humanized nanobodies of the invention can be obtained in any suitable manner known per se (i.e., as indicated under points (1)-(8) above) and thus are not strictly limited to polypeptides that have been obtained using a polypeptide that comprises a naturally occurring $V_HH$ domain as a starting material. Humanized nanobodies may have several advantages, such as a reduced immunogenicity, compared to the corresponding naturally occurring $V_HH$ domains. Such humanization generally involves replacing one or more amino acid residues in the sequence of a naturally occurring $V_HH$ with the amino acid residues that occur at the same position in a human VH domain, such as a human VH3 domain. The humanizing substitutions should be chosen such that the resulting humanized nanobodies still retain the favorable properties of nanobodies as defined herein. The skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_HH$ domains on the other hand.

For example, both "humanization" and "camelization" can be performed by providing a nucleotide sequence that encodes a naturally occurring $V_HH$ domain or VH domain, respectively, and then changing, in a manner known per se, one or more codons in the nucleotide sequence in such a way that the new nucleotide sequence encodes a "humanized" or "camelized" nanobody of the invention, respectively. This nucleic acid can then be expressed in a manner known per se, so as to provide the desired nanobody of the invention. Alternatively, based on the amino acid sequence of a naturally occurring VHH domain or VH domain, respectively, the amino acid sequence of the desired humanized or camelized Nanobody of the invention, respectively, can be designed and then synthesized de novo using techniques for peptide synthesis known per se. Also, based on the amino acid sequence or nucleotide sequence of a naturally occurring $V_HH$ domain or VH domain, respectively, a nucleotide sequence encoding the desired humanized or camelized Nanobody of the invention, respectively, can be designed and then synthesized de novo using techniques for nucleic acid synthesis known per se, after which the nucleic acid thus obtained can be expressed in a manner known per se, so as to provide the desired nanobody of the invention. Other suitable methods and techniques for obtaining the nanobodies of the invention and/or nucleic acids encoding the same, starting from naturally occurring VH sequences or preferably VHH sequences, will be clear from the skilled person, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a nanobody of the invention or a nucleotide sequence or nucleic acid encoding the same.

Also within the scope of the invention are natural or synthetic analogs, mutants, variants, alleles, homologs and orthologs (herein collectively referred to as "variants") of the immunoglobulin single variable domains of the invention as defined herein. Some particularly preferred, but non-limiting examples of immunoglobulin single variable domains, as well as combinations of CDR sequences are mentioned in Table 14, which lists the CDR sequences that are present in a number of preferred, but non-limiting immunoglobulin single variable domains of the invention. Thus, according to one embodiment of the invention, the term "immunoglobulin single variable domain of the invention" in its broadest sense also covers such variants, in particular variants of the nanobodies of SEQ ID NO:3, SEQ ID NO:4, SEQ ID NO:7, SEQ ID NO:8, SEQ ID NO:112, SEQ ID NO:114, SEQ ID NO:116, SEQ ID NOS:126-155 (see Table 4, Table 14). Generally, in such variants, one or more amino acid residues may have been replaced, deleted and/or added, compared to the nanobodies of the invention as defined herein. Such substitutions, insertions or deletions may be made in one or more of the framework regions and/or in one or more of the CDRs, and in particular variants of the CDRs of the nanobodies of SEQ ID NO:3, SEQ ID NO:4, SEQ ID NO:7, SEQ ID NO:8, SEQ ID NO:112, SEQ ID NO:114, SEQ ID NO:116, SEQ ID NOS:126-155, the CDRs corresponding to SEQ ID NOS: 156-251 (Table 14). Variants, as used herein, are sequences wherein each or any framework region and each or any complementarity determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST.[50,51] Software for performing BLAST analyses is publicly available through the National Center for Biotechnology Information (on the worldwide web at ncbi.nlm.nih.gov/). Such variants of immunoglobulin single variable domains may be of particular advantage since they may have improved potency or other desired properties.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about two, about five, about ten, up to about twenty, up to about thirty or up to about fifty or more amino acids. A protein or a fragment thereof may contain more than one deletion.

An "insertion" or "addition" is that change in an amino acid or nucleotide sequences which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about one, about three, about five, about ten, up to about twenty, up to about thirty or up to about fifty or more amino acids. A protein or fragment thereof may contain more than one insertion.

A "substitution," as used herein, results from the replacement of one or more amino acids or nucleotides by different amino acids or nucleotides, respectively as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

By means of non-limiting examples, a substitution may, for example, be a conservative substitution (as described herein) and/or an amino acid residue may be replaced by another amino acid residue that naturally occurs at the same position in another $V_H H$ domain. Thus, any one or more substitutions, deletions or insertions, or any combination thereof, that either improve the properties of the nanobody of the invention or that at least do not detract too much from the desired properties or from the balance or combination of desired properties of the nanobody of the invention (i.e., to the extent that the nanobody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may, for example, involve introducing a limited number of possible substitutions and determining their influence on the properties of the nanobodies thus obtained.

According to particularly preferred embodiments, variants of the immunoglobulin single variable domains, in particular the nanobodies of the present invention may have a substitution, deletion or insertion, of one, two or three amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3, as listed in Table 14. More preferably, variants of the immunoglobulin single variable domains, in particular the nanobodies, of the present invention may have a conservative substitution (as defined herein) of one, two or three amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3, as listed in Table 14.

Further, depending on the host organism used to express the immunoglobulin single variable domain of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example, to allow site-specific pegylation.

Examples of modifications, as well as examples of amino acid residues within the immunoglobulin single variable domain, preferably the nanobody sequence, that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the immunoglobulin single variable domain of the invention, and in particular of one or more functional groups, residues or moieties that confer one or more desired properties or functionalities to the immunoglobulin single variable domain of the invention. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFvs and single domain antibodies), for which reference is, for example, made to *Remington's Pharmaceutical Sciences,* 16th ed., Mack Publishing Co., Easton, Pa. (1980). Such functional groups may, for example, be linked directly (for example, covalently) to a immunoglobulin single variable domain of the invention, or optionally via a suitable linker or spacer, as will again be clear to the skilled person. One of the most widely used techniques for increasing the half-life and/or reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFvs); reference is made to, for example, Chapman, *Nat. Biotechnol.,* 54, 531-545 (2002); by Veronese and Harris, *Adv. Drug Deliv. Rev.* 54, 453-456 (2003), by Harris and Chess, *Nat. Rev. Drug. Discov.,* 2, (2003) and in WO04060965. Various reagents for pegylation of proteins are also commercially available, for example, from Nektar Therapeutics, USA. Preferably, site-directed pegylation is used, in particular via a cysteine-residue (see, for example, Yang et al., *Protein Engineering,* 16, 10, 761-770 (2003). For example, for this purpose, PEG may be attached to a cysteine residue that naturally occurs in a nanobody of the invention, a nanobody of the invention may be modified so as to suitably introduce one or more cysteine residues for attachment of PEG, or an amino acid sequence comprising one or more cysteine residues for attachment of PEG may be fused to the N- and/or C-terminus of a nanobody of the invention, all using techniques of protein engineering known per se to the skilled person. Preferably, for the immunoglobulin single variable domains and proteins of the invention, a PEG is used with a molecular weight of more than 5000, such as more than 10,000 and less than 200,000, such as less than 100,000; for example, in the range of 20,000-80,000. Another, usually less preferred modification comprises N-linked or O-linked glycosylation, usually as part of co-translational and/or post-translational modification, depending on the host cell used for expressing the immunoglobulin single variable domain or polypeptide of the invention. Another technique for increasing the half-life of an immunoglobulin single variable domain may comprise the engineering into bifunctional constructs (for example, one nanobody against the target MMR and one against a serum protein such as albumin) or into fusions of immunoglobulin single variable domains with peptides (for example, a peptide against a serum protein such as albumin).

Yet another modification may comprise the introduction of one or more detectable labels or other signal-generating groups or moieties, depending on the intended use of the labeled nanobody. Suitable labels and techniques for attaching, using and detecting them will be clear to the skilled person and, for example, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled nanobodies and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, diethyl-enetriaminepentaacetic acid (DTPA) or ethylenediaminetetraacetic acid (EDTA). Yet another modification may comprise the introduction of a functional group that is one part of a specific binding pair, such as the biotin-(strept)avidin binding pair. Such a functional group may be used to link the nanobody of the invention to another protein, polypeptide or chemical compound that is bound to the other half of the binding pair, i.e., through formation of the binding pair. For example, a nanobody of the invention may be conjugated to biotin, and linked to another protein, polypeptide, compound or carrier conjugated to avidin or streptavidin. For example, such a conjugated nanobody may be used as a reporter, for example, in a diagnostic system where a detectable signal-producing agent is conjugated to avidin or streptavidin. Such binding pairs may, for example, also be used to bind the nanobody of the invention to a carrier, including carriers suitable for pharmaceutical purposes. One non-limiting example are the liposomal formulations described by Cao and Suresh, *Journal of Drug Targeting*, 8, 4, 257 (2000). Such binding pairs may also be used to link a therapeutically active agent to the nanobody of the invention.

According to a preferred embodiment, the immunoglobulin single variable domain of the present invention is fused to a detectable label, either directly or through a linker. Preferably, the detectable label is a radio-isotope or radioactive tracer, which is suitable for medical applications, such as in in vivo nuclear imaging. Examples include, without the purpose of being limitative, $^{99m}Tc$, $^{123}I$, $^{125}I$, $^{111}In$, $^{18}F$, $^{64}Cu$, $^{67}Ga$, $^{68}Ga$, and any other radio-isotope which can be used in animals, in particular mouse or human. According to a specific embodiment, the detectable label is $^{99m}Tc$.

In still another embodiment, the immunoglobulin single variable domain of the present invention is fused to a moiety selected from the group consisting of a toxin, or to a cytotoxic drug, or to an enzyme capable of converting a prodrug into a cytotoxic drug, or to a radionuclide, or coupled to a cytotoxic cell, either directly or through a linker. Specific, but non-limiting examples of such moieties are described in the Example section.

As used herein, "linkers" are peptides of 1 to 50 amino acids length and are typically chosen or designed to be unstructured and flexible. These include, but are not limited to, synthetic peptides rich in Gly, Ser, Thr, Gln, Glu or further amino acids that are frequently associated with unstructured regions in natural proteins.[49] Non-limiting examples of suitable linker sequences are described in the Example section, and include $(G_4S)_3$ (GGGGSGGGGSGGGGS; SEQ ID NO:121), llama IgG2 hinge (AHHSEDPSSKAPKAPMA; SEQ ID NO:122) or human IgA hinge (SPSTPPTPSPSTP-PAS SEQ ID NO:123) linkers.

In a particular embodiment, the immunoglobulin single variable domains of the invention are in a "multivalent" form and are formed by bonding, chemically or by recombinant DNA techniques, together two or more monovalent immunoglobulin single variable domains. Non-limiting examples of multivalent constructs include "bivalent" constructs, "trivalent" constructs, "tetravalent" constructs, and so on. The immunoglobulin single variable domains comprised within a multivalent construct may be identical or different. In another particular embodiment, the immunoglobulin single variable domains of the invention are in a "multi-specific" form and are formed by bonding together two or more immunoglobulin single variable domains, of which at least one with a different specificity. Non-limiting examples of multi-specific constructs include "bi-specific" constructs, "tri-specific" constructs, "tetra-specific" constructs, and so on. To illustrate this further, any multivalent or multispecific (as defined herein) immunoglobulin single variable domain of the invention may be suitably directed against two or more different epitopes on the same antigen, for example, against two or more different parts of the MMR ectodomain; or may be directed against two or more different antigens, for example, against MMR and one or more other marker of Table 1. Preferably, a monovalent immunoglobulin single variable domain of the invention is such that it will bind to the MMR (as described herein) with an affinity less than 500 nM, preferably less than 200 nM, more preferably less than 10 nM, such as less than 500 µM. Multivalent or multispecific immunoglobulin single variable domains of the invention may also have (or be engineered and/or selected for) increased avidity and/or improved selectivity for the desired MMR, and/or for any other desired property or combination of desired properties that may be obtained by the use of such multivalent or multispecific immunoglobulin single variable domains.

In a further aspect, the present invention also provides a polypeptide comprising any of the immunoglobulin single variable domains according to the invention, either in a monovalent, multivalent or multi-specific form. Thus, polypeptides comprising monovalent, multivalent or multi-specific nanobodies are included here as non-limiting examples.

In still another aspect, the invention also relates to a pharmaceutical composition comprising a therapeutically effective amount of a immunoglobulin single variable domain of the invention, and at least one of pharmaceutically acceptable carrier, adjuvant or diluent.

A "carrier," or "adjuvant," in particular a "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. So, pharmaceutically acceptable carriers are inherently non-toxic and nontherapeutic, and they are known to the person skilled in the art. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. Carriers or adjuvants may be, as a non limiting example, Ringer's solution, dextrose solution or Hank's solution. Non aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

As used herein, the terms "therapeutically effective amount," "therapeutically effective dose" and "effective amount" mean the amount needed to achieve the desired result or results. As used herein, "pharmaceutically acceptable" means a material that is not biologically or otherwise undesirable, i.e., the material may be administered to an individual along with the compound without causing any undesirable biological effects or interacting in a deleterious manner with any of the other components of the pharmaceutical composition in which it is contained.

Certain of the above-described immunoglobulin single variable domains may have therapeutic utility and may be administered to a subject having a condition in order to treat the subject for the condition.

Accordingly, in a second aspect, the invention relates to a method of preventing and/or treating cancer, comprising administering a pharmaceutically effective amount of an immunoglobulin single variable domain of the invention or a pharmaceutical composition derived thereof to a subject in need thereof.

As used herein, the term "preventing cancer" means inhibiting or reversing the onset of the disease, inhibiting or reversing the initial signs of the disease, inhibiting the appearance of clinical symptoms of the disease. As used herein, "treating cancer" or "treating a subject or individual having cancer" includes substantially inhibiting the disease, substantially slowing or reversing the progression of the disease, substantially ameliorating clinical symptoms of the disease or substantially preventing the appearance of clinical symptoms of the disease. In particular, it includes inhibition of the replication of cancer cells, inhibition of the spread of cancer, reduction in tumor size, lessening or reducing the number of cancerous cells in the body, and/or amelioration or alleviation of the symptoms of cancer. A treatment is considered therapeutic if there is a decrease in mortality and/or morbidity, and may be performed prophylactically, or therapeutically. A variety of subjects or individuals are treatable. Generally the "subjects" are mammals or mammalian, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

As used herein, the term "cancer" refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer.

In a specific embodiment, the invention relates to a method of inhibiting tumor growth or tumor metastases in a mammal in need thereof comprising selectively targeting TAM subpopulations linked to different intratumoral regions, such as hypoxic or normoxic regions of a solid tumor. As a specific embodiment, the above method comprises administering to the mammal a pharmaceutically effective amount of an immunoglobulin single variable domain or a pharmaceutical composition or a polypeptide according to the invention, in particular an immunoglobulin single variable domain fused to a toxin, or to a cytotoxic drug, or to an enzyme capable of converting a prodrug into a cytotoxic drug, or to a radionuclide, or coupled to a cytotoxic cell, and the like (see also Example section).

As used herein, "TAM subpopulations" refer to distinct subsets of tumor-associated macrophages (TAMs) that are present in a tumor environment, which are characterized by the differential expression of molecular markers. For a detailed description of different TAM subpopulations, reference is made to the Example section, in particular Examples 1 to 8, and Example 24, and Table 1. For example, the macrophage mannose receptor is one of the molecular markers which is specifically expressed on a TAM subpopulation which resides predominantly in the hypoxic regions of a tumor. According to particular embodiments, a TAM subpopulation can be defined as MHC II$^{low}$ or MHC II$^{hi}$. In a preferred embodiment, the TAM subpopulation is defined as MHC II$^{low}$.

The immunoglobulin single variable domain and/or pharmaceutical composition may be administered by any suitable method within the knowledge of the skilled man. The administration of a nanobody as described above or a pharmaceutically acceptable salt thereof may be by way of oral, inhaled or parenteral administration. In particular embodiments the nanobody is delivered through intrathecal or intracerebroventricular administration. The active compound may be administered alone or preferably formulated as a pharmaceutical composition. An amount effective to treat a certain disease or disorder that express the antigen recognized by the nanobody depends on the usual factors such as the nature and severity of the disorder being treated and the weight of the mammal. However, a unit dose will normally be in the range of 0.01 to 50 mg, for example, 0.01 to 10 mg, or 0.05 to 2 mg of nanobody or a pharmaceutically acceptable salt thereof. Unit doses will normally be administered once or more than once a day, for example, two, three, or four times a day, more usually one to three times a day, such that the total daily dose is normally in the range of 0.0001 to 1 mg/kg; thus a suitable total daily dose for a 70 kg adult is 0.01 to 50 mg, for example, 0.01 to 10 mg or more usually 0.05 to 10 mg. It is greatly preferred that the compound or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colorants, flavorings, and wetting agents. The tablets may be coated according to well known methods in the art. Suitable fillers for use include cellulose, mannitol, lactose and other similar agents. Suitable disintegrants include starch, polyvinylpyrrolidone and starch derivatives such as sodium starch glycolate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example, methyl or propyl p-hydroxybenzoate or sorbic acid, and if desired conventional flavoring or coloring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example, between 1 and 5 microns, such as between 2 and 5 microns. A favored inhaled dose will be in the range of 0.05 to 2 mg, for example, 0.05 to 0.5 mg, 0.1 to 1 mg or 0.5 to 2 mg. For parenteral administration, fluid unit dose forms are prepared containing a compound of the present invention and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned. All these medicaments can be intended for human or veterinary use.

The efficacy of the immunoglobulin single variable domains of the invention, and of compositions comprising the same, can be tested using any suitable in vitro assay, cell-based assay, in vivo assay and/or animal model known per se, or any combination thereof, depending on the specific disease or disorder involved.

In a specific embodiment it should be clear that the therapeutic method of the present invention against cancer can also be used in combination with any other cancer therapy known in the art such as irradiation, chemotherapy or surgery.

Reliable hypoxia tracers that can be used for non-invasive tumor imaging are currently unavailable or limiting. The availability of such tracers would represent a significant progress in the field of radiotherapy, since they would allow the radiotherapist to adapt the radiation dose, depending on the targeted tumor region (hypoxic versus normoxic). The identification of tumor-associated macrophage (TAM) subsets that are situated in hypoxic/normoxic environments allows for the identification of macrophage-specific biomarkers that can be used for non-invasive imaging of hypoxic/normoxic areas in tumors. For example, MMR represents such a marker, since it is preferentially expressed on the hypoxic MHC II$^{low}$ TAMs. Due to their small size and high tumor penetrance, nanobodies are the ideal format for non-invasive imaging. Nanobodies raised against markers that are preferentially expressed on the hypoxic MHC II$^{low}$ TAMs can be used for the imaging of hypoxia in tumors. The anti-MMR nanobodies can be used in this respect.

Other applications of TAM subset-specific nanobodies, coupled to tracers for imaging (for example, Near Infrared Fluorescent or NIRF tracers), include but are not limited to (i) accurately quantifying the amount of TAM or TAM subsets inside any given tumor, which can be of prognostic value, (ii) assessing the impact of therapy—including TAM-directed therapies as presently claimed—on the amount and/or the activation state of TAM, (iii) visualizing hypoxic/normoxic regions within the tumor.

Accordingly, in a further aspect, the present invention also encompasses a method of in vivo imaging tumor cells in a subject, the method comprising the step of:
  administering to the subject an immunoglobulin single variable domain according to the invention fused to a detectable label.

As used herein, "tumor cells" or simply "tumor" refers to the tumor tissue as a whole, including different cell types that are present in a tumor environment. Tumor cells include cancer cells but also non-transformed host cells, or tumor-associated stroma cells. Examples of tumor-associated stroma cells include myeloid cells, in particular tumor-associated macrophages.

Preferably, the above described method may further comprise one or more of the following steps of:
- selectively targeting and/or visualizing tumor-associated macrophage (TAM) subpopulations linked to different intratumoral regions, in particular wherein the intratumoral regions include a hypoxic or normoxic region of a solid tumor;
- determining a relative percentage of the TAM subpopulations, and optionally assessing the impact of a cancer therapy on the relative percentage of the tumor-associated macrophage subpopulations;

Further, in still another aspect, the present invention envisages a method of diagnosing cancer or prognosing cancer aggressiveness in a subject suffering from or suspected to suffer from cancer comprising the steps of:
- utilizing any of the immunoglobulin single variable domains according to the invention to determine the relative percentage of tumor-associated macrophage subpopulations in the subject; and
- diagnosing cancer or prognosing cancer aggressiveness in the subject according to the relative percentage of the TAM subpopulations; and optionally
- assessing the impact of a cancer therapy on the relative percentage of the tumor-associated macrophage subpopulations.

In particular embodiments, the method comprises the steps of (i) providing a sample from the individual comprising cancer cells or suspected to comprise cancer cells; (ii) determining in the sample the relative percentage of TAM subpopulations; (iii) classifying the individual as having a good/prognosis or diagnosing the individual as having cancer according to the results of step (ii). To further illustrate this, reference is made to Example 19.

A sample may comprise any clinically relevant tissue sample, such as a tumor biopsy or fine needle aspirate, or a sample of bodily fluid, such as blood, plasma, serum, lymph, ascitic fluid, cystic fluid, urine or nipple exudate. The sample may be taken from a human, or, in a veterinary context, from non-human animals such as ruminants, horses, swine or sheep, or from domestic companion animals such as felines and canines. The sample may also be paraffin-embedded tissue sections. It is understood that the cancer tissue includes the primary tumor tissue as well as a organ-specific or tissue-specific metastasis tissue.

In the context of the present invention, prognosing an individual suffering from or suspected to suffer from cancer refers to a prediction of the survival probability of individual having cancer or relapse risk which is related to the invasive or metastatic behavior (i.e., malignant progression) of tumor tissue or cells. As used herein, "good prognosis" means a desired outcome. For example, in the context of cancer, a good prognosis may be an expectation of no recurrences or metastasis within two, three, four, five years or more of initial diagnosis of cancer. "Poor prognosis" means an undesired outcome. For example, in the context of cancer, a poor prognosis may be an expectation of a recurrence or metastasis within two, three, four, or five years of initial diagnosis of cancer. Poor prognosis of cancer may indicate that a tumor is relatively aggressive, while good prognosis may indicate that a tumor is relatively nonaggressive.

As used herein, the terms "determining," "measuring," "assessing," and "assaying" are used interchangeably and include both quantitative and qualitative determinations. In particular, ways to determine the relative percentage of TAM subpopulations are known to the person skilled in the art, for example, by using flow cytometry, and is illustrated into more detail, but without the purpose of being limitative, in the Example section.

Next, it is commonly known that finding tumor-specific markers for antibody-based targeting remains a difficult task. This is especially true when targeting the tumor stroma, since stromal antigens are typically not restricted to tumors. This may hamper the usefulness of these tools both for diagnostic and therapeutic applications. Therefore, a strategy was developed to reduce the targeting of tracers to healthy organs to background levels, while preserving an efficient targeting of the tumor. Unexpectedly, it was found that co-injecting monovalent labeled nanobody directed against the macrophage mannose receptor and excess of unlabeled bivalent immunoglobulin single variable domain directed against the same target, blocked all extratumoral sites, while only slightly affecting tumor-specific tracer uptake. The monovalent-labeled—bivalent-unlabeled immunoglobulin single variable domain approach as described herein is especially attractive since bivalent immunoglobulin single variable domains do not efficiently compete for free binding sites in the tumor, while they block extratumoral sites much more efficiently.

Thus, according to a preferred embodiment, any of the above described methods for in vivo imaging, diagnosis/prognosis or treatment of cancer may comprise an additional step of co-administering a monovalent labeled immunoglobulin single variable domain according to the invention and an unlabeled bivalent form of an immunoglobulin single variable domain directed against the same target (macrophage mannose receptor) to block extratumoral binding sites. According to a preferred embodiment, the unlabeled bivalent form of the anti-MMR immunoglobulin single variable domain may comprise two identical or two different immunoglobulin single variable domains, as long as at least one of the immunoglobulin single variable domains is directed against the same target (macrophage mannose receptor). As used herein, "unlabeled" refers to the absence of a detectable label, in particular a radio-isotope or radio-active tracer as defined hereinbefore. It should be clear that this does not exclude the absence of another modification (as defined hereinbefore).

A further aspect of the invention relates to a method for producing an immunoglobulin single variable domain according to the invention or a polypeptide comprising an immunoglobulin single variable domain according to the invention, the method comprising the steps of:
- expressing, in a suitable host cell or expression system, a nucleic acid sequence encoding an immunoglobulin single variable domain or a polypeptide comprising an immunoglobulin single variable domain according to the invention; and optionally
- isolating and/or purifying the immunoglobulin single variable domain or the polypeptide.

Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the immunoglobulin single variable domains can be done according to techniques known by the skilled person in the art.

The following examples more fully illustrate preferred features of the invention, but are not intended to limit the invention in any way. Those having ordinary skill in the art and access to the teachings herein will recognize additional modifications and embodiments within the scope thereof. Therefore, the present invention is limited only by the claims attached herein. All of the starting materials and reagents disclosed below are known to those skilled in the art, and are available commercially or can be prepared using well-known techniques.

EXAMPLES

Material and Methods to the Examples
Mice and Cell Lines

Female Balb/c and C57BL/6 mice were purchased from Harlan. Balb/c $CX_3CR1^{GFP/GFP}$ mice were a gift from Dr. Grégoire Lauvau (Universite de Nice-Sophia Antipolis, France) and Dr. Frédéric Geissmann (King's College London, UK). C57BL/6 MMR-deficient, CCR2-deficient and MMTVPyMT mice were provided by Etienne Pays (Universite Libre de Bruxelles), Frank Tacke (Aachen University) and Massimiliano Mazzone (KULeuven), respectively. All animal studies were approved by and performed according to the guidelines of the institutional review board. The Balb/c mammary adenocarcinoma cell line) TS/A[10] was provided by Dr. Vincenzo Bronte (Istituto Oncologico Veneto, Italy). The Balb/c mammary adenocarcinoma TS/A and 3LL-R clone of the C57BL/6 Lewis Lung Carcinoma and were injected subcutaneously (sc) in the flank or in the fat pads ($3 \times 10^6$ cells). 12 to 14 days after inoculation, TS/A and 3LL-R tumor-bearing mice were imaged. MMTV-PyMT mice bearing macroscopic tumors were consecutively imaged with distinct tracers 48 to 72 hours apart. Tumor dissection and flow cytometry were performed 96 hours after the last scan.

Tumor Preparation, Flow Cytometry and Cell Sorting

Tumors were chopped and incubated for 25 minutes (37° C.) with 10 U/ml Collagenase typeI, 400 U/ml Collagenase typeIV and 30 U/ml DNAseI (Worthington). Density gradients (Axis-Shield) were used to remove tissue debris and dead cells.

Commercial antibodies used for cell surface stainings are found in Table 2. Non-labeled anti-CCR2 (MC-21) was a gift of Dr. Matthias Mack (University of Regensburg, Germany). To prevent aspecific binding, rat anti-mouse CD16/CD32 (clone 2.4G2, BD Biosciences) was used. Nanobodies were labeled using Nanobodies were labeled using the Alexafluor®488 or Alexafluor®647 Protein Labeling kit (Invitrogen) according to the manufacturers' instructions.

To purify TAMs, CD11b$^+$ cells were isolated via MACS using anti-CD11b microbeads (Miltenyi Biotec). Subsequently, cells were sorted using a BD FACSAria™ II (BD Biosciences).

In Vivo Labeling of Blood Monocytes

Latex labeling of blood monocytes was performed as described earlier.[19,20] Briefly, to label Ly6C$^{low}$ monocytes and track their infiltration in tumors, mice were injected intravenously (iv) with 250 µl of 0.5 µm fluoresbrite yellow-green microspheres (Polysciences) diluted 1:25 in PBS. Twenty-four hours later, mice received sc TS/A injections. To label and track Ly6C$^{hi}$ monocytes, mice were injected iv with 250 µl of clodronate liposomes. Eighteen hours later, mice received iv latex injection and sc TS/A injection. Clodronate was a gift from Roche and was incorporated into liposomes as previously described.[21]

Bromodeoxyuridine Labeling and Ki67 Stainings

Tumor-bearing mice (14 days pi) were given an initial intraperitoneal injection of 1 mg BrdU (BD Biosciences), followed by continuous BrdU administration in the drinking water at a concentration of 0.8 mg/ml (Sigma). Tumors were collected after consecutive time points and BrdU intracellular stainings were performed following the manufacturer's instructions (BrdU labeling Kit, BD Biosciences). PE-labeled anti-Ki67 or matching isotype controls (BD Biosciences) was added together with FITC-labeled anti-BrdU in the final step of the intracellular staining protocol.

RNA Extraction, cDNA Preparation and Quantitative Real-Time PCR

RNA was extracted using TRIzol (Invitrogen) and was reverse-transcribed with oligo(dT) and SuperScript II RT (Invitrogen), following the manufacturer's instructions. Quantitative real-time PCR was performed in an iCycler, with iQ SYBR Green Supermix (Bio-Rad) using gene-specific primers (Table 2). PCR cycles consisted of 1-minute denaturation at 94° C., 45-second annealing at 55° C., and 1-minute extension at 72° C. Gene expression was normalized according to the expression of ribosomal protein S12.

Intracellular TNFα and iNOS Stainings

For intracellular TNFα stainings, freshly isolated TAMs were cultured in vitro for 1 hour, after which Brefeldin A (BD Biosciences) was added. Five hours later cells were fixed, permeabilized (Fix/Perm kit, eBioScience) and stained with anti-TNFα. For intracellular iNOS stainings, freshly isolated TAMs were cultured in vitro with or without 10 U/ml IFNγ and/or 10 ng/ml LPS. 12 hours later cells were fixed, permeabilized and stained with anti-iNOS. Normalized delta-Median Fluorescence Intensity (ΔMFI) was calculated as follows: [(MFI iNOS staining)−(MFI isotype staining)]/(MFI iNOS staining) FACS data were acquired using a BD FACSCanto II (BD Biosciences).

Measurement of Arginase Activity

The arginase activity in the lysate of 5 10$^5$ sorted TAMs was measured as described earlier.[22]

Immunohistochemistry and Hypoxia Measurements

For hypoxia stainings, tumor-bearing mice were injected with 80 mg/kg body weight pimonidazole (Hypoxyprobe-1, HP-1, HPI Inc.) and 2 hours later tumors were collected.

For immunohistochemistry, tumors were snap-frozen in liquid nitrogen and 5 µm sections were made. Sections were fixed for 10 minutes in ice-cold aceton. To block aspecific binding sites, sections were incubated 30 minutes with 10% normal donkey serum (Jackson ImmunoResearch Laboratories). For CD11b, MHC II and anti-HP-1 triple stainings, sections were: (1) incubated 30 minutes with purified rat anti-CD11b (BD Biosciences) and purified rabbit anti-HP-1 (HPI Inc.) (2) incubated 30 minutes with F(ab')$_2$ donkey anti-Rat/Cy3 (Jackson ImmunoResearch Laboratories) and F(ab')$_2$ donkey anti-rabbit/Cy5 (Jackson ImmunoResearch Laboratories) (3) remaining anti-rat binding sites were blocked with 5% normal rat serum (Jackson ImmunoResearch Laboratories) (4) incubated 30 minutes with rat anti-MHC II/alexa-fluor 488 (M5/114.15.2 Biolegend). Rat anti-MECA32 (Pan-endothelial cell antigen) was from BD Biosciences. Sections were mounted with fluorescent mounting medium (Dako). Pictures were acquired with a Plan-Neofluar 10×/0.30 or Plan-Neofluar 20×/0.50 (Carl Zeiss) objective on a Zeiss Axioplan 2 microscope (Carl Zeiss) equipped with an Orca-R2 camera (Hamamatsu) and Smartcapture 3 software (Digital Scientific UK). For flow cytometric HP-1 measurements, tumor single cell suspensions were made, and cells were fixed and permeabilized using the BD Biosciences Fix/Perm kit. Finally, rat anti-HP1/FITC (HPI Inc.) was added for 30 minutes at 37° C.

Determining Latex Phagocytosis In Vivo and In Vitro

For measuring in vivo latex uptake by TAMs, tumor-bearing mice were injected iv with 250 µl of yellow-green latex microspheres (Polysciences) diluted 1:25 in PBS. 1-2 hours later, tumor single cell suspensions were made and latex uptake by tumor CD11b$^+$ cells was assessed via FACS. For in vitro latex uptake, freshly isolated TAMs were cultured in 96-well plates for 40 minutes at 4° C. or 37° C., in the presence of latex (diluted 1:5000).

Chorioallantoic Membrane Angiogenesis Assays

Chorioallantoic membrane (CAM) assays were performed as described earlier.[23] Briefly, fertilized white leghorn chicken eggs (Wyverkens, Halle, Belgium) were incubated at 37° C. for three days prior to removing 3 ml of albumen to detach the shell from the developing CAM. Next, a window was made in the eggshell to expose the CAM. At day 9, sterile absorbable gelatin sponges (1-2 mm$^3$; Hospithera, Brussels, Belgium) were impregnated with 5×10$^4$ sorted TAM subsets and placed on the CAM. Sponges were also loaded with PBS/0.1% BSA (1 mg/ml, <50 µg/embryo) as negative control and with recombinant human VEGF-A$_{165}$ (100 µg/ml, <5 µg/embryo) as positive control. At day 13, membranes were fixed with 4% paraformaldehyde and the area around the implants was analyzed using a Zeiss Lumar V.12 stereomicroscope with NeoLumar S1.5× objective (15× magnification). Digital images were captured using an AxioCam MRc5 and processed with Axiovision 4.5 Software (Zeiss). To determine the number of blood vessels, a grid containing three concentric circles with diameters of 4, 5, and 6 mm was positioned on the surface of the CAM and all vessels radiating from the sample spot and intersecting the circles were counted under a stereomicroscope.

DQ-OVA Processing, MLR Assays, Suppression Assays

To assess TAM antigen processing, tumor single cell suspensions were incubated for 15 minutes at 0° C. or 37° C. in the presence of 10 µg/ml DQ-OVA (Molecular Probes), allowing for antigen uptake. After thorough washing, cells could further process DQ-OVA intracellularly during different time intervals, at 0° C. or 37° C. Following each time interval, cells were surface labeled and DQ-OVA fluorescence in each TAM subset was measured via FACS.

For Mixed Leukocyte Reaction (MLR) assays, T cells were purified from C57BL/6 spleens, by first depleting CD11c$^+$ and CD19$^+$ cells on a MACS LD column using anti-CD11c and anti-CD19 microbeads (Miltenyi biotech) and subsequently positively selecting CD4$^+$ or CD8$^+$ T cells using anti-CD4 or anti-CD8 microbeads (Miltenyi biotech). 2×10$^5$ purified C57BL/6 T cells were cultured with 5×10$^4$ sorted Balb/c TAMs or cDCs, in round-bottom 96-well plates. Three days later $^3$H-thymidine was added and cells were allowed to proliferate for another 18 hours before incorporated radioactivity was measured.

For T-cell suppression assays, 1×10$^5$ (1:2), 5×10$^4$ (1:4), 2.5×10$^4$ (1:8) or 1.25×10$^4$ (1:16) sorted TAMs or cDCs were added to 2×10$^5$ naive Balb/c splenocytes, in flat-bottom 96-well plates. These co-cultures were promptly stimulated with 1 µg/ml anti-CD3, 24 hours later $^3$H-thymidine was added and cells were allowed to proliferate for another 18 hours before incorporated radioactivity was measured. L-NMMA (0.5 mM, Sigma), nor-NOHA (0.5 mM, Calbiochem), or both, were added from the beginning of the culture. The Relative % suppression of proliferation was calculated as described earlier.[24] (% Suppression without inhibitor)/(% Suppression with inhibitor)×100, with % Suppression calculated as [1-(proliferation of splenocytes)/(proliferation splenocytes+TAMs)]×100.

Sorting of Splenic Conventional DCs

To purify splenic conventional DCs, spleens were flushed with 200 U/ml collagenase III (Worthington) and squashed. Subsequently, CD11c$^+$ cells were enriched via MACS, using anti-CD11c microbeads (Miltenyi Biotec), after which CD11c$^+$MHC II$^{hi}$B220$^-$Ly6C$^-$ DCs were sorted using a BD FACSAria™ II (BD Biosciences).

Statistics

Statistical significance was determined by the Student's t test, using Microsoft Excel or GraphPad Prism 4.0 software. Differences were considered significant when P≤0.05. Geometric means and confidence intervals were determined using Microsoft Excel.

Where multiple comparisons are made (nine to ten different organs), the p-values of the student's t test were adjusted by Holm's procedure.[42] The R environment[43] and the multtest package[44] were used for statistical analyses and figures. The significance of the student t tests and corrections for multiple testing was set to 0.05.

Generation of Mono- and Bivalent Anti-MMR Nanobodies

The anti-MMR Nanobody (Nb) clone 1 was isolated from an immune phage library in a similar way as described before.[30,31] In brief, an alpaca (Vicugna pacos) was immunized with 100 µg MMR (R&D Systems) six times at weekly intervals. mRNA prepared from peripheral blood lymphocytes was used to make cDNA with the Ready-to-Go You-prime-first-strand beads (GE Healthcare). The gene sequences encoding the VHHs were PCR amplified using the CALL001/CALL002 and A6E/38 primer pairs. These PCR fragments were ligated into the pHEN4 phagemid vector after digestion with the PstI and BstEII restriction enzymes. Using M13K07 helper phage infection, the VHH library was expressed on phages and specific Nanobody-phages were enriched by several consecutive rounds of in vitro selection on microtiter plates (Nunc). Individual colonies were screened in ELISA for antigen recognition with non-specific phage particles serving as a negative control. The VHH genes of the clones that scored positive in ELISA were recloned into the expression vector pHEN6 using the restriction enzymes PstI and BstEII. Expression in the periplasm and purification of Nanobody was performed as described previously.[28]

Bivalent Nanobodies were generated by recombinantly attaching a linker sequence 3' of the VHH sequence using PCR primer biNbF (5'-CCG GCC ATG GCC CAG GTG CAG CTT CAG GAG TCT GG AGG AGG-3'; SEQ ID NO:117) and primers biNbG4SR (5'-TGA TTC CTG CAG CTG CAC CTG ACT ACC GCC GCC TCC AGA TCC ACC TCC GCC ACT ACC GCC TCC GCC TGA GGA GAC GGT GAC CTG GGT C-3'; SEQ ID NO:118), biNbg2cR (5'-TGA TTC CTG CAG CTG CAC CTG TGC CAT TGG AGC TTT GGG AGC TTT GGA GCT GGG GTC TTC GCT GTG GTG CGC TGA GGA GAC GGT GAC CTG GGT C-3'; SEQ ID NO:119), biNbIgAR (5'-TGA TTC CTG CAG CTG CAC CTG ACT TGC CGG TGG TGT GGA TGG TGA TGG TGT GGG AGG TGT AGA TGG GCT TGA GGA GAC GGT GAC CTG GGT C-3'; SEQ ID NO:120) which code for a (G$_4$5)$_3$ (GGGGSGGGGSGGGGS; SEQ ID NO:121), llama IgG2 hinge (AHHSEDPSSKAPKAPMA; SEQ ID NO:122) or human IgA hinge (SPSTPPTPSPSTPPAS; SEQ ID NO:123) linker respectively. These PCR fragments were inserted 5' of the VHH gene in the original VHH expression vector with a PstI/BstEII restriction digest. After ligation, the resulting bivalent anti-MMR Nanobody vector was expressed as described above.

Construction and Production Anti-MMR-PE38 Immunotoxins

Anti-MMR-PE38 toxin fusions were generated using the anti-MMR bivalent Nanobodies as templates. The PE38 (recombinant *Pseudomonas* Exotoxin A[33] gene was PCR amplified from the pET28aCD11scFv-PE38 vector[32] using the PE38HF (5'-ATT GAA TTC TAT TAG TGG TGG TGG TGG TGG TGC TCG AGT G -3'; SEQ ID NO:124) and PE38bisR (5'-TTA ACT GCA GAT GGC CGA AGA GGG CGG CAG CCT-3'; SEQ ID NO:125) primers. During this PCR reaction a PstI and EcoRI restriction site were introduced 5' and 3' of the PE38 gene respectively. Both the PE38 PCR fragments and the pHEN6 vectors containing bivalent anti-MMR Nanobody genes with a $(G_4S)_3$ (GGGGSGGGGSGGGGS; SEQ ID NO:121), llama IgG2 hinge (AHHSEDPSSKAPKAPMA; SEQ ID NO:122) or human IgA hinge (SPSTPPTPSPSTPPAS; SEQ ID NO:123) linker were digested using PstI and EcoRI restriction enzymes. By ligating the PE38 gene fragment in the pHEN6 vector fragments, the PE38 gene was fused to the 3' end of the anti-MRR Nanobody-linker gene. The resulting immunotoxin constructs were produced and purified in the same manner as the mono- and bivalent anti-MMR Nanobody constructs.

Surface Plasmon Resonance

Affinity analysis was performed using a BIAcore T100 (GE Healthcare) with HEPES-buffered saline running buffer (10 mM HEPES with 0.15 M NaCl, 3.4 mM EDTA and 0.005% surfactant P20 at pH 7.4). MRR was immobilized on a CM5 chip in acetate buffer 50 mM (pH 5.0), resulting in 2100 RU MMR coated on the chip. A second channel on the same chip was activated/deactivated in a similar way and served as a negative control. The MMR Nanobodies were used as analytes in eleven different concentrations, ranging from 1 to 2000 nM, at a flow rate of 10 ml/min. Glycine-HCl 50 mM (pH 2.0) was used for elution. The kinetic and equilibrium parameters (kd, ka and $K_D$) values were calculated from the combined sensogram of all concentrations using BIAcore T100 evaluation software 2.02 (GE Healthcare).

Nanobody Purification

All Nanobody proteins were purified from *E. coli* periplasmic extracts using immobilized metal affinity chromatography (IMAC) on Ni-NTA resin (Sigma-Aldrich, St. Louis, Mo.) followed by size exclusion chromatography (SEC) on Superdex 75 HR 10/30 (Pharmacia, Gaithersburg, Md.) in phosphate buffered saline pH 7.4 (PBS).

Nanobody Labeling and In Vitro Characterization of $^{99m}$Tc-Labeled Nanobodies Nanobodies were labeled with $^{99m}$Tc at their hexahistidine tail. For the labeling, $[^{99m}Tc(H_2O)_3(CO)_3]^+$ was synthesized by adding 1 mL of $^{99m}TcO4^-$ (0.74-3.7 GBq) to an Isolink kit (Mallinckrodt Medical BV) containing 4.5 mg of sodium boranocarbonate, 2.85 mg of sodium tetraborate.$10H_2O$, 8.5 mg of sodium tartrate.$2H_2O$, and 7.15 mg of sodium carbonate, pH 10.5. The vial was incubated at 100° C. in a boiling bath for 20 minutes. The freshly prepared $[^{99m}Tc(H_2O)_3(CO)_3]^+$ was allowed to cool at room temperature for 5 minutes and neutralized with 125 µL of 1 M HCl to pH 7-8. $[^{99m}Tc(H_2O)_3(CO)_3]^+$ was added to 50 µL of 1 mg/mL monovalent Nanobody or 2 mg/ml bivalent Nanobody, together with 50 µL of carbonate buffer, pH 8. The mixture was incubated for 90 minutes at 52° C. in a water bath. The labeling efficiency was determined by instant thin-layer chromatography in acetone as mobile phase and analyzed using a radiometric chromatogram scanner (VCS-201; Veenstra). When the labeling yield was less than 90%, the $^{99m}$Tc-Nanobody solution was purified on a NAP-5 column (GE Healthcare) pre-equilibrated with phosphate-buffered saline (PBS) and passed through a 0.22 µm Millipore filter to eliminate possible aggregates.

Pinhole SPECT-microCT Imaging Procedure

Mice were intravenously injected with 100-200 µl 45-155 MBq (about 5-10 µg) of $^{99m}$Tc-Nanobody, with or without an excess of concentrated monovalent or bivalent unlabeled Nanobody. Mice were anesthetized with a mixture of 18.75 mg/kg ketamine hydrochloride (Ketamine 1000®, CEVA, Brussels, Belgium) and 0.5 mg/kg medetomidin hydrochloride (Domitor®, Pfizer, Brussels, Belgium) 10-15 minutes before pinhole SPECT acquisition.

MicroCT imaging was followed by pinhole SPECT on separate imaging systems. MicroCT was performed using a dual source CT scanner (Skyscan 1178, Skyscan, Aartselaar, Belgium) with 60 kV and 615 mA at a resolution of 83 µm. The total body scan time was 2 minutes. Image reconstruction was performed using filtered backprojection (Nrecon, Skyscan, Aartselaar, Belgium). Total body pinhole SPECT was performed at 60 minutes or 180 minutes post-injection (p.i.) using a dual headed gamma camera (e.cam$^{180}$ Siemens Medical Solutions, IL, USA), mounted with two multi-pinhole collimators (three pinholes of 1.5 mm in each collimator, 200 mm focal length, 80 mm radius of rotation). Images were acquired over 360 degrees in 64 projections of 10 s into 128×128 matrices resulting in a total imaging time of 14 minutes. The SPECT images were reconstructed using an iterative reconstruction algorithm (OSEM) modified for the three pinhole geometry and automatically reoriented for fusion with CT based on six $^{57}$Co landmarks.

Image Analysis

Image viewing and quantification was performed using AMIDE Medical Image Data Examiner software. Ellipsoid regions of interest (ROIs) were drawn around the tumor and major organs. Uptake was calculated as the counts in the tissue divided by the injected activity counts and normalized for the ROI size (% IA/cm$^3$). High-resolution image 3D-reconstructions were generated using OsiriX Imaging Software.

Biodistribution Analysis

Thirty minutes after microCT/SPECT acquisition, mice were sacrificed with a lethal dose of pentobarbital (Nembutal; CEVA). Tumor, kidneys, liver, lungs, muscle, spleen, lymph nodes, bone, heart, and blood were removed and weighed, and the radioactivity was measured using an automated γ-counter (Cobra II Inspector 5003; Can berra-Packard). Tissue and organ uptake was calculated as percentage of injected activity per gram of tissue (% IA/g), corrected for decay.

Immunofluorescence Stainings

Mice were injected intravenously with 500 µg Alexafluor647-labeled Nbs and intraperitoneally with 80 mg/kg pimonidazole [hypoxyprobe-1, HPI, Inc.] for hypoxia stainings Two hours later, tumors were fixed in 4% paraformaldehyde, rehydrated overnight (20% sucrose) and sectioned (5 µm). Antibodies were: rat anti-F4/80/alexa-fluor488 (CI:A3-1, Serotec), F(ab') 2 donkey anti-rabbit/Cy3 Jacksonlmmuno). Pictures were acquired with a Plan-Neofluar 10×/0.30 or 20×/0.50 (Carl Zeiss) objective on a Zeiss Axioplan2 microscope with an Orca-R2 camera (Hamamatsu) and Smartcapture 3 software (Digital Scientific UK).

Activation of Immune Cells In Vitro and In Vivo

Mono- or bivalent α-MMR and BCII10 Nbs were added in varying concentrations to bone marrow-derived dendritic cells (BMDCs) or bone marrow-derived macrophages (BM-DMs) (0.2 µg/ml, 2 µg/ml and 20 µg/ml for monovalent Nbs and 0.4 µg/ml, 4 µg/ml and 40 µg/ml for bivalent Nbs) for 24 hours in vitro in the presence or absence of LPS (10 ng/ml).

For assessment of the effect of α-MMR Nb in vivo, naïve mice and 13 days 3LL-R tumor-bearing mice were injected intravenously with 5 µg monovalent Nb+200 µg bivalent Nb.

After 0 hours, 6 hours and 24 hours, blood serum was collected by heart puncture, incubated for 30 minutes at 37° C. and centrifuged (1000×g, 10 minutes).

Cytokines and chemokines were quantified in culture supernatants or blood serum with specific sandwich ELISAs for IL-10 (BD Biosiences), TNF (R&D Systems), CCL17 (R&D Systems), IL1Ra (R&D Systems) or CCL22 (R&D Systems) in accordance with the protocol provided by the manufacturer.

Generation of Anti-Human MMR and Anti-Human/Mouse MMR Cross-Reactive Nanobodies

The anti-human macrophage mannose receptor (MMR) and anti-human/mouse MMR cross-reactive nanobodies (Nbs) were isolated from an immune phage library in a similar way as described before.[29, 30, 31] However, in order to generate cross-reactive Nbs, an alternating immunization schedule was carried out. An alpaca (Vicugna pacos) was immunized with 100 µg human MMR (R&D Systems #2534) followed by 100 µg mouse MMR (R&D Systems #2535) one week later. This alternating schedule was maintained for a total of 6 weeks and both proteins were mixed with the Gerbu adjuvant before injection. After immunization, blood was collected and the peripheral blood lymphocytes were isolated. mRNA was extracted from these cells using TRIzol (Invitrogen) and was reverse-transcribed with oligo(dT) and SuperScript II RT (Invitrogen), following the manufacturer's instructions. The gene sequences encoding the variable domains (VHHs) were PCR amplified, with the leader sequence specific CALL001 (5'-GTC CTG GCT CTC TTC TAC AAG G-3'; SEQ ID NO:252) and $CH_2$ exon specific CALL002 (5'-GGT ACG TGC TGT TGA ACT GTT CC-3'; SEQ ID NO:253) primers. After 1% agarose gel separation, the 600 bp fragment VHH-$CH_2$ fragment was isolated from gel and re-amplified using the nested primers A6E (5'-GAT GTG CAG CTG CAG GAG TCT GGR GGA GG-3'; SEQ ID NO:254) and PMCF (5'-CTA GTG CGG CCG CTG AGG AGA CGG TGA CCT GGG T-3'; SEQ ID NO:255) specific for the framework-1 and framework-4 regions, respectively. These PCR fragments were ligated into the phagemid vector pMECS, a variant of pHEN4,[52] after digestion with the PstI and NotI restriction enzymes. The pMECS differs from the pHEN4 in coding for a HA (YPYDVPDYGS; SEQ ID NO:256) and 6xhistidine tag fusion at the C-terminus of the Nb instead of a HA tag only fusion. Ligated material was transformed in freshly prepared E. coli TG1 cells and plated on LB plates with ampicillin. The colonies were scraped from the plates, washed and stored at −80° C. in LB-medium supplemented with glycerol (50% final concentration). Using M13VCS helper phage infection, the VHH library was expressed on phages. Specific Nanobody-phages were enriched by several consecutive rounds of in vitro selection on antigen coated to wells of microtiter plates (Nunc). For isolation of human/mouse MMR cross-reactive Nbs, screening was performed using human and mouse MMR alternatingly. Bound phage particles were eluted with 100 mM triethylamine (pH 11.0), immediately neutralized with 1 M Tris-HCl (pH 7.4) and used to infect E. coli TG1 cells. Individual colonies were picked and expression of recombinant Nanobody-M13 protein III by addition of 1 mM isopropyl-β-D-thiogalac-topyranoside (IPTG). The periplasmic extract of each clone was subsequently tested in ELISA for human MMR recognition with non-specific antigen coated wells serving as a negative control. Human/mouse MMR cross-reactive Nbs were also screened in a similar fashion against mouse MMR, only clones reactive with both human and mouse antigens were withheld as cross-reactive Nbs. Each ELISA was performed on plates coated with 1 µg/ml MMR in 100 mM $NaHCO_3$ buffer pH=8.8. After coating the plates are washed with PBS+0.05% Tween-20 (PBST) and blocked for two hours with PBS+0.05% Tween-20+2% non-fat dry milk-powder (Nestle) (PBSM). The PE extracts are then incubated for 1 hour on the plate and then washed with PBST followed by 1 hour incubation of 0.5 µg/ml mouse anti-HA tag antibody (16B12, Covance) in PBSM. After washing with PBST, 1.5 µg/ml alkaline phosphatase conjugated anti-mouse antibody (Sigma) in PBSM in added to the plate for 1 hour followed by PBST washing. Finally, the ELISA is developed using 2 mg/ml alkaline phosphatise substrate (Sigma) in AP-buffer (100 mM NaCl, 50 mM $MgCl_2$, 100 mM Tris pH=9.5) and the optical density signal at 405 nm is measured.

Expression and Purification of Anti-Human MMR and Anti-Human/Mouse MMR Cross-Reactive Nanobodies The pMECS-Nb plasmids of the clones that scored positive in ELISA were transformed into E. coli WK6 cells. These cells stop translation at the TAG codon and therefore express the Nbs without a phage protein fusion. Production of recombinant VHH was performed in shaker flasks by growing the bacteria in Terrific Broth supplemented with 0.1% glucose and ampicillin until an absorbance at 600 nm between 0.6 and 0.9 was reached. VHH expression was then induced with 1 mM IPTG for 16 hours at 28° C. After pelleting the cells, the periplasmic proteins were extracted by osmotic shock. This periplasmic extract was loaded on a nickel-nitrilotriacetic acid (Thermo Scientific), and after washing, the bound proteins were eluted in PBS with 500 mM imidazol. The eluted fraction was dialyzed to Vivaspin 2 centrifugal concentrators (Sartorius). The final purity of the protein was checked by SDS-PAGE. The final yield was determined from UV absorption at 280 nm using the calculated theoretical extinction coefficient of the VHH.

Example 1

Figure 6:
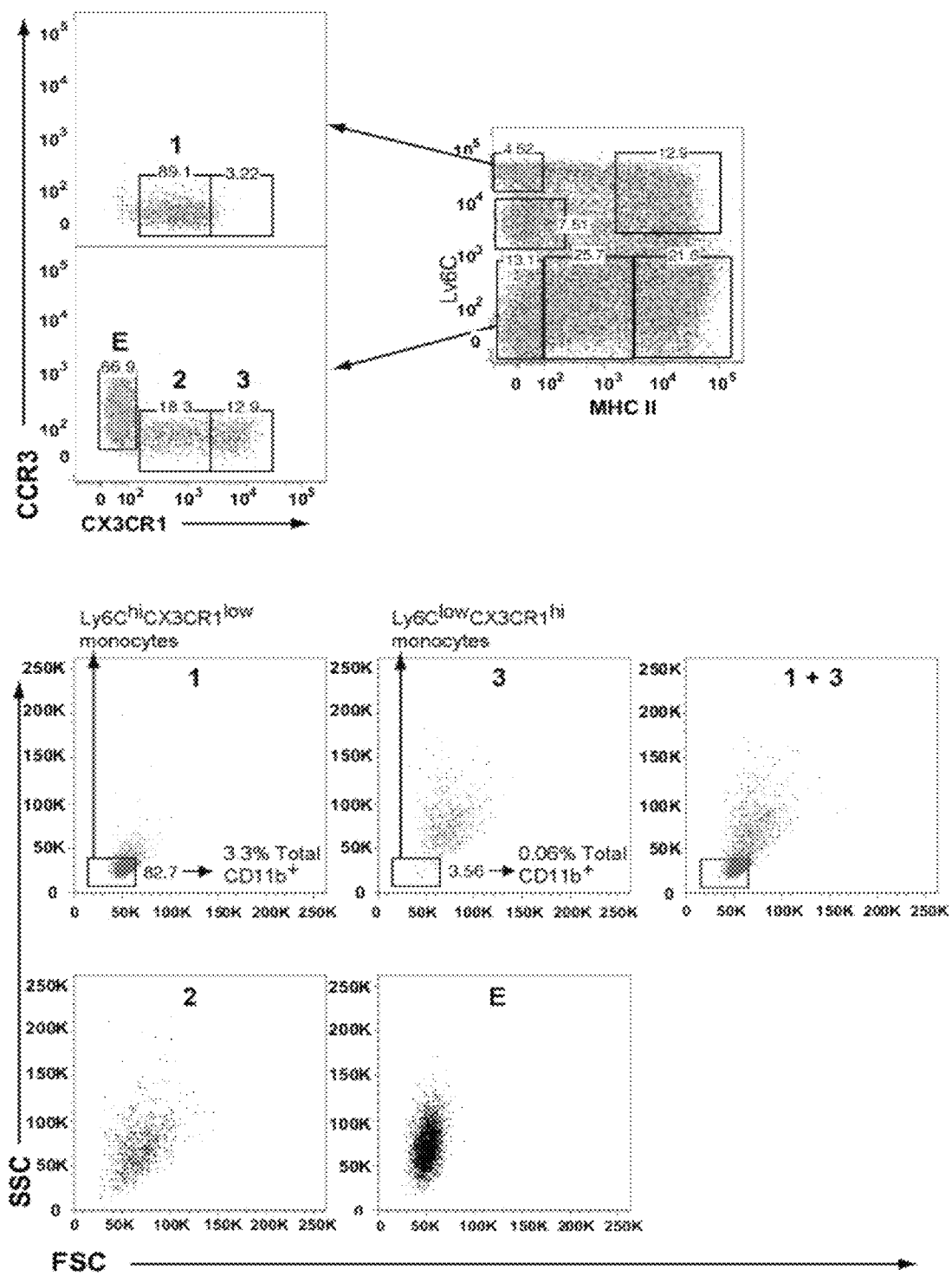
FIG. 6: Identifying Ly6C$^{hi}$ and Ly6C$^{low}$ monocytes in tumors. Eleven-day-old tumors were collected from CX$_3$CR1$^{GFP/+}$ reporter mice. Within the gated CD11b$^+$ population, Ly6C$^{hi}$MHC II$^-$ and Ly6C$^{low}$MHC II$^-$ cells were subgated and their respective CX$_3$CR1 vs. CCR3 plots are shown. Ly6C$^{hi}$MHC II$^-$ cells were CCR3–CX$_3$CR1$^{low}$ (Gate 1). Ly6C$^{low}$MHC II$^-$ cells could be subdivided in CCR3$^-$CX$_3$CR1$^{low}$ (Gate 2), CCR3$^-$CX$_3$CR1$^{hi}$ (Gate 3) and CCR3$^+$CX$_3$CR1– cells (Gate E, comprising of eosinophils). Forward vs. Side Scatter plots for the distinct gates are shown in the bottom panel. Similar results were seen at different time points of tumor growth. For the indicated time point, results are representative of three independent experiments.

TS/A Tumors are Highly Infiltrated with a Heterogeneous Population of Myeloid Cells Containing Distinct Granulocyte and Monocyte/Macrophage Subsets To study the tumor-infiltrating myeloid compartment, we employed the Balb/c mammary adenocarcinoma model TS/A. Subcutaneous tumors contained a large $CD11b^+$ fraction, indicating a high infiltration of myeloid cells (FIG. 1A). Interestingly, this $CD11b^+$ population was heterogeneous and encompassed at least 7 subsets, which could be readily distinguished based on their differential expression of MHC class II and Ly6C (FIG. 1A). $Ly6C^{hi}MHC\ II^-$ cells (Gate 1: FIG. 1A) were $F4/80^+CX_3CR1^{low}CCR2^{hi}CD62L^+$, did not express the granulocyte markers Ly6G or CCR3 and had a small size and granularity ($FSC^{low}SSC^{low}$), indicating that they were $Ly6C^{hi}$ monocytes (FIGS. 1A, 1C and FIG. 6). The $CD11b^+MHC\ II^+$ cells in Gates 2-4 were reminiscent of macrophages, having an enlarged macrophage-like scatter and expressing high levels of F4/80 (FIGS. 1A, 1C). Remarkably, distinct subsets of tumor-associated macrophages (TAMs) were clearly distinguishable: $Ly6C^{int}MHC\ II^{hi}$ ($Ly6C^{int}$ TAMs, Gate 2), $Ly6C^{low}MHC\ II^{hi}$ ($MHC\ II^{hi}$ TAMs, Gate 3) and $Ly6C^{low}MHC\ II^{low}$ ($MHC\ II^{low}$ TAMs, Gate 4). The majority of $Ly6C^{low}MHC\ II^-$ cells were $CCR3^+CX_3CR1^-$ eosinophils (Gate 5: FIG. 1A and Gate E: FIG. 6). However, $Ly6C^{low}MHC\ II^-$ cells also consisted of $CCR3^-CX_3CR1^{li}$ (Gate 2: FIG. 6) and $CCR3^-CX_3CR1^{hi}$ (Gate 3: FIG. 6) cells, the latter possibly resembling $Ly6C^{low}CX_3CR1^{hi}$ monocytes. However, the majority of these $CX_3CR1^{hi}$ cells did not have a monocyte scatter, suggesting they were TAMs (FIG. 6). This suggests that Ly6C$^{low}$ monocytes were not present in significant amounts in these tumors. Finally, TS/A tumors were also infiltrated with CCR3$^+$Ly6C$^{int}$ eosinophils (Gate 6: FIG. 1A), and Ly6G$^{hi}$ neutrophils (Gate 7: FIG. 1A).

Interestingly, the relative percentages of these distinct myeloid subpopulations dramatically changed as tumors progressed (FIG. 1B). Within the TAM compartment, the percentage of Ly6C$^{int}$ TAMs decreased, while the Ly6C$^{low}$MHC II$^{low}$ TAM subset became gradually more prominent, reaching up to 60% of the myeloid tumor-infiltrate in large tumors (>10 mm).

Example 2

Ly6C$^{hi}$ Monocytes are the Precursors of all TAM Subsets in TS/A Tumors

Figure 2:
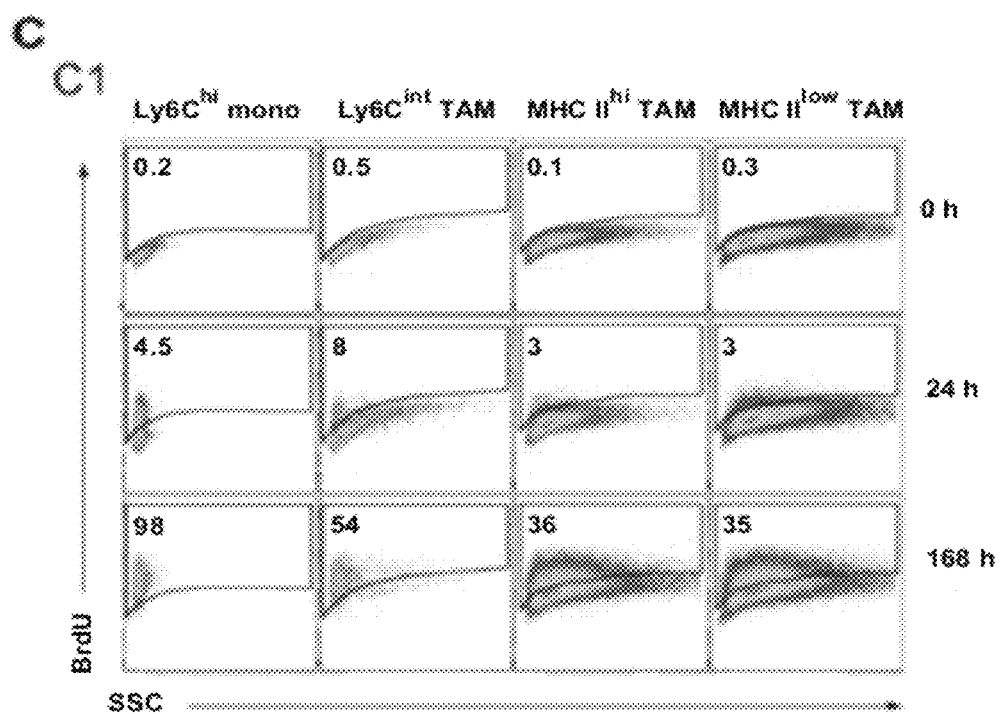
FIG. 2: Infiltration of latex-labeled monocytes in tumors and kinetics of BrdU incorporation in the distinct TAM subsets. (A) Six-day-old tumors were collected from control mice or mice in which the Ly6Clow or Ly6Chi monocytes were labeled. Plots are gated on CD11b+ cells. n=3 experiments. (B1) 6-, 12- or 19-day-old tumors were collected from untreated mice (control) or mice in which the Ly6Chi monocytes were labeled (latex injected). Plots are gated on CD11b+ cells. (B2) Ly6C vs. MHC II plots of tumor single-cell suspensions from latex injected mice at 6, 12 or 19 days p.i, either gated on the total CD11b+ population or on the latex+CD11b+ population. n=3 experiments. (C) Two weeks tumor-bearing mice were left untreated (0 hours) or continuously given BrdU for the indicated time, after which BrdU incorporation in tumor cells was measured. C1 shows how BrdU+ cells were gated in the different TAM subsets. n=2 BrdU-kinetic experiments (D) The intracellular expression of Ki67 was assessed via flow cytometry. Shaded histograms are isotype controls. n>3.

Macrophages typically derive from circulating blood-borne precursors such as monocytes. The presence of Ly6C$^{hi}$, but not Ly6C$^{low}$, monocytes in TS/A tumors suggested that the former could be more efficiently recruited to tumors and function as the TAM precursor. To investigate this, we selectively labeled Ly6C$^{hi}$ or Ly6C$^{low}$ monocyte subsets in vivo with fluorescent latex beads, using a previously described procedure.[11, 12]. This method has been validated to stably label the respective monocyte subsets for 5 to 6 days in naïve mice. Hence, TS/A was injected after Ly6C$^{low}$ or Ly6C$^{hi}$ monocyte labeling and tumors were collected 6 days pi. No appreciable numbers of tumor-infiltrating latex$^+$monocytes were observed when applying the Ly6C$^{low}$ labeling strategy (FIG. 2A). In contrast, Ly6C$^{hi}$ labeling resulted in the detection of a significant fraction of CD11b$^+$latex$^+$ monocytes, illustrating that Ly6C$^{hi}$ monocytes are the main tumor-infiltrating monocyte subset. With this approach, latex$^+$ cells could be detected up to 19 days post tumor injection (FIG. 2B), allowing a follow-up of the monocyte progeny in the course of tumor growth. At day 6, latex$^+$Ly6C$^{hi}$ monocytes had differentiated into latex$^+$Ly6C$^{int}$ TAMs, and to some extent also into latex$^+$MHC and latex$^+$MHC II$^{low}$ TAMs (FIG. 2B). From day 12 onward, the majority of latex$^+$Ly6C$^{hi}$ monocytes had converted into latex$^+$MHC II$^{hi}$ and latex$^+$ MHC II$^{low}$ TAMs. Together, these data demonstrate that all TAM subsets can be derived from Ly6C$^{hi}$ monocytes.

Example 3

Ly6C$^{int}$, MHC II$^{hi}$ and MHC TAMs have Distinct Differentiation Kinetics and Turnover Rates To determine the turnover rate and differentiation kinetics of the monocyte/TAM subsets, BrdU was administered continuously to tumor-bearing animals and its incorporation was measured at consecutive time points. Tumor-infiltrating Ly6C$^{hi}$ monocytes quickly became BrdU$^+$, reaching plateau values after 48 hours of BrdU administration (FIG. 2D). This indicates a rapid monocyte turnover rate and/or proliferation of monocytes inside tumors. Remarkably, intratumoral Ly6C$^{hi}$ monocytes were Ki67$^+$, suggesting a proliferative potential (FIG. 2C). In contrast, TAMs were non-proliferating (Ki6T) and hence unable to directly incorporate BrdU. Therefore, BrdU$^+$ TAMs must differentiate from BrdU$^+$ monocytes, resulting in a lag phase of BrdU positivity. Indeed, only a minor fraction of MHC II$^{hi}$ and MHC II$^{low}$ TAMs were BrdU$^+$ upon 24 hours BrdU administration (FIG. 2D). However, compared with these subsets, Ly6C$^{int}$ TAMs incorporated BrdU at a faster rate, with a higher percentage being BrdU$^+$ already at 24 hours. These results suggest that monocytes first give rise to Ly6C$^{int}$ TAMs, which then differentiate into MHC II$^{hi}$ and MHC II$^{low}$ TAMs. MHC II$^{hi}$ and MHC II$^{low}$ TAMs incorporated BrdU slowly and with similar kinetics, arguing for a comparable and low turnover rate.

Example 4

MHC II$^{hi}$ and MHC II$^{low}$ TAMs Differ at the Molecular Level

Efforts have been made before to characterize TAMs at the molecular level.[13, 14] We characterized the distinct TAM subsets at the gene and protein level. The gene expression of sorted MHC II$^{hi}$ and MHC II$^{low}$ TAMs (FIG. 7A) was analyzed via qRT-PCR (Table 1). Ly6C$^{int}$ TAMs, constituting only a minor fraction in larger tumors, were not included in this analysis. Interestingly, when comparing MHC II$^{hi}$ with MHC II$^{low}$ TAMs (Table 1 hi/low), M2-associated genes such as Arg1 (Arginase-1), Cd163, Stab1 (Stabilin-1) and Mrc1 (MMR) were higher expressed in the MHC II$^{low}$ subset. In contrast, more M1-type, pro-inflammatory genes such as Nos2 (iNOS), Ptgs2 (Cox2), Il1b, Il6 and Il12b were up-regulated in MHC II$^{hi}$ TAMs. This differential activation state was also reflected at the protein level. Membrane expression of the M2 markers macrophage mannose receptor (MMR), macrophage scavenger receptor 1 (SR-A) and IL-4Rα were clearly higher on MHC II$^{low}$ TAMs, while the M1-associated marker CD11c, was only expressed on MHC II$^{hi}$ TAMs (FIG. 1C). Moreover, while arginase activity was observed in both TAM subsets, it was significantly higher for MHC II$^{low}$ TAMs (FIG. 3A). In the same vein, TNFα, which has previously been reported to associate with a M2 phenotype in tumors,[15, 16] was produced by both TAM subsets, but a significantly higher percentage of MHC II$^{low}$ TAMs were found to be TNFα$^+$ (FIG. 3B). While iNOS protein was not detected in freshly isolated TAMs, it could be induced by IFN-γ and/or LPS stimulation (FIG. 3C). Interestingly, IFN-γ or LPS induced iNOS more efficiently in MHC II$^{hi}$ TAMs, with a higher fraction of these cells becoming iNOS$^+$. Together, these data indicate that the identified TAM subsets have a differential activation state, with MHC II$^{low}$ TAMs being more M2-oriented.

TAM subsets also showed a markedly distinct chemokine expression pattern (Table 1). Notably, mRNAs for chemokines typically involved in lymphocyte attraction, such as Ccl5, Cx$_3$cl1, Cxcl11, Cxcl10, Cxcl9 and the CCR4 ligands Ccl17 and Ccl22 were up-regulated in MHC II$^{hi}$ TAMs. In contrast, mRNAs for monocyte/macrophage chemoattractants, such as Ccl6, the CCR2 ligands Ccl7, Ccl2 and Ccl12 and the CCR5/CCR1 ligands Ccl4, Ccl3 and Ccl9 were significantly higher in MHC II$^{low}$ TAMs. Furthermore, at the protein level, a differential expression of the chemokine receptors CX$_3$CR1 and CCR2 was observed, with MHC II$^{hi}$ TAMs being CX$_3$CR1$^{hi}$CCR2$^-$, while MHC II$^{low}$ TAMs were CX$_3$CR1$^{low}$CCR2$^+$ (FIG. 1C).

Both TAM subsets expressed many potentially pro-angiogenic genes, including Vegfa, Mmp9, Pgf, Spp1 and cathD (Table 1). However, several angiostatic factors such as angpt2, Cxcl9, Cxcl10 and Cxcl11 were up-regulated in the MHC II$^{hi}$ fraction. One of the most differentially expressed genes (higher in MHC II$^{low}$ TAMs) was Lyve1.

We conclude that MHC II$^{hi}$ and MHC II$^{low}$ TAMs have a distinguishing profile of molecules involved in inflammation (M1/M2), chemotaxis and angiogenesis.

Example 5

MHC II$^{low}$ TAMs are Enriched in Regions of Hypoxia, while MHC II$^{hi}$ TAMs are Mainly Normoxic Tumors often harbor regions of hypoxia, a factor which is known to influence macrophage function.[9] To visualize hypoxia in TS/A tumors, tumor-bearing mice were injected with pimonidazole (Hypoxyprobe-1, HP-1) and tumor sections were stained for hypoxic adducts and blood vessels. FIG. 4A shows that tumors indeed contained a large number of hypoxic cells, primarily in regions with a less developed vasculature. Interestingly, staining sections for HP-1, CD11b and MHC II demonstrated that many CD11b$^+$MHC II$^-$ cells (which in large tumors are mainly MHC II$^{low}$ TAMs) were HP-1$^+$ (FIG. 4B). Interestingly however, the majority of CD11b$^+$MHC II$^+$ cells were HP-1$^-$. This indicates that while a significant fraction of MHC II$^{low}$ TAMs resided in hypoxic areas, MHC II$^{hi}$ TAMs were mainly normoxic. Importantly, HP-1 adducts could also be detected through intracellular flow cytometry on freshly isolated TAMs. Again, the highest signal was seen in MHC II$^{low}$ TAMs, confirming they were the most hypoxic TAM subset (FIG. 4C).

Figure 8:
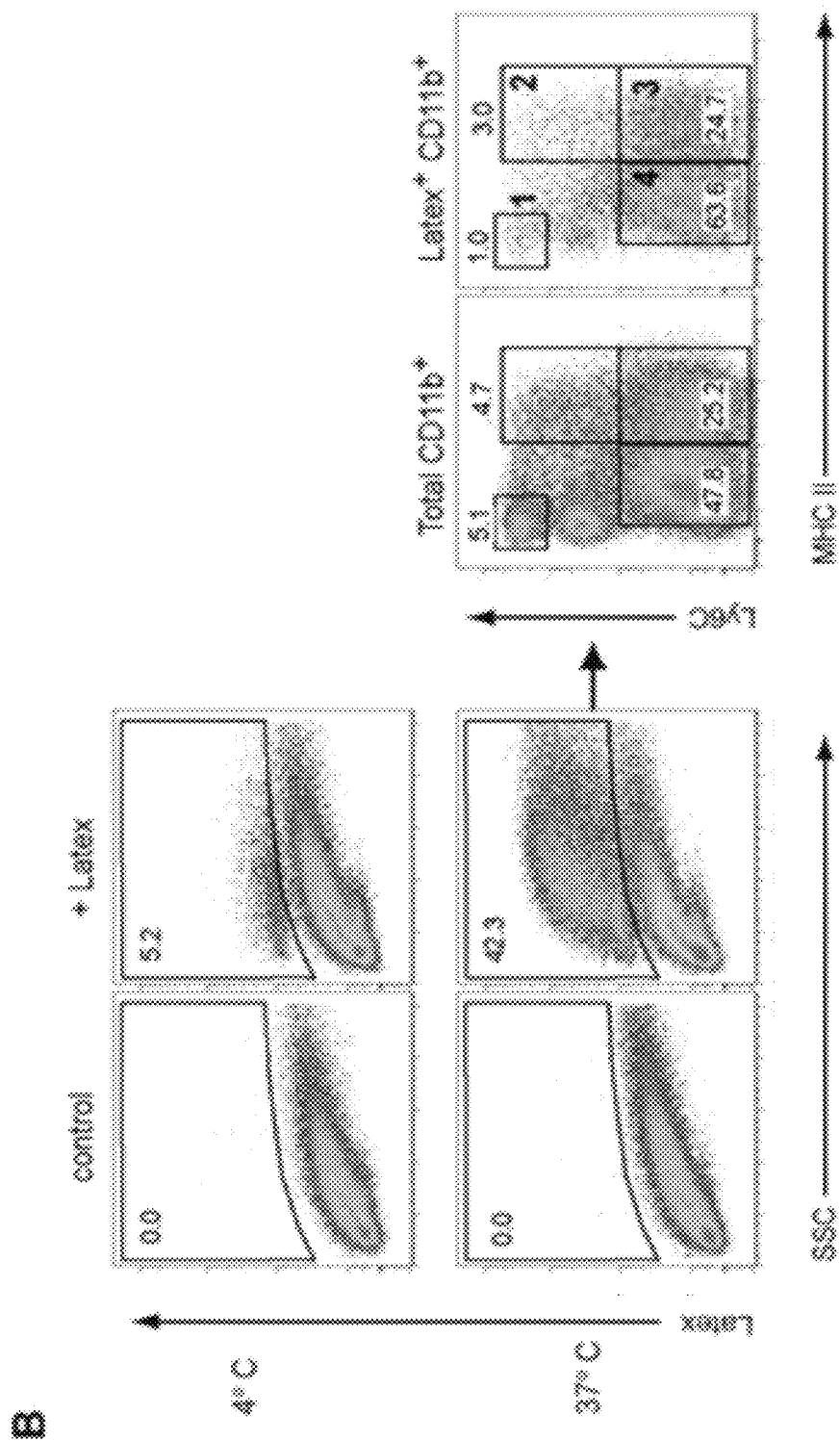
FIG. 8: Latex bead uptake by TAM subsets in vivo and in vitro. (A) Three weeks tumor-bearing mice were injected iv with fluorescent latex beads and 2 hours later, tumors were collected to assess latex uptake by the CD11b+ population. The depicted SSC vs. latex plot is on gated CD11b+ cells and shows how latex+ cells are gated. The percentage of Ly6Chi monocytes, Ly6Cint TAMs, MHC II$^{hi}$ TAMs and MHC II$^{low}$ TAMs within the total CD11b+ gate or CD11b+Latex+ gate is depicted for five individual groups of tumors from three independent experiments. (B) Tumor single cell suspensions were cultured in vitro, at 4° C. or 37° C., in the absence (control) or presence of latex beads for 40 minutes. Latex+ cells within the CD11b+ population were gated and their percentages are given. The percentage of the distinct monocyte/TAM subsets within the total CD11b+ gate or CD11b+Latex+ gate is depicted for five individual groups of tumors from three independent experiments for cells cultured at 37° C.
Figure 8:
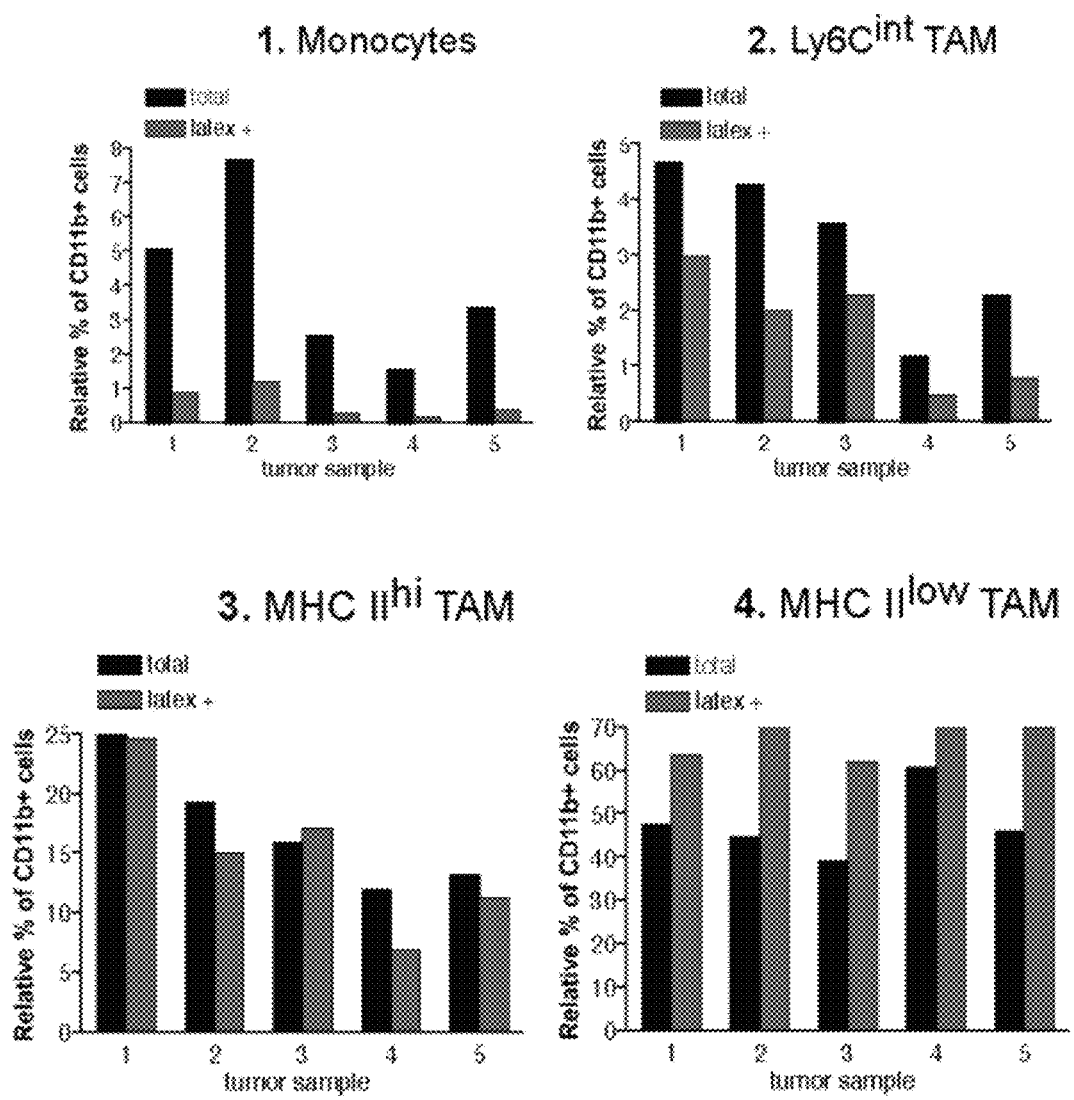

A consequence of MHC II$^{low}$ TAMs being in hypoxic regions should be a reduced access to blood-transported molecules. To test this, fluorescent latex particles were injected iv in tumor-bearing mice. 1 to 2 hours later a fraction of tumor-associated CD11b$^+$ cells were found to be latex$^+$ (FIG. 8A). However, latex uptake was not equal in all TAM subsets. Indeed, in relative terms, MHC II$^{low}$ TAMs phagocytosed less latex than monocytes and other TAM subsets. This was not due to an inherently reduced phagocytic capacity of MHC II$^{low}$ TAMs, since the latter showed the highest phagocytic latex uptake in vitro (FIG. 8B). These data suggest that the reduced in vivo latex uptake of MHC II$^{low}$ TAMs was due to a restricted access to latex particles which further substantiates the enrichment of MHC II$^{low}$ TAMs in hypoxic regions.

Example 6

MHC II$^{low}$ TAMs Show a Superior Pro-Angiogenic Activity In Vivo

Hypoxia initiates an angiogenic program.[17] In addition, our gene profiling revealed the expression of angiogenesis-regulating molecules in TAMs. To directly test the pro-angiogenic activity of both TAM subsets in vivo, we employed the chorioallantoic membrane (CAM) assay. Sorted MHC II$^{hi}$ or MHC II$^{low}$ TAMs were implanted on developing CAMs, while BSA or rhVEGF served as negative and positive controls, respectively. rhVEGF induced the outgrowth of allantoic vessels specifically directed towards the implants (FIG. 5A). Interestingly, compared with BSA controls, the presence of MHC II$^{hi}$ or MHC II$^{low}$ TAMs significantly increased the number of implant-directed vessels, demonstrating a pro-angiogenic activity for both TAM subsets. However, the vessel count for implants containing MHC II$^{low}$ TAMs was on average two-fold higher than with MHC II$^{hi}$ TAMs. These data show that MHC II$^{low}$ TAMs had a superior pro-angiogenic activity in vivo.

Example 7

Figure 9:
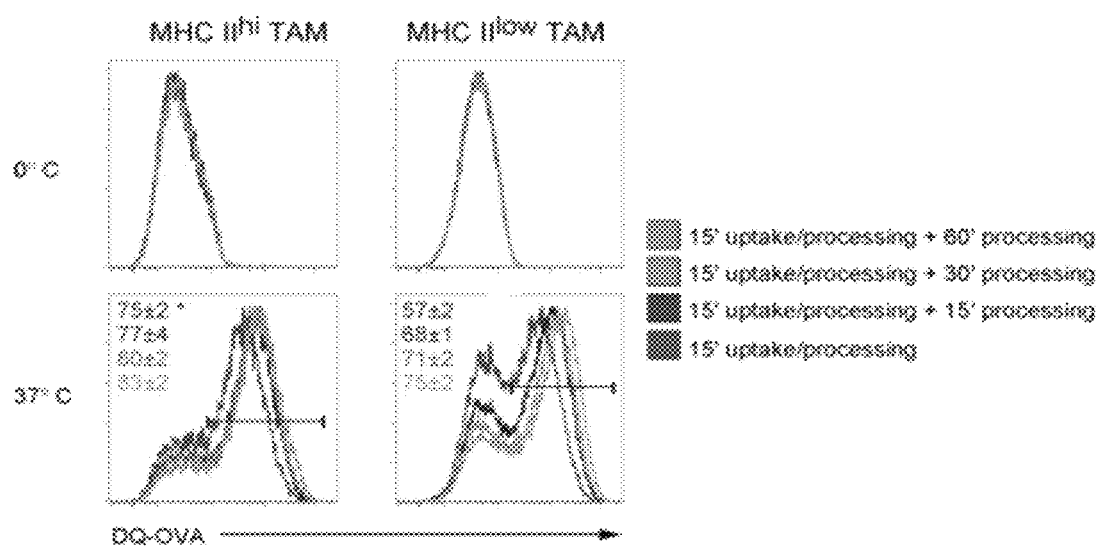
FIG. 9: DQ-OVA processing by TAM subsets. TAMs were allowed to phagocytose and process DQ-OVA for 15 minutes at 0° C. or 37° C. Free DQ-OVA was subsequently removed from the culture medium and TAMs were given an additional 15, 30 and 60 minutes to process internalized DQ-OVA. DQ-OVA processing results in the formation of fluorescent peptides and fluorescence intensities for the gated TAM subsets are shown in histogram plots. Values are the mean percentage cells within the indicated gate±SEM from three independent experiments. p-values were calculated for these means between MHC II$^{hi}$ vs. MHC II$^{low}$ TAMs for each time point. * $p<0.05$
Figure 10:
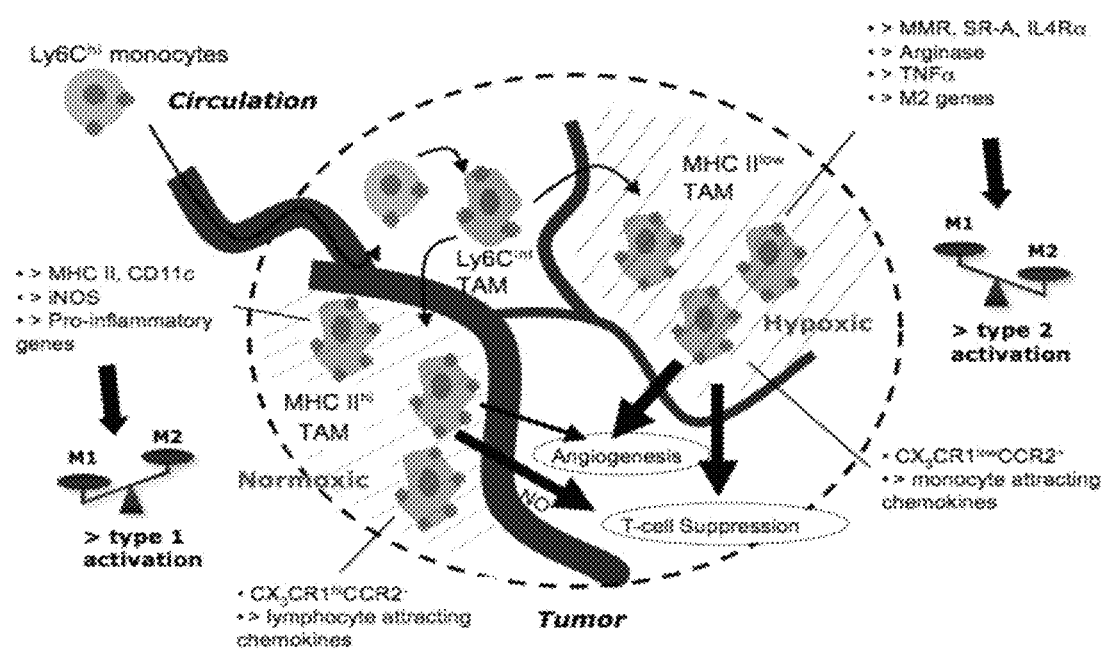
FIG. 10: Schematic summary.

TAMs are Poor Antigen-Presenters, but can Efficiently Suppress T-Cell Proliferation We wondered whether the TAM subsets were able to process internalized antigens and activate T cells. Both TAM subsets took up and processed DQ-Ovalbumin (DQ-OVA) at 37° C. However, examining DQ-OVA processing at consecutive time points indicated that processing naïve more slowly in the MHC II$^{low}$ fraction (FIG. 9). To investigate whether TAMs could directly activate naïve T cells, a mixed leukocyte reaction (MLR) assay was used. Hereto, sorted MHC II$^{hi}$ or MHC II$^{low}$ TAMs were cultured with purified allogeneic C57BL/6 CD4$^+$ or CD8$^+$ T cells. Sorted splenic CD11c$^{hi}$MHC II$^{hi}$ conventional DCs (cDCs) (FIG. 7B) were used as a reference T-cell-stimulating population.[18] Compared with cDCs, MHC II$^{hi}$ or MHC II$^{low}$ TAMs induced poor proliferation of allogeneic CD4$^+$ or CD8$^+$ T cells (FIG. 5B), suggesting a limited antigen-presenting capacity or, alternatively, a T-cell suppressive capacity that overrules antigen-presentation.

To investigate the latter possibility, T cells were polyclonally activated in the presence of TAMs or cDCs. Interestingly, as opposed to cDCs, both MHC II$^{hi}$ and MHC II$^{low}$ TAMs equally suppressed anti-CD3-induced T-cell proliferation in a dose-dependent manner (FIG. 5C). In an attempt to identify the suppressive molecules responsible for TAM-mediated suppression, inhibitors of iNOS (L-NMMA) and arginase (N or Noha) were added to the co-cultures (FIG. 5D). Blocking iNOS significantly reduced T-cell suppression by MHC II$^{hi}$ TAMs, demonstrating a role for nitric oxide in its suppressive mechanism. In contrast, iNOS inhibition only had a minor effect on the suppressive potential of MHC II$^{low}$ TAMs, showing that both subsets employ different T-cell suppressive mechanisms.

Example 8

Similar TAM Subsets in Other Tumor Models

Interestingly, the TAM subsets identified in TS/A tumors, were also present in other tumor models. Both in the Lewis Lung Carcinoma (LLC) model and in the mammary carcinoma model 4T1, MHC II$^{hi}$ and MHC II$^{low}$ TAMs could be identified (FIG. 13A). Furthermore, as in TS/A, typical M2 markers such as MMR and IL4Rα were higher expressed on MHC II$^{low}$ TAMs, while M1 markers such as CD11c were higher on MHC II$^{hi}$ TAMs (FIG. 13B). This indicates that our initial findings in TS/A are not restricted to a single tumor model or even to a single carcinoma type (mammary vs. lung carcinoma). The dynamics of TAM subsets in the LLC model resembled that of TS/A, with MHC II$^{low}$ TAMs accumulating over time and forming the majority of myeloid cells in established tumors (FIG. 13C, LLC). However, 4T1 tumors did not adhere to this trend and instead MHC II$^{hi}$ TAMs accumulated as tumors progressed (FIG. 13C, 4T1). These data indicate that the accumulation of TAM subsets over time can vary from one tumor type to another, which possibly reflects differences in tumor architecture. Therefore, these findings provide a rationale for classifying tumors based on the relative percentage of TAM subsets (with tumor volume taken into account). This might be useful for devising a tailored therapy and/or as a prognostic factor.

Example 9

Nanobodies Against the Macrophage Mannose Receptor (CD206-MMR)

As outlined in the Examples above, TAMs can adopt different phenotypes and functional specializations. For example, TAMs located in hypoxic tumor regions were found to be extremely pro-angiogenic, suggesting that they play an important role in tumor vascularization. Interestingly, we have identified CD206 (macrophage mannose receptor) as a membrane marker which is specifically expressed on this tumor-promoting TAM subset. Anti-CD206 (anti-MMR) nanobodies, which are the smallest available antigen-binding entities, were created (see also Example 14) in order to target these cells in vivo. It was shown that the newly created anti-CD206 Nbs bind strongly to TAMs, but not to other myeloid cell types such as monocytes and granulocytes or any other tumor resident cells. These and other nanobodies against any of the markers of Table 1 are used for non-invasive imaging of TAMs using SPECT/Micro-CT. These nanobodies are also used to create immunotoxins for the therapeutical targeting of these cells in pre-clinical tumor models or for antibody-directed enzyme prodrug therapies (ADEPT).

Example 10

In Vivo Imaging Using Macrophage Mannose Receptor Nanobodies

In a next step, we performed in vivo imaging using Macrophage Mannose Receptor (MMR) targeting nanobodies. The nanobodies were labeled at their hexahistidine-tail with $^{99m}$Tc at elevated temperatures by tricarbonyl-chemistry. Purified, $^{99m}$Tc-labeled Nanobodies were injected intravenously in mice and total body scans were made using pinhole SPECT and micro-CT.

Figure 11:
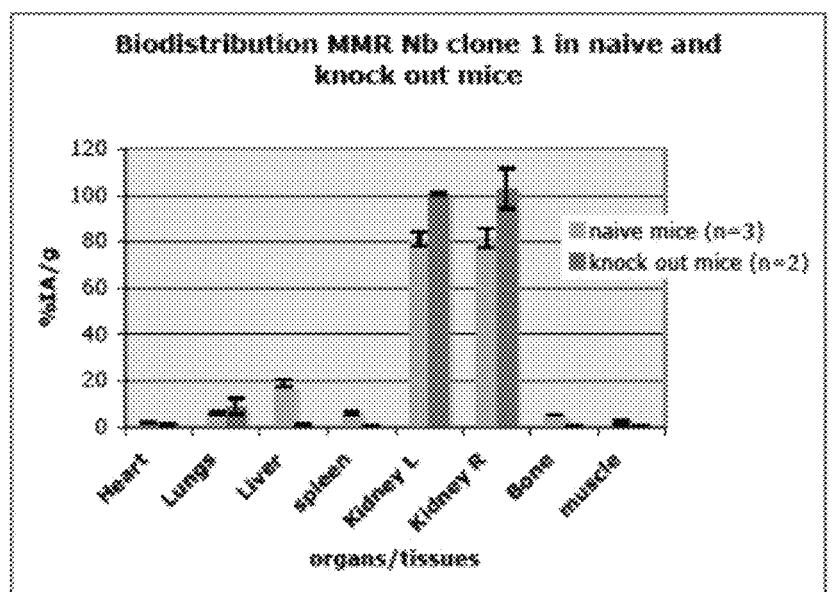
FIG. 11: Biodistribution MMR Nb in naïve and knockout mice.

The first step in the in vivo evaluation was the study of the biodistribution in healthy mice. This allows to evaluate physiological sites of specific accumulation and to determine the pharmacokinetic properties of the imaging probes. MMR nanobodies show uptake in organs such as lungs, spleen and liver. The blood clearance is fast with less than 1% IA (injected activity)/ml remaining in blood at 1 hour 30 minutes post injection. We also tested MMR nanobodies in MMR knock-out mice where the uptake in liver and spleen dropped below 1% IA/g (FIG. 11). These data indicate that the accumulation in organs such as liver and spleen is related to MMR expression and therefore specific. Only the accumulation in lungs appears to be MMR-unrelated.

Figure 12:
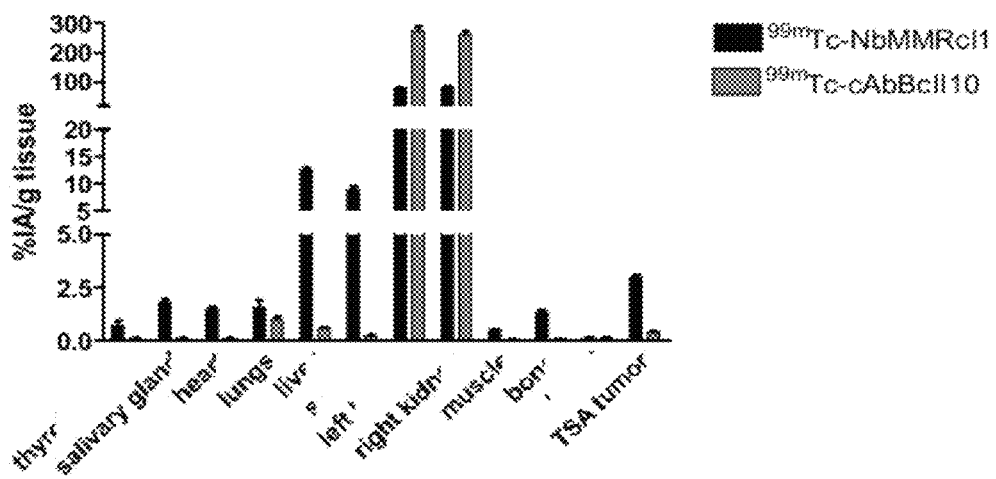
FIG. 12: Uptake experiments of MMR Nb in TS/A tumor-bearing mice.

Next, $^{99m}$Tc-labeled MMR Nanobodies and a control Nanobody recognizing a target not present in mice (the cAb-BcII10 nanobody, raised against subunit 10 of the β-lactamase BcII enzyme of *Bacillus cereus*) were inoculated in TS/A tumor-bearing mice. Uptake of the MMR Nanobody in liver, spleen, lungs, kidneys and blood was similar as before (FIG. 12), whereas accumulation of the control Nanobody was below 1% IA/g for all organs except for lungs and kidneys. Interestingly, the MMR Nanobody showed significant accumulation in the subcutaneous TS/A tumor (>2.5% IA/g), whereas the uptake of the control Nanobody in the subcutaneous tumor had dropped below 0.5% IA/g at 1h30 post injection.

Example 11

TAM Targeting Using Anti-CD206 Nb-Toxins

Anti-CD206 Nbs are covalently linked to a protein toxin for TAM cell killing. Candidate toxins are the diphtheria toxin or the *Pseudomonas* exotoxin. It is investigated whether Nb-toxin conjugates are able to induce TAM cell death both in vitro and in vivo. Next, the effect of Nb-toxin treatment on tumor growth is assessed. For this, different injection schemes and doses are evaluated, ideally obtaining tumor regression coupled to a low overall toxicity. Further, it is investigated whether in vivo TAM depletion results in reduced tumor angiogenesis. This is done by immunohistochemically counting the number of blood vessels in tumors of Nb-toxin treated or untreated mice.

Alternatively, TAM killing might alleviate immune suppression or induce an inflammatory environment favoring the development of anti-tumor immunity. Thereto, it is investigated whether Nb-toxin treatment expands tumor-infiltrating T cells (TILs). The activation of TILs is assessed by evaluating the expression of certain membrane markers and through intracellular measurement of cytokine production. $CD8^+$ cytotoxic TILs are purified and their tumor killing potential is directly assessed in vitro. The impact of anti-tumor immunity is also evaluated by repeating the Nb-toxin treatment in $Rag2^{-/-}$ or SCID mice, which do not have functional T or B cells.

Example 12

Targeting Tumors Using an Anti-CD206 Nb-Enzyme/Prodrug Strategy

The observation that CD206 is expressed on TAMs from several independent tumor models, makes it a potential tumor-targeting marker for a variety of different cancers. CD206 is therefore an interesting candidate for developing antibody-directed enzyme prodrug therapies (ADEPT). In ADEPT an antibody is coupled to an enzyme which is able to convert a prodrug into a cytotoxic drug. We have previously proven that this also works with the Nb format.[25] Anti-CD206 Nbs can, for example, be coupled to β-lactamase, an enzyme which is able to release phenylenediamine mustard from the prodrug 7-(4-carboxybutanamido) cephalosporin mustard. Anti-CD206 Nb-enzyme conjugates can be injected in tumor-bearing mice, subsequently allowing clearance of unbound Nbs after which the prodrug is administered. This will result in a high toxicity at the tumor site, killing TAMs but also other bystander tumor cells, while having a low overall toxicity in the animal. We evaluate the efficacy of anti-CD206 Nb enzyme-prodrug therapies for inducing tumor regression in our preclinical tumor models.

Example 13

MMR as a Marker for the Differential Targeting of Tam Subsets In Vivo

Figure 14:
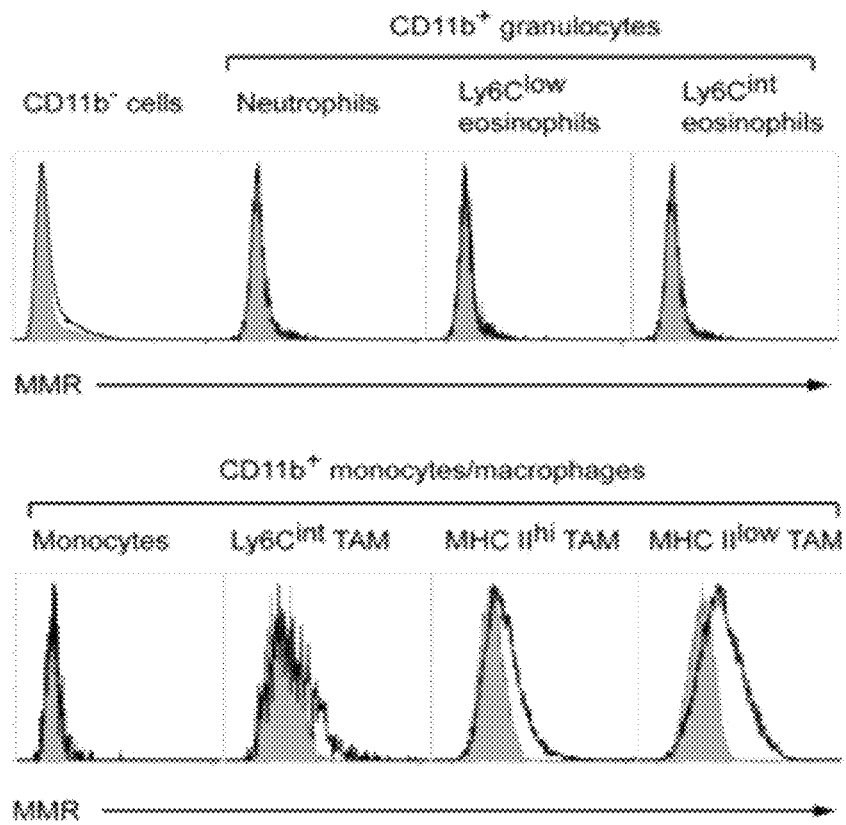
FIG. 14. MMR expression on distinct cell types present in TS/A tumor suspensions. Single cell suspensions were made from TS/A tumors and MMR expression was evaluated on the indicated cell populations using an anti-MMR monoclonal antibody. Shaded histograms represent isotype control.
Figure 15:
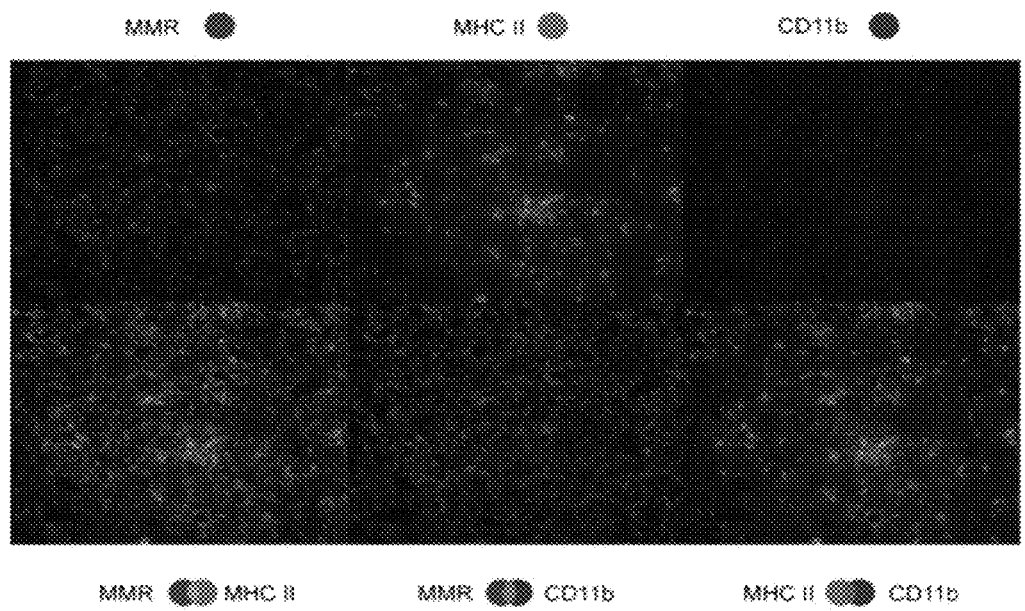
FIG. 15. Anti-MMR clone 1 differentially labels TAM subsets in TS/A tumor sections. TS/A tumors were collected from three weeks tumor-bearing mice and frozen sections were triple-stained for MMR (red), MHC II (green) and CD11b (blue).

In the above Examples, it was shown that in tumor single cell suspensions, MMR was differentially expressed between MHC $II^{hi}$ and MHC $II^{low}$ TAMs, as assessed by flow cytometry using anti-MMR monoclonal antibodies. In addition, MMR was not/poorly expressed on $CD11b^-$ cells, granulocytes, monocytes and $Ly6C^{int}$ TAMs in the TS/A mouse mammary carcinoma model (FIG. 14). We next set out to investigate MMR expression patterns in tumor sections. TS/A mammary carcinoma sections were triple-stained for MMR (red), CD11b (blue) and MHC II (green) (FIG. 15). MMR and CD11b staining almost completely co-localized, showing that MMR cells were indeed TAMs. Interestingly however, MMR expression poorly co-localized with $CD11b^+MHC\ II^+$ cells (the majority corresponding to MHC $II^{hi}$ TAMs), indicating that MMR staining was mainly restricted to MHC $II^{low}$ TAMs. Therefore, MMR can be used for differentially targeting MHC $II^{hi}$ and MHC $II^{low}$ TAMs on tumor sections. Together with our flow cytometric results this indicates that MMR can be an interesting marker for specifically targeting MHC $II^{low}$ TAMs in vivo.

Example 14

Generation of Anti-MMR Monovalent and Bivalent Nanobodies

Nanobodies (Nb) were raised against the recombinant extracellular portion of MMR (α-MMR Nb), as described in the Materials and Methods (see also Example 9; Table 4). The binding characteristics of the monovalent anti-MMR nanobodies were compared using surface Plasmon resonance measurements (Table 5). Nanobody clone 1 demonstrated an eight-fold higher apparent affinity for immobilized recombinant MMR compared to nanobody clone 3 ($K_D$=2.31×10$^{-8}$ M versus 1.91×10$^{-7}$ M, respectively), and became hence the nanobody of choice for the remaining of this study. In addition, SPR competition studies demonstrated that pretreatment with nanobody clone 1 does not preclude nanobody clone 3 binding, and vice versa, suggesting that anti-MMR Nb clone 1 and Nb clone 3 bind to non-overlapping epitopes (data not shown). Further, bivalent nanobodies were constructed by linking two anti-MMR nanobody 1 entities using (G$_4$S)$_3$ (GGGGSGGGGSGGGGS; SEQ ID NO:121), llama IgG2 hinge (AHHSEDPSSKAPKAPMA; SEQ ID NO:122) or human IgA hinge (SPSTPPTPSPSTPPAS SEQ ID NO:123) linkers. These bivalent anti-MMR molecules showed a five-fold higher avidity compared to the monovalent clone 1 nanobody, which can be attributed largely to three-fold increase in $K_D$. The different linkers used for bivalent nanobody construction did not seem to have a significant effect on the affinity of the molecules for the MMR antigen. As a negative control nanobody in all experiments, we consistently used α-BCII10 Nb, which is a binder of the β-lactamase BCII enzyme of *Bacillus cereus*.

Example 15

Ex Vivo Characterization of Anti-MMR Nanobodies

Figure 16:
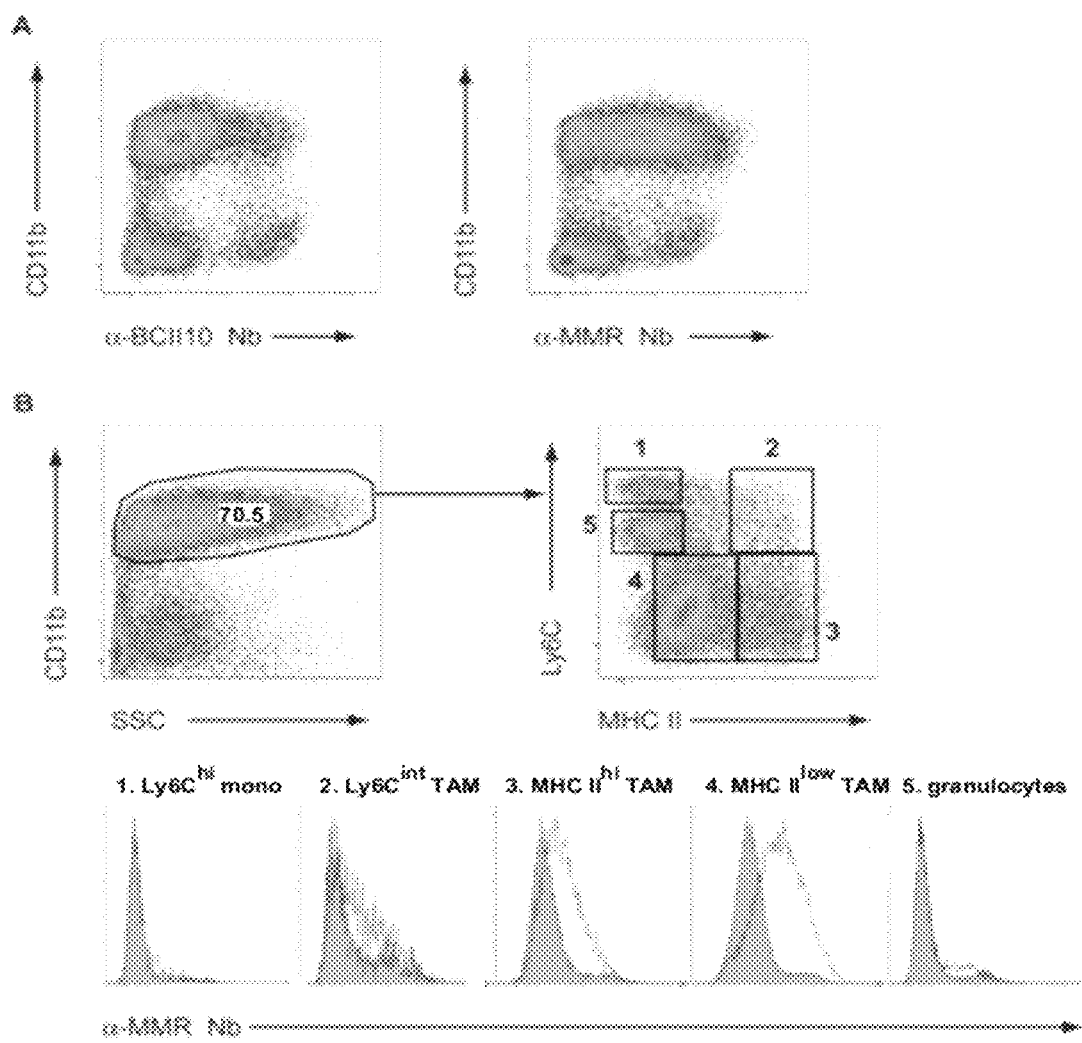
FIG. 16. anti-MMR Nb differentially binds to TAM subsets in tumor single cell suspensions. (A) Single-cell suspensions of 21-day old TS/A tumors were stained with the indicated markers. anti-BCII10 Nb served as negative control. (B) Staining of anti-MMR Nb clone 1 was examined on the gated myeloid subsets. Shaded histograms represents staining with anti-BCII10 Nb.

To investigate whether the anti-MMR Nb could bind to TAMs ex vivo, single cell suspensions were made of subcutaneous TS/A tumors and flow cytometric analyses were performed (FIG. 16). The anti-MMR Nb bound to a subset of CD11b$^+$ cells, but not to CD11b$^-$ cells (FIG. 16A). Within the CD11b$^+$ fraction, anti-MMR Nb did not bind to monocytes (FIG. 16B, gate 1), granulocytes (Gate 5) and only very weakly to Ly6C$^{int}$ TAMs (gate 2). Staining was therefore restricted to MHC II$^{hi}$ (gate 3) and MHC II$^{low}$ TAMs (gate 4), with the latter subset binding anti-MMR Nb to a much greater extent. These results are therefore in line with our previous observations using anti-MMR monoclonal antibodies. We conclude that in ex vivo tumor suspensions, the anti-MMR Nb stained mature TAMs and more intensely the MHC II$^{low}$ subset.

Example 16

Figure 17:
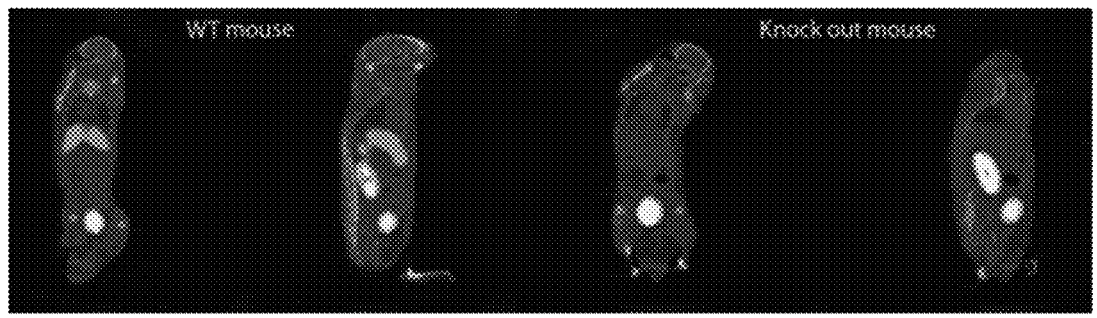
FIG. 17. Coronal and sagittal views of fused Pinhole SPECT and Micro-CT images of naive WT or MMR$^{-/-}$ mice 1 hour after injection with $^{99m}$Tc labeled anti-MMR Nb clone 1. (A) In WT mice anti-MMR Nb shows kidney/bladder elimination and uptake in several organs. (B) In MMR$^{-/-}$ mice anti-MMR Nb shows primarily kidney/bladder elimination.

Assessment of the Biodistribution and Specificity of Anti-MMR Nanobody Clone 1 and its Bivalent Derivative in Naive Mice Using Pinhole SPECT/Micro-CT Analysis Next, we wished to assess whether the anti-MMR Nb clone 1 could be used for targeting and imaging of MMR-expressing cells in vivo. In first instance, this was investigated in naive mice. To this end, anti-MMR monovalent Nb were labeled with $^{99m}$Tc and injected intravenously in naive C57BL/6 mice. Three hours post injection, total-body scans were acquired using pinhole SPECT and micro-CT (FIG. 17), images were quantified and tracer uptake expressed as percentage injected activity per gram cubic centimeter (% IA/cm$^3$) (Table 6). To ascertain the specificity of the anti-MMR Nb and to prove that any potential targeting was not due to aspecific retention, anti-MMR Nb were also injected in naive C57BL/6 MMR$^{-/-}$ mice. In MMR$^{-/-}$ mice, SPECT/micro-CT images show a high tracer uptake in the kidneys and urinary activity in the bladder, indicative of renal clearance, but only low background-level retention is seen in other organs (FIG. 17, Table 6). The only exception were the lungs, suggesting that lung-targeting was aspecific. In contrast, WT mice showed an increased retention of the anti-MMR Nb in several organs, including heart, bone, spleen and liver, with the latter two showing the most intense signals (FIG. 17). These results indicate that the anti-MMR monovalent Nb has a high in vivo specificity and can efficiently target organs such as the liver and spleen. A similar experiment was performed with the different bivalent anti-MMR Nb constructs, all of which showing an even increased uptake in the liver as compared to the monovalent molecule and a concomitant reduction in clearance via the kidneys (Table 7). Again, retention of bivalent anti-MMR Nb in all organs, except the lung, is MMR-specific and is absent in MMR$^{-/-}$ mice. As was expected, retention of the control cAbBCII10 Nb is very low in all organs, resulting in a massive clearance via the kidneys (Table 7).

Example 17

Tumor-Targeting Potential and Specificity of Anti-MMR Nanobodies

Figure 18:
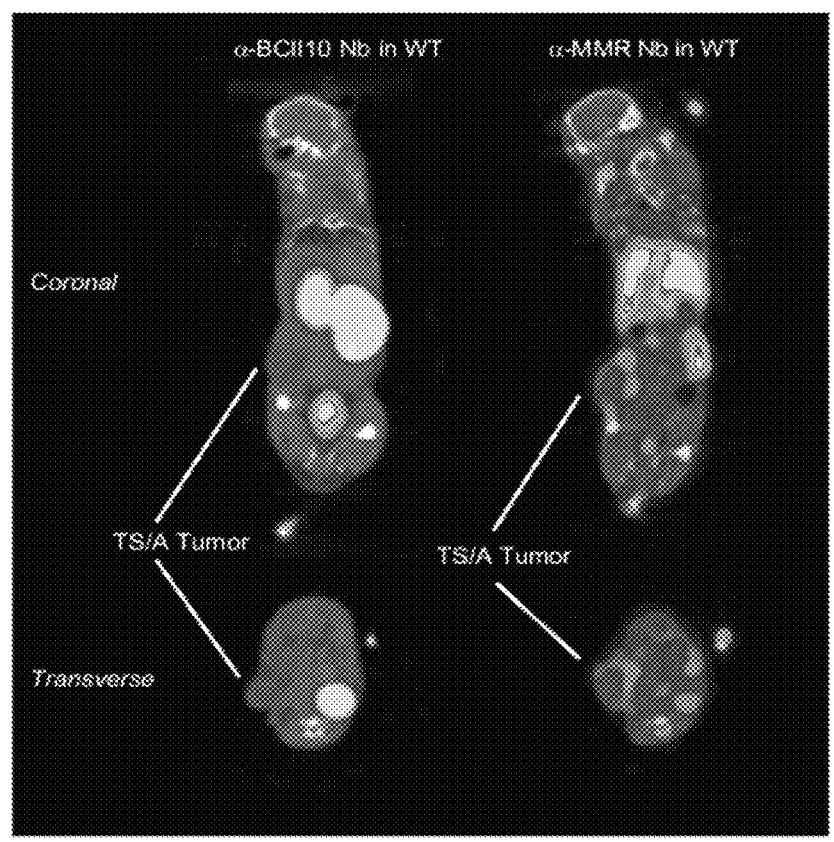
FIG. 18. Coronal and transverse views of fused Pinhole SPECT and Micro-CT images of WT TS/A tumor-bearing mice 3 hours after injection with $^{99m}$Tc labeled cAbBCII10 or anti-MMR Nb.
Figure 19:
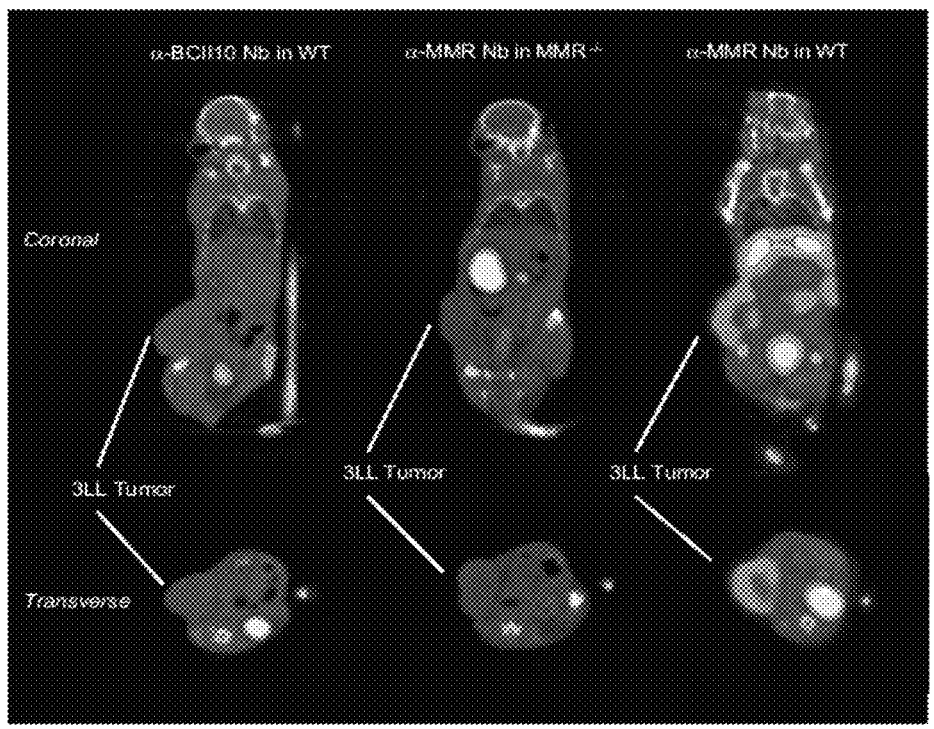
FIG. 19. Coronal and transverse views of fused Pinhole SPECT and Micro-CT images of WT and MMR$^{-/-}$ 3LL tumor-bearing mice 3 hours after injection with $^{99m}$Tc labeled cAbBCII10 or anti-MMR Nb.

Next, we set out to investigate whether the anti-MMR Nb could be used to target TAMs in vivo. Hereto, $^{99m}$Tc-labeled anti-MMR Nbs were injected intravenously in TS/A (Balb/c) and 3LL-R (C57BL/6) tumor-bearing mice and SPECT/micro-CT and ex vivo dissection analyses were performed. $^{99m}$Tc-labeled cAbBCII10 Nbs were used as negative controls. In addition, to further ascertain the specificity of tumor uptake, 3LL-R tumors were also grown in C57BL/6 MMR$^{-/-}$ mice. In these mice, 3LL-R tumors grew progressively and the distinct TAM subsets remained present as assessed by flow cytometry (data not shown). Interestingly, as observed by SPECT/micro-CT imaging, both TS/A and 3LL-R tumors showed a clear uptake of anti-MMR Nb, which was significantly higher than tumor uptake of cAbBCII10 Nb (FIGS. 18 and 19). These findings were confirmed through ex vivo dissection analysis, where the activity in the tumor and organs was assessed and expressed as injected activity per gram (% IA/g): TS/A tumor uptake was 3.02±0.10% IA/g for anti-MMR Nb and 0.40±0.03% IA/g for cAbBCII10 (Table 8); 3LL-R tumor uptake was 3.02±0.19% IA/g for anti-MMR Nb and 0.74±0.03% IA/g for cAbBCII10 (Table 9). Importantly, in 3LL-R tumor-bearing MMR$^{-/-}$ mice, tumor uptake of anti-MMR Nb was reduced by ten-fold (0.33±0.03% IA/g, Table 9), showing that targeting in WT mice was receptor-specific.

Example 18

Figure 20:
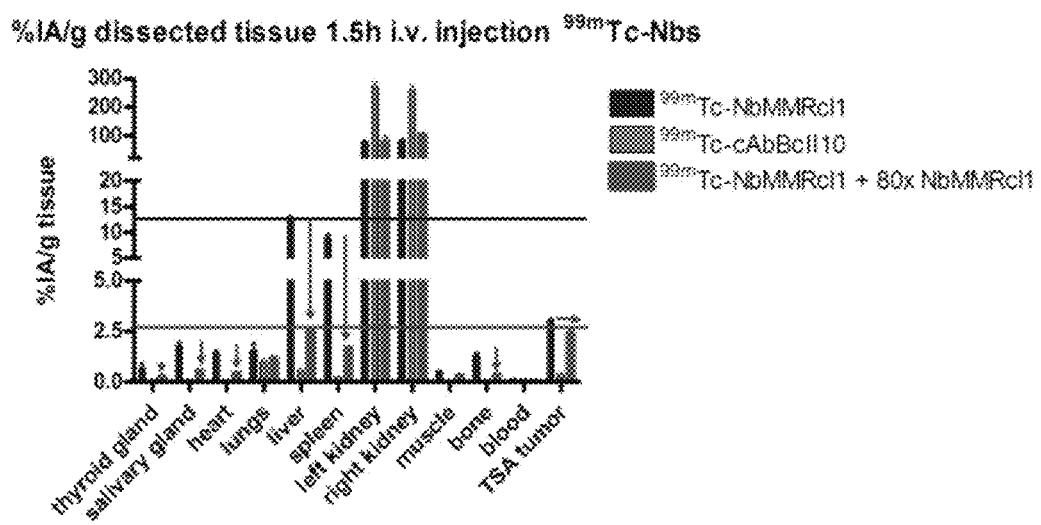
FIG. 20. Uptake values of $^{99m}$Tc-labeled monovalent anti-MMR Nb clone 1 in TS/A tumor-bearing mice upon co-injection with an eighty-fold excess of cold monovalent anti-MMR Nb, based on dissection at 3 hours post injection. Tracer uptake is expressed as injected activity per gram (% IA/g).

Blocking of Extratumoral Binding Sites by Excess Monovalent or Bivalent Anti-MMR Nb Both in the TS/A and 3LL-R model, $^{99m}$Tc-labeled anti-MMR Nb accumulates to a higher extent in liver and spleen than in the tumor. Therefore, we sought for ways to minimize binding of labeled tracer in these extratumoral sites, while preserving tumor targeting. In first instance, we co-injected an eighty-fold excess of cold unlabeled anti-MMR Nb and subsequently evaluated the biodistribution of $^{99m}$Tc-labeled anti-MMR Nb. This strategy results in a strongly reduced accumulation of labeled Nb in all organs, except for the tumor, resulting in a similar level of specific uptake in tumor and liver (FIG. 20). Next, we hypothesized that the inherently enhanced biodistribution of bivalent anti-MMR Nb to the liver and its enhanced in vivo retention (lower clearance via the kidneys) could be exploited to block the extratumoral binding sites more efficiently. To this end, we co-injected $^{99m}$Tc-labelled anti-MMR Nb with a twenty-fold excess of cold bivalent anti-MMR and assessed the specific uptake of labeled Nb in distinct organs. Remarkably, while the retention of monovalent anti-MMR in all organs is reduced to the aspecific background level seen with the control Nb cAb-BCII10, the uptake in tumors is only slightly diminished (FIG. 21). As a result, the specific uptake of labeled anti-MMR Nb is highest in the tumor.

Example 19

The Relative Abundance of TAM Subsets Correlates with Tumor Aggressiveness

Figure 23:
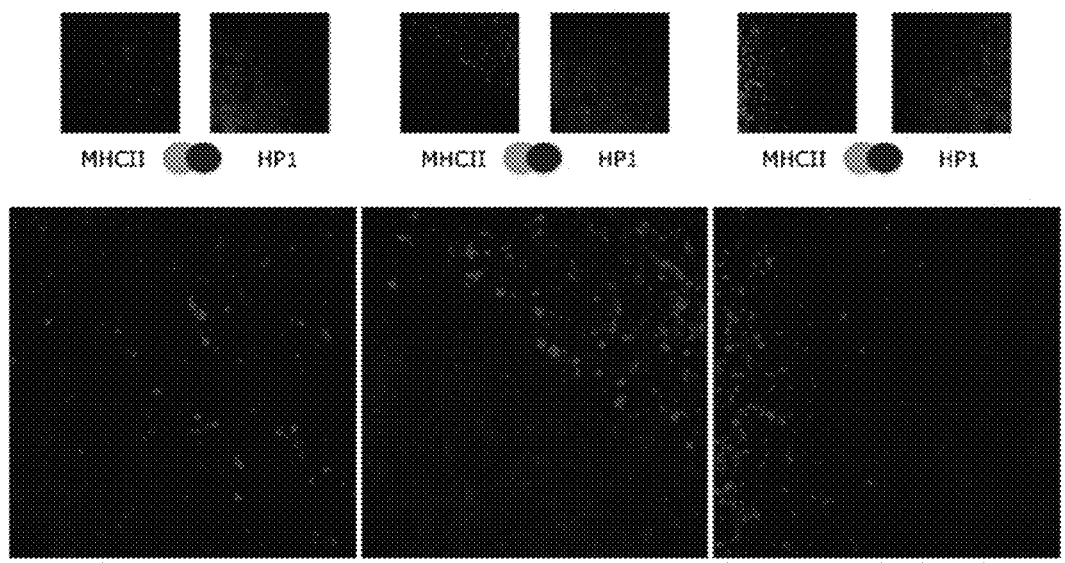
FIG. 23. MHC II$^{hi}$ TAM are located outside of hypoxic regions in 3LL-R tumors. 3LL-R tumors were collected from 12-days tumor-bearing mice and frozen sections were double-stained for MHC II (green) and Hypoxyprobe (blue). Pictures are shown from three distinct regions within the same tumor.

To assess whether the relative abundance of TAM subsets correlates with tumor aggressiveness, we injected high and low malignant 3LL lung carcinoma variants and evaluated the TAM subset distribution in the corresponding tumors. 3LL-R lung carcinoma cells establish rapidly growing tumors upon subcutaneous inoculation, reaching a tumor volume of about 1000 mm$^3$ within 12 days (FIG. 22). In these tumors, the MHC II$^{high}$ TAM subpopulation, which is located in normoxic regions, is outnumbered by the MHC II$^{low}$ subset (FIGS. 22 and 23). In contrast, 3LL-S tumors grow much slower (1000 mm$^3$ within about 35 days) and are dominated by the MHC II$^{high}$ TAM subset (FIG. 22). A similar observation is made when comparing fast growing T241 fibrosarcoma tumors with slow growing T241-HRG tumors (data not shown). Together, these data indicate that the relative abundance of TAM subsets can be prognostic for tumor aggressiveness.

Example 20

Evaluation of the Anti-MMR-PE38 Immunotoxin

The anti-MMR Nb clone 1 was fused to the *Pseudomonas* exotoxin A as described in Materials and Methods, creating an MMR-specific immunotoxin. It was shown that the recombinant production of this immunotoxin results in a functional toxic moiety, with the ability to kill cancer (3LL-R, 3LL-S) and macrophage cell lines (J774) in vitro (data not shown). In vivo administration of the toxin does not result in lethality, even at the highest dose used (data not shown). Further, the ability of the immunotoxin to specifically eliminate MMR-positive cells in vivo is assessed, in particular MMR$^+$MHC II$^{low}$ TAM in tumors, and the consequences of TAM subset elimination for tumor characteristics (growth, metastasis, vessel density, vessel functionality, . . . ) is evaluated.

Example 21

α-MMR Nb Clone 1 Targets Hypoxic Tumor-Associated Macrophages In Vivo

Figure 24:
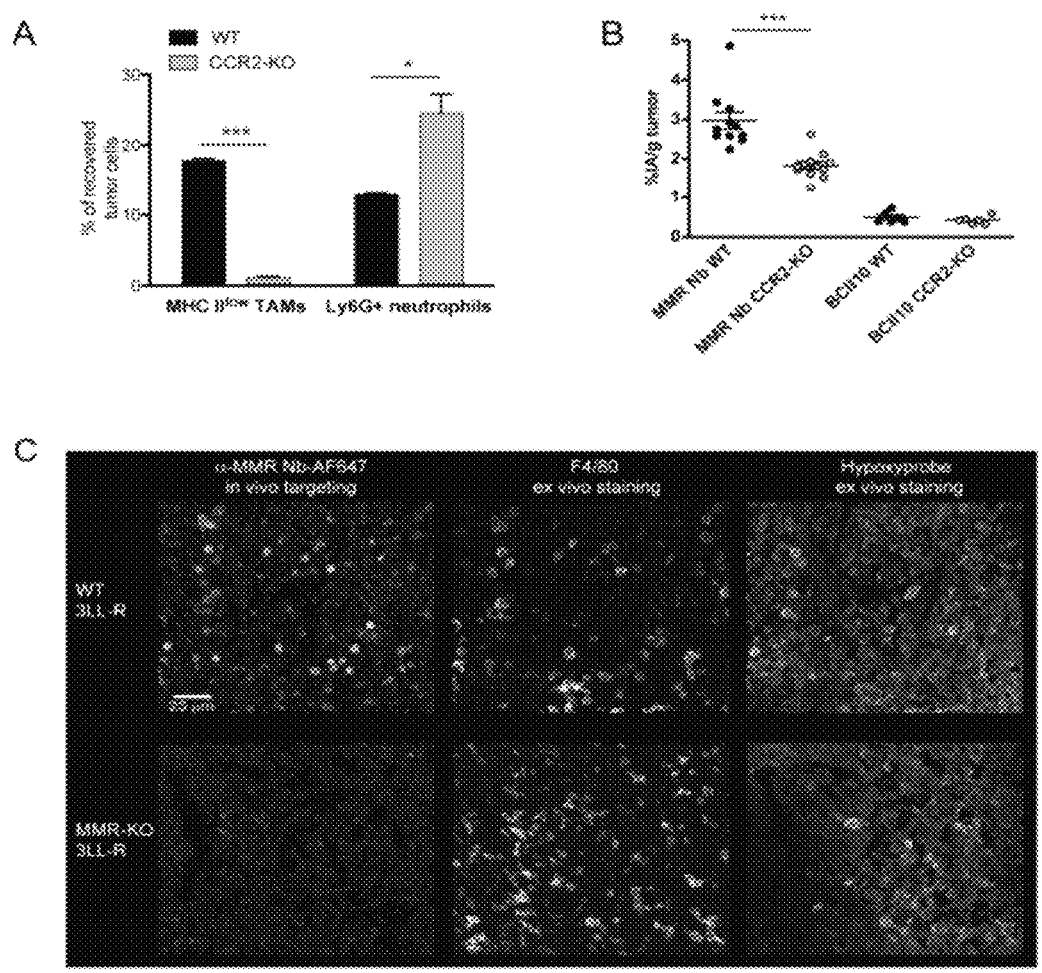
FIG. 24. α-MMR Nb targeting in WT and CCR2-KO tumor-bearing mice. (A) Percentages of MHC II$^{low}$ TAMs and Ly6G$^+$ neutrophils in tumor single-cell suspensions of WT and CCR2-KO tumors. Mean±SEM (n=4) (B) Uptake values of $^{99m}$Tc-labeled α-MMR Nb c11 or Nb BCII10 in WT or CCR2-KO mice 12 days post 3LL-R injection. *** p<0.001 (C) AF647-labeled α-MMR Nb c11 and pimonidazole were injected i.v. in 3LL-R WT or MMR-KO tumor-bearers. Two hours later, tumors were collected and stained for F4/80 and hypoxyprobe. (D) Overlays of α-MMR Nb-AF647, hypoxyprobe and F4/80 signals in WT 3LL-R tumors.
Figure 24:
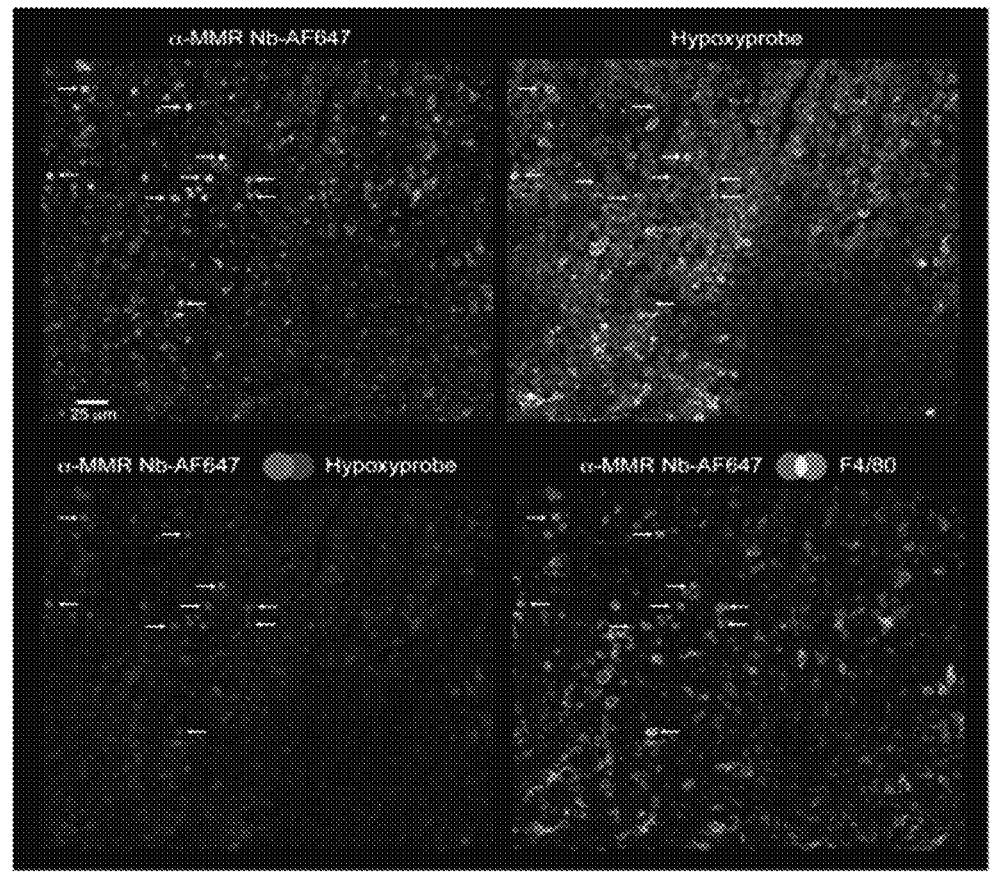

Having established that α-MMR Nb c11 specifically targeted MMR cells in tumors, we wished to ascertain whether this was due to TAM targeting. Previous work showed that CCR2-deficiency can result in a significant decrease in TAM infiltration with only a minimal effect on tumor growth, resulting from the compensatory influx of tumor-promoting neutrophils.$^{(45, 46)}$ To investigate whether CCR2-deficiency affected the numbers of TAMs and in particular MHC II$^{low}$ TAMs in our model, flow cytometric analyses were performed on single-cell suspensions of equally sized s.c. 3LL-R tumors grown in WT or CCR$^2$-KO mice. This showed that CCR$^2$-deficiency led to a dramatic reduction in the number of MHC II$^{low}$ TAMs, while infiltration of Ly6G$^+$MMR$^-$ neutrophils was significantly increased (FIG. 24A). Next, we compared the tumor-uptake of $^{99m}$Tc-labeled α-MMR Nb c11 injected in WT vs CCR2-KO 3LL-R tumor-bearing mice. $^{99m}$Tc-labeled α-MMR Nb showed a similar biodistribution in the organs/tissues of CCR2-KO vs WT tumor-bearers (Table 10). Importantly however, uptake of $^{99m}$Tc-labeled α-MMR Nb was significantly reduced in CCR2-KO tumors: 2.97±0.22% IA/g in WT vs 1.83±0.1% IA/g in CCR2-KO tumors (FIG. 3B). This indicates that TAMs residing in solid tumors are indeed targets of α-MMR Nbs in vivo.

Since MHC II$^{low}$ MMR$^+$ TAM were shown to associate with hypoxic regions, we next assessed whether α-MMR Nbs preferentially label hypoxic TAM in vivo. Hereto, AF647-coupled α-MMR Nbs were injected i.v. in s.c. 3LL-R WT or MMR-KO tumor-bearing mice. Two hours later, tumors were collected, sectioned and stained for the hypoxia marker pimonidazole (hypoxyprobe) and the macrophage marker F4/80. Interestingly, AF647 fluorescence almost completely co-localized with F4/80 staining in WT tumors, but was absent from MMR-KO tumors (FIG. 24C). In addition, the majority of AF647(bright) cells were located in hypoxic areas and stained with pimonidazole (FIGS. 24C and 24D). These results convincingly show that α-MMR Nbs can target hypoxic tumor regions in vivo, where they bind to the residing MMR macrophages.

Example 22

Strategies for Increasing the Tumor-to-Tissue Ratio of $^{99m}$Tc-Labeled α-MMR Nb c11

Figure 25:
FIG. 25. Increasing tumor-to-tissue ratios of $^{99m}$Tc-α-MMR Nb tracer uptake by excess unlabeled bivalent α-MMR Nb c11. (A) Overview of different Nb constructs. (B) Mono and bivalent $^{99m}$Tc-labeled Nbs were injected in s.c. TS/A or 3LL-R tumor-bearing mice and uptake values were calculated 3 hours post injection via organ dissection (C) s.c. TS/A tumor-bearing mice were injected with $^{99m}$Tc-labeled Nb BCII10, $^{99m}$Tc-labeled α-MMR Nb c11 or $^{99m}$Tc-labeled α-MMR Nb+twenty-fold molar excess of unlabeled bivalent α-MMR Nb c11. C1: uptake values of $^{99m}$Tc-α-MMR Nb (expressed as injected activity per gram (% IA/g)) at 3 hours post injection. Mean±SEM (n=6). C2: α-MMR Nb-to-background ratio, calculated as $^{99m}$Tc-α-MMR Nb uptake values/$^{99m}$Tc-Nb BCII10. C3: tumor-to-tissue ratio of $^{99m}$Tc-α-MMR Nb, calculated as "tracer uptake in the tumor"/"tracer uptake in the organ." Statistical significance was tested between $^{99m}$Tc-α-MMR Nb and $^{99m}$Tc-α-MMR Nb+cold Nb *p<0.05, p<0.01, *p<0.001.
Figure 25:
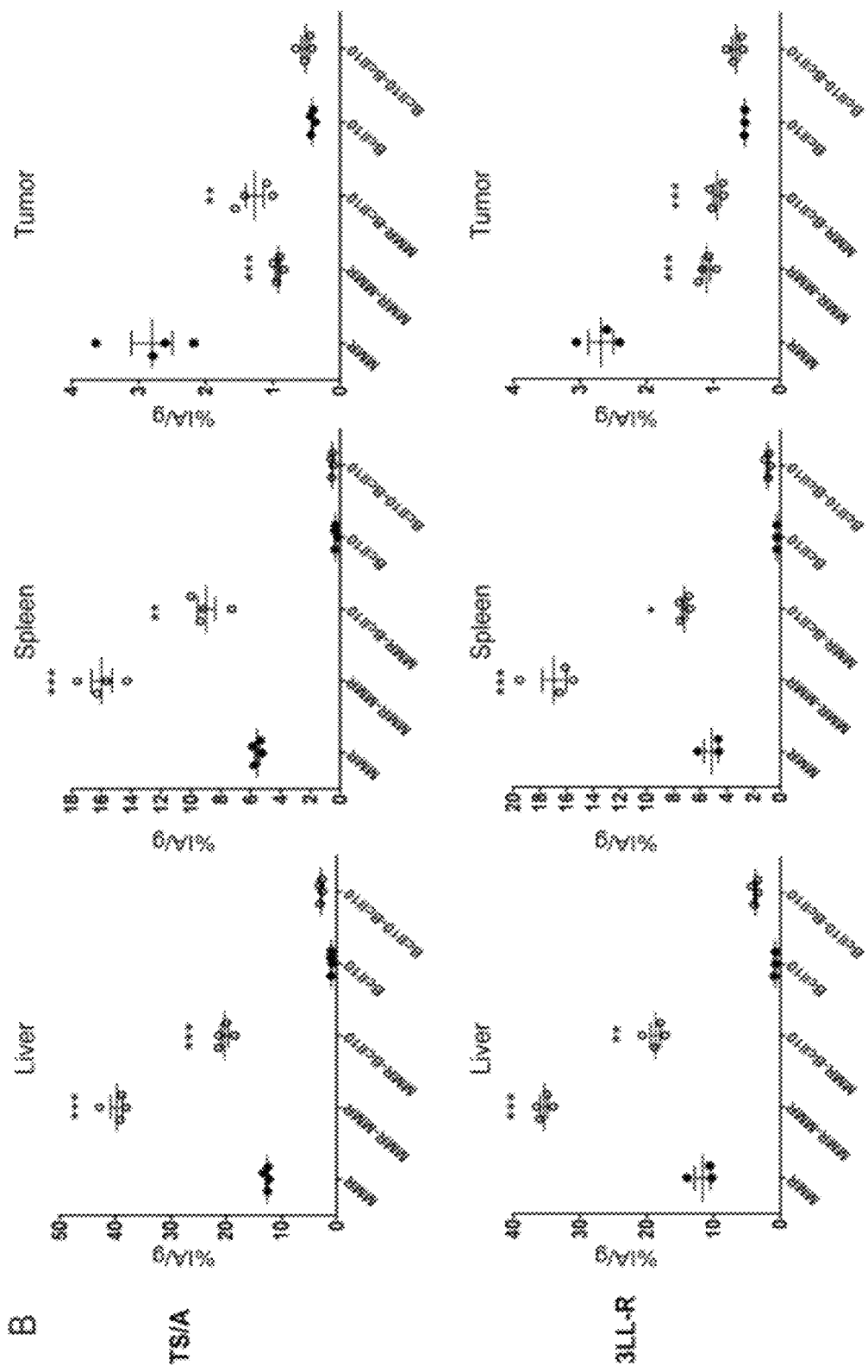
Figure 25:
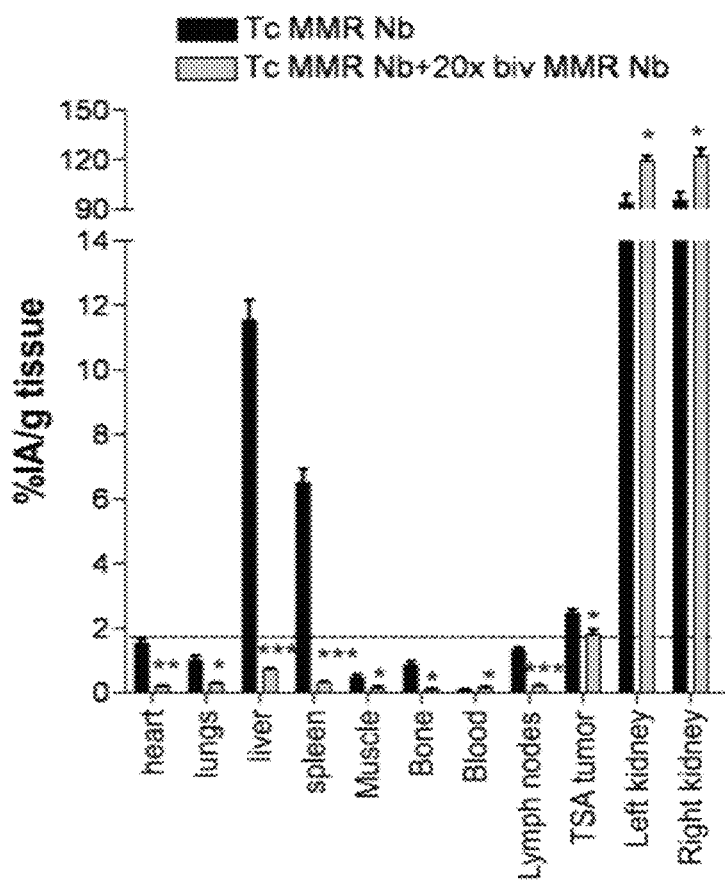
Figure 26:
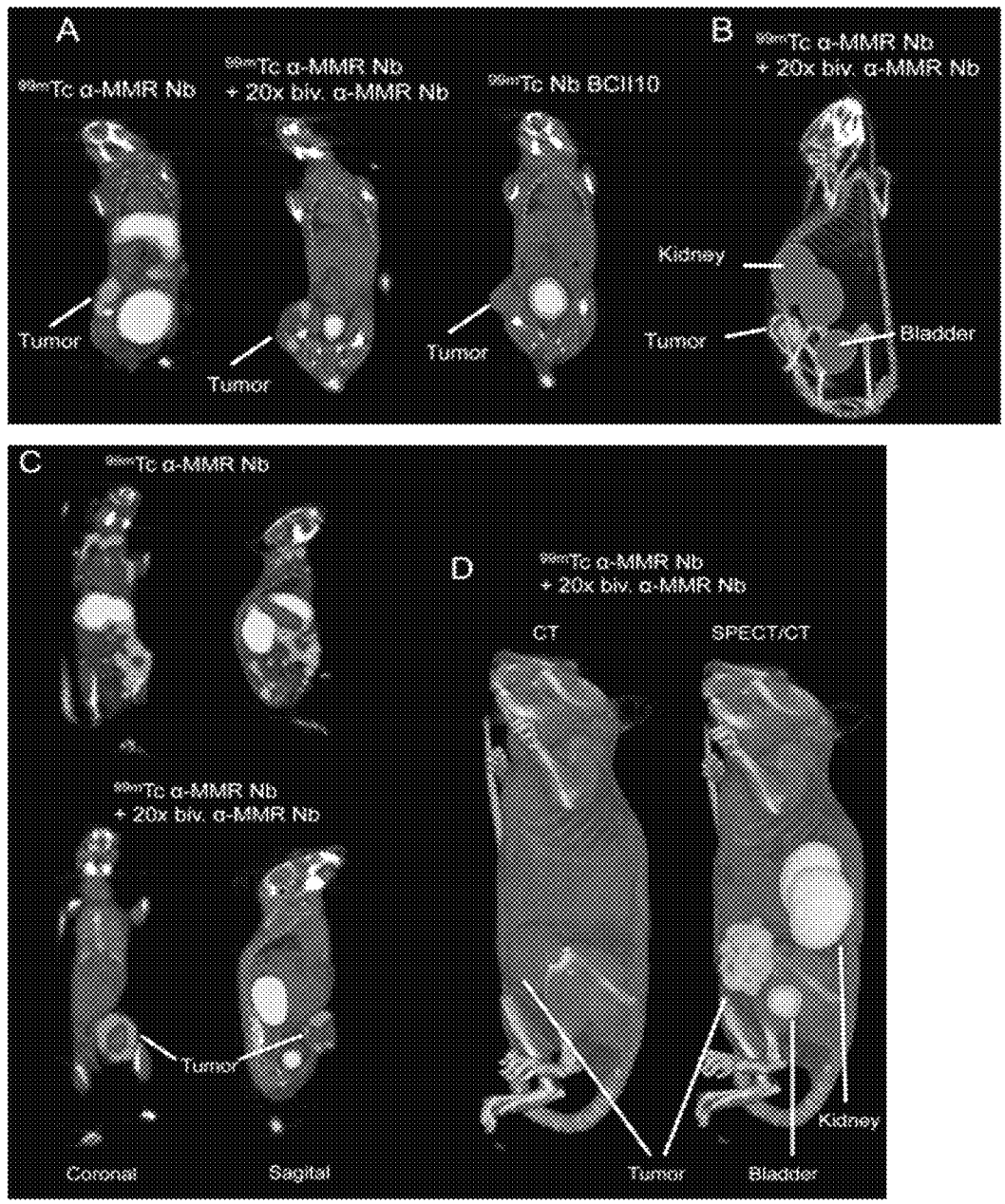
FIG. 26. Fused Pinhole SPECT/Micro-CT images of mice co-injected with $^{99m}$Tclabeled α-MMR Nb with excess unlabeled bivalent α-MMR Nb. (A) Coronal views of subcutaneous TS/A-bearing mice 3 hours after injection of $^{99m}$Tc-labeled α-MMR Nb c11, $^{99m}$Tc-labeled α-MMR Nb c11+twenty-fold molar excess of unlabeled bivalent α-MMR Nb c11 or $^{99m}$Tc-labeled Nb BCII10. (B) 3D reconstruction of SPECT/CT images of a subcutaneous TS/A-bearing mouse injected with indicated tracer, 3 hours p.i. (planar view; Video 1 for 3D view: data not shown) (C) Coronal and sagittal views of mice bearing orthotopic TS/A tumors in the mammary gland 3 hours after injection with indicated tracers. (D) High-resolution 3D reconstruction of CT and SPECT/CT images of an orthotopic TS/A-bearing mouse injected with indicated tracer, 3 hours p.i. (planar view; Video 2 for 3D view: data not shown).
Figure 27:
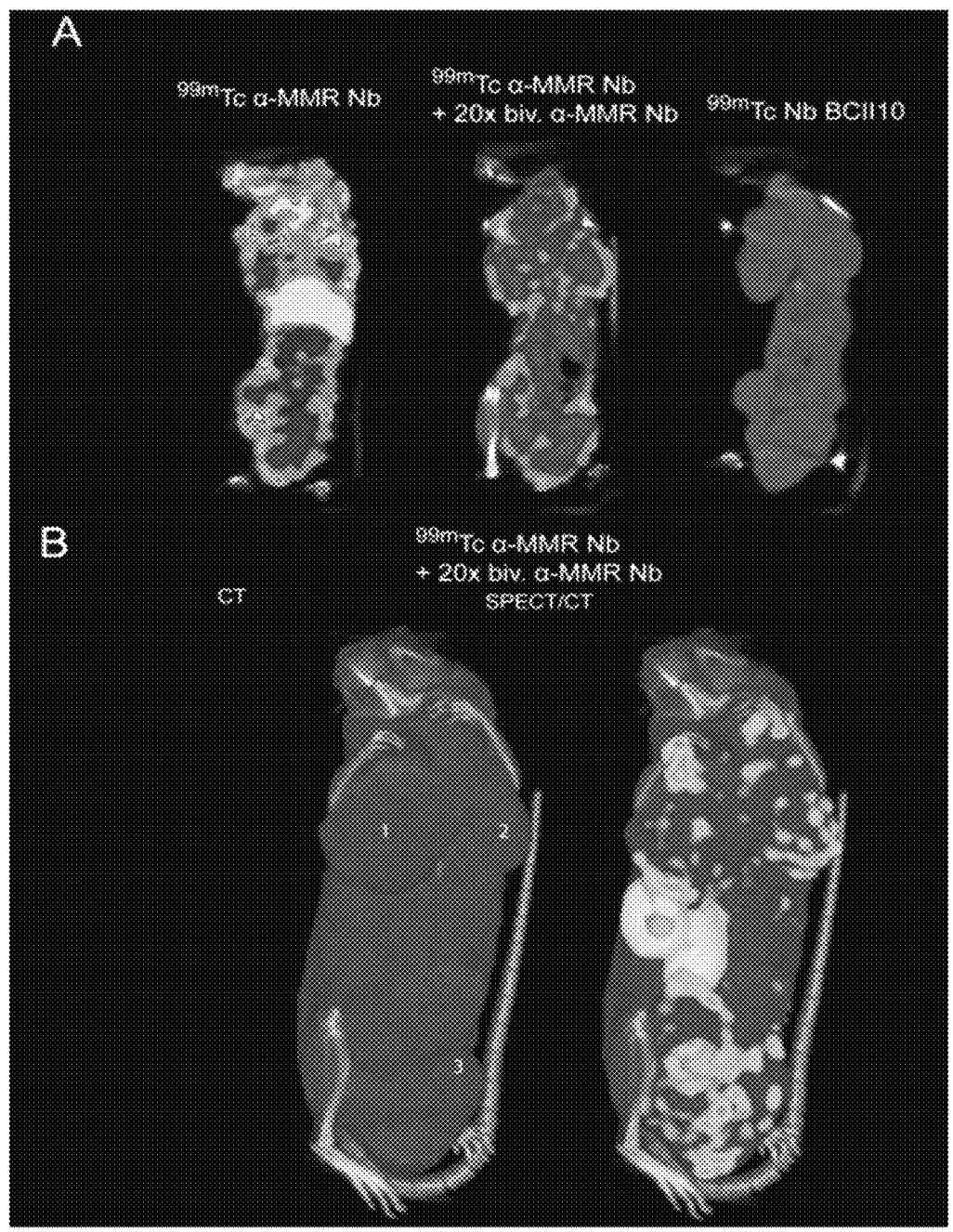
FIG. 27. α-MMR Nb-based imaging and TAM targeting in MMTV-PyMT mice. (A) A MMTV-PyMT mouse with multiple macroscopic nodules was consecutively (48- to 76-hour intervals) injected with indicated tracers; images were taken 3 hours p.i. Coronal views are shown. n=3 (B) High-resolution 3D reconstruction of CT and SPECT/CT images of the same mouse after injection of $^{99m}$Tc-labeled α-MMR Nb and blocking bivalent α-MMR Nb. Out of multiple nodules, the numbers indicate those tumors that were chosen for dissection (C) FACS analysis of single-cell suspensions from the tumors indicated in (B).
Figure 27:
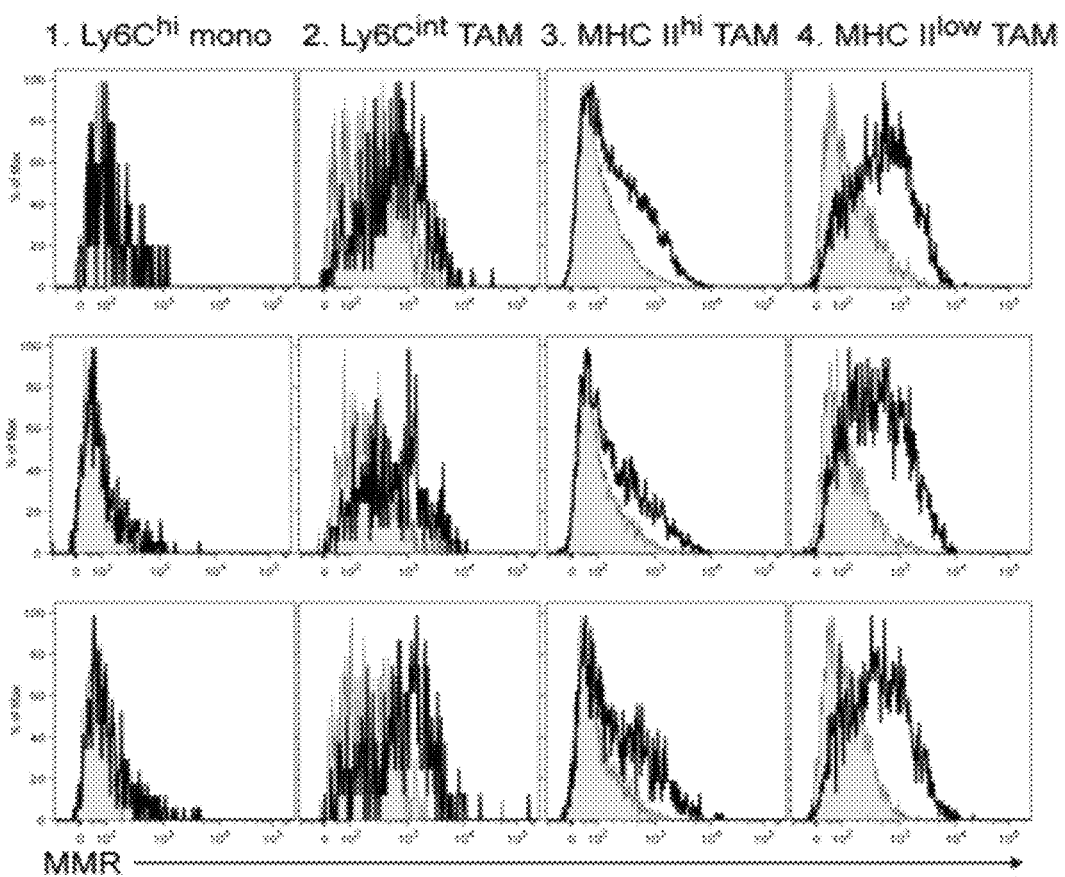

A methodology for the specific in vivo targeting of a tracer to TAMs, but not to other sites in the body, could be of important diagnostic and therapeutic significance. However, both in the TS/A and 3LL-R model, $^{99m}$Tc-labeled anti-MMR Nb accumulates to a higher extent in liver and spleen as compared to tumor. Therefore, we aimed to minimize binding of labeled tracer in these extratumoral sites, while preserving tumor targeting. The efficient tumor targeting potential of nanobodies is thought to be a direct result of their small size. To investigate this, a series of larger bivalent Nbs were created (FIG. 25A). First, αMMR-αMMR bivalent Nbs were made by cloning three different peptide linkers with increasing proline content (glycineserine linker, part of the llama IgG2c hinge or part of the human IgA hinge) between two Nb c11 sequences (as described in Example 14). All these bivalent Nbs showed a five-fold higher avidity compared to the monovalent Nb c11, which can be largely attributed to a three-fold increase in $K_D$ (Table 5) and displayed a very similar in vivo biodistribution (Table 7). In addition, using the llama IgG2c linker, αMMR-BCII10 bispecific Nbs and BCII10-BCII10 bivalent Nbs were generated and their in vivo biodistribution was evaluated in TS/A and 3LL-R tumor-bearing mice. Interestingly, αMMR-BCII10 and especially αMMR-αMMR Nbs showed a significantly enhanced targeting of liver and spleen, but a dramatically reduced targeting of tumor, as compared to monovalent α-MMR Nbs (FIG. 25B). Hence, these bivalent Nbs seem to possess desirable features to efficiently block extratumoral binding sites while preserving intratumoral binding sites. To test this, we co-injected $^{99m}$Tc-labeled monovalent α-MMR Nb with a twenty-fold molar excess of unlabeled bivalent αMMR-αMMR Nb and assessed the specific uptake of labeled Nb in distinct organs. While the retention of monovalent $^{99m}$Tc-labeled α-MMR Nb is reduced in all organs to the aspecific background level seen with Nb BCII10, the uptake in tumors is only slightly diminished (FIG. 25C). As a result, the tumor-to-tissue ratio of labeled α-MMR Nb is dramatically increased and tracer uptake is highest in the tumor. This allowed the tumor to be clearly distinguishable in SPECT/micro-CT imaging of mice bearing subcutaneous tumors (FIGS. 26A and 26B). Importantly, very similar imaging data were obtained when TS/A tumors were grown orthotopically in the mammary fat pad (FIGS. 5C and 5D), for which the presence of the two main TAM subsets as described above (Example X). Finally, imaging studies were performed in transgenic MMTV-PyMT mice, which spontaneously develop mammary tumors.[33] Hereto, a mouse bearing multiple macroscopic tumors was consecutively imaged (48-hour intervals to allow complete elimination and decay of the $^{99m}$Tc tracer) with either $^{99m}$Tc-labeled α-MMR Nb, $^{99m}$Tc-labeled BCII10 Nb or $^{99m}$Tc-labeled α-MMR Nb co-injected with unlabeled bivalent αMMR-αMMR Nb. When $^{99m}$Tclabeled α-MMR Nb was injected alone, tumors were not easily distinguishable due to high extratumoral uptake (FIG. 27A). However, co-injecting unlabeled bivalent αMMR-αMMR Nb minimalized extratumoral Nb retention and resulted in tracer uptake in the most prominent macroscopic nodules as seen via high-resolution 3D CT reconstructions (FIG. 27B). Notably, FACS analysis showed that for all three selected tumors highlighted in FIG. 6B, distinct TAM subpopulations were present, whereby MMR expression was highest on the MHC II$^{low}$ TAMs (FIG. 27C).

Example 23

Effect of Mono- and Bivalent α-MMR Nb c11 on Immune Cell Activation

Figure 28:
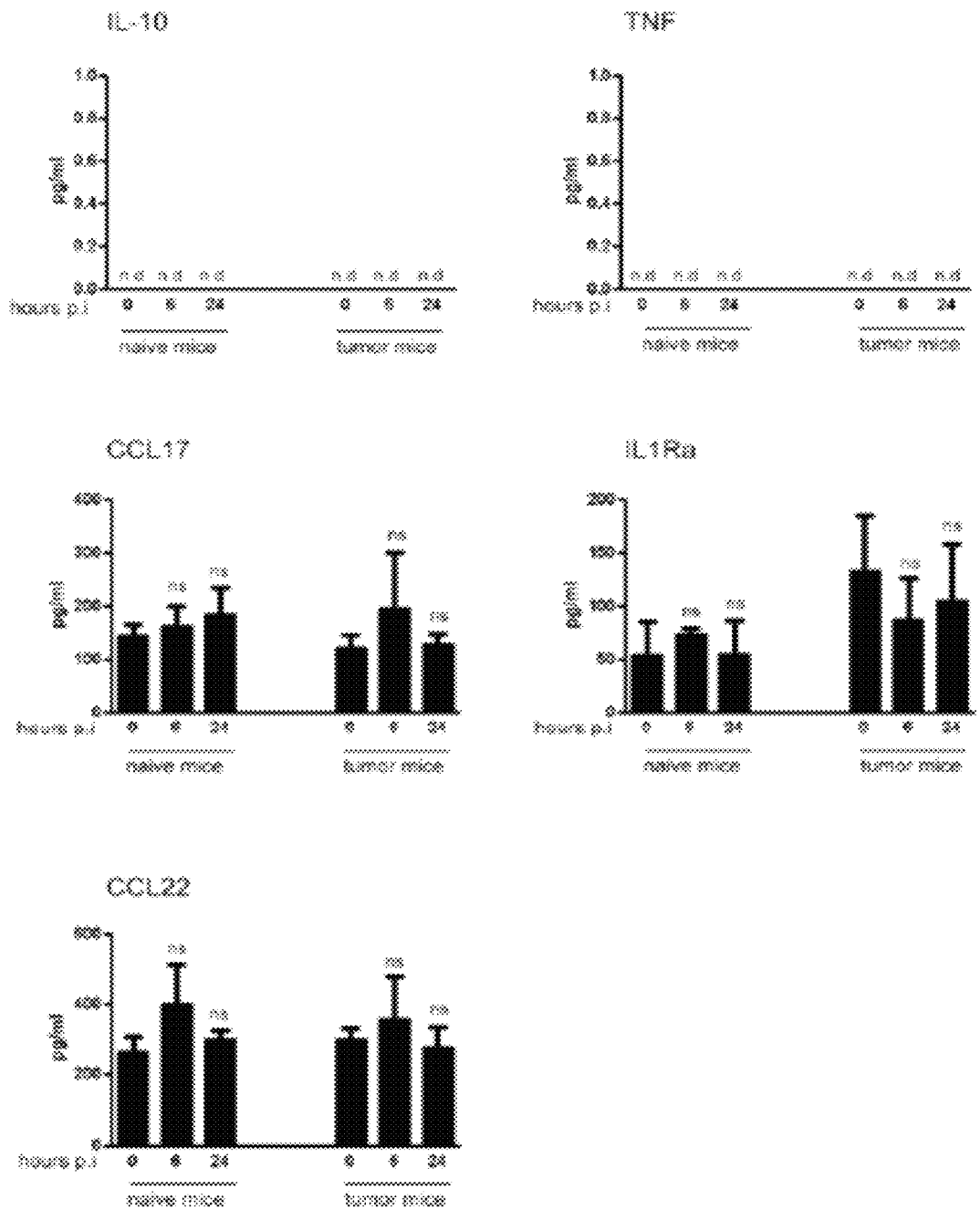
FIG. 28. Effect of mono- and bivalent α-MMR Nb on immune cell activation in vivo. To assess whether Nbs elicit a functional response in vivo, naive mice and 13 days 3LL-R tumor-bearing mice were left untreated or were stimulated (i.v. injection) with 5 µg monovalent Nb+200 µg bivalent Nb for 6 or 24 hours. Cytokine and chemokine production was assessed by sandwich ELISA on blood serum. Values are the mean±SEM of three experiments.

Monoclonal anti-MMR antibodies are known to potentially activate macrophages and DCs.[47] To assess whether mono- or bivalent α-MMR Nb c11 elicits a response, Nbs were added in varying concentrations to bone-marrow derived DCs (BMDCs) or macrophages (BMDMs) in vitro or were injected at a high dose in vivo. Monovalent α-MMR Nbs did not alter cytokine/chemokine production by BMDCs nor BMDMs in vitro, with or without LPS stimulation (data not shown). With the highest concentration of bivalent Nb (40 µg/ml) we observed a small, but significant, increase in TNF production by DCs and TNF and IL1Ra production by macrophages in vitro. Importantly however, the highest in vivo dose of Nb used in this study (5 µg monovalent Nb+200 µg bivalent Nb) did not induce any significant increase in the serum cytokine levels, both for naive and tumor-bearing mice (FIG. 28). Overall, we conclude that anti-MMR Nbs are innovative tools for the targeting and imaging of hypoxic MMR$^+$ TAMs without the risk of inducing overt innate immune responses in vivo.

Example 24

Relevance of MMR as a Marker for Tumor-Promoting Tams in Human Tumors

In order to test the relevancy of MMR as a marker for tumor-promoting TAMs in human tumors, we assessed MMR and CD68 (as human macrophage marker) expression in paraffin-embedded sections of human breast cancer samples (VUB-UZ Brussel). Using immunohistochemistry on consecutive slides of the same specimen and one double staining on a single slide, we could demonstrate the presence of CD68 positive macrophages in both tumor and fibrotic foci within the tumor region. Immunostaining for MMR clearly shows that the macrophages found in fibrotic foci do co-express MMR (data not shown). Since fibrotic foci within the tumor region is known to be a marker of hypoxia and worse prognosis,[48] the presence of MMR$^+$ macrophages could function as an indicator of severe hypoxia in human tumors as well, similar to what we show for mouse tumors.

In summary, these studies shows that in human breast cancer samples, MMR$^+$ TAMS are clearly detected and are enriched in fibrotic foci which are known to be a marker for intratumoral hypoxia and correlate with a poor prognosis.

Example 25

Selection of Anti-Human MMR Nbs

Figure 29:
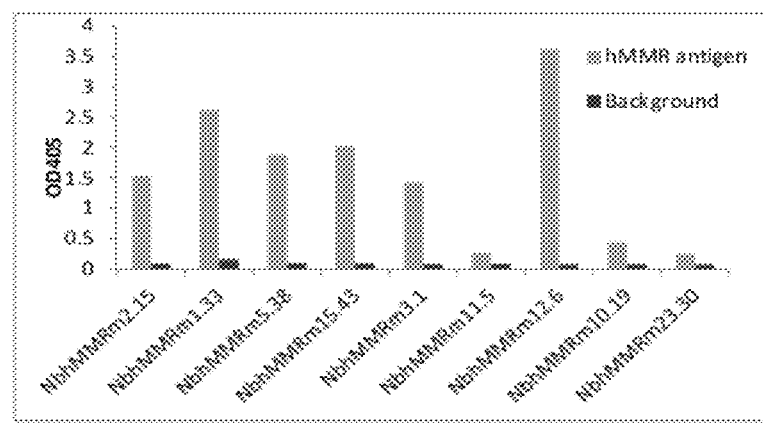
FIG. 29. PE-ELISA on human MMR. Summary of the selected anti-human MMR Nb clones. A clone was selected when the OD405 nm was at least three times higher on specific antigen as compared to irrelevant milk-blocking proteins.

Next, anti-human MMR nanobodies were generated (see also Material and Method section). After four panning rounds of an anti human/anti mouse MMR phage bank on human MMR, up to 100-fold enrichments for hMMR reactive phages were observed per panning round. Therefore, 188 colonies from all rounds were selected for PE-expression. These PE-extracts were used in PE-ELISAs to determine which clones react effectively to hMMR. In total 100 clones were selected based on these results (FIG. 29). Additionally, the DNA and protein sequence of the selected clones was determined (Table 11) and double clones or premature stopping clones were discarded.

Example 26

Selection of Anti-Human/Mouse MMR Cross-Reactive Nbs

Figure 30:
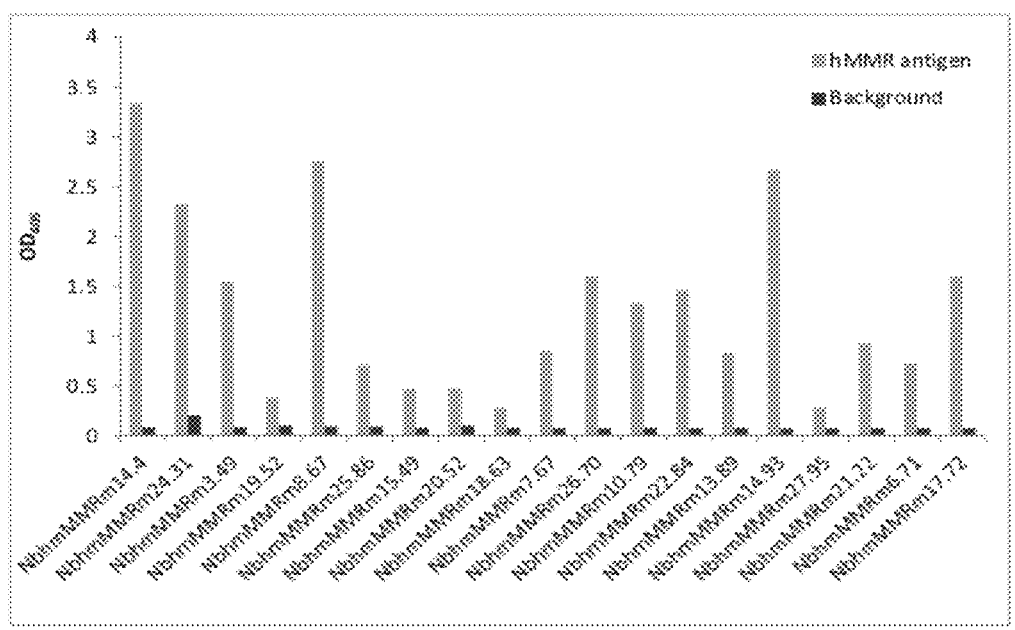
FIG. 30. PE-ELISA on human MMR. Summary of the selected anti-human/mouse MMR cross-reactive Nb clones. A clone was selected when the OD405 nm was at least three times higher on specific antigen as compared to irrelevant milk-blocking proteins.
Figure 31:
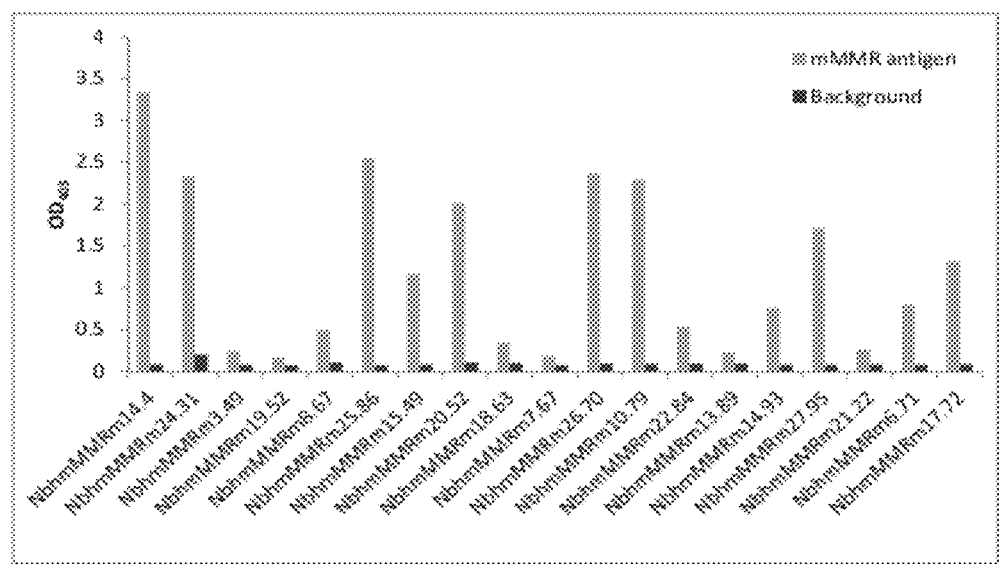
FIG. 31. PE-ELISA on mouse MMR Summary of the selected anti-human/mouse MMR cross-reactive Nb clones.

Next, anti-human/mouse MMR cross-reactive nanobodies were generated (see also Material and Method section). The anti human/anti mouse MMR phage bank was alternatingly screened on human and mouse MMR for a total of four rounds, resulting in up to 100-fold enrichments for hMMR/mMMR reactive phages from the second panning round. Therefore, 188 colonies from the second and third rounds were selected for PE-expression. These PE-extracts were used in PE-ELISAs to determine which clones react effectively to MMR, clones were selected after the ELISA on hMMR (FIG. 30). These clones were then screened for binding on mouse MMR (FIG. 31). Only clones[42] that reacted to both antigens were withheld as true cross-reactive Nbs. These clones were sequenced (Table 12) and divided into families based on their CDR3 regions.

Example 27

Production of Representative Set of Anti-Human or Anti-Human/Mouse MMR Nbs

A set of representative clones was selected for Nb production in *E. Coli*: (1) anti-human Nbs: NbhMMRm1.33, NbhMMRm10.19, NbhMMRm23.30, NbhMMRm2.15, NbhMMRm3.1, NbhMMRm5.38, NbhMMRm12.6, NbhMMRm11.5, NbhMMRm15.43, NbhMMRm16.95; (2) anti-human/mouse Nbs: NbhmMMRm14.4, NbhmMMRm6.71, NbhmMMRm24.31, NbhmMMRm20.52, NbhmMMRm3.49, NbhmMMRm22.84, NbhmMMRm19.52, NbhMMRm21.22, NbhmMMRm14.93, NbhmMMRm15.49, NbhmMMRm17.72, NbhmMMRm10.79, NbhmMMRm7.67, NbhMMRm4.83 Each clone was grown in a two-liter culture. After expression and osmotic shock, the resulting extract was purified on 1 ml of Ni-NTA resin. The resulting 5 ml of eluted Nb was dialyzed to PBS after which the concentration was determined using a Nanodrop device and purity was assessed on Coomassie stained SDS-PAGE gels. The nanobodies all produced between 0.7 and 9 mg Nb/1 E. coli culture (Table 13).

TABLE 1

Gene expression profile of MHC II$^{hi}$ versus MHC II$^{low}$ TAMs

| Gene | GeneID | hi/low | hi/low | 90% CI | p | ΔCt hi |
|---|---|---|---|---|---|---|
| Ccl17 | MGI: 1329039 | | 30 | [19-47] | ** | 8.1 ± 0.3 |
| Cx3cl1 | MGI: 1097153 | | 9.2 | [4.4-19] | * | 12.2 ± 0.5 |
| Cxcl11 | MGI: 1860203 | | 7.4 | [4.2-13] | ** | 9.2 ± 0.1 |
| Ccl5 | MGI: 98262 | | 6.1 | [4.1-8.9] | * | 5.4 ± 0.4 |
| Il6 | MGI: 96559 | | 5.9 | [1.8-19] | | 14 ± 0.9 |
| Cxcl10 | MGI: 1352450 | | 5.9 | [4.3-8.2] | * | 5.4 ± 0.4 |
| Cxcl9 | MGI: 1352449 | | 5.3 | [4.2-6.6] | *** | 6.4 ± 0.0 |
| Il12b | MGI: 96540 | | 4.0 | [1.6-10] | | 12.4 ± 0.4 |
| Il1b | MGI: 96543 | | 3.6 | [2.6-5.1] | *** | 2.9 ± 0.1 |
| Pgf | MGI: 105095 | | 3.3 | [0.68-16] | | 9.5 ± 0.5 |
| Mmp9 | MGI: 97011 | | 2.9 | [1.9-4.2] | | 4.0 ± 0.5 |
| Ptgs2 (Cox2) | MGI: 97798 | | 2.3 | [1.1-5.0] | | 7.3 ± 0.6 |
| Nos2 (iNOS) | MGI: 97361 | | 2.3 | [1.4-3.8] | * | 8.8 ± 0.1 |
| Angpt2 | MGI: 1202890 | | 2.1 | [1.6-2.7] | ** | 9.2 ± 0.1 |
| Ccl22 | MGI: 1306779 | | 2.0 | [1.9-2.2] | * | 11.5 ± 0.3 |
| Tek (Tie2) | MGI: 98664 | | 1.8 | [1.5-2.2] | | 5.7 ± 0.4 |
| Vegfa | MGI: 103178 | | 1.6 | [1.3-2.0] | | 6.2 ± 0.2 |
| Thbs2 (TSP2) | MGI: 98738 | | 1.2 | [0.9-1.8] | | 13 ± 0.0 |
| Il1a | MGI: 96542 | | 1.2 | [1.0-1.3] | | 6.8 ± 0.4 |
| Il10 | MGI: 96537 | | 1.0 | [0.69-1.5] | | 9.2 ± 0.3 |
| Cxcl16 | MGI: 1932682 | | 0.97 | [0.67-1.4] | | 4.1 ± 0.0 |
| Tnf | MGI: 104798 | | 0.93 | [0.64-1.3] | | 5.1 ± 0.3 |
| Thbs1 (TSP1) | MGI: 98737 | | 0.89 | [0.79-1.00] | | 6.2 ± 0.2 |
| Cx3cr1 | MGI: 1333815 | | 0.85 | [0.63-1.2] | | 7.4 ± 0.2 |
| Mif | MGI: 96982 | | 0.79 | [0.67-0.93] | | 3.9 ± 0.1 |
| Igf1 | MGI: 96432 | | 0.78 | [0.63-0.97] | | 10.3 ± 0.4 |
| Mmp14 | MGI: 101900 | | 0.77 | [0.53-1.1] | | 8.3 ± 0.1 |
| Ccr2 | MGI: 106185 | | 0.71 | [0.39-1.3] | | 6.5 ± 0.5 |
| Plau (uPA) | MGI: 97611 | | 0.71 | [0.62-0.81] | | 5.7 ± 0.1 |
| Ccl11 | MGI: 103576 | | 0.7 | [0.39-1.2] | | 12.6 ± 0.3 |
| Adamts1 | MGI: 109249 | | 0.68 | [0.44-1.0] | | 14.1 ± 0.3 |
| Ccl1 | MGI: 98258 | | 0.65 | [0.43-0.99] | | 12.5 ± 0.5 |
| Tgfb1 | MGI: 98725 | | 0.64 | [0.58-0.70] | * | 4.5 ± 0.2 |
| Cxcl1 | MGI: 108068 | | 0.64 | [0.51-0.79] | | 3.5 ± 0.1 |

TABLE 1-continued

Gene expression profile of MHC II$^{hi}$ versus MHC II$^{low}$ TAMs

| Ccl8 | MGI: 101878 | | 0.57 | [0.33-0.98] | | 6.5 ± 0.4 |
|---|---|---|---|---|---|---|
| Il4ra | MGI: 105367 | | 0.50 | [0.44-0.57] | | 10.6 ± 0.2 |
| Arg1 | MGI: 88070 | | 0.48 | [0.46-0.51] | ** | 1.7 ± 0.1 |
| Spp1 | MGI: 98389 | | 0.45 | [0.40-0.51] | * | 1.0 ± 0.1 |
| Ccl12 | MGI: 108224 | | 0.44 | [0.30-0.64] | * | 2.7 ± 0.2 |
| Ccl6 | MGI: 98263 | | 0.39 | [0.27-0.57] | * | 1.9 ± 0.3 |
| Ccl4 | MGI: 98261 | | 0.34 | [0.24-0.48] | ** | 4.8 ± 0.4 |
| Ctsd | MGI: 88562 | | 0.33 | [0.30-0.36] | ** | 4.4 ± 0.2 |
| Ccl9 | MGI: 104533 | | 0.33 | [0.27-0.39] | ** | 2.5 ± 0.3 |
| Ccl3 | MGI: 98260 | | 0.33 | [0.25-0.43] | ** | 6.0 ± 0.2 |
| Timp2 | MGI: 98753 | | 0.30 | [0.15-0.59] | * | 4.8 ± 0.5 |
| Ccl2 | MGI: 98259 | | 0.26 | [0.19-0.36] | * | 2.7 ± 0.4 |
| Ccl7 | MGI: 99512 | | 0.25 | [0.18-0.35] | ** | 2.9 ± 0.5 |
| Mrc1 (MMR) | MGI: 97142 | | 0.23 | [0.21-0.25] | *** | 4.2 ± 0.0 |
| Stab1 | MGI: 2148742 | | 0.22 | [0.16-0.29] | ** | 5.5 ± 0.2 |
| CD163 | MGI: 2135946 | | 0.16 | [0.12-0.21] | ** | 9.6 ± 0.1 |
| Lyve1 | MGI: 2136348 | | 0.033 | [0.019-0.06] | * | 8.5 ± 0.1 |

Figure 3:
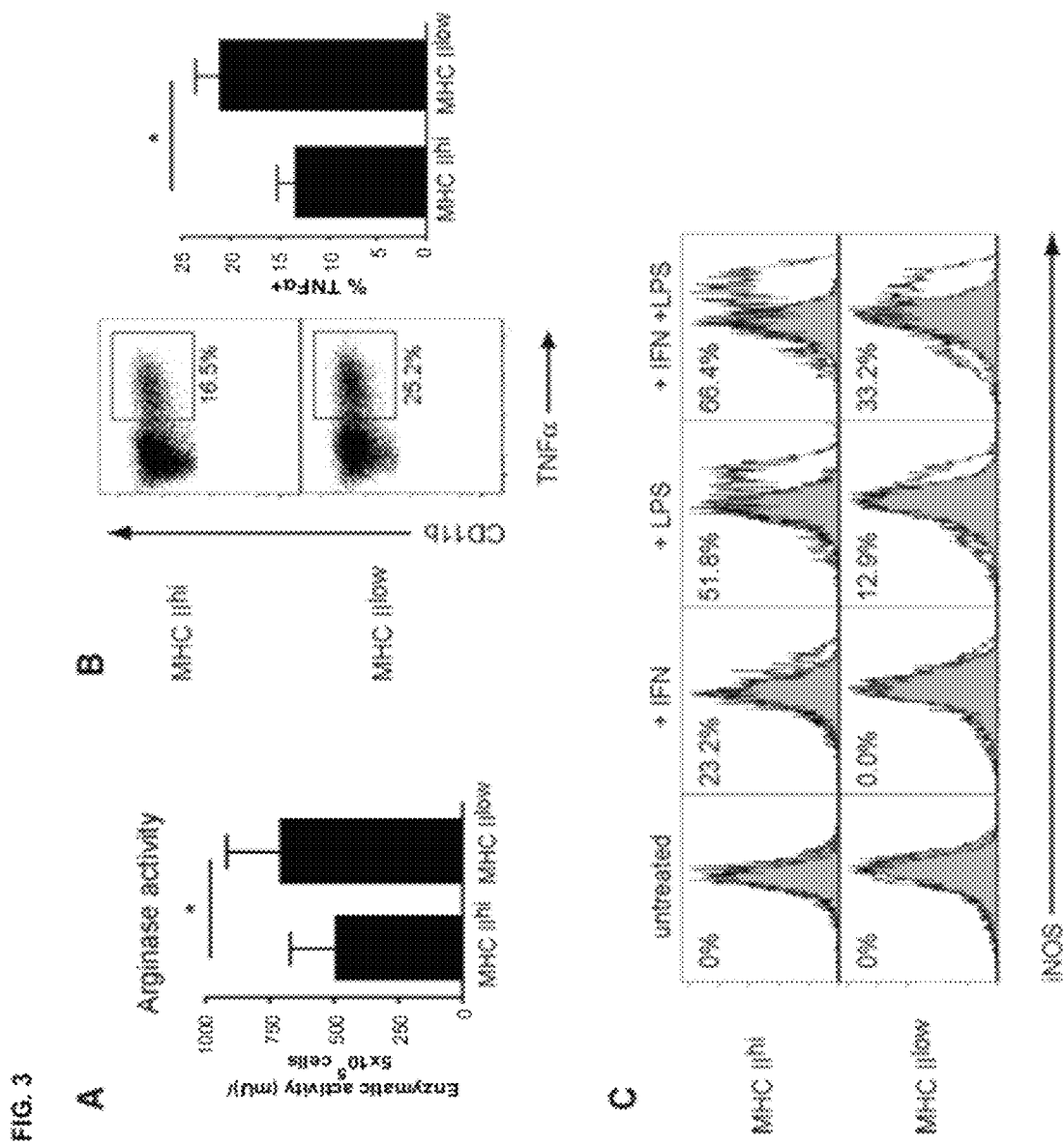
FIG. 3: Arginase, TNFα, and iNOS protein expression in MHC II$^{hi}$ and MHC II$^{low}$ TAMs. (A) Arginase enzymatic activity (mU) was measured in lysates of sorted TAMs. Values are the mean±SEM of three experiments. * $p<0.05$ (B) TNFα production by TAMs was measured using intracellular FACS. Bar diagrams represent the mean percentage TNFa+ TAMs±SEM from three experiments. * $p<0.05$ (C) LPS were left untreated or stimulated with IFNγ, LPS or LPS+IFNγ for 12 hours. Subsequently, iNOS expression was evaluated using intracellular FACS. The percentage iNOS+ cells is shown as normalized ΔMFI (see Materials & Methods). n=2 experiments.
Figure 5:
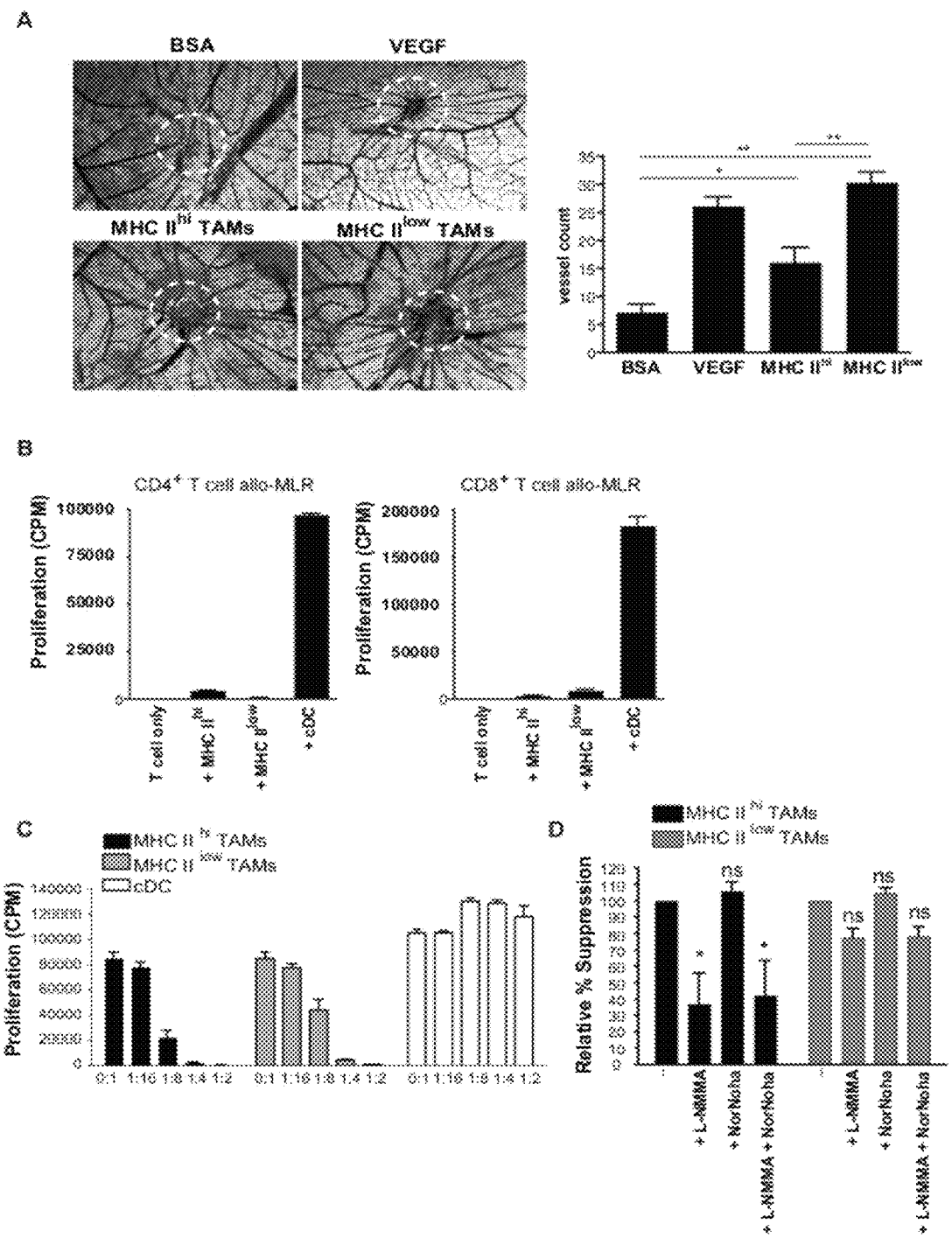
FIG. 5: Differential functions of TAM subsets. (A) Sorted TAMs were grafted on the developing chorioallantoic membrane from fertilized chicken eggs. BSA and rhVEGF grafting were used as negative and positive controls, respectively. At day 13, the number of vessels growing towards the implants was quantified. Values are the mean number of implant-directed vessels±SEM of eight individual eggs/condition of two experiments. * $p<0.05$; ** $p<0.01$. (B) Sorted TAM subsets or splenic Balb/c cDCs were cultured in the presence of purified C57BL/6 CD4+ or CD8+ T cells and T-cell proliferation was assessed. Graphs represent the average level of 3H-thymidine incorporation, expressed as Counts Per Minute (CPM), ±SEM. n=3 experiments. (C) Sorted TAM subsets or splenic Balb/c cDC were added to naive Balb/c splenocytes. Co-cultures were stimulated with anti-CD3 and proliferation was assessed. n=3 experiments. (D) TAM subsets and Balb/c splenocytes were cultured at a 1:4 ratio and treated with anti-CD3 with or without the indicated inhibitors. Values represent the mean±SD of the relative percentage suppression taken over three experiments. * $p<0.05$

| Protein | Gene | GeneID |
|---|---|---|
| Table 1 Legend | | |
| FIG. 1 | D7Rik132 (S12) | MGI: 1338854 |
| CD11b | Itgam (Cd11b) | MGI: 96607 |
| Ly6C | Ly6c1 (Ly6c) | MGI: 96882 |
| Ly6G | Ly6g | MGI: 109440 |
| CX$_3$CR1 | Cx3cr1 | MGI: 1333815 |
| F4/80 | Emr1 | MGI: 106912 |
| CD62L | Sell (Cd62l) | MGI: 98279 |
| CD49d | Itga4 (Cd49d) | MGI: 96603 |
| CD162 | Selplg (Cd162) | MGI: 106689 |
| CD11c | Itgax (Cd11c) | MGI: 96609 |
| CD43 | Spn (Cd43) | MGI: 98384 |
| SR-A | Msr1 | MGI: 98257 |
| IL4-Rα | Il4ra | MGI: 105367 |
| CD80 | Cd80 | MGI: 101775 |
| CD86 | Cd86 | MGI: 101773 |
| PD-L1 | Cd274 | MGI: 1926446 |
| PD-L2 | Pdcd1lg2 | MGI: 1930125 |
| FIG. 3 | | |
| Arginase | Arg1 | MGI: 88070 |
| FIG. 5 | | |
| CD4 | Cd4 | MGI: 88335 |
| CD8 | Cd8a | MGI: 88346 |

>5
2-5
0.5-2
0.5-0.2
<0.2

TAM subsets were sorted from 3 weeks tumor-bearing mice and their gene expression was assessed using qRT-PCR. The expression of each gene was normalized based on the S12 gene and is shown as the relative expression in MHC II$^{hi}$ vs. MHC II$^{low}$ TAMs (hi/low). Values are the geometric means of three to four independent experiments and are color-coded according to the level of induction. Accompanying 90% confidence intervals and p-values are shown.
*p < 0.05;
**p < 0.01;
***p < 0.001.
$C_T$ represents the threshold cycle.
The $\Delta C_T$ was calculated for MHC II$^{hi}$ TAMs and is defined as ($C_T$(gene) − $C_T$(S12)); values represent mean ± SEM.
Lower ΔCt corresponds to higher expression levels.

TABLE 2

| Markers | Clone | Manufacturer |
|---|---|---|
| CD11b PE-Cy7 | M1/70 | BD Bioscience |
| Ly6C AF647/AF488 | ER-MP20 | Serotec |
| Ly6G PE/FITC | 1A8 | BD Bioscience |
| IA/IE PE/FITC | M5/114.15.2 | BD Bioscience |
| IA/IE PercpCy5.5 | M5/114.15.2 | Serotec |
| IA/IE FITC | M5/114.15.2 | eBioscience |
| F4/80 PE/FITC | CI:A3-1 | Serotec |
| CCR3 FITC | 83101 | R&D Systems |
| CD62L PE | SK11 | BD Bioscience |
| CD11c PE | HL3 | BD Bioscience |
| CD43 PE | S7 | BD Bioscience |
| CD49d PE | 9C10(MFR4.B) | BD Bioscience |
| CD162 PE | 2PH1 | BD Bioscience |
| MMR PE/FITC | MR5D3 | Serotec |
| SR-A PE | 2F8 | Serotec |
| IL4Rα | mIL4RM1 | BD Bioscience |
| Tie-2 PE | TEK4 | eBioscience |
| CD80 FITC | 16-10A1 | BD Bioscience |
| CD86 FITC | GL-1 | BD Bioscience |
| PD-L1/PE | MIH5 | eBioscience |
| PD-L2/PE | TY25 | eBioscience |
| anti-TNFα/APC | MP6-XT22 | BD Bioscience |
| Rabbit anti-iNOS | (M19) | Santa Cruz |
| anti-Rabbit/APC | polyclonal | Invitrogen |

TABLE 3

List of gene specific primers

| GENE | FORWARD PRIMER | REVERSE PRIMER |
|---|---|---|
| CCL17 | CCCATGAAGACCTTCACCTC (SEQ ID NO: 9) | CATCCCTGGAACACTCCACT (SEQ ID NO: 10) |
| CX3CL1 | ACTCCTTGATTGGTGGAAGC (SEQ ID NO: 11) | CAAAATGGCACAGACATTGG (SEQ ID NO: 12) |
| CXCL11 | TCCTTTCCCCAAATATCACG (SEQ ID NO: 13) | CAGCCATCCCTACCATTCAT (SEQ ID NO: 14) |
| CCL5 | GTGCCCACGTCAAGGAGTAT (SEQ ID NO: 15) | AGCAAGCAATGACAGGGAAG (SEQ ID NO: 16) |
| IL6 | GTCTTCTGGAGTACCATAGC (SEQ ID NO: 17) | GTCAGATACCTGACAACAGG (SEQ ID NO: 18) |
| CXCL10 | TCTGAGTCCTCGCTCAAGTG (SEQ ID NO: 19) | CCTTGGGAAGATGGTGGTTA (SEQ ID NO: 20) |
| CXCL9 | TCAACAAAAGAGCTGCCAAA (SEQ ID NO: 21) | GCAGAGGCCAGAAGAGAGAA (SEQ ID NO: 22) |
| IL12B | GAAAGACCCTGACCATCACT (SEQ ID NO: 23) | CCTTCTCTGCAGACAGAGAC (SEQ ID NO: 24) |
| IL1B | GTGTGGATCCAAAGCAATAC (SEQ ID NO: 25) | GTCTGCTCATTCATGACAAG (SEQ ID NO: 26) |
| PGF | GCACTGTGTGCCGATAAAGA (SEQ ID NO: 27) | TACCTCCGGGAAATGACATC (SEQ ID NO: 28) |
| MMP9 | TGAATCAGCTGGCTTTTGTG (SEQ ID NO: 29) | GTGGATAGCTCGGTGGTGTT (SEQ ID NO: 30) |
| PTGS2 (COX2) | CAGGCTGAACTTCGAAACAG (SEQ ID NO: 31) | CAGCTACGAAAACCCAATCA (SEQ ID NO: 32) |
| NOS2 | GCTTCTGGTCGATGTCATGAG (SEQ ID NO: 33) | TCCACCAGGAGATGTTGAAC (SEQ ID NO: 34) |
| ANGPT2 | GCATGTGGTCCTTCCAACTT (SEQ ID NO: 35) | GATCCTCAGCCACAACCTTC (SEQ ID NO: 36) |
| CCL22 | TGACTTGGGTCCTTGTCCTC (SEQ ID NO: 37) | AAGGAAGCCACCAATGACAC (SEQ ID NO: 38) |
| TEK (TIE2) | ACTTCGCAGGAGAACTGGAG (SEQ ID NO: 39) | AAGAAGCTGTTGGGAGGACA (SEQ ID NO: 40) |
| VEGFA | CAGGCTGCTGTAACGATGAA (SEQ ID NO: 41) | AATGCTTTCTCCGCTCTGAA (SEQ ID NO: 42) |

TABLE 3-continued

List of gene specific primers

| GENE | FORWARD PRIMER | REVERSE PRIMER |
|---|---|---|
| THBS2 (TSP2) | GAAAGCATACCTGGCTGGAC (SEQ ID NO: 43) | ACAAAAGAGCCGTACCTGGA (SEQ ID NO: 44) |
| IL1A | TTTCAAAAGGAAGGGGACAA (SEQ ID NO: 45) | CCACCTAGAAAACCCTGCTG (SEQ ID NO: 46) |
| IL10 | ACTCAATACACACTGCAGGTG (SEQ ID NO: 47) | GGACTTTAAGGGTTACTTGG (SEQ ID NO: 48) |
| CXCL16 | GTCTCCTGCCTCCACTTTCT (SEQ ID NO: 49) | CTAAGGGCAGAGGGGCTATT (SEQ ID NO: 50) |
| TNF | CCTTCACAGAGCAATGACTC (SEQ ID NO: 51) | GTCTACTCCCAGGTTCTCTTC (SEQ ID NO: 52) |
| THBS1 (TSP1) | CGTTGCCATTGGAATAGAGA (SEQ ID NO: 53) | TGGCAAAGAGTCAAAACTGG (SEQ ID NO: 54) |
| CX3CR1 | CACCATTAGTCTGGGCGTCT (SEQ ID NO: 55) | GATGCGGAAGTAGCAAAAGC (SEQ ID NO: 56) |
| MIF | CTTTTAGCGGCACGAACGAT (SEQ ID NO: 57) | AAGAACAGCGGTGCAGGTAA (SEQ ID NO: 58) |
| IGF1 | TGACATGCCCAAGACTCAGA (SEQ ID NO: 59) | AGGTTGCTCAAGCAGCAAAG (SEQ ID NO: 60) |
| MMP14 | CCGGTACTACTGCTGCTCCT (SEQ ID NO: 61) | CACACACCGAGCTGTGAGAT (SEQ ID NO: 62) |
| CCR2 | CTCAGTTCATCCACGGCATA (SEQ ID NO: 63) | CAAGGCTCACCATCATCGTA (SEQ ID NO: 64) |
| PLAU (UPA) | TCTCCTGGGCAAGTGTAGGA (SEQ ID NO: 65) | GCCTGTGCAGAGTGAACAAA (SEQ ID NO: 66) |
| CCL11 | CTCCACAGCGCTTCTATTCC (SEQ ID NO: 67) | CTTCTTCTTGGGGTCAGCAC (SEQ ID NO: 68) |
| ADAMTS1 | CTGGGCAAGAAATCTGATGA (SEQ ID NO: 69) | TGGTTGTGGCAGGAAAGATA (SEQ ID NO: 70) |
| CCL1 | GGATGTTGACAGCAAGAGCA (SEQ ID NO: 71) | CTCATCTTCACCCCGGTTAG (SEQ ID NO: 72) |
| TGFB1 | CCAAGGAGACGGAATACAGG (SEQ ID NO: 73) | TCTCTGTGGAGCTGAAGCAA (SEQ ID NO: 74) |
| CXCL1 | TCATAGCCACACTCAAGAATG (SEQ ID NO: 75) | AAGCAGAACTGAACTACCATC (SEQ ID NO: 76) |
| CCL8 | TCTACGCAGTGCTTCTTTGC (SEQ ID NO: 77) | CCACTTCTGTGTGGGGTCTA (SEQ ID NO: 78) |
| IL4RA | GCAGATGGCTCATGTCTGAA (SEQ ID NO: 79) | CTCTGGGAAGCTGGGTGTAG (SEQ ID NO: 80) |
| ARG1 | TCACCTGAGCTTTGATGTCG (SEQ ID NO: 81) | TTATGGTTACCCTCCCGTTG (SEQ ID NO: 82) |
| SPP1 | GCTTGGCTTATGGACTGAGG (SEQ ID NO: 83) | CTTGTCCTTGTGGCTGTGAA (SEQ ID NO: 84) |
| CCL12 | GCCTCCTGCTCATAGCTACC (SEQ ID NO: 85) | GGGTCAGCACAGATCTCCTT (SEQ ID NO: 86) |
| CCL6 | ATGTCCAGCTTTGTGGGTTC (SEQ ID NO: 87) | AGGTCAGGTTCCGCAGATAA (SEQ ID NO: 88) |
| CCL4 | CCCACTTCCTGCTGTTTCTC (SEQ ID NO: 89) | GAGCAAGGACGCTTCTCAGT (SEQ ID NO: 90) |
| CTSD | CCTTCGCGATTATCAGAATCC (SEQ ID NO: 91) | TACTTATGGTGGACCCAGCA (SEQ ID NO: 92) |

TABLE 3-continued

List of gene specific primers

| GENE | FORWARD PRIMER | REVERSE PRIMER |
|---|---|---|
| Ccl9 | CCAGATCACACATGCAACAG (SEQ ID NO: 93) | CTATAAAAATAAACACTTAGAGCCA (SEQ ID NO: 94) |
| Ccl3 | CGGAAGATTCCACGCCAATTC (SEQ ID NO: 95) | GGTGAGGAACGTGTCCTGAAG (SEQ ID NO: 96) |
| Timp2 | ATCGAACCCAGAGTGGAATG (SEQ ID NO: 97) | GCTAGAAACCCCAGCATGAG (SEQ ID NO: 98) |
| Ccl2 | CACTCACCTGCTGCTACTCATTCACGGATTCACAGAGAGGGAAAAATGG (SEQ ID NO: 99) | (SEQ ID NO: 100) |
| Ccl7 | GACAAAGAAGGGCATGGAAG (SEQ ID NO: 101) | CATTCCTTAGGCGTGACCAT (SEQ ID NO: 102) |
| Mrc1 (MMR) | GCAAATGGAGCCGTCTGTGC (SEQ ID NO: 103) | CTCGTGGATCTCCGTGACAC (SEQ ID NO: 104) |
| Stab1 | ACGGGAAACTGCTTGATGTC (SEQ ID NO: 105) | ACTCAGCGTCATGTTGTCCA (SEQ ID NO: 106) |
| CD163 | GAGCATGAATGAAGTGTCCG (SEQ ID NO: 107) | TGCTGAAGTTGTCGTCACAC (SEQ ID NO: 108) |
| Lyve1 | CTGGCTGTTTGCTACGTGAA (SEQ ID NO: 109) | CATGAAACTTGCCTCGTGTG (SEQ ID NO: 110) |

TABLE 4

Anti- mouse CD206 (MMR) nanobodies (anti-MMR nanobody clone 1 and 3): monovalent en bivalent constructs and nanobodies

| | |
|---|---|
| DNA seq + His tag (clone 1) SEQ ID NO: 1 | CAGGTGCAGCTGCAGGAGTCTGGAGGAGGCTTGGTGCAGCCTGGGGGGTCT CTGAGACTCTCCTGTGCAGCCTCTGGAAACATCTTCAGTATCAATGCCATCG GCTGGTACCGCCAGGCTCCAGGGAAGCAGCGCGAGTTGGTCGCAACTATTA CTCTTAGTGGTAGCACAAACTATGCAGACTCCGTGAAGGGCCGATTCTCCAT CTCCAGAGACAACGCCAAGAACACGGTGTATCTGCAAATGAACAGCCTGAA ACCTGAGGACACGGCCGTCTATTACTGTAATGCTAACACCTATAGCGACTCT GACGTTTATGGCTACTGGGGCCAGGGGACCCAGGTCACCGTCTCCTCACACC ACCATCACCATCAC |
| DNA seq - His tag (clone 1) SEQ ID NO: 2 | CAGGTGCAGCTGCAGGAGTCTGGAGGAGGCTTGGTGCAGCCTGGGGGGTCT CTGAGACTCTCCTGTGCAGCCTCTGGAAACATCTTCAGTATCAATGCCATCG GCTGGTACCGCCAGGCTCCAGGGAAGCAGCGCGAGTTGGTCGCAACTATTA CTCTTAGTGGTAGCACAAACTATGCAGACTCCGTGAAGGGCCGATTCTCCAT CTCCAGAGACAACGCCAAGAACACGGTGTATCTGCAAATGAACAGCCTGAA ACCTGAGGACACGGCCGTCTATTACTGTAATGCTAACACCTATAGCGACTCT GACGTTTATGGCTACTGGGGCCAGGGGACCCAGGTCACCGTCTCCTCA |
| Protein + His tag (clone 1) SEQ ID NO: 3 | QVQLQESGGGLVQPGGSLRLSCAASGNIFSINAIGWYRQAPGKQRELVATITLS GSTNYADSVKGRFSISRDNAKNTVYLQMNSLKPEDTAVYYCNANTYSDSDVY GYWGQGTQVTVSSHHHHHH |
| Protein - His tag (clone 1) SEQ ID NO: 4 | QVQLQESGGGLVQPGGSLRLSCAASGNIFSINAIGWYRQAPGKQRELVATITLS GSTNYADSVKGRFSISRDNAKNTVYLQMNSLKPEDTAVYYCNANTYSDSDVY GYWGQGTQVTVSS |
| DNA seq + His tag (clone 3) SEQ ID NO: 5 | CAGGTGCAGCTGCAGGAGTCTGGAGGAGGATTGGTGCAGGCTGGGGGCTCT CTGAGACTCTCCTGTGCAGCCTCTGGACGCACCTTCAGTAGAGATGCCATGG GCTGGTTCCGCCAGGCTCCAGGGAAGGAGCGTGAGTTTGTAGCAGGTATTA GCTGGAGTGGTGGTAGCACATACTATGCAGACTCCGTGAAGGGCCGATTCA CCATCTCCAGGGACGGCGCCAAGAACACGGTAAATCTGCAAATGAACAGCC TGAAACCTGAGGACACGGCCGTTTATTACTGTGCAGCATCGTCGATTTATGG GAGTGCGGTAGTAGATGGGCTGTATGACTACTGGGGCCAGGGGACCCAGGT CACCGTCTCCTCACACCACCATCACCATCAC |

TABLE 4-continued

Anti- mouse CD206 (MMR) nanobodies (anti-MMR nanobody clone 1 and 3): monovalent en bivalent constructs and nanobodies

| | |
|---|---|
| DNA seq - His tag (clone 3) SEQ ID NO: 6 | CAGGTGCAGCTGCAGGAGTCTGGAGGAGGATTGGTGCAGGCTGGGGGCTCT CTGAGACTCTCCTGTGCAGCCTCTGGACGCACCTTCAGTAGAGATGCCATGG GCTGGTTCCGCCAGGCTCCAGGGAAGGAGCGTGAGTTTGTAGCAGGTATTA GCTGGAGTGGTGGTAGCACATACTATGCAGACTCCGTGAAGGGCCGATTCA CCATCTCCAGGGACGGCGCCAAGAACACGGTAAATCTGCAAATGAACAGCC TGAAACCTGAGGACACGGCCGTTTATTACTGTGCAGCATCGTCGATTTATGG GAGTGCGGTAGTAGATGGGCTGTATGACTACTGGGGCCAGGGGACCCAGGT CACCGTCTCCTCA |
| Protein + His tag (clone 3) SEQ ID NO: 7 | QVQLQESGGGLVQAGGSLRLSCAASGRTFSRDAMGWFRQAPGKEREFVAGIS WSGGSTYYADSVKGRFTISRDGAKNTVNLQMNSLKPEDTAVYYCAASSIYGSA VVDGLYDYWGQGTQVTVSSHHHHHH |
| Protein - His tag (clone 3) SEQ ID NO: 8 | QVQLQESGGGLVQAGGSLRLSCAASGRTFSRDAMGWFRQAPGKEREFVAGIS WSGGSTYYADSVKGRFTISRDGAKNTVNLQMNSLKPEDTAVYYCAASSIYGSA VVDGLYDYWGQGTQVTVSS |
| DNA seq + His tag (MMR biv IgA) SEQ ID NO: 111 | CAGGTGCAGCTTCAGGAGTCTGGAGGAGGCTTGGTGCAGCCTGGGGGGTCT CTGAGACTCTCCTGTGCAGCCTCTGGAAACATCTTCAGTATCAATGCCATCG GCTGGTACCGCCAGGCTCCAGGGAAGCAGCGCGAGTTGGTCGCAACTATTA CTCTTAGTGGTAGCACAAACTATGCAGACTCCGTGAAGGGCCGATTCTCCAT CTCCAGAGACAACGCCAAGAACACGGTGTATCTGCAAATGAACAGCCTGAA ACCTGAGGACACGGCCGTCTATTACTGTAATGCTAACACCTATAGCGACTCT GACGTTTATGGCTACTGGGGCCAGGGGACCCAGGTCACCGTCTCCTCAAGC CCATCTACACCTCCCACACCATCACCATCCACACCACCGGCAAGTCAGGTGC AGCTGCAGGAGTCTGGAGGAGGCTTGGTGCAGCCTGGGGGGTCTCTGAGAC TCTCCTGTGCAGCCTCTGGAAACATCTTCAGTATCAATGCCATCGGCTGGTA CCGCCAGGCTCCAGGGAAGCAGCGCGAGTTGGTCGCAACTATTACTCTTAG TGGTAGCACAAACTATGCAGACTCCGTGAAGGGCCGATTCTCCATCTCCAG AGACAACGCCAAGAACACGGTGTATCTGCAAATGAACAGCCTGAAACCTGA GGACACGGCCGTCTATTACTGTAATGCTAACACCTATAGCGACTCTGACGTT TATGGCTACTGGGGCCAGGGGACCCAGGTCACCGTCTCCTCACACCACCATC ACCATCAC |
| Protein + His tag (MMR biv IgA) SEQ ID NO: 112 | QVQLQESGGGLVQPGGSLRLSCAASGNIFSINAIGWYRQAPGKQRELVATITLS GSTNYADSVKGRFSISRDNAKNTVYLQMNSLKPEDTAVYYCNANTYSDSDVY GYWGQGTQVTVSSSPSTPPTPSPSTPPASQVQLQESGGGLVQPGGSLRLSCAAS GNIFSINAIGWYRQAPGKQRELVATITLSGSTNYADSVKGRFSISRDNAKNTVYL QMNSLKPEDTAVYYCNANTYSDSDVYGYWGQGTQVTVSSHHHHHH |
| DNA seq + His tag (MMR biv (Gly4Ser)3) SEQ ID NO: 113 | CAGGTGCAGCTTCAGGAGTCTGGAGGAGGCTTGGTGCAGCCTGGGGGGTCT CTGAGACTCTCCTGTGCAGCCTCTGGAAACATCTTCAGTATCAATGCCATCG GCTGGTACCGCCAGGCTCCAGGGAAGCAGCGCGAGTTGGTCGCAACTATTA CTCTTAGTGGTAGCACAAACTATGCAGACTCCGTGAAGGGCCGATTCTCCAT CTCCAGAGACAACGCCAAGAACACGGTGTATCTGCAAATGAACAGCCTGAA ACCTGAGGACACGGCCGTCTATTACTGTAATGCTAACACCTATAGCGACTCT GACGTTTATGGCTACTGGGGCCAGGGGACCCAGGTCACCGTCTCCTCAGGC GGAGGCGGTAGTGGCGAGGTGGATCTGGAGGCGGCGGTAGTCAGGTGCA GCTGCAGGAGTCTGGAGGAGGCTTGGTGCAGCCTGGGGGGTCTCTGAGACT CTCCTGTGCAGCCTCTGGAAACATCTTCAGTATCAATGCCATCGGCTGGTAC CGCCAGGCTCCAGGGAAGCAGCGCGAGTTGGTCGCAACTATTACTCTTAGT GGTAGCACAAACTATGCAGACTCCGTGAAGGGCCGATTCTCCATCTCCAGA GACAACGCCAAGAACACGGTGTATCTGCAAATGAACAGCCTGAAACCTGAG GACACGGCCGTCTATTACTGTAATGCTAACACCTATAGCGACTCTGACGTTT ATGGCTACTGGGGCCAGGGGACCCAGGTCACCGTCTCCTCACACCACCATC ACCATCAC |
| Protein + His tag (MMR biv (Gly4Ser)3) SEQ ID NO: 114 | QVQLQESGGGLVQPGGSLRLSCAASGNIFSINAIGWYRQAPGKQRELVATITLS GSTNYADSVKGRFSISRDNAKNTVYLQMNSLKPEDTAVYYCNANTYSDSDVY GYWGQGTQVTVSSGGGGSGGGGSGGGGSQVQLQESGGGLVQPGGSLRLSCAA SGNIFSINAIGWYRQAPGKQRELVATITLSGSTNYADSVKGRFSISRDNAKNTVY LQMNSLKPEDTAVYYCNANTYSDSDVYGYWGQGTQVTVSSHHHHHH |
| DNA seq + His tag (MMR biv g2c) SEQ ID NO: 115 | CAGGTGCAGCTTCAGGAGTCTGGAGGAGGCTTGGTGCAGCCTGGGGGGTCT CTGAGACTCTCCTGTGCAGCCTCTGGAAACATCTTCAGTATCAATGCCATCG GCTGGTACCGCCAGGCTCCAGGGAAGCAGCGCGAGTTGGTCGCAACTATTA CTCTTAGTGGTAGCACAAACTATGCAGACTCCGTGAAGGGCCGATTCTCCAT CTCCAGAGACAACGCCAAGAACACGGTGTATCTGCAAATGAACAGCCTGAA ACCTGAGGACACGGCCGTCTATTACTGTAATGCTAACACCTATAGCGACTCT GACGTTTATGGCTACTGGGGCCAGGGGACCCAGGTCACCGTCTCCTCAGCG CACCACAGCGAAGACCCCAGCTCCAAAGCTCCCAAAGCTCCAATGGCACAG GTGCAGCTGCAGGAGTCTGGAGGAGGCTTGGTGCAGCCTGGGGGGTCTCTG AGACTCTCCTGTGCAGCCTCTGGAAACATCTTCAGTATCAATGCCATCGGCT |

TABLE 4-continued

Anti- mouse CD206 (MMR) nanobodies (anti-MMR nanobody clone 1 and 3): monovalent en bivalent constructs and nanobodies

|  |  |
|---|---|
|  | GGTACCGCCAGGCTCCAGGGAAGCAGCGCGAGTTGGTCGCAACTATTACTC<br>TTAGTGGTAGCACAAACTATGCAGACTCCGTGAAGGGCCGATTCTCCATCTC<br>CAGAGACAACGCCAAGAACACGGTGTATCTGCAAATGAACAGCCTGAAACC<br>TGAGGACACGGCCGTCTATTACTGTAATGCTAACACCTATAGCGACTCTGAC<br>GTTTATGGCTACTGGGGCCAGGGGACCCAGGTCACCGTCTCCTCACACCACC<br>ATCACCATCAC |
| Protein + His tag<br>(MMR biv g2c)<br>SEQ ID NO: 116 | QVQLQESGGGLVQPGGSLRLSCAASGNIFSINAIGWYRQAPGKQRELVATITLS<br>GSTNYADSVKGRFSISRDNAKNTVYLQMNSLKPEDTAVYYCNANTYSDSDVY<br>GYWGQGTQVTVSSAHHSEDPSSKAPKAPMAQVQLQESGGGLVQPGGSLRLSC<br>AASGNIFSINAIGWYRQAPGKQRELVATITLSGSTNYADSVKGRFSISRDNAKNT<br>VYLQMNSLKPEDTAVYYCNANTYSDSDVYGYWGQGTQVTVSSHHHHHH |

TABLE 5

SPR kinetic and equilibrium parameters for anti-MMR Nanobodies and bivalent Nanobody 1 derivatives.

| Sample | $k_a$ | SE ($k_a$) | $k_d$ | SE ($k_d$) | $K_D$ | Chi$^2$ |
|---|---|---|---|---|---|---|
| Anti-MMR Nb1 | 5.76E+05 | 1.4E+3 | 0.01331 | 2.1E−5 | 2.31E−08 | 0.558 |
| Anti-MMR Nb3 | 9.73E+04 | 1.6E+2 | 0.01859 | 2.2E−5 | 1.91E−07 | 0.190 |
| biv MMR linker 1 GS | 1.04E+06 | 4.9E+3 | 0.004404 | 1.4E−5 | 4.22E−09 | 3.56 |
| biv MMR linker 2 g2c | 1.02E+06 | 4.8E+3 | 0.004107 | 1.4E−5 | 4.04E−09 | 2.50 |
| biv MMR linker 3 IgA | 9.13E+05 | 1.5E+4 | 0.004285 | 5.3E−5 | 4.69E−09 | 2.25 |

Nb: Nanobody;
biv: bivalent;
GS: (Gly$_4$Ser)$_3$ linker;
g2c: llama IgG2 hinge linker;
IgA: human IgA hinge linker;
SE: standard error.

TABLE 6

Uptake values of $^{99m}$Tc-labeled anti-MMR Nb clone 1 in naive and MMR$^{-/-}$ mice based on Pinhole SPECT/micro-CT at 1 hour post injection. Tracer uptake is expressed as percentage injected activity per gram cubic centimeter (% IA/cm$^3$).

| Organs/Tissues | MMR Nb in WT (% IA/cm$^3$) | MMR Nb in MMR$^{-/-}$ (% IA/cm$^3$) |
|---|---|---|
| Heart | 2.04 ± 0.21 | 1.13 ± 0.12 |
| Lungs | 5.96 ± 0.16 | 9.06 ± 2.43 |
| Liver | 18.66 ± 0.87 | 0.91 ± 0.16 |
| Spleen | 6.17 ± 0.31 | 0.34 ± 0.21 |
| Kidney Left | 80.98 ± 1.65 | 100.58 ± 0.4 |
| Kidney Right | 81.65 ± 2.32 | 102.82 ± 6.17 |
| Muscle | 1.74 ± 0.50 | 0.39 ± 0.22 |
| Bone | 5.02 ± 0.01 | 0.46 ± 0.02 |

TABLE 7

Uptake values of $^{99m}$Tc-labeled bivalent anti-MMR Nb constructs (with (G$_4$S)$_3$, llama IgG2 hinge or human IgA hinge linkers), monovalent anti-MMR Nb clone 1, and control cAbBCII10 Nb in naive and MMR$^{-/-}$ mice based on Pinhole SPECT/micro-CT at 1 hour post injection. Tracer uptake is expressed as percentage injected activity per gram cubic centimeter (% IA/cm$^3$).

| Organs-Tissues | (G4S)3 WT (% IA/cm3) | (G4S)3 MMR−/− (% IA/cm3) | Llama IgG2c WT (% IA/cm3) | Llama IgG2c MMR−/− (% IA/cm3) | Human IgA WT (% IA/cm3) | Human IgA MMR−/− (% IA/cm3) | MMR Nb WT (% IA/cm3) | cAbBCII10 WT (% IA/cm3) |
|---|---|---|---|---|---|---|---|---|
| Heart | 1.549 ± 0.057 | 0.541 ± 0.013 | 1.416 ± 0.147 | 0.440 ± 0.070 | 1.395 ± 0.083 | 0.505 ± 0.057 | 2.793 ± 0.043 | 0.693 ± 0.128 |
| Lungs | 1.053 ± 0.082 | 1.246 ± 0.038 | 0.987 ± 0.167 | 1.271 ± 0.130 | 0.936 ± 0.086 | 1.169 ± 0.161 | 2.543 ± 0.417 | 1.837 ± 0.271 |
| Liver | 20.857 ± 0.215 | 0.930 ± 0.081 | 20.491 ± 0.578 | 1.658 ± 0.077 | 21.571 ± 0.435 | 1.176 ± 0.044 | 13.670 ± 0.741 | 2.637 ± 0.203 |
| Spleen | 14.018 ± 1.669 | 0.634 ± 0.042 | 13.618 ± 1.497 | 1.347 ± 0.300 | 13.805 ± 1.353 | 0.477 ± 0.007 | 13.070 ± 0.251 | 0.933 ± 0.113 |
| Kidney Left | 26.381 ± 2.054 | 225.129 ± 13.936 | 24.257 ± 1.129 | 193.162 ± 8.114 | 26.728 ± 3.014 | 210.760 ± 14.414 | 160.443 ± 13.153 | 415.643 ± 15.162 |
| Kidney Right | 26.074 ± 2.227 | 212.682 ± 6.308 | 24.599 ± 2.053 | 202.343 ± 0.779 | 24.947 ± 2.463 | 214.144 ± 11.751 | 159.003 ± 13.700 | 408.597 ± 22.588 |
| Muscle | 0.251 ± 0.034 | 0.224 ± 0.010 | 0.158 ± 0.023 | 0.216 ± 0.015 | 0.212 ± 0.045 | 0.205 ± 0.004 | ND | ND |
| Bone | 1.466 ± 0.062 | 0.282 ± 0.016 | 1.041 ± 0.114 | 0.254 ± 0.030 | 1.089 ± 0.138 | 0.263 ± 0.022 | ND | ND |

TABLE 8

Uptake values of $^{99m}$Tc-labeled anti-MMR or cAbBCII10 Nb in TS/A tumor-bearing WT mice, based on dissection at 3 hours post injection. Tracer uptake is expressed as injected activity per gram tissue (% IA/g).

| Organs/Tissues | anti-MMR Nb in WT (% IA/g) | cAbBcII10 Nb in WT (% IA/g) |
|---|---|---|
| Heart | 1.45 ± 0.12 | 0.10 ± 0.01 |
| Lungs | 1.55 ± 0.36 | 0.98 ± 0.12 |
| Liver | 12.60 ± 0.54 | 0.59 ± 0.02 |
| Spleen | 8.95 ± 0.60 | 0.24 ± 0.01 |
| Kidney Left | 79.67 ± 2.32 | 273.25 ± 14.76 |
| Kidney Right | 80.78 ± 3.62 | 261.16 ± 11.35 |
| Muscle | 0.52 ± 0.03 | 0.05 ± 0.01 |
| Bone | 1.33 ± 0.10 | 0.08 ± 0.01 |
| Blood | 0.13 ± 0.02 | 0.14 ± 0.01 |
| Tumor | 3.02 ± 0.10 | 0.40 ± 0.03 |

TABLE 9

Uptake values of $^{99m}$Tc-labeled anti-MMR or cAbBCII10 Nb in 3LL tumor-bearing WT or MMR$^{-/-}$ mice, based on dissection at 3 hours post injection. Tracer uptake is expressed as injected activity per gram (% IA/g).

| Organs/Tissues | anti-MMR Nb in WT (% IA/g) | anti-MMR Nb in MMR$^{-/-}$ (% IA/g) | cAbBcII10 Nb in WT (% IA/g) |
|---|---|---|---|
| Heart | 2.02 ± 0.11 | 0.06 ± 0.01 | 0.17 ± 0.01 |
| Lungs | 1.46 ± 0.05 | 1.02 ± 0.70 | 0.58 ± 0.04 |
| Liver | 9.55 ± 1.02 | 1.36 ± 1.06 | 1.03 ± 0.03 |
| Spleen | 4.61 ± 0.50 | 0.17 ± 0.02 | 0.41 ± 0.03 |
| Kidney Left | 108.61 ± 16.11 | 153.29 ± 27.22 | 368.79 ± 10.10 |
| Kidney Right | 88.60 ± 21.70 | 154.90 ± 20.71 | 305.21 ± 54.67 |
| Muscle | 0.61 ± 0.05 | 0.05 ± 0.02 | 0.08 ± 0.02 |
| Bone | 1.69 ± 0.10 | 0.06 ± 0.01 | 0.13 ± 0.01 |
| Blood | 0.10 ± 0.01 | 0.09 ± 0.01 | 0.24 ± 0.01 |
| Tumor | 3.02 ± 0.19 | 0.33 ± 0.03 | 0.74 ± 0.03 |

TABLE 10

Uptake values of $^{99m}$Tc-labeled α-MMR Nb in s.c. 3LL-R tumor-bearing WT or CCR2-KO mice, based on dissection at 3 hours post injection. Tracer uptake is expressed as injected activity per gram (% IA/g).

| Organs/Tissues | α-MMR Nb in WT (% IA/g) | α-MMR Nb in CCR2-KO (% IA/g) |
|---|---|---|
| Heart | 1.77 ± 0.06 | 1.94 ± 0.08 |
| Lungs | 1.54 ± 0.25 | 1.21 ± 0.10 |
| Liver | 14.1 ± 0.83 | 15.9 ± 0.65 |
| Spleen | 5.80 ± 0.25 | 7.14 ± 0.34 |
| Kidney Left | 103 ± 6.72 | 92.0 ± 7.56 |
| Kidney Right | 105 ± 7.55 | 92.7 ± 9.3 |
| Muscle | 0.36 ± 0.03 | 0.46 ± 0.06 |
| Bone | 1.04 ± 0.06 | 1.01 ± 0.03 |
| Blood | 0.16 ± 0.01 | 0.17 ± 0.01 |
| Tumor | 2.96 ± 0.22 | 1.81 ± 0.11 |

TABLE 11

Anti-human MMR Nbs selected after ELISA on human MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 257).

| Name | SEQ ID NO: | Sequence |
|---|---|---|
| NbhMMR m1.33 | 126 | QVQLQESGGGLVQPGGSLRLSCAASGFTLDNYTVANPRQAPGKEREGVSC ISSSSGSTNYADSVKGRFTISRDNSKKSVYLQMNSLKPEDTAIYTCAASRAP FYTSGYYFPDSTCVAASYDYWGQGTQVTVSS |
| NbhMMR m10.19 | 127 | QVQLQESGGGLVQPGGSLKLSCAASGSIFSIKTMGWYRQAPGKQRELVAAI TSGGSTNYADSVKGRFTISRDNAKNTVYLQMNSLKPEDTAVYYCNADGV VANDQFYDFYWGQGTQVTVSS |
| NbhMMR m23.30 | 128 | QVQLQESGGGLVQAGDSLSISCAASGDTFNHYSWGWFRQAPGKAREFVA AISWNGGSKYADSVKGRFAISRDIAKNTVSLQMNSLEPEDTAVYYCAADF RFYNDWEDDWSWRVYWGQGTQVTVSS |
| NbhMMR m2.15 | 129 | QVQLQESGGGLVQPGESLRLSCKLSGFTLDYYDIGWFRQAPGKEPEGVSCI SSICKSANYADSVKGRFTISRDNVKNTVYLQMNSLKPEDTAIYYCAAEROT PYNDGDCIRASYDYWGQGIQVTVSS |
| NbhMMR m3.1 | 130 | QVQLQESGGGLVQPGGSLRLSCAASGFTLDYYAIGWFRQAPGKEREGISCI SYRGSTTYADSVKGRFTISKDNAKNTAYLQMNNLKPEDTGIYYCAAGFV CYNYDTWGPGTQVTVSS |
| NbhMMR m5.38 | 131 | QVQLQESGGGLVQAGGSLRLSCAASGFTDDDYDIGWFRQAPGKEREGVSC ISSSGSTYYADSVKGRFTISSDNAKNTVYLQMNSLKPEDTAVYYCAADFP FWDSGSYYVPGCRHATYDYWGQGTQVTVSS |
| NbhMMR m12.6 | 132 | QVQLQESGGGLVQPGGSLRLSCVVSGSFLSINHMGWYRQVSGEQRELVAA ITSSSSTNYADSVKGRFTISPDSAKNTVYLQMNSLKPEDTAVYYCHADAL TMLPPPDFWGQGTQVTVSS |

TABLE 11-continued

Anti-human MMR Nbs selected after ELISA on human MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 257).

| Name | SEQ ID NO: | Sequence |
|---|---|---|
| NbhMMR m11.5 | 133 | QVQLQESGGGLVQPGGSLMLSCAASGNIFTINRMGWYRQAPGKQRELVA AITSGGHTNYADSVKGRFTISRDNAKNTVYLQMNSLKPEDTAVYYCNAAI VTMFSFVSDYWGQGTQVTVSS |
| NbhMMR m15.43 | 134 | QVQLQESGGTLVQPGGSLRLSCAASGSTFSINNMGWYRQAPGKQRELVAG ITGGNTHYADSVKGRFTISRDNAKNTMYLQMNGLKPEDTAVYYCNANWG AYWGQGTQVTVSS |
| NbhMMR m16.95 | 135 | QVQLQESGGGLVQPGGSLGLSCAASGRIASISAMGWYRQAPGKQRELVAA ITGSGRTNYADSVKGRFTISRDNAKNTVYLQMNSLKPEDTAVYYCNLLMV DYGLGLCTDYWGQGTQVTVSS |
| NbhMMR m4.83 | 136 | QVQLQESGGGLVQPGGSLRLSCAASGPGFKLDYYAIAWFRQAPGKEREGV SCIGSSCSGLTTYVENSVKDRFTISRDNAQNTVYLHMNSLKPEDTGIYYCA ADTTYYCSEPVWRHPYGSWGQGTQVTVSS |

CDR1 (red), CDR2 (green) and CDR3 (blue) domains are also indicated, and are listed separately in Table 14.

TABLE 12

Anti-human/mouse MMR cross-reactive Nbs selected after ELISA on human MMR and mouse MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 257).

| Name | SEQ ID NO: | Sequence |
|---|---|---|
| NbhmMMRm14.4 | 137 | QVQLQESGGGLVQAGDSLRLSCAASGRTFSINYMGWYRQAPGKQRELVA AITSGGSTNYADSVKGRFTISRDNAKNTMYLQMNSLKPEDTAVYYCNAD MDSSLSCETVDVWGQGTQVTVSS |
| NbhmMMRm6.71 | 138 | QVQLQESGGGLVQAGGSLRLSCAASGGTFDDSVIGWFRQAPGKEREGVSC ISSNCGTTHYASPVKGRFTISDNAKNTVYLQMNSLKPEDTAVYYCAAHTP HKGSPGTSASTFNWGQGTQVTVSS |
| NbhmMMRm24.31 | 139 | QVQLQESGGGLVQPGGSLRLSCTATGFTLKHHHIGWLRQAPGKEREGVAS INSGGSTHYADSVQGRFTISRDNAKNTVFLQMNSLKSEDTAVYYCAPLA RYYGLNGQPSSYGYWGQGTQVTVSS |
| NbhmMMRm20.52 | 140 | QVQLQESGGGLVQAGGSLRLSCAASGRIPSAYAMGWFRQAPGKEREFVA AIGPSGLSTDYADSVKGRFTISRDSAKNMVYLQMNSLKPEDTALYHCAAR TVSAPPSAAWGYGYWGQGTQVTVSS |
| NbhmMMRm3.49 | 141 | QVQLQESGGGLVQPGGSLRLSCAASGFSLDYYAIGWFRQAPGKEREGISCI SYKGSSTTYADSVKGRFTISKDNAKNTAYLQMNSLKPEDTGIYSCAAGFV CYNTDYWGQGTQVTVSS |
| NbhmMMRm22.84 | 142 | QVQLQESGGGLVQPGGSLRLSCAASGRTPSNYVNYAMGWFRQFPGKERE FVASISNSSVTTYYADSVKGRFTISRDNAKNTVYLQMNSLKPEDTAVYYC AAHLAQVSDYATPDEHQPGAWGQGTQVTVSS |
| NbhmMMRm19.52 | 143 | QVQLQESGGGLVQAGGSLRLSCLASGDTFSNYVMAWFRQAPGKEREIVA AIRLSGAKYVPDSVKGRFTISRDNAKNAMYLQMTSLKPEDTARYYCAAG HIWGQYAYWGQGTQVTVSS |
| NbhmMMRm21.22 | 144 | QVQLQESGGGLVQAGGSLRLSCAASGRTFSSAAMGWFRQAPGKEREPVA LIHLDDGETYYADIAKGRFTLSKDNAKNSVYLQMNSLKPEDTAVYYCAV RCRPDDNYEYWGQGTQVTVSS |
| NbhmMMRm14.93 | 145 | QVQLQESGGGLVQAGDSLRLSCAASGRTFSINYMGWYRQAPGKQRELVA AITSGNSSNYADSVKGRFTISRDNAKKTMYLQMNSLKPEDTAVYYCNAD MDSSLSGSYYEVWGQGTQVTVSS |

TABLE 12-continued

Anti-human/mouse MMR cross-reactive Nbs selected after ELISA on human MMR and mouse MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 257).

| Name | SEQ ID NO: | Sequence |
|---|---|---|
| NbhmMMRm15.49 | 146 | QVQLQESGGGLVQAGGSLRLSCAASGSTFSINNMGWYRQAPGKQRELVA GITKKNTHYADSVKGRFTISRDNAKNTMYLQMNSLKPEDTAVYYCNANW GANWGQGTQVTVSS |
| NbhmMMRm17.72 | 147 | QVQLQESGGGLVQPGGSLRLSCAASGSIVSINAMGWYRQAPGKQRELVAG VTGSGRTNLADSVKGRFTISRDNAKNTVYLQMNSLKPEDTAVYYCNVLVI GPLSGYDYWGQGTQVTVSS |
| NbhmMMRm10.79 | 148 | QVQLQESGGGLVQPGGSLKLSCAASGSIFSIKTMGWYRQAPGKQRELVAA VSSGGSTNYADSVKGRFTISRDNAKNAVYLQMNSLKPEDTAVYYCNADG VVAWDQPYDNYWGQGTQVTVSS |

CDR1 (red), CDR2 (green) and CDR3 (blue) domains are also indicated, and are listed separately in Table 14.

TABLE 13

Production yields and physico-chemical characteristics of the anti-human MMR and anti-human/mouse MMR cross-reactive Nbs. All Nbs produce between 0.7 and 9 mg/l *E. coli* culture.

| Name | number of A.A. Nb + HA + His | MW Nb + HA + His (dalton) | Theoretical pi | Extinction coefficient (assuming all Cys form cystines) | Estimated production capacity (g/l *E. Coli*) |
|---|---|---|---|---|---|
| anti-human MMR Nbs | | | | | |
| NbhMMRm1.33 | 152 | 16545 | 6.30 | 30620 | 0.7 |
| NbhMMRm10.19 | 140 | 15188 | 6.63 | 31525 | 3.7 |
| NbhMMRm23.30 | 144 | 16150 | 5.71 | 63035 | 2.3 |
| NbhMMRm2.15 | 146 | 16095 | 5.58 | 29130 | 1.6 |
| NbhMMRm3.1 | 137 | 14961 | 6.63 | 30620 | 1.1 |
| NbhMMRm5.38 | 150 | 16535 | 5.51 | 36120 | 1.2 |
| NbhMMRm12.6 | 138 | 15011 | 6.13 | 23045 | 1.7 |
| NbhMMRm11.5 | 139 | 15106 | 7.17 | 26025 | 6.8 |
| NbhMMRm15.43 | 131 | 14266 | 8.00 | 30035 | 6.2 |
| NbhMMRm16.95 | 140 | 15025 | 7.17 | 26025 | 5.6 |
| NbhMMRm4.83 | 149 | 16395 | 6.70 | 36120 | 3.0 |
| anti-human/anti-mouse MMR Nbs | | | | | |
| NbhmMMRm14.4 | 141 | 15275 | 6.29 | 26025 | 1.6 |
| NbhmMMRm6.71 | 144 | 15295 | 5.70 | 24660 | 2.4 |
| NbhmMMRm24.31 | 144 | 15793 | 8.00 | 26025 | 1.0 |
| NbhmMMRm20.52 | 143 | 15431 | 8.00 | 30035 | 5.4 |
| NbhmMMRm3.49 | 137 | 14875 | 6.63 | 29130 | 1.6 |
| NbhmMMRm22.84 | 149 | 16628 | 7.25 | 35995 | 4.2 |
| NbhmMMRm19.52 | 136 | 14986 | 8.59 | 31525 | 4.1 |
| NbhmMMRm21.22 | 137 | 15045 | 5.91 | 26025 | 2.1 |
| NbhmMMRm14.93 | 141 | 15289 | 6.63 | 26025 | 2.6 |
| NbhmMMRm15.49 | 131 | 14226 | 8.00 | 30035 | 4.0 |
| NbhmMMRm17.72 | 138 | 14896 | 7.18 | 24535 | 3.4 |
| NbhmMMRm10.79 | 140 | 15130 | 6.63 | 31525 | T.B.D |
| NbhmMMRm7.67 | 137 | 15153 | 7.18 | 30035 | 4.0 |
| NbhmMMRm8.67 | 151 | 16635 | 6.76 | 40005 | 2.0 |
| NbhmMMRm13.89 | 139 | 15096 | 6.70 | 30035 | 5.4 |
| NbhmMMRm18.63 | 135 | 14393 | 7.18 | 34045 | 9.0 |
| NbhmMMRm25.86 | 135 | 14891 | 6.29 | 24535 | 3.9 |
| NbhmMMRm26.70 | 140 | 15299 | 7.18 | 24535 | 6.0 |
| NbhmMMRm27.95 | 140 | 15392 | 7.22 | 24535 | 1.0 |

T.B.D.: to be determined

TABLE 14

CDRs of MMR-specific nanobodies

| Nanobody reference number | SEQ ID NO[1] | CDR1 | CDR2 | CDR3 |
|---|---|---|---|---|
| Nanobody clone 1 | 4 | SGNIFSINAIG (SEQ ID NO: 156) | TITLSGSTN (SEQ ID NO: 188) | NTYSDSDVYGY (SEQ ID NO: 220) |
| Nanobody clone 3 | 8 | SGRTFSRDAMG (SEQ ID NO:157) | GISWSGGST (SEQ ID NO: 189) | SSIYGSAVVDGLYDY (SEQ ID NO: 221) |
| NbhMMRm1.33 | 126 | GFTLDNYTVA (SEQ ID NO: 158) | CISSSGGST (SEQ ID NO: 190) | ERAPPYYSGYYFFDSTCVAASYDY (SEQ ID NO: 222) |
| NbhMMRm10.19 | 127 | GSIFSIKTMG (SEQ ID NO: 159) | AITSGGST (SEQ ID NO: 191) | DGVVAWDQPYDNY (SEQ ID NO: 223) |
| NbhMMRm23.30 | 128 | GDTFNHYSWG (SEQ ID NO: 160) | AISWNGGS (SEQ ID NO: 192) | DRRPYNDWWDDWSWWVY (SEQ ID NO: 224) |
| NbhMMRm2.15 | 129 | GFTLDYYDIG (SEQ ID NO: 161) | CISSIGGSA (SEQ ID NO: 193) | EAQTPYNDGDCTRASYDY (SEQ ID NO: 225) |
| NbhMMRm3.1 | 130 | GFTLDYYAIG (SEQ ID NO: 162) | CISYKGGST (SEQ ID NO: 194) | GFVCYNYDY (SEQ ID NO: 226) |
| NbhMMRm5.38 | 131 | GFTDDDYDIG (SEQ ID NO: 163) | CISSSDGST (SEQ ID NO: 195) | DFFRWDSGSYYVRGCRHATYDY (SEQ ID NO: 227) |
| NbhMMRm12.6 | 132 | GSFLSINHMG (SEQ ID NO: 164) | AITSGGST (SEQ ID NO: 196) | DALTMLPPFDF (SEQ ID NO: 228) |
| NbhMMRm11.5 | 133 | GNIFTINRMG (SEQ ID NO: 165) | AITSGGNT (SEQ ID NO: 197) | AIVTMTSPYSDY (SEQ ID NO: 229) |
| NbhMMRm15.43 | 134 | GSTFSINNMG (SEQ ID NO: 166) | GITGGNT (SEQ ID NO: 198) | NWGAY (SEQ ID NO: 230) |
| NbhMMRm16.95 | 135 | GRIASISAMG (SEQ ID NO: 167) | AITGSGRT (SEQ ID NO: 199) | LMVDYGLGLGTDY (SEQ ID NO: 231) |
| NbhMMRm4.83 | 136 | PGFKLDYYAIA (SEQ ID NO: 168) | CIGGSGSGLT (SEQ ID NO: 200) | DTYYYCSKRVWRNDYGS (SEQ ID NO: 232) |
| NbhmMMRm14.4 | 137 | GRTFSINYMG (SEQ ID NO: 169) | AITSGSGST (SEQ ID NO: 201) | DMDSSLSGGYVDV (SEQ ID NO: 233) |
| NbhmMMRm6.71 | 138 | GGTFDDSVIG (SEQ ID NO: 170) | CISSNDGTT (SEQ ID NO: 202) | ETPSIGSPCTSASYDY (SEQ ID NO: 234) |
| NbhmMMRm24.31 | 139 | GFTLKNHHIG (SEQ ID NO: 171) | SINSSGGST (SEQ ID NO: 203) | LRRYYGLNLDPGSYDY (SEQ ID NO: 235) |
| NbhmMMRm20.52 | 140 | GRIFSAYAMG (SEQ ID NO: 172) | AISRSGDST (SEQ ID NO: 204) | RTVSAPPSAAWGYGY (SEQ ID NO: 236) |
| NbhmMMRm3.49 | 141 | GFSLDYYAIG (SEQ ID NO: 173) | CISYKGGST (SEQ ID NO: 205) | GFVCYNYDY (SEQ ID NO: 237) |
| NbhmMMRm22.84 | 142 | GRTFSNYVNYAMG (SEQ ID NO: 174) | SISWSSVTT (SEQ ID NO: 206) | HLAQYSDYAYRDPHQFGA (SEQ ID NO: 238) |
| NbhmMMRm19.52 | 143 | GDTFSNYVMA (SEQ ID NO: 175) | AIRLSGAR (SEQ ID NO: 207) | GHTWGQYAY (SEQ ID NO: 239) |
| NbhmMMRm21.22 | 144 | GRTFSSAAMG (SEQ ID NO: 176) | LINLDDGET (SEQ ID NO: 208) | RGRFDDNYEY (SEQ ID NO: 240) |

TABLE 14-continued

CDRs of MMR-specific nanobodies

| Nanobody reference number | SEQ ID NO[1] | CDR1 | CDR2 | CDR3 |
|---|---|---|---|---|
| NbhmMMRm14.93 | 145 | GRTFSINYMG (SEQ ID NO: 177) | AITSGSGST (SEQ ID NO: 209) | DMDSSLSGGYVDV (SEQ ID NO: 241) |
| NbhmMMRm15.49 | 146 | GSTFSINNMG (SEQ ID NO: 178) | GITGGNT (SEQ ID NO: 210) | NWGAY (SEQ ID NO: 242) |
| NbhmMMRm17.72 | 147 | GSIVSINAMG (SEQ ID NO: 179) | LVTGSGRT (SEQ ID NO: 211) | LVIGPLEGYDY (SEQ ID NO: 243) |
| NbhmMMRm10.79 | 148 | GSIFSIKTMG (SEQ ID NO: 180) | AVSSGGST (SEQ ID NO: 212) | DGVVAWDQPYDNY (SEQ ID NO: 244) |
| NbhmMMRm7.67 | 149 | GRTFSVNAMA (SEQ ID NO: 181) | SITSSGLDT (SEQ ID NO: 213) | ERWDNGMVY (SEQ ID NO: 245) |
| NbhmMMRm8.67 | 150 | GSMFSINAWG (SEQ ID NO: 182) | SITSGGGST (SEQ ID NO: 214) | ERWDGYALGYSPNH GSGHRPYNY (SEQ ID NO: 246) |
| NbhmMMRm13.89 | 151 | GSIFSINAWG (SEQ ID NO: 183) | EITSSGST (SEQ ID NO: 215) | VAVTFTTPRSDY (SEQ ID NO: 247) |
| NbhmMMRm18.63 | 152 | GSIISINAMA (SEQ ID NO: 184) | AISSGGST (SEQ ID NO: 216) | GGGWRPGA (SEQ ID NO: 248) |
| NbhmMMRm25.86 | 153 | GFTVSTSMIN (SEQ ID NO: 185) | DVLPSGST (SEQ ID NO: 217) | NRETMPPF (SEQ ID NO: 249) |
| NbhmMMRm26.70 | 154 | GFPFSSAPMS (SEQ ID NO: 186) | YIGYTGTIT (SEQ ID NO: 218) | GYARLIADSDLV (SEQ ID NO: 250) |
| NbhmMMRm27.95 | 155 | GFPFNIYPMS (SEQ ID NO: 187) | YISHGGTTT (SEQ ID NO: 219) | GYARLMTDSELV (SEQ ID NO: 251) |

[1]Nanobody sequences without His tag

TABLE 15

Amino acid sequences of human and mouse macrophage mannose receptor

| Name | SEQ ID NO | Amino acid sequence |
|---|---|---|
| Human MMR (MRC1) | 258 | MRLPLLLVFASVIPGAVLLLDTRQFLIYNEDHKRCVDAVSPSAVQ TAACNQDAESQKFRWVSESQIMSVAFKLCLGVPSKTDWVAITLY ACDSKSEFQKWECKNDTLLGIKGEDLFFNYGNRQEKNIMLYKGS GLWSRWKIYGTTDNLCSRGYEAMYTLLGNANGATCAFPFKFENK WYADCTSAGRSDGWLWCGTTTDYDTDKLFGYCPLKFEGSESLW NKDPLTSVSYQINSKSALTWHQARKSCQQQNAELLSITEIHEQTYL TGLTSSLTSGLWIGLNSLSFNSGWQWSDRSPFRYLNWLPGSPSAE PGKSCVSLNPGKNAKWENLECVQKLGYICKKGNTTLNSFVIPSES DVPTHCPSQWWPYAGHCYKIHRDEKKIQRDALTTCKEGGDLTS IHTIEELDFIISQLGYEPNDELWIGLNDIKIQMYFEWSDGTPVTFTK WLRGEPSHENNRQEDCVVMKGKDGYWADRGCEWPLGYICKMK SRSQGPEIVEVEKGCRKGWKKHHFYCYMIGHTLSTFAEANQTCN NENAYLTTIEDRYEQAFLTSFVGLRPEKYFWTGLSDIQTKGTFQW TIEEEVRFTHWNSDMPGRKPGCVAMRTGIAGGLWDVLKCDEKA KFVCKHWAEGVTHPPKPTTTPEPKCPEDWGASSRTSLCFKLYAK GKHEKKTWFESRDFCRALGGDLASINNKEEQQTIWRLITASGSYH KLFWLGLTYGSPSEGFTWSDGSPVSYENWAYGEPNNYQNVEYC GELKGDPTMSWNDINCEHLNNWICQIQKGQTPKPEPTPAPQDNPP VTEDGWVIYKDYQYYFSKEKETMDNARAFCKRNFGDLVSIQSES EKKFLWKYVNRNDAQSAYFIGLLISLDKKFAWMDGSKVDYVSW ATGEPNFANEDENCVTMYSNSGFWNDINCGYPNAFICQRHNSSIN ATTVMPTMPSVPSGCKEGWNFYSNKCFKIFGFMEEERKNWQEAR KACIGFGGNLVSIQNEKEQAFLTYHMKDSTFSAWTGLNDVNSEH TFLWTDGRGVHYTNWGKGYPGGRRSSLSYEDADCVVIIGGASNE AGKWMDDTCDSKRGYICQTRSDPSLTNPPATIQTDGFVKYGKSS YSLMRQKFQWHEAETYCKLHNSLIASILDPYSNAFAWLQMETSN ERVWIALNSNLTDNQYTWTDKWRVRYTNWAADEPKLKSACVY |

TABLE 15-continued

Amino acid sequences of human and mouse macrophage mannose receptor

| Name | SEQ ID NO | Amino acid sequence |
|---|---|---|
| | | LDLDGYWKTAHCNESFYFLCKRSDEIPATEPPQLPGRCPESDHTA
WIPFHGHCYYIESSYTRNWGQASLECLRMGSSLVSIESAAESSFLS
YRVEPLKSKTNFWIGLFRNVEGTWLWINNSPVSFVNWNTGDPSG
ERNDCVALHASSGFWSNIHCSSYKGYICKRPKIIDAKPTHELLTTK
ADTRKMDPSKPSSNVAGVVIIVILLILTGAGLAAYFFYKKRRVHLP
QEGAFENTLYFNSQSSPGTSDMKDLVGNIEQNEHSVI |
| Recombinant human MMR (R&D systems) | 259 | LLDTRQFLIYNEDHKRCVDAVSPSAVQTAACNQDAESQKFRWVS
ESQIMSVAFKLCLGVPSKTDWVAITLYACDSKSEFQKWECKNDT
LLGIKGEDLFFNYGNRQEKNIMLYKGSGLWSRWKIYGTTDNLCS
RGYEAMYTLLGNANGATCAFPFKFENKWYADCTSAGRSDGWL
WCGTTTDYDTDKLFGYCPLKFEGSESLWNKDPLTSVSYQINSKSA
LTWHQARKSCQQQNAELLSITEIHEQTYLTGLTSSLTSGLWIGLNS
LSFNSGWQWSDRSPFRYLNWLPGSPSAEPGKSCVSLNPGKNAKW
ENLECVQKLGYICKKGNTTLNSFVIPSESDVPTHCPSQWWPYAGH
CYKIHRDEKKIQRDALTTCRKEGGDLASIHTIEEFDFIISQLGYEPN
DELWIGLNDIKIQMYFEWSDGTPVTFTKWLRGEPSHENNRQEDC
VVMKGKDGYWADRGCEWPLGYICKMKSRSQGPEIVEVEKGCRK
GWKKHHFYCYMIGHTLSTFAEANQTCNNENAYLTTIEDRYEQAF
LTSFVGLRPEKYFWTGLSDIQTKGTFQWTIEEEVRFTHWNSDMPG
RKPGCVAMRTGIAGGLWDVLKCDEKAKFVCKHWAEGVTHPPKP
TTTPEPKCPEDWGASSRTSLCFKLYAKGKHEKKTWFESRDFCRAL
GGDLASINNKEEQQTIWRLITASGSYHKLFWLGLTYGSPSEGFTW
SDGSPVSYENWAYGEPNNYQNVEYCGELKGDPTMSWNDINCEH
LNNWICQIQKGQTPKPEPTPAPQDNPPVTEDGWVIYKDYQYYFSK
EKETMDNARAFCKRNFGDLVSIQSESEKKFLWKYVNRNDAQSAY
FIGLLISLDKKFAWMDGSKVDYVSWATGEPNFANEDENCVTMYS
NSGFWNDINCGYPNAFICQRHNSSINATTVMPTMPSVPSGCKEGW
NFYSNKCFKIFGFMEEERKNWQEARKACIGFGGNLVSIQNEKEQA
FLTYHMKDSTFSAWTGLNDVNSEHTFLWTDGRGVHYTNWGKG
YPGGRRSSLSYEDADCVVIIGGASNEAGKWMDDTCDSKRGYICQ
TRSDPSLTNPPATIQTDGFVKYGKSSYSLMRQKFQWHEAETYCKL
HNSLIASILDPYSNAFAWLQMETSNERVWIALNSNLTDNQYTWT
DKWRVRYTNWAADEPKLKSACVYLDLDGYWKTAHCNESFYFL
CKRSDEIPATEPPQLPGRCPESDHTAWIPFHGHCYYIESSYTRNWG
QASLECLRMGSSLVSIESAAESSFLSYRVEPLKSKTNFWIGLFRNV
EGTWLWINNSPVSFVNWNTGDPSGERNDCVALHASSGFWSNIHC
SSYKGYICKRPKIIDAKPTHELLTTKADTRKMDPSKHHHHHH |
| Mouse MMR (Mrc 1) | 260 | MRLLLLLAFISVIPVSVQLLDARQFLIYNEDHKRCVDALSAISVQT
ATCNPEAESQKFRWVSDSQIMSVAFKLCLGVPSKTDWASVTLYA
CDSKSEYQKWECKNDTLFGIKGTELYFNYGNRQEKNIKLYKGSG
LWSRWKVYGTTDDLCSRGYEAMYSLLGNANGAVCAFPPFKFENK
WYADCTSAGRSDGWLWCGTTTDYDKDLFGFCPLHFEGSERLW
NKDPLTGILYQINSKSALTWHQARASCKQQNADLLSVTEIHEQMY
LTGLTSSLSSGLWIGLNSLSVRSGWQWAGGSPFRYLNWLPGSPSS
EPGKSCVSLNPGKNAKWENLECVQKLGYICKKGNNTLNPFIIPSA
SDVPTGCPNQWWPYAGHCYRIHREEKKIQKYALQACRKEGGDL
ASIHSIEEFDFIFSQLGYEPNDELWIGLNDIKIQMYFEWSDGTPVTF
TKWLPGEPSHENNRQEDCVVMKGKDGYWADRACEQPLGYICK
MVSQSHAVVPEGADKGCRKGWKRHGFYCYLIGSTLSTFTDANHT
CTNEKAYLTTVEDRYEQAFLTSLVGLRPEKYFWTGLSDVQNKGT
FRWTVDEQVQFTHWNADMPGRKAGCVAMKTGVAGGLWDVLS
CEEEKAKFVCKHWAEGVTRPPEPTTTPEPKCPENWGTTSKTSMCF
KLYAKGKHEKKTWFESRDFCKAIGGELASIKSKDEQQVIWRLITS
SGSYHELFWLGLTYGSPSEGFTWSDGSPVSYENWAYGEPNNYQN
VEYCGELKGDPGMSWNDINCEHLNNWICQIQKGKTLLPEPTPAPQ
DNPPVTADGWVIYKDYQYYFSKEKETMDNARAFCKKNFGDLATI
KSESEKKFLWKYINKNGGQSPYFIGMLISMDKKFIWMDGSKVDF
VAWATGEPNFANDDENCVTMYTNSGFWNDINCGYPNNFICQRH
NSSINATAMPTTPTTPGGCKEGWHLYKNKCFKIFGFANEEKKSW
QDARQACKGLKGNLVSIENAQEQAFVTYHMRDSTFNAWTGLNDI
NAEHMFLWTAGQGVHYTNWGKGYPGGRRSSLSYEDADCVVIG
GNSREAGTWMDDTCDSKQGYICQTQTDPSLPVSPTTTPKDGFVT
YGKSSYSLMKLKLPWHEAETYCKDHTSLLASILDPYSNAFAWMK
MHPFNVPIWIALNSNLTNNEYTWTDRWRVRYTNWGADEPKLKS
ACVYMDVDGYWRTSYCNESFYFLCKKSDEIPATEPPQLPGKCPES
EQTAWIPFYGHCYYFESSFTRSWGQASLECLRMGASLVSIETAAE
SSFLSYRVEPLKSKTNFWIGMFRNVEGKWLWLNDNPVSFVNWKT
GDPSGERNDCVVLASSSGLWNNIHCSSYKGFICKMPKIIDPVTTHS
SITTKADQRKMDPQPKGSSKAAGVVTVVLLIVIGAGVAAYFFYK
KRHALHIPQEATFENTLYFNSNLSPGTSDTKDLMGNIEQNEHAII |

TABLE 15-continued

Amino acid sequences of human and mouse macrophage mannose receptor

| Name | SEQ ID NO | Amino acid sequence |
|---|---|---|
| Recombinant mouse MMR (R&D systems) | 261 | LLDARQFLIYNEDHKRCVDALSAISVQTATCNPEAESQKFRWVSD SQIMSVAFKLCLGVPSKTDWASVTLYACDSKSEYQKWECKNDTL FGIKGTELYFNYGNRQEKNIKLYKGSGLWSRWKVYGTTDDLCSR GYEAMYSLLGNANGAVCAFPFKFENKWYADCTSAGRSDGWLW CGTTTDYDKDKLFGFCPLHFEGSERLWNKDPLTGILYQINSKSAL TWHQARASCKQQNADLLSVTEIHEQMYLTGLTSSLSSGLWIGLNS LSVRSGWQWAGGSPFRYLNWLPGSPSSEPGKSCVSLNPGKNAKW ENLECVQKLGYICKKGNNTLNPFIIPSASDVPTGCPNQWWPYAGH CYRIHREEKKIQKYALQACRKEGGDLASIHSIEEFDFIFSQLGYEPN DELWIGLNDIKIQMYFEWSDGTPVTFTKWLPGEPSHENNRQEDCV VMKGKDGYWADRACEQPLGYICKMVSQSHAVVPEGADKGCRK GWKRHGFYCYLIGSTLSTFTDANHTCTNEKAYLTTVEDRYEQAF LTSLVGLRPEKYFWTGLSDVQNKGTFRWTVDEQVQFTHWNADM PGRKAGCVAMKTGVAGGLWDVLSCEEKAKFVCKHWAEGVTRP PEPTTTPEPKCPENWGTTSKTSMCFKLYAKGKHEKKTWFESRDFC KAIGGELASIKSKDEQQVIWRLITSSGSYHELFWLGLTYGSPSEGF TWSDGSPVSYENWAYGEPNNYQNVEYCGELKGDPGMSWNDINC EHLNNWICQIQKGKTLLPEPTPAPQDNPPVTADGWVIYKDYQYYF SKEKETMDNARAFCKKNFGDLATIKSESEKKFLWKYINKNGGQS PYFIGMLISMDKKFIWMDGSKVDFVAWATGEPNFANDDENCVT MYTNSGFWNDINCGYPNNFICQRHNSSINATAMPTTPTTPGGCKE GWHLYKNKCFKIFGFANEEKKSWQDARQACKGLKGNLVSIENA QEQAFVTYHMRDSTFNAWTGLNDINAEHMFLWTAGQGVHYTN WGKGYPGGRRSSLSYEDADCVVVIGGNSREAGTWMDDTCDSKQ GYICQTQTDPSLPVSPTTTPKDGFVTYGKSSYSLMKLKLPWHEAE TYCKDHTSLLASILDPYSNAFAWMKMHPFNVPIWIALNSNLTNNE YTWTDRWRVRYTNWGADEPKLKSACVYMDVDGYWRTSYCNES FYFLCKKSDEIPATEPPQLPGKCPESEQTAWIPFYGHCYYFESSFTR SWGQASLECLRMGASLVSIETAAESSFLSYRVEPLKSKTNFWIGM FRNVEGKWLWLNDNPVSFVNWKTGDPSGERNDCVVLASSSGLW NNIHCSSYKGFICKMPKIIDPVTTHSSITTKADQRKMDPQPKGSSK AHHHHHH |
| Human MMR (MRC1)-ectodomain | 262 | LLDTRQFLIYNEDHKRCVDAVSPSAVQTAACNQDAESQKFRWVS ESQIMSVAFKLCLGVPSKTDWVAITLYACDSKSEFQKWECKNDT LLGIKGEDLFFNYGNRQEKNIMLYKGSGLWSRWKIYGTTDNLCS RGYEAMYTLLGNANGATCAFPFKFENKWYADCTSAGRSDGWL WCGTTTDYDTDKLFGYCPLKFEGSESLWNKDPLTSVSYQINSKSA LTWHQARKSCQQQNAELLSITEIHEQTYLTGLTSSLTSGLWIGLNS LSFNSGWQWSDRSPFRYLNWLPGSPSAEPGKSCVSLNPGKNAKW ENLECVQKLGYICKKGNTTLNSFVIPSESDVPTHCPSQWWPYAGH CYKIHRDEKKIQRDALTTCRKEGGDLTSIHTIEELDFIISQLGYEPN DELWIGLNDIKIQMYFEWSDGTPVTFTKWLRGEPSHENNRQEDC VVMKGKDGYWADRGCEWPLGYICKMKSRSQGPEIVEVEKGCRK GWKKHHFYCYMIGHTLSTFAEANQTCNNENAYLTTIEDRYEQAF LTSFVGLRPEKYFWTGLSDIQTKGTFQWTIEEEVRFTHWNSDMPG RKPGCVAMRTGIAGGLWDVLKCDEKAKFVCKHWAEGVTHPPKP TTTPEPKCPEDWGASSRTSLCFKLYAKGKHEKKTWFESRDFCRAL GGDLASINNKEEQQTIWRLITASGSYHKLFWLGLTYGSPSEGFTW SDGSPVSYENWAYGEPNNYQNVEYCGELKGDPTMSWNDINCEH LNNWICQIQKGQTPKPEPTPAPQDNPPVTEDGWVIYKDYQYYFSK EKETMDNARAFCKRNFGDLVSIQSESEKKFLWKYVNRNDAQSAY FIGLLISLDKKFAWMDGSKVDYVSWATGEPNFANEDENCVTMYS NSGFWNDINCGYPNAFICQRHNSSINATTVMPTMPSVPSGCKEGW NFYSNKCFKIFGFMEEERKNWQEARKACIGFGGNLVSIQNEKEQA FLTYHMKDSTFSAWTGLNDVNSEHTFLWTDGRGVHYTNWGKG YPGGRRSSLSYEDADCVVIIGGASNEAGKWMDDTCDSKRGYICQ TRSDPSLTNPPATIQTDGFVKYGKSSYSLMRQKFQWHEAETYCKL HNSLIASILDPYSNAFAWLQMETSNERVWIALNSNLTDNQYTWT DKWRVRYTNWAADEPKLKSACVYLDLDGYWKTAHCNESFYFL CKRSDEIPATEPPQLPGRCPESDHTAWIPFHGHCYYIESSYTRNWG QASLECLRMGSSLVSIESAAESSFLSYRVEPLKSKTNFWIGLFRNV EGTWLWINNSPVSFVNWNTGDPSGERNDCVALHASSGFWSNIHC SSYKGYICKRPKIIDAKPTHELLTTKADTRKMDPSK |

TABLE 15-continued

Amino acid sequences of human and mouse macrophage mannose receptor

| Name | SEQ ID NO | Amino acid sequence |
|---|---|---|
| Mouse MMR (Mrc1)-ectodomain | 263 | LLDARQFLIYNEDHKRCVDALSAISVQTATCNPEAESQKFRWVSD SQIMSVAFKLCLGVPSKTDWASVTLYACDSKSEYQKWECKNDTL FGIKGTELYFNYGNRQEKNIKLYKGSGLWSRWKVYGTTDDLCSR GYEAMYSLLGNANGAVCAFPFKFENKWYADCTSAGRSDGWLW CGTTTDYDKDKLFGFCPLHFEGSERLWNKDPLTGILYQINSKSAL TWHQARASCKQQNADLLSVTEIHEQMYLTGLTSSLSSGLWIGLNS LSVRSGWQWAGGSPFRYLNWLPGSPSSEPGKSCVSLNPGKNAKW ENLECVQKLGYICKKGNNTLNPFIIPSASDVPTGCPNQWWPYAGH CYRIHREEKKIQKYALQACRKEGGDLASIHSIEEFDFIFSQLGYEPN DELWIGLNDIKIQMYFEWSDGTPVTFTKWLPGEPSHENNRQEDCV VMKGKDGYWADRACEQPLGYICKMVSQSHAVVPEGADKGCRK GWKRHGFYCYLIGSTLSTFTDANHTCTNEKAYLTTVEDRYEQAF LTSLVGLRPEKYFWTGLSDVQNKGTFRWTVDEQVQFTHWNADM PGRKAGCVAMKTGVAGGLWDVLSCEEKAKFVCKHWAEGVTRP PEPTTTPEPKCPENWGTTSKTSMCFKLYAKGKHEKKTWFESRDFC KAIGGELASIKSKDEQQVIWRLITSSGSYHELFWLGLTYGSPSEGF TWSDGSPVSYENWAYGEPNNYQNVEYCGELKGDPGMSWNDINC EHLNNWICQIQKGKTLLPEPTPAPQDNPPVTADGWVIYKDYQYYF SKEKETMDNARAFCKKNFGDLATIKSESEKKFLWKYINKNGGQS PYFIGMLISMDKKFIWMDGSKVDFVAWATGEPNFANDDENCVT MYTNSGFWNDINCGYPNNFICQRHNSSINATAMPTTPTTPGGCKE GWHLYKNKCFKIFGFANEEKKSWQDARQACKGLKGNLVSIENA QEQAFVTYHMRDSTFNAWTGLNDINAEHMFLWTAGQGVHYTN WGKGYPGGRRSSLSYEDADCVVVIGGNSREAGTWMDDTCDSKQ GYICQTQTDPSLPVSPTTTPKDGFVTYGKSSYSLMKLKLPWHEAE TYCKDHTSLLASILDPYSNAFAWMKMHPFNVPIWIALNSNLTNNE YTWTDRWRVRYTNWGADEPKLKSACVYMDVDGYWRTSYCNES FYFLCKKSDEIPATEPPQLPGKCPESEQTAWIPFYGHCYYFESSFTR SWGQASLECLRMGASLVSIETAAESSFLSYRVEPLKSKTNFWIGM FRNVEGKWLWLNDNPVSFVNWKTGDPSGERNDCVVLASSSGLW NNIHCSSYKGFICKMPKIIDPVTTHSSITTKADQRKMDPQPKGSSK A |

REFERENCES

1. Mantovani A., P. Allavena, A. Sica, F. Balkwill. Cancer-related inflammation. *Nature* 2008; 454:436-44.
2. Pollard J. W. Tumor-educated macrophages promote tumor progression and metastasis. *Nat. Rev. Cancer* 2004; 4:71-8.
3. Lin E. Y., J. F. Li, L. Gnatovskiy, et al. Macrophages regulate the angiogenic switch in a mouse model of breast cancer. *Cancer Res.* 2006; 66:11238-46.
4. Lewis C. E., J. W. Pollard. Distinct role of macrophages in different tumor microenvironments. *Cancer Res.* 2006; 66:605-12.
5. Varol C., S. Yona, S. Jung. Origins and tissue-context-dependent fates of blood monocytes. *Immunol. Cell Biol.* 2009; 87:30-8.
6. Auffray C., M. H. Sieweke, F. Geissmann. Blood monocytes: development, heterogeneity, and relationship with dendritic cells. *Annu. Rev. Immunol.* 2009; 27:669-92.
7. Martinez F. O., L. Helming, S. Gordon. Alternative activation of macrophages: an immunologic functional perspective. *Annu. Rev. Immunol.* 2009; 27:451-83.
8. Sica A., T. Schioppa, A. Mantovani, P. Allavena. Tumor-associated macrophages are a distinct M2 polarised population promoting tumour progression: potential targets of anti-cancer therapy. *Eur. J. Cancer* 2006; 42:717-27.
9. Lewis C., C. Murdoch. Macrophage responses to hypoxia: implications for tumor progression and anti-cancer therapies. *Am. J. Pathol.* 2005; 167:627-35.
10. Nanni P., C. de Giovanni, P. L. Lollini, G. Nicoletti, G. Prodi. TS/A: a new metastasizing cell line from a BALB/c spontaneous mammary adenocarcinoma. *Clin. Exp. Metastasis* 1983; 1:373-80.
11. Tacke F., F. Ginhoux, C. Jakubzick, N. van Rooijen, M. Merad, G. J. Randolph. Immature monocytes acquire antigens from other cells in the bone marrow and present them to T cells after maturing in the periphery. *J. Exp. Med.* 2006; 203:583-97.
12. Tacke F., D. Alvarez, T. J. Kaplan, et al. Monocyte subsets differentially employ CCR2, CCR5, and CX3CR1 to accumulate within atherosclerotic plaques. *J. Clin. Invest.* 2007; 117:185-94.
13. Ojalvo L. S., W. King, D. Cox, J. W. Pollard. High-density gene expression analysis of tumor-associated macrophages from mouse mammary tumors. *Am. J. Pathol.* 2009; 174:1048-64.
14. Biswas S. K., L. Gangi, S. Paul, et al. A distinct and unique transcriptional program expressed by tumor-associated macrophages (defective NF-kappaB and enhanced IRF-3/STAT1 activation). *Blood* 2006; 107:2112-22.
15. Hagemann T., J. Wilson, F. Burke, et al. Ovarian cancer cells polarize macrophages toward a tumor-associated phenotype. *J. Immunol.* 2006; 176:5023-32.
16. Hagemann T., T. Lawrence, I. McNeish, et al. "Re-educating" tumor-associated macrophages by targeting NF-kappaB. *J. Exp. Med.* 2008; 205:1261-8.
17. Pugh C. W., P. J. Ratcliffe. Regulation of angiogenesis by hypoxia: role of the HIF system. *Nat. Med.* 2003; 9:677-84.
18. Reis e Sousa C. Dendritic cells in a mature age. *Nat. Rev. Immunol.* 2006; 6:476-83.
19. Tacke F., F. Ginhoux, C. Jakubzick, N. van Rooijen, M. Merad, G. J. Randolph. Immature monocytes acquire antigens from other cells in the bone marrow and present them to T cells after maturing in the periphery. *J. Exp. Med.* 2006; 203:583-597.

20. Tacke F., D. Alvarez, T. J. Kaplan, et al. Monocyte subsets differentially employ CCR2, CCR5, and CX3CR1 to accumulate within atherosclerotic plaques. *J. Clin. Invest.* 2007; 117:185-194.
21. Van Rooijen N., A. Sanders. Liposome mediated depletion of macrophages: mechanism of action, preparation of liposomes and applications. *J. Immunol. Methods* 1994; 174:83-93.
22. Liu Y., J. A. Van Ginderachter, L. Brys, P. De Baetselier, G. Raes, A. B. Geldhof. Nitric oxide-independent CTL suppression during tumor progression: association with arginase-producing (M2) myeloid cells. *J. Immunol.* 2003; 170:5064-5074.
23. Movahedi B., C. Gysemans, D. Jacobs-Tulleneers-Thevissen, C. Mathieu, D. Pipeleers. Pancreatic duct cells in human islet cell preparations are a source of angiogenic cytokines interleukin-8 and vascular endothelial growth factor. *Diabetes* 2008; 57:2128-2136.
24. Movahedi K., M. Guilliams, J. Van den Bossche, et al. Identification of discrete tumor-induced myeloid-derived suppressor cell subpopulations with distinct T cell-suppressive activity. *Blood* 2008; 111:4233-4244.
25. Cortez-Retamozo V., N. Backmann, P. D. Senter, U. Wernery, P. De Baetselier, S. Muyldermans and H. Revets. Efficient cancer therapy with a nanobody-based conjugate. *Cancer Res.* 2004; 64:2853-2857.
26. Hamers-Casterman C., Atarhouch T., Muyldermans S., Robinson G., Hamers C., Songa E., Bendahman N & Hamers R., 1993, Nature 363, p. 446-448.
27. Desmyter A., T. Transue., M. Ghahroudi, M. Dao-Thi, F. Poortmans, R. Hamers, S. Muyldermans and L. Wyns, 1996, *Nat. Struct. Biol.*, p. 803-811.
28. Conrath K., M. Lauwereys, M. Galleni, A. Matagne, J-M. Frere, J. Kinne, L. Wyns, and S. Muyldermans (2001). β-Lactamase Inhibitors Derived from Single-Domain Antibody Fragments Elicited in the Camelidae Antimicrob Agents. *Chemother* 45, 2807-2812
29. Saerens D., G. Ghassabeh, S. Muyldermans, 2008, *Current Opinion in Pharmacology* 8, p. 600-608.
30. Saerens D., J. Kinne, E. Bosmans, U. Wernery, S. Muyldermans, K. Conrath (2004). Single domain antibodies derived from dromedary lymph node and peripheral blood lymphocytes sensing conformational variants of prostate-specific antigen. *J. Biol. Chem.* 279: 51965-72.
31. Saerens D., B. Stijlemans, T. N. Baral, G. T. Nguyen Thi, U. Wernery, S. Magez, P. De Baetselier, S. Muyldermans, K. J. Conrath. Parallel selection of multiple anti-infectome Nanobodies without access to purified antigens (2008) *Immunol. Methods* 329: 138-50.
32. Huarte E., J. R. Cubillos-Ruiz, Y. C. Nesbeth, U. K. Scarlett, D. G. Martinez, R. J. Buckanovich, F. Benencia, R. V. Stan, T. Keler, P. Sarobe, C. L. Sentman, J. R. Conejo-Garcia. (2008) Depletion of dendritic cells delays ovarian cancer progression by boosting antitumor immunity. *Cancer Res.* 68: 7684-91.
33. Hwang J., D. J. Fitzgerald, S. Adhya, I. Pastan (1987) Functional domains of *Pseudomonas* exotoxin identified by deletion analysis of the gene expressed in *E. coli. Cell.* 48:129-36.
34. Harris N., M. Super, M. Rits, G. Chang, R. A. Ezekowitz. (1992) Characterization of the murine macrophage mannose receptor: demonstration that the down-regulation of receptor expression mediated by interferon-gamma occurs at the level of transcription. *Blood* 80: 2363-73.
35. Lefranc M. P., C. Pommie, et al. (2003). "IMGT unique numbering for immunoglobulin and T cell receptor variable domains and Ig superfamily V-like domains." *Developmental and Comparative Immunology* 27(1): 55-77.
36. Grivennikov S. I., F. R. Greten, M. Karin. Immunity, inflammation, and cancer. Cell. 2010; 140:883-99.
37. Hofmeister V., D. Schrama, J. C. Becker. Anti-cancer therapies targeting the tumor stroma. *Cancer Immunol. Immunother.* 2008; 57:1-17.
38. Zafir-Lavie I., Y. Michaeli, Y. Reiter. Novel antibodies as anticancer agents. *Oncogene.* 2007; 26:3714-33.
39. Condeelis J., J. W. Pollard. Macrophages: obligate partners for tumor cell migration, invasion, and metastasis. *Cell.* 2006; 124:263-6.
40. Wesolowski J., V. Alzogaray, J. Reyelt, M. Unger, K. Juarez, M. Urrutia, A. Cauerhiff, W. Danquah, B. Rissiek, F. Scheuplin, N. Schwarz, S. Adriouch, O. Boyer, M. Seman, A. Licea, D. V. Serreze, F. A. Goldbaum, F. Haag, and F. Koch-Nolte. (2009). Single domain antibodies: promising experimental and therapeutic tools in infection and immunity *Med. Microbiol. Immunol.* 198, 157-174.
41. Riechmann and Muyldermans *J. Immunol. Methods* 2000; 240: 185-195.
42. Holm S. A Simple Sequentially Rejective Multiple Test Procedure. *Scand. J Stat.* 1979; 6:65-70.
43. Ihaka R., R. R. Gentleman. A Language for Data Analysis and Graphics. *J. Comput. Graph. Stat.* 1996; 5:299-314.
44. Katherine S. Pollard HNG, Yongchao Ge, Sandra Taylor and Sandrine Dudoit. multtest: Resampling-based multiple hypothesis testing. R package version 2.7.1. 2011 [cited; Available from: worldwide web at CRAN.Rproject.org/package=multtest.
45. Sawanobori Y., S. Ueha, M. Kurachi, T. Shimaoka, J. E. Talmadge, J. Abe, et al. Chemokine-mediated rapid turnover of myeloid-derived suppressor cells in tumor-bearing mice. *Blood* 2008; 111:5457-66.
46. Pahler J. C., S. Tazzyman, N. Erez, Y. Y. Chen, C. Murdoch, H. Nozawa, et al. Plasticity in tumor-promoting inflammation: impairment of macrophage recruitment evokes a compensatory neutrophil response. *Neoplasia.* 2008; 10:329-40.
47. Chieppa M., G. Bianchi, A. Doni, A. Del Prete, M. Sironi, G. Laskarin, et al. Crosslinking of the mannose receptor on monocyte-derived dendritic cells activates an anti-inflammatory immunosuppressive program. *J. Immunol.* 2003; 171:4552-60.
48. Colpaert C. G., P. B. Vermeulen, S. B. Fox, A. L. Harris, L. Y. Dirix, E. A. Van Marck. The presence of a fibrotic focus in invasive breast carcinoma correlates with the expression of carbonic anhydrase 1x and is a marker of hypoxia and poor prognosis. *Breast Cancer Res. Treat.* 2003; 81:137-47.
49. Dosztányi Z., V. Csizmok, P. Tompa, and I. Simon (2005). IUPred: web server for the prediction of intrinsically unstructured regions of proteins based on estimated energy content. *Bioinformatics* (Oxford, England), 21(16), 3433-4.
50. Higgins & Sharp, *CABIOS* 5:151 (1989)
51. Altschul S. F., W. Gish, W. Miller, E. W. Myers, D. J. Lipman. Basic local alignment search tool. *J. Mol. Biol.* 1990; 215:403-10.
52. Arbabi Ghahroudi M., A. Desmyter, L. Wyns, R. Hamers, S. Muyldermans. Selection and identification of single domain antibody fragments from camel heavy-chain antibodies. *FEBS Lett.* 1997; 414:521-6.

What is claimed is:

1. A method of in vivo imaging tumor-associated macrophages (TAM) in a subject, the method comprising:
   administering to the subject an immunoglobulin single variable domain labeled with a detectable label, wherein the immunoglobulin single variable domain specifically binds to a macrophage mannose receptor selected from the group consisting of SEQ ID NO: 260 and SEQ ID NO: 258, and wherein the immunoglobulin single variable domain comprises a nanobody sequence ($V_HH$) selected from the group consisting of SEQ ID NO: 4, SEQ ID NO: 130, SEQ ID NO: 131, SEQ ID NO: 137, SEQ ID NO: 139, SEQ ID NO: 141, and SEQ ID NO: 144, and
   Imaging TAM in the subject to which the labeled immunoglobulin single variable domain binds.

2. The method according to claim 1, the method further comprising:
   co-administering to the subject an unlabeled bivalent form of the immunoglobulin single variable domain to block extratumoral binding sites for the immunoglobulin single variable domain in the subject.

3. The method according to claim 2, wherein the imaged TAM are MHC II$^{low}$.

4. The method according to claim 1, wherein the subject is mammalian.

5. The method according to claim 4, wherein the subject is human.

6. The method according to claim 1, wherein the imaged TAM are located in the hypoxic regions of a solid tumor.

7. The method according to claim 1, wherein the imaged TAM are associated with mammary adenocarcinoma cells or lung carcinoma cells.

8. The method according to claim 1, wherein the nanobody sequence comprises SEQ ID NO:4.

9. The method according to claim 1, wherein the nanobody sequence comprises SEQ ID NO:130.

10. The method according to claim 1, wherein the nanobody sequence comprises SEQ ID NO:131.

11. The method according to claim 1, wherein the nanobody sequence comprises SEQ ID NO:137.

12. The method according to claim 1, wherein the nanobody sequence comprises SEQ ID NO:139.

13. The method according to claim 1, wherein the nanobody sequence comprises SEQ ID NO:141.

14. The method according to claim 1, wherein the nanobody sequence comprises SEQ ID NO:144.

* * * * *